United States Patent
Imperiali et al.

(10) Patent No.: US 11,597,751 B2
(45) Date of Patent: Mar. 7, 2023

(54) GLYCAN-BINDING PROTEINS AND RELATED COMPOSITIONS AND METHODS

(71) Applicant: Massachusetts Institute of Technology, Cambridge, MA (US)

(72) Inventors: Barbara Imperiali, Cambridge, MA (US); Cristina Zamora, Medford, MA (US); Elizabeth Ward, Somerville, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 74 days.

(21) Appl. No.: 16/818,827

(22) Filed: Mar. 13, 2020

(65) Prior Publication Data
US 2020/0362000 A1 Nov. 19, 2020

Related U.S. Application Data

(60) Provisional application No. 62/848,891, filed on May 16, 2019.

(51) Int. Cl.
C07K 14/47 (2006.01)
(52) U.S. Cl.
CPC .................................... *C07K 14/47* (2013.01)
(58) Field of Classification Search
None
See application file for complete search history.

(56) References Cited

U.S. PATENT DOCUMENTS

| | | | |
|---|---|---|---|
| 9,422,548 | B2 | 8/2016 | Pecorari et al. |
| 2010/0159527 | A1 | 6/2010 | Martin et al. |
| 2012/0258460 | A1 | 10/2012 | Cheng et al. |
| 2014/0322825 | A1 | 10/2014 | Pancer et al. |
| 2016/0143990 | A1 | 5/2016 | Kitten |
| 2019/0113512 | A1 | 4/2019 | Sikes Johnson et al. |

FOREIGN PATENT DOCUMENTS

WO  WO 2007/011891 A2  1/2007

OTHER PUBLICATIONS

Gera et al.,"Highly stable binding proteins derived from the hyperthermophilic Sso7d scaffold", Journal of Molecular Biology 409: 601-616 (Year: 2011).*
Traxlmayr et al.,"Strong enrichment of aromatic residues in binding sites from a charge-neutralized hyperthermostable Sso7d scaffold library", The Journal of Biological Chemistry vol. 291, No. 432, pp. 22496-22508 (Year: 2016).*
Gao et al.,"Unique Binding Specificities of Proteins toward Isomeric Asparagine-Linked Glycans", Cell Chemical Biology 26, 535-547 (Year: 2019).*
Banno et al. Development of a sugar-binding residue prediction system from protein sequences using support vector machine. Comput Biol Chem. 2017;66:36-43. doi: 10.1016/j.compbiolchem.2016.10.009.
Barre et al., Mannose-binding plant lectins: different structural scaffolds for a common sugar-recognition process. *Biochimie.* 2001;83(7):645-651. doi:10.1016/s0300-9084(01)01315-3. Abstract only.
Baumann et al., DNA-binding surface of the Sso7d protein from Sulfolobus solfataricus. J Mol Biol. 1995;247(5):840-846. doi:10.1006/jmbi.1995.0184.
Flint et al. Ligand-mediated dimerization of a carbohydrate-binding molecule reveals a novel mechanism for protein-carbohydrate recognition. J Mol Biol. 2004;337(2):417-426. doi:10.1016/j.jmb.2003.12.081.
Gera et al., Highly stable binding proteins derived from the hyperthermophilic Sso7d scaffold. J Mol Biol. 2011;409(4):601-616. doi:10.1016/j.jmb.2011.04.020.
Hong et al. Sugar-binding proteins from fish: selection of high affinity "lambodies" that recognize biomedically relevant glycans. ACS Chem Biol. 2013;8(1):152-160. doi:10.1021/cb300399s.
Lammerts Van Bueren et al., Carbohydrate-binding modules. CAZypedia. 2018.
Luo et al. Recognition of the Thomsen-Friedenreich pancarcinoma carbohydrate antigen by a lamprey variable lymphocyte receptor. J Biol Chem. 2013;288(32):23597-23606. doi:10.1074/jbc.M113.480467.
Ng et al., Structural analysis of monosaccharide recognition by rat liver mannose-binding protein. J Biol Chem. 1996;271(2):663-674. doi:10.1074/jbc.271.2.663.
Proft, Sortase-mediated protein ligation: an emerging biotechnology tool for protein modification and immobilisation. Biotechnol Lett. 2010;32(1):1-10. doi:10.1007/s10529-009-0116-0.
Stanley, Galectin-1 Pulls the Strings on VEGFR2. Cell. 2014;156(4):625-626. doi:10.1016/j.cell.2014.01.059.
Traxlmayr et al. Strong Enrichment of Aromatic Residues in Binding Sites from a Charge-neutralized Hyperthermostable Sso7d Scaffold Library. J Biol Chem. 2016;291(43):22496-22508. doi:10.1074/jbc.M116.741314.
Wong et al. An intermolecular binding mechanism involving multiple LysM domains mediates carbohydrate recognition by an endopeptidase. Acta Crystallogr D Biol Crystallogr. 2015;71(Pt 3):592-605. doi:10.1107/S139900471402793X.

(Continued)

*Primary Examiner* — Anand U Desai
(74) *Attorney, Agent, or Firm* — Wolf, Greenfield & Sacks, P.C.

(57) ABSTRACT

Glycan-binding proteins, and compositions thereof, are generally described, including methods of making and using such proteins. The proteins may include scaffolds based on easily evolvable DNA-binding proteins, with binding sites able to specifically bind to mono- or disaccharides, such as monosaccharide-binding determinants, disaccharide-binding determinants, more complex carbohydrates, etc. In certain aspects, a protein may be generated starting from a small DNA-binding protein, such as Sso7d. Such glycan-binding proteins may have numerous applications, including in enzyme-linked immunosorbent assays (ELISAs), glycan characterization, cell selection, flow cytometry, histology, imaging, arrays, affinity purification, enzyme-linked visualization, binding to a target for pharmaceutical purposes, etc.

20 Claims, 18 Drawing Sheets
Specification includes a Sequence Listing.

(56) References Cited

OTHER PUBLICATIONS

International Search Report and Written Opinion for PCT/US2020/022732 dated Aug. 13, 2020.

International Preliminary Report on Patentability for PCT/US2020/022732 dated Jun. 15, 2020.

Chua et al., Galectin-10, a potential biomarker of eosinophilic airway inflammation. PLoS One. 2012;7(8):e42549. doi: 10.1371/journal.pone.0042549. Epub Aug. 6, 2012. PMID: 22880030; PMCID: PMC3412795.

Gilbert et al., Editorial overview: Carbohydrate-protein interactions and glycosylation: integrating structural biology, informatics and systems modelling to understand glycan structure and glycan-protein interactions. Curr Opin Struct Biol. Oct. 2016;40:v-viii. doi: 10.1016/j.sbi.2016.11.009. Epub Nov. 27, 2016. PMID: 27899244.

Kebriaei et al., Droplet Frequency Sensor: a new modality for sensitive, label-free, inline biochemical detection. IEEE. Transducers. 2017;642-645.

Song et al., Novel fluorescent glycan microarray strategy reveals ligands for galectins. Chem Biol. Jan. 30, 2009;16(1):36-47. doi: 10.1016/j.chembiol.2008.11.004. PMID: 19171304; PMCID: PMC2662446.

Toscano et al., Dissecting the pathophysiologic role of endogenous lectins: glycan-binding proteins with cytokine-like activity? Cytokine Growth Factor Rev. Feb.-Apr. 2007;18(1-2):57-71. doi: 10.1016/j.cytogfr.2007.01.006. Epub Feb. 22, 2007. PMID: 17321195.

\* cited by examiner

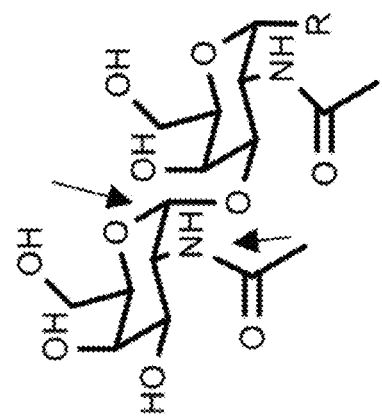
FIG. 2C GalNAcα1-3GalNAcα
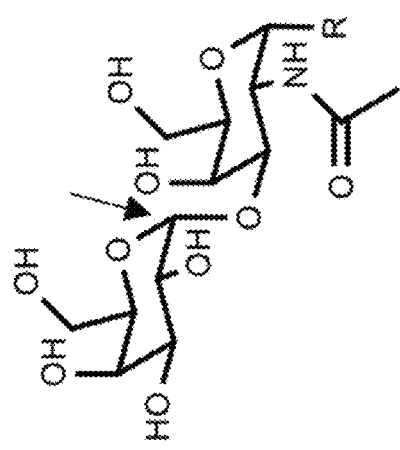
FIG. 2B Galα1-3GalNAcα
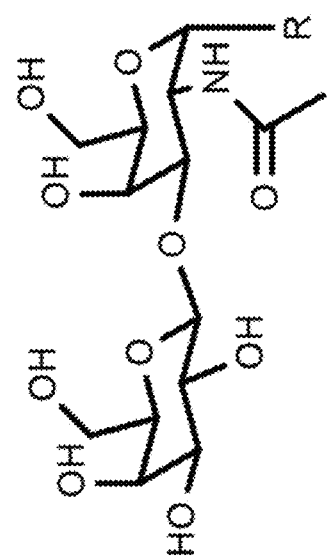
FIG. 2A Galβ1-3GalNAcα (TF)

Neu5Gc

Neu5Ac (sialic acid)

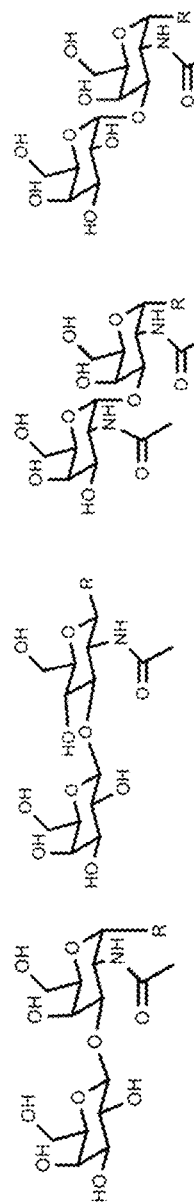
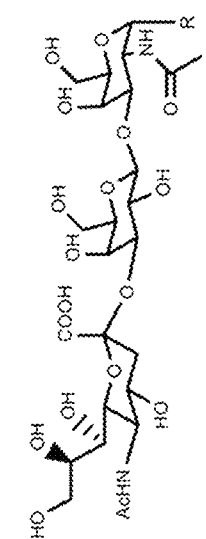
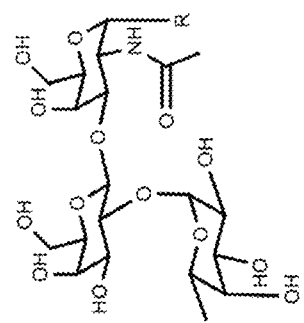
FIG. 9A Galβ1-3GalNAcα (TF antigen)
FIG. 9B Galβ1-3GlcNAβ (Le<sup>c</sup>)
FIG. 9C GalNAcα1-3GalNAcα
FIG. 9D Galα1-3GalNAcα
FIG. 9E NeuSAcα2-3Galβ1-3GalNAcα (Sia-TF)
FIG. 9F Fucα1-2Galβ1-3GalNAcα (H3)

GLYCAN-BINDING PROTEINS AND RELATED COMPOSITIONS AND METHODS

RELATED APPLICATIONS

This application claims priority to U.S. Provisional Patent Application Ser. No. 62/848,891, filed on May 16, 2019, and entitled "Glycan-Binding Proteins and Related Compositions and Methods," which is hereby incorporated by reference in its entirety.

GOVERNMENT SPONSORSHIP

This invention was made with Government support under Grant No. R21 AI130776 awarded by the National Institutes of Health (NIH). The Government has certain rights in the invention.

TECHNICAL FIELD

Glycan-binding proteins and related compositions and methods are generally described.

SUMMARY

Glycan-binding proteins, and compositions thereof, are generally described. Inventive methods of making and using the glycan-binding proteins are also described. The subject matter of the present invention involves, in some cases, interrelated products, alternative solutions to a particular problem, and/or a plurality of different uses of one or more systems and/or articles.

Certain aspects are related to compositions. In one aspect, a composition comprises a protein having at least 55% homology to the following sequence:

```
                                        (SEQ ID NO: 3)
ATVKFTYQGEEKQVDISKIK(s1)(s2)DEGGG(s3)SEKDAPKELLQML
EKQ
``` wherein (s1) consists of 7 amino acid residues and is not KKVWRVG (SEQ ID NO: 407), (s2) consists of 7 amino acid residues and is not QMISFTY (SEQ ID NO: 408), (s3) consists of 7 amino acid residues and is not ATGRGAV (SEQ ID NO: 409). In some embodiments, the protein specifically binds to a monosaccharide or disaccharide-binding determinant.

In another aspect, a composition comprises a protein having at least 55% homology to the following sequence:

```
                                        (SEQ ID NO: 4)
ATVKFTYQGEEKQVDISKIKKX¹VX²RX³GQX⁴IX⁵FX⁶YDEGGGAX⁷GX⁸
GX⁹VSEKDAPKELLQMLEKQ,
``` wherein each of $X^1$, $X^2$, $X^3$, $X^4$, $X^5$, $X^6$, $X^7$, $X^8$, and $X^9$ is independently an amino acid residue, with the proviso that $X^1$, $X^2$, $X^3$, $X^4$, $X^5$, $X^6$, $X^7$, $X^8$, and $X^9$ cannot simultaneously be K, W, V, M, S, T, T, R, and A, respectively. In some cases, the protein specifically binds to a monosaccharide or disaccharide-binding determinant.

In another aspect, a composition comprises a protein having 55-99% homology to the following sequence:

```
                                        (SEQ ID NO: 1)
ATVKFTYQGEEKQVDISKIKKVWRVGQMISFTYDEGGGATGRGAVSEKDA
PKELLQMLEKQ,
``` wherein the protein specifically binds to a monosaccharide or disaccharide-binding determinant.

In yet another aspect, a composition comprises a first glycan-binding portion and a second glycan-binding portion. In some cases, each of the first glycan-binding portion and the second glycan-binding portion independently has at least 55% homology to Sso7d.

In addition, certain aspects are related to methods. For example, in one aspect, a method of producing a glycan-binding protein comprises providing a protein scaffold, wherein the protein scaffold comprises Sso7d, generating one or more variants of the protein scaffold, determining binding and/or binding selectivity of the one or more variants to a monosaccharide or disaccharide-binding determinant, selecting a variant exhibiting increased binding and/or binding selectivity to the monosaccharide or disaccharide-binding determinant from the one or more variants, and repeating the generating, determining and selecting steps, using the variant exhibiting increased binding and/or binding selectivity to the monosaccharide or disaccharide-binding determinant in each repeat.

In another aspect, a method of producing a glycan-binding protein comprises providing a protein scaffold, wherein the protein scaffold has no more than 200 amino acid residues, with a binding face area of less than or equal to 6 square nanometers ($nm^2$), generating one or more variants of the protein scaffold, determining binding and/or binding selectivity of the one or more variants to a monosaccharide or disaccharide-binding determinant, selecting a variant exhibiting increased binding and/or binding selectivity to the monosaccharide or disaccharide-binding determinant from the one or more variants, and repeating the generating, determining and selecting steps, using the variant exhibiting increased binding and/or binding selectivity to the monosaccharide or disaccharide-binding determinant in each repeat.

A large variety of proteins are described herein. For example, in one set of embodiments, the protein is selected from Sequence List 1. In another set of embodiments, the protein is selected from Sequence List 2.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIG. 2A illustrates the structure of Galβ1-3GalNAcα (TF or Thomsen-Friedenrich antigen).

FIG. 2B illustrates the structure of Galα1-3GalNAcα, with arrows towards various points of differentiation from the TF antigen.

FIG. 2C illustrates the structure of GalNAcα1-3GalNAcα, with arrows towards various points of differentiation from the TF antigen.

FIGS. 9A-9F illustrate disaccharides (or disaccharide motifs within trisaccharides) bound by glycan-binding proteins, in accordance with some embodiments described herein.

BRIEF DESCRIPTION OF THE SEQUENCES

Figure 1:
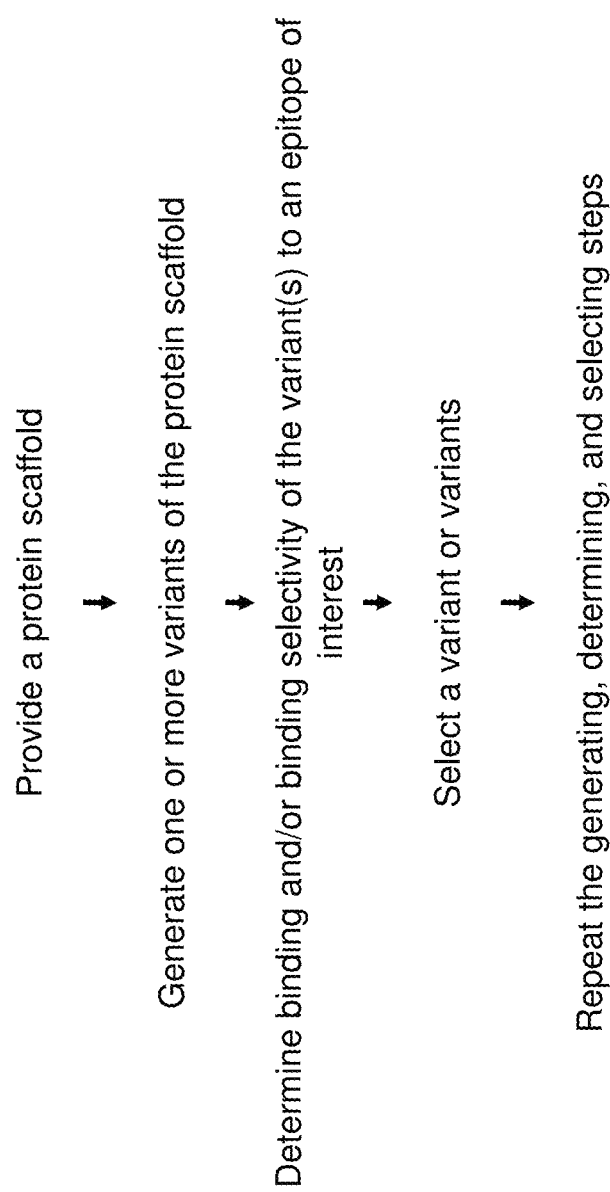
FIG. 1 illustrates a flowchart of methods of generating a glycan-binding protein, in some embodiments.

SEQ ID NO: 1 is a reduced-charge variant of Sso7d (rcSso7d), having a sequence:

ATVKFTYQGEEKQVDISKIKKVWRVGQMISFTYDEGGGATGRGAVSEKDA

PKELLQMLEKQ.

SEQ ID NO: 2 is Sso7d, a protein from *S. solfataricus* having a sequence:

ATVKFKYKGEEKQVDISKIKKVWRVGKMISFTYDEGGGKTGRGAVSEKDA

PKELLQMLEKQK.

SEQ ID NO: 3 is ATVKFTYQGEEKQVDISKIK(s1)(s2)DEGGG(s3) SEKDAPKELLQMLEKQ, where (s1) consists of 7 amino acid residues and is not KKVWRVG (SEQ ID NO: 407), (s2) consists of 7 amino acid residues and is not QMISFTY (SEQ ID NO: 408), and (s3) consists of 7 amino acid residues and is not ATGRGAV (SEQ ID NO: 409).

SEQ ID NO: 4 is the following amino acid sequence: ATVKFTYQGEEKQVDISKIKKX$^1$VX$^2$RX$^3$GQX$^4$IX$^5$FX$^6$YDEGGGAX$^7$GX$^8$GX$^9$VSE KDAPKELLQMLEKQ, where each of X$^1$, X$^2$, X$^3$, X$^4$, X$^5$, X$^6$, X$^7$, X$^8$, and X$^9$ is independently an amino acid residue, with the proviso that X$^1$, X$^2$, X$^3$, X$^4$, X$^5$, X$^6$, X$^7$, X$^8$, and X$^9$ cannot simultaneously be K, W, V, M, S, T, T, R, and A, respectively.

SEQ ID NO: 5 is M11.1, an artificial protein having the following sequence:

ATVKFTYQGEEKQVDISKIKWVIRWGQHIAFKYDEGGGAAGYGWVSEKDA

PKELLQMLEKQ.

SEQ ID NO: 6 is M11.2, an artificial protein having the following sequence:

ATVKFTYQGEEKQVDISKIKWVNRWGQRIYFKYDEGGGAAGYGWVSEKDA

PKELLQMLEKQ.

SEQ ID NO: 7 is M11.1.2, an artificial protein having the following sequence:

ATVKYTYRGEEKRVDISKIKWVNRWGQHLAFKYDKGGGAAGYGWVSEKDA

PKELLQMLEKR.

SEQ ID NO: 8 is M11.1.3, an artificial protein having the following sequence:

ATVKSTYRGEEKQVDISKIKWVIRWGQHLAFKYDEGGGAAGYGWVSEKDA

PKELLQMLEKQ.

SEQ ID NO: 9 is M11.1.5, an artificial protein having the following sequence:

ATVKFTYRGEEKQVDISKIKWVNRWGQHLAFKYDVGGGAAGYGWMSEKDAP

KELLQMLEKR.

SEQ ID NO: 10 is M18.1, an artificial protein having the following sequence:

ATVKFTYQGEEKQVDISKIKWVIRLGRTIMFKYDEGGGANGYGKVSEKDA

PKELLQMLEKQ.

SEQ ID NO: 11 is M18.2, an artificial protein having the following sequence:

ATVKFTYQGEEKQVDISKIKWVVRLGQVIMFKYDEGGGANGYGKVSEKDA

PKELLQMLEKQ.

SEQ ID NO: 12 is M18.2.2, an artificial protein having the following sequence:

ATVKFTYRGEEKQVDISKIKWVVRLGQVIMFKYGEGGGSNGYGRVSEKDA
PKELRQMLEKR.

SEQ ID NO: 13 is M18.2.5, an artificial protein having the following sequence:

ATVKFTYRGEEKQVDISKIKWVVRLGQVIMFKYDEGGGASGYGRVSEKDA
PKELLQMLEK.

DETAILED DESCRIPTION

Glycan-binding proteins, and compositions thereof, are generally described, including methods of making and using such proteins. The proteins may include scaffolds based on easily evolvable DNA-binding proteins, with binding sites able to specifically bind to mono- or disaccharides, such as monosaccharide-binding determinants, disaccharide-binding determinants, in more complex carbohydrates, etc. In certain aspects, a protein may be generated starting from a small DNA-binding protein, such as Sso7d. Such glycan-binding proteins may have numerous applications, including in enzyme-linked immunosorbent assays (ELISAs), glycan characterization, cell selection, flow cytometry, histology, imaging, arrays, affinity purification, enzyme-linked visualization, binding to a target for pharmaceutical purposes, etc.

Certain aspects of the invention are generally directed to proteins able to bind to glycans, for example, via specific binding. Glycans are generally sugars or carbohydrates, alone or conjugated to other entities, such as proteins, lipids, small molecules, or the like. The glycans may include any number of saccharide units, including monosaccharides, disaccharides, and larger polysaccharides. Glycans can be homo- or heteropolymers of monosaccharide residues, and can be linear or branched. The glycan may comprise only saccharide units, or other non-saccharide units as well, for example, as in glycoproteins, glycolipids, glyconucleic acids, proteoglycans, etc.

In some cases, glycan-binding proteins such as those discussed herein may be relatively small or low-molecular weight, and can accordingly bind to small glycan-binding determinants, e.g., monosaccharides or disaccharides within an overall glycan structure, e.g., via specific binding. Such glycan-binding determinants that the protein can bind may be a single monosaccharide or disaccharide, or in some cases, the glycan-binding determinant may be part of a larger structure, e.g., such as those noted above.

In contrast, other carbohydrate-binding proteins known to the art are typically significantly larger, and are unable to specifically bind to or recognize single monosaccharide or disaccharide-binding determinants. Glycan-binding proteins such as these may be useful in a variety of immunological, therapeutic, diagnostic, or technological roles such as those discussed herein.

In addition, certain embodiments of the invention are generally directed to systems and methods for making such glycan-binding proteins. In some cases, a DNA-binding protein may be used as a protein scaffold and engineered, e.g., using directed evolution, to produce a glycan-binding protein. In some cases, e.g., after multiple generations, proteins with high specificities of binding to glycans may be developed.

In some cases, the protein scaffold may be one that is readily evolvable. The protein scaffold may also, in certain embodiments, have a binding site (e.g., a binding pocket) that has dimensions compatible with monosaccharide and/or disaccharide binding, and/or have a binding site (e.g., a binding pocket) that has dimensions similar to those of any monosaccharide or disaccharide motif of interest within a glycan.

In addition, in certain embodiments, the protein scaffold may be devoid of disulfides. In some cases, the protein scaffold may be stable to a wide range of temperatures and/or pH values. In addition, such protein scaffolds may be one that can be readily functionalized chemically or conjugated to other entities, for example, to generate clustered or branched assemblies. For example, in one set of embodiments, two such protein scaffolds may be linked together.

As one non-limiting example, in some embodiments, Sso7d (or a reduced-charge variant thereof) can be used as a protein scaffold. Native or wild-type Sso7d arises from *Sulfolobus solfataricus*, where it binds DNA and does not ordinarily bind glycans. However, the Sso7d scaffold can be used to develop glycan-binding proteins, as discussed herein. For instance, in some embodiments, the Sso7d protein scaffold is mutated, for example, by error-prone PCR, to generate variants. These variants are then, in some cases, analyzed to determine binding efficiency to a target glycan, for instance, using Yeast-Surface Display (YSD) selections with magnetic bead-immobilized glycans. The variant or variants with the best binding and/or binding selectivity to the target glycan (e.g., a specific monosaccharide or disaccharide-binding determinant) are then selected, and the process is optionally repeated one or more times (e.g., the variant(s) undergo a session of random mutation, the variants generated from this session of mutation are analyzed via YSD, and the variant(s) with the best binding and/or binding selectivity to the target of interest are selected). As many repetitions can be done as desired and/or as required to achieve the desired binding constant and/or binding selectivity.

Based on techniques such as these, or others described herein, modified Sso7d proteins can be developed that can bind to various glycans, for example, but not limited to, a disaccharide (e.g. the dihexose Galβ1-3GalNAcα, also named the TF antigen, FIG. 2A) or a monosaccharide (e.g. the nonulosonic acid named Neu5Ac, FIG. 3A) and certain embodiments of the invention are also generally directed to such modified Sso7d proteins. In some cases, the binding may be relatively specific, for example, with a $K_D$ of less than $10^{-5}$ M, or other values such as those described herein.

In certain embodiments, glycan-binding proteins such as those discussed herein can be used in various applications. In some cases, the protein can be modified further. For example, a glycan-binding protein could be attached to another glycan-binding protein to, for example, increase the binding and/or binding selectivity even further. As another example, in certain instances, a glycan-binding protein could be attached to another structure (e.g., a fluorophore) to, for example, functionalize the protein for a particular use, such as use for ELISAs, therapeutics, glycan characterization, cell selection, flow cytometry, histology, imaging, arrays, affinity purification, and/or enzyme-linked visualization, among other applications. A variety of applications involving the binding of a glycan to a glycan-binding protein, e.g., specifically, thus may be realized.

The above discussion illustrates various non-limiting examples of some embodiments. However, other embodiments of glycan-binding proteins and compositions thereof are also possible, as discussed below.

Certain aspects are related to systems and methods for producing glycan-binding proteins and compositions thereof. Non-limiting examples of such glycan-binding proteins are discussed below. Exemplary directed evolution methods of producing glycan-binding proteins are described in relation to FIG. 1. However, it should be understood that the methods described herein have broader utility, and are not limited to generating the glycan-binding proteins described herein. In addition, it should be understood that other methods may be used instead of the methods described in FIG. 1, including other directed evolution methods as well as other methods, such as ab initio calculations, to produce glycan-binding proteins and other proteins such as those described herein.

Thus, some embodiments are generally directed to directed evolution method of producing a protein, such as a glycan-binding protein. As an example of a directed evolution method, in FIG. 1, the method comprises providing a protein scaffold and generating one or more variants of the scaffold, determining binding and/or selectivity of those variants (for example, to a binding determinant of interest, such as to a monosaccharide and/or disaccharide) and selecting those that meet desired criteria (e.g., improved binding and/or selectivity). These steps can be repeated in some cases.

Certain methods, including certain directed evolution methods, start with the identification of a suitable protein scaffold. The protein scaffold may then be randomly mutated under directed evolution to produce a protein having one or more desired characteristics, such as the ability to bind a glycan, in some cases specifically.

Figure 8B:
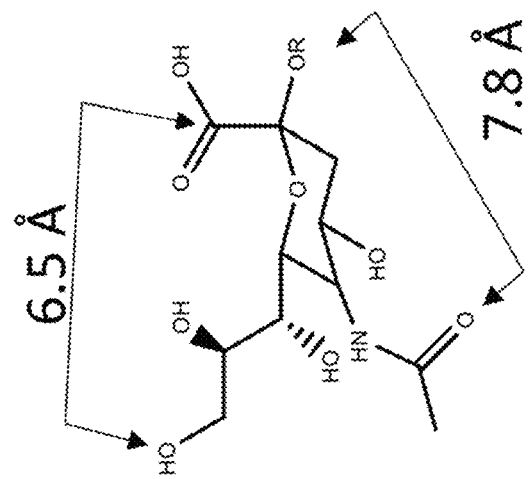
FIG. 8B illustrates the dimensions of an example monosaccharide (i.e., NeuN5Ac).
Figure 8A:
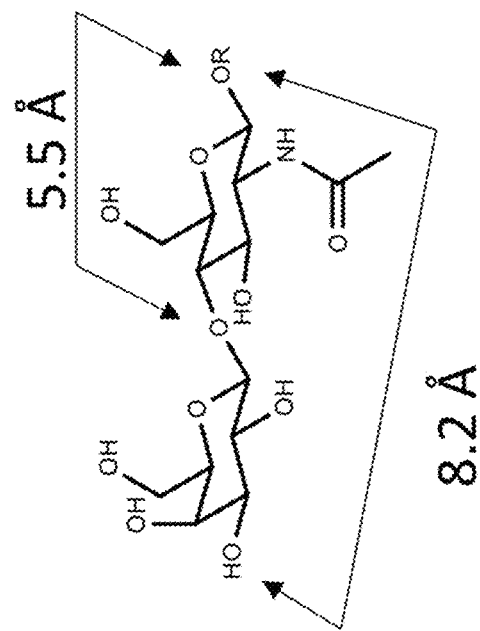
FIG. 8A illustrates the dimensions of an example disaccharide (i.e., TF antigen).

In some cases, the protein scaffold may be one that has a binding site (e.g., a binding pocket) that has dimensions compatible with monosaccharide and/or disaccharide binding, and/or have a structure that has dimensions similar to those of any monosaccharide or disaccharide motif of interest within a glycan In some cases the binding site may be one that is evolvable, e.g., as the protein scaffold is evolved using directed evolution. For example, the protein scaffold may be one that has a binding site (e.g., a binding pocket) that has dimensions compatible with monosaccharide and/or disaccharide binding, and/or have a binding site (e.g., a binding pocket) that has dimensions similar to those of any monosaccharide or disaccharide motif of interest within a glycan Examples of such dimensions are shown in FIGS. 8A-8B; in FIG. 8A, the dimensions of a typical disaccharide (the dihexose Galβ1-3GalNAcα) are shown; in FIG. 8B, the dimensions of a typical monosaccharide (the nonulosonic acid Neu5Ac) are shown. It should be understood that these dimensions are exemplary, and that other monosaccharides or disaccharides will have dimensions slightly different from these. However, the dimensions of the binding site of the protein scaffold may have dimensions comparable to these. For example, the binding site may have a largest dimension that is smaller than 30 Angstroms, smaller than 25 Angstroms, smaller than 20 Angstroms, smaller than 15 Angstroms, smaller than 10 Angstroms, smaller than 9.8 Angstroms, smaller than 9.6 Angstroms, smaller than 9.4 Angstroms, smaller than 9.2 Angstroms, smaller than 9.0 Angstroms, smaller than 8.8 Angstroms, smaller than 8.6 Angstroms, smaller than 8.4 Angstroms, smaller than 8.2 Angstroms, smaller than 8.0 Angstroms, smaller than 7.8 Angstroms, smaller than 7.6 Angstroms, smaller than 7.4 Angstroms, smaller than 7.2 Angstroms, smaller than 7.0 Angstroms, etc.

In some cases, the protein scaffold may be selected to have a binding face area of at least 1, at least 2, at least 3, at least 4, at least 5, at least 6, or at least 7 square nanometers ($nm^2$). The protein scaffold, in some instances, has a binding face area of less than or equal to 6, less than or equal to 5, less than or equal to 4, or less than or equal to 3 square nanometers ($nm^2$). Combinations of these ranges are also possible (e.g., 2-6 square nanometers ($nm^2$)). The binding face area can be calculated by looking at the binding site of the protein scaffold, finding the longest dimension of that site, and multiplying it by the dimension of the site at a 90 degree angle from the longest dimension. For example, if the longest dimension is 30 Angstroms and the orthogonal dimension is 15 Angstroms, then the binding face area would be 450 Angstroms$^2$ (1.5×3.0) or 4.5 $nm^2$.

The protein scaffold itself may, in some cases, be one that is based on a relatively small protein, for example, one that is slightly greater than these dimensions. This may, for example, allow for multiple scaffolds to be conjugated together with minimal additional sequences. For example, the protein scaffold may be one that has a relatively low number of amino acids, e.g., less than 250 amino acids. In certain cases, the protein scaffold has less than or equal to 200 amino acid residues, less than or equal to 175 amino acid residues, less than or equal to 150 amino acid residues, less than or equal to 125 amino acid residues, less than or equal to 100 amino acid residues, or less than or equal to 75 amino acid residues. In accordance with some embodiments, the protein scaffold has greater than or equal to 25 amino acid residues, greater than or equal to 50 amino acid residues, greater than or equal to 75 amino acid residues, greater than or equal to 100 amino acid residues, or greater than or equal to 150 amino acid residues. Combinations of these ranges are also possible (e.g., the protein scaffold may have between 50-100 amino acid residues, between 50-75 amino acid residues, between 75-100 amino acid residues, or the like).

In certain instances, the protein scaffold has a maximum dimension of less than or equal to 200 Angstroms, less than or equal to 150 Angstroms, less than or equal to 100 Angstroms, less than or equal to 50 Angstroms, less than or equal to 40 Angstroms, less than or equal to 30 Angstroms, less than or equal to 25 Angstroms, less than or equal to 20 Angstroms, less than or equal to 15 Angstroms, less than or equal to 10 Angstroms, less than or equal to 7 Angstroms, or less than or equal to 3 Angstroms. In addition, according to some embodiments, the protein scaffold has a maximum dimension of greater than or equal to 5 Angstroms, greater than or equal to 9 Angstroms, greater than or equal to 12 Angstroms, greater than or equal to 15 Angstroms, greater than or equal to 18 Angstroms, greater than or equal to 20 Angstroms, greater than or equal to 25 Angstroms, greater than or equal to 30 Angstroms, greater than or equal to 40 Angstroms, etc. Combinations of these ranges are also possible (e.g., the protein scaffold may have a maximum dimension of between 15-20 Angstroms, between 20-25 Angstroms, between 10-30 Angstroms, etc.).

In addition, in some embodiments, the protein scaffold may be substantially devoid of disulfides or cysteine residues. Cysteines may cause problems with respect to disulfide bond formation, which can significantly alter the molecular structure of the protein scaffold, e.g., during the directed evolution process. For example, there may be no more than 4, 3, 2, or 1 cysteines within the protein scaffold.

In some cases, no cysteines are present. Similarly, the protein scaffold may have fewer than or equal to 2, or 1 disulfide bonds, or the protein scaffold may be free of disulfide bonds.

In some cases, the protein scaffold may be selected to have a relatively high melting temperature ($T_m$), i.e., the protein scaffold may exhibit high thermal stability. For example, the protein scaffold may exhibit a melting temperature of greater than or equal to 50° C., greater than or equal to 60° C., greater than or equal to 70° C., greater than or equal to 80° C., greater than or equal to 90° C. greater than or equal to 100° C., greater than or equal to 125° C., greater than or equal to 150° C., etc. In some cases, the melting temperature may be less than or equal to 150° C., less than or equal to 125° C., less than or equal to 100° C., less than or equal to 90° C., or less than or equal to 80° C. Combinations of these ranges are also possible (e.g., 60° C. to 125° C. (inclusive)). The melting temperature or melting point is generally the temperature at which the protein begins to denature or lose its shape or 3D conformation. Accordingly, melting temperature can be determined, for example, by increasing the temperature and observing any changes in three-dimensional structure using circular dichroism (CD), differential scanning calorimetry (DSC) measurements, or the like.

The protein scaffolds may also be selected to be stable to a wide range of pH conditions. For example, the protein scaffold may be stable at a pH of greater than or equal to 1, greater than or equal to 2, greater than or equal to 3, greater than or equal to 4, greater than or equal to 5, or greater than or equal to 6. In some embodiments, the protein scaffold may be stable at a pH of less than or equal to 12, less than or equal to 11, less than or equal to 10, less than or equal to 9, or less than or equal to 8. Combinations of these ranges are also possible. For example, in some cases, the protein and/or the protein scaffold used to generate a glycan-binding protein are stable within a pH of between 2-11, or within a pH between 1-12. pH stability can be determined, for example, by adjusting the pH of the solution and observing changes in three-dimensional structure (e.g., using CD) after 30 minutes.

In some cases, a protein scaffold may be selected to be readily functionalized chemically or conjugated to other entities, for example, to generate clustered or branched assemblies. For example, the protein scaffold may be one that is capable of chemical functionalization, array display, and/or conjugation. This may be useful, for example, to generate clustered and branched assemblies to exploit avidity effects, which can be important in glycan binding in some cases. In certain embodiments, the size of the protein scaffold may be sufficiently compact, e.g., having the dimensions as discussed above, so that non-binding components of the scaffold do not substantially interfere with conjugation of glycan readers for binding multivalent glycans and more complex glycan targets. For example, in some embodiments, two protein scaffolds may be linked or conjugated together, e.g., to bind to more complex glycan targets. In some cases, the protein scaffold may be selected to be amenable to high-yield protein expression in *Escherichia coli* and facile bioconjugation to fluorophores, purification tags, biocompatible resins, 2-dimensional (2D) arrays, or the like. In addition, in some embodiments, the protein scaffold may be selected to be compatible with yeast surface display, in the presence and/or in the absence of $Ca^{2+}$ or any other metal ion or cofactor.

Examples of protein scaffolds that may be suitable to produce glycan-binding proteins, such as those discussed herein, include Affibody, Fn3 domain, DARPins, Lambody, and Sso7d, these are summarized in Table 1.

TABLE 1

| SCAFFOLD | # Residues | WT $T_m$ (° C.) |
|---|---|---|
| Affibody | 58 | 78 |
| Fn3 domain | 94 | 84 |
| DARPins | 130-190 | variable |
| Lambody | 217 | n/d |
| Sso7d | 63 | 98 |

Thus, in one set of embodiments, the protein scaffold may be Sso7d (e.g., from *Sulfolobus solfataricus*), or variants thereof. Sso7d has the following sequence:

```
                                          (SEQ ID NO: 2)
ATVKFKYKGEEKQVDISKIKKVWRVGKMISFTYDEGGGKTGRGAVSEKDA

PKELLQMLEKQK
```

In addition, the protein scaffold may be based on the reduced-charge variant of Sso7d (rcSso7d), for example, comprising the following sequence:

```
                                          (SEQ ID NO: 1)
ATVKFTYQGEEKQVDISKIKKVWRVGQMISFTYDEGGGATGRGAVSEKDA

PKELLQMLEKQ.
```

Thus, in certain cases, the protein scaffold may be based on Sso7d or rcSso7d, with 10, 9, 8, 7, 6, 5, 4, 3, 2, or 1 changed residues. In some cases, the protein scaffold may be based on rcSso7d, but with greater than or equal to 70%, greater than or equal to 80%, greater than or equal to 90%, greater than or equal to 95%, or greater than or equal to 99% homology. The protein scaffold may also have less than or equal to 99%, less than or equal to 95%, less than or equal to 90%, or less than or equal to 85% homology to Sso7d or rcSso7d. Combinations of these ranges are also possible (e.g., 90-99% homology).

In certain embodiments, the method comprises generating one or more variants of the protein scaffold, e.g., as is shown in FIG. 1. Any number of variants may be generated. In addition, a variety of methods may be used to generate variants of the protein scaffold. For example, in some embodiments, error-prone PCR can be used to mutate the protein scaffold randomly. Other non-limiting examples include various experimental techniques (such as error-prone PCR, chemical mutagenesis, UV irradiation, etc.), or computer-based approaches (e.g., altering the amino acid sequence, e.g., randomly or with particular mutations, such as relatively conservative mutations). In some cases, site-directed mutagenesis techniques may be used (e.g., focused on one or more of the variable residue portions of a protein scaffold, such as those discussed herein). In other cases, the mutations may be randomly generated, e.g., without regard to any particular focus within the protein scaffold.

In some embodiments, the variants of the protein scaffold that are generated include, on average, greater than or equal to 1 amino acid, greater than or equal to 2 amino acids, greater than or equal to 3 amino acids, greater than or equal to 5 amino acids, etc., in each round of mutation. In certain embodiments, there may be less than or equal to 5 amino acids, less than or equal to 4 amino acids, less than or equal to 3 amino acids, or less than or equal to 2 amino acids that were mutated in a protein scaffold in a round of mutation. Combination of these ranges are also possible. In some cases, the number of mutations in a protein scaffold may not be deterministic, i.e., in techniques, such as error-prone PCR, that generate random mutations within a protein scaffold.

In some cases, the variant protein scaffolds may be studied to determine which ones exhibit desired characteristics. For example, the variants exhibiting increased binding and/or binding selectivity to the target of interest (e.g., the monosaccharide or disaccharide-binding determinant) may be determined. In some embodiments, binding and/or binding selectivity of the one or more variants to a target of interest, such as a glycan, may be used. Examples of potential targets include monosaccharide or disaccharide-binding determinants, more complex carbohydrates, or the like, e.g., as discussed herein.

For example, in accordance with certain embodiments, binding and/or binding selectivity may be determined based on binding of the variants to a target of interest, such as a monosaccharide or disaccharide-binding determinant. Non-limiting examples of monosaccharide-binding determinants include hexoses (e.g., glucose, galactose, fructose, etc.), hexosamines (e.g. glucosamine, galactosamine), heptoses or heptuloses (e.g., sedoheptulose, mannoheptulose, L-glycero-D-manno-heptose, etc.), octoses or octulosonic acids (e.g., methylthiolincosamide), nonoses or nonulosonic (sialic) acids (e.g., Kdn, Neu5Gc, Neu, Neu2en5Ac), and Neu5Ac (sialic acid) etc., as well as derivatives thereof having one or more additional substitutions at the hydroxyl groups, e.g., on C-4, C-7, C-8, and/or C-9 (such as O-acetyl, O-methyl, O-sulfate, O-lactyl, or phosphate groups, etc.), octulosonic acids and derivatives thereof (e.g. KDO or keto-deoxyoctulosonate), and nonulosonic acids and derivatives thereof (e.g. Leg or legionaminic acid, Pse or pseudaminic acid, etc.). Non-limiting examples of disaccharide-binding determinants include dihexoses (e.g., sucrose, lactose, maltose, etc.), diheptoses, and Galβ1-3GalNAcα (TF or Thomsen-Friedenrich antigen). Those of ordinary skill in the art will be familiar with other monosaccharide or disaccharide-binding determinants as well that can be used in other embodiments, e.g., as a target of interest. Many of these have been widely discussed in the scientific literature.

Thus, one or more variants may be selected that exhibit increased binding and/or binding selectivity to a target, such as a monosaccharide or disaccharide-binding determinant. In some cases, for example, variants exhibiting improved binding (e.g., as measured by the dissociation constant or $K_D$) may be selected, for example, improvements of at least 5% or at least 10% in $K_D$ in a given round of mutation/selection. It will be understood that generally, higher affinities produce smaller $K_D$ values, as discussed below. Thus, such improved variants can be determined by determining $K_D$ values, and selecting those that meet some suitable criteria, e.g., by selecting variants that have less than a certain $K_D$ value, by selecting a certain number or percentage of variants as ranked by their $K_D$ values, or the like (e.g., the 5% or 10% of variants with the lowest $K_D$ values, etc.).

In some cases, variants that are selected may be those that are able to specifically bind to a target, such as a glycan. For example, specific binding may be observed with $K_D$ values of less than $10^{-5}$ M, less than $10^{-6}$ M, less than $10^{-7}$ M, less than $10^{-8}$ M, less than $10^{-9}$ M, less than $10^{-10}$ M, etc.

A variety of methods of determining $K_D$ values can be used, e.g., based on the glycan or other target. For example, one suitable technique is yeast-surface display (YSD), e.g., using with magnetic bead-immobilized glycans as discussed below. The yeast (and the variants) can be sorted, for example, using fluorescence-activated cell sorting (FACS) or other flow cytometry techniques. Other non-limiting examples include expression in alternative systems (e.g. bacteria, insect cells, mammalian cells, or the like), biolayer interferometry traces, surface plasmon resonance (SPR) traces, binding to immobilized glycan arrays, or the like. In addition, it should be understood that other methods of determining binding or selectively may be used, instead of and/or in in addition to determining $K_D$ values.

Figure 7:
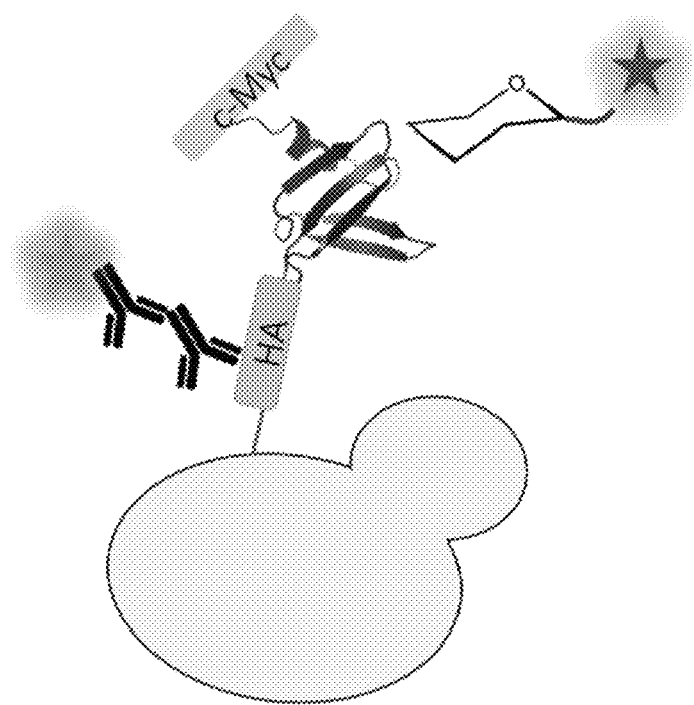
FIG. 7 illustrates a yeast-surface display of a glycan-binding protein binding a sugar-binding determinant, in accordance with certain embodiments.

Thus, in some embodiments, the determination and/or selection are accomplished using Yeast-Surface Display (YSD) selections with magnetic bead-immobilized glycans. For example, in FIG. 7, yeast-surface display is used to determine whether a variant binds a sugar-binding determinant of interest (e.g., a monosaccharide or disaccharide-binding determinant). Moreover, in certain embodiments, YSD will be used in the presence or in the absence of $Ca^{2+}$ or other metal ion or cofactor. Accordingly, in some cases, the protein scaffold is compatible with YSD in the presence of $Ca^{2+}$ and/or in the absence of $Ca^{2+}$.

In certain embodiments, the above steps (e.g., generating, determining, and selecting) may be repeated, using the variant exhibiting increased binding and/or binding selectivity as the next protein scaffold that binds to the target (e.g., a monosaccharide or disaccharide-binding determinant) in each repeat. In some instances, the generating, determining, and selecting steps are repeated, for example, until one or more variants with the desired binding and/or binding selectivity is obtained, e.g., as discussed herein. In some embodiments, these steps are repeated at least once, at least 5 times, at least 10 times, at least 20 times, or more in some cases. In certain instances, these steps are repeated less than or equal to 25 times, less than or equal to 20 times, less than or equal to 10 times, less than or equal to 5 times, or less than or equal to 2 times. Combinations of these ranges are also possible (e.g., 1-2 times).

In certain cases, once the variant has been characterized and/or its sequence has been identified, the generated protein can then be made with other common techniques available in the art. For example, the protein could be synthesized or it could be expressed in cells, such as in *E. coli*. Those of ordinary skill in the art will be aware of systems and methods for expressing a protein from its nucleic acid sequence.

Another aspect of the present invention is generally related to glycan-binding proteins and compositions thereof, e.g., generated using the techniques discussed above, or other techniques. The protein, in accordance with certain embodiments, may be able to bind to a glycan-binding determinant including any of those described herein e.g., via specific binding. For example, the protein may exhibit binding to a monosaccharide or a disaccharide-binding determinant, e.g., with $K_D$ values of less than $10^{-5}$ M, less than $10^{-6}$ M, less than $10^{-7}$ M, less than $10^{-8}$ M, less than $10^{-9}$ M, less than $10^{-10}$ M, etc. In addition, the protein can exhibit selective binding to a target glycan in certain embodiments, e.g. as compared to other glycans having similar structures. For example, the protein may be able to tightly bind to single copies of a binding determinant and/or distinguish differences at the atomic level.

As an example, as discussed, certain glycan-binding proteins are generally based on rcSso7d used as a protein scaffold. Native Sso7d is a DNA-binding protein, but does not significantly bind glycans. It forms an SH3-domain-like fold with five beta (β)-strands and an alpha (α)-helix at the C-terminus. In certain embodiments, the protein rcSso7d has a similar, or identical, three-dimensional structure to that of native Sso7d. For example, in certain cases, the protein has an SH3-domain-like fold. The protein, in some instances, has five beta (β)-strands. The protein has an alpha (α)-helix at the C-terminus, in certain embodiments. The three-dimensional structure of the protein may be considered similar to that of Sso7d if it has one or more of (i) an SH3-domain-like fold, (ii) five beta (β)-strands, or (iii) an alpha (α)-helix at the C-terminus.

In some cases, for example, the glycan-binding protein may exhibit a certain degree of homology to Sso7d (SEQ ID NO: 2), or to modified Sso7d sequences such as those described herein, for instance, the reduced-charge variant of Sso7d (rcSso7d) shown as SEQ ID NO: 1. For instance, the glycan-binding protein may exhibit 50% or greater, 55% or greater, 60% or greater, 65% or greater, 68% or greater, 70% or greater, 75% or greater, 80% or greater, 85% or greater, 90% or greater, 95% or greater homology, 97% or greater, or 99% to one or more of the sequences disclosed herein, for example, Sso7d, a modified Sso7d such as the reduced-charge variant of Sso7d (rcSso7d) of SEQ ID NO: 1, or other scaffold protein such as affibodies, Fn3 domains, DARPins, Lambodies, or the like. The glycan-binding protein may also have 99% or less, 95% or less, 90% or less, 85% or less, 80% or less, 75% or less, 70% or less, 65% or less, or 60% or less homology to one or more of those sequences. Combinations of these ranges are also possible (e.g., 55-90% homology, 68-90% homology, 75-90% homology, and 75-85% homology, etc.). As mentioned, there may be variants from the original scaffold protein, e.g., caused by directed evolution or other techniques descried herein, that allow the protein to bind to glycans. Thus, in some cases, the homology may exclude 100% (i.e., exclude wild-type scaffold proteins), since such proteins may not be able to bind glycans, or bind to glycans very poorly.

In some embodiments, the glycan-binding protein may have at least 1, at least 2, at least 3, at least 4, at least 5, at least 6, at least 8, at least 10, at least 12, at least 14, at least 16, at least 18, at least 20, at least 22, at least 24, at least 26, at least 28, at least 30, at least 32, at least 34, at least 36, at least 38, and/or no more than 40, no more than 38, no more than 36, no more than 34, no more than 32, no more than 30, no more than 28, no more than 26, no more than 24, no more than 22, no more than 20, no more than 18, no more than 16, no more than 14, no more than 12, no more than 10, no more than 8, no more than 6, no more than 5, no more than 4, no more than 3, or no more than 2 mutations relative to the initial scaffold protein, e.g., to Sso7d, a modified Sso7d such as the reduced charge variant of Sso7d (rcSso7d) of SEQ ID NO: 1, or other scaffold protein such as affibodies, Fn3 domains, DARPins, Lambodies, or the like. As a non-limiting example, a scaffold protein may have 2-4, 6-8, or 10-14 mutations relative to SEQ ID NO: 1 or SEQ ID NO: 2.

In addition, in some cases, the glycan-binding protein may have at least 34 amino acids, at least 37 amino acids, at least 40 amino acids, at least 43 amino acids, at least 46 amino acids, at least 49 amino acids, at least 52 amino acids, at least 55 amino acids, or at least 58 amino acids of one or more of the sequences in the same order. In certain embodiments, the protein may have 61 or fewer amino acids, 58 or fewer amino acids, 55 or fewer amino acids, 52 or fewer amino acids, 49 or fewer amino acids, 46 or fewer amino acids, 43 or fewer amino acids, 40 or fewer amino acids, or 37 or fewer amino acids of one or more of the sequences disclosed above in the same order. Combinations of these ranges are also possible (e.g., 37-58 amino acids of the sequences disclosed above in the same order).

In some embodiments, the amino acids may be contiguous or noncontiguous. For example, the following sequence (discussed in Example 2, Sequence List 1) has 45 amino acids (shown in underlining) of SEQ ID NO: 1:

(SEQ ID NO: 14)
ATVKFTYRGEEKQVGVSRVKSVHRIGQWIKFWYDEGSGAYGRGYVSEKDA

PEELLQMLEKRGSEQKLISEEDL.

Notably, in this example, some of the homologous amino acids are contiguous (e.g., the following 7 amino acid stretch: ATVKFTY (SEQ ID NO: 15)) while others are noncontiguous (e.g., the following 8 homologous amino acids in an 18 amino acid stretch: GVSRVKSVHRIGQWIKFW (SEQ ID NO: 16)). In some cases, there may be additional amino acids that are not present in the protein scaffold, before, after, and/or in between contiguous sections. For example, in the above example, the protein has 12 amino acids at the end of its sequence that are not present in the protein scaffold (SEQ ID NO: 1). Similarly, in certain instances, there may be sections of the protein scaffold that are missing from the protein. For example, in the above example, the protein contains the sequence QVGVSRVKSV (SEQ ID NO: 410) while the protein scaffold (SEQ ID NO: 1) contains the sequence QVDISKIKKV (SEQ ID NO: 411). In this case, the protein scaffold has an extra amino acid (11 amino acids compared to 10 amino acids). Lastly, in this example, since there are 45 amino acids of the protein scaffold in the protein, 62 amino acids in the protein scaffold, and 73 amino acids in the protein, the protein has 72.6% (45/62) homology to the protein scaffold (SEQ ID NO:1).

As mentioned, certain embodiments of the invention are generally directed to modified Sso7d sequences that are able to bind to a glycan, for instance specifically. In some instances, the protein may be able to bind to a monosaccharide or disaccharide-binding determinant. For example, in some cases, the Sso7d, or a reduced charge variant thereof, may be modified in one or more surface-exposed residues on the protein. For instance, in one set of embodiments, 1, 2, 3, 4, 5, 6, 7, 8, or 9 or more surface-exposed residues may be modified. As a specific non-limiting example, certain embodiments of the invention are generally directed to the following sequence:

ATVKFTYQGEEKQVDISKIKKX$^1$VX$^2$RX$^3$GQX$^4$IX$^5$FX$^6$YDEGGGAX$^7$GX$^8$

GX$^9$VSEKDAPKELLQMLEKQ, where each of $X^1$, $X^2$, $X^3$, $X^4$, $X^5$, $X^6$, $X^7$, $X^8$, and $X^9$ is independently an amino acid residue, with the proviso that $X^1$, $X^2$, $X^3$, $X^4$, $X^5$, $X^6$, $X^7$, $X^8$, and $X^9$ cannot all be K, W, V, M, S, T, T, R, and A, respectively (SEQ ID NO: 4). However, it should be understood that individually, one or more of these substitutions may still be made, e.g., 1, 2, 3, 4, 5, 6, 7, or 8 of the substitutions of $X^1$ with K, $X^2$ with W, $X^3$ with V, $X^4$ with M, $X^5$ with S, $X^6$ with T, $X^7$ with T, $X^8$ with R, and $X^9$ with A can be made in various embodiments.

In addition, other embodiments of the invention are generally directed to sequences that are homologous to any of the above sequences, e.g., sequences exhibiting 50% or greater, 55% or greater, 60% or greater, 65% or greater, 68% or greater, 70% or greater, 75% or greater, 80% or greater, 85% or greater, 90% or greater, 95% or greater homology, 97% or greater, and/or 99% or less, 95% or less, 90% or less, 85% or less, 80% or less, 75% or less, 70% or less, 65% or less, or 60% or less homology to this sequence. Combinations of these ranges are also possible (e.g., 55-90% homology, 68-90% homology, 75-90% homology, and 75-85% homology, etc.).

In certain cases, the protein may be a modified Sso7d sequences that are able to bind to a glycan, e.g. specifically. For example, the protein may be able to bind to a monosaccharide or disaccharide-binding determinant. In one embodiment, the protein has the following sequence:

```
                                         (SEQ ID NO: 3)
ATVKFTYQGEEKQVDISKIK(s1)(s2)DEGGG(s3)SEKDAPKELLQML
EKQ.
```

In this sequence, (s1), (s2), and (s3) represent regions of a reduced charge Sso7d variant that are surface-exposed, and may be modified. For example, independently within each of (s1), (s2), and (s3), 1, 2, 3, 4, 5, 6, or 7 of the amino acid residues within these sequences may be modified. In the initial variant, (s1) is KKVWRVG (SEQ ID NO: 407), (s2) is QMISFTY (SEQ ID NO: 408), and (s3) is ATGRGAV (SEQ ID NO: 409), and one or more of (s1), (s2), and (s3) may be modified, e.g., to have a sequence different than these. Thus, for example, in one embodiment, (s1) consists of 7 amino acid residues and is not KKVWRVG (SEQ ID NO: 407), (s2) consists of 7 amino acid residues and is not QMISFTY (SEQ ID NO: 408), and (s3) consists of 7 amino acid residues and is not ATGRGAV (SEQ ID NO: 409).

In some embodiments, 1, 2, or 3 of positions 2, 4, and 6 of (s1) may be modified, e.g., with a different amino acid residue, for example, as in $KX^1VX^2RX^3G$ (SEQ ID NO: 412), where each of $X^1$, $X^2$, and $X^3$ independently are amino acid residues, although $X^1$, $X^2$, and $X^3$ cannot simultaneously be K, W, and V, respectively. In some embodiments, 1, 2, or 3 of positions 2, 4, and 6 of (s2), e.g., with a different amino acid residue, for example, as in $QX^4IX^5FX^6Y$ (SEQ ID NO: 413), where each of $X^4$, $X^5$, and $X^6$ independently are amino acid residues, although $X^4$, $X^5$, and $X^6$ cannot simultaneously be M, S, and T. In some embodiments, 1, 2, or 3 of positions 2, 4, and 6 of (s3), e.g., with a different amino acid residue. In addition, in certain cases, the substitution is not with cysteine, for example, as in $AX^7GX^8GX^9V$ (SEQ ID NO: 414), where each of $X^7$, $X^8$, and $X^9$ independently are amino acid residues, although $X^7$, $X^8$, and $X^9$ cannot simultaneously be T, R, and A.

In addition, other embodiments of the invention are generally directed to sequences that are homologous to any of the above-described sequences, e.g., sequences exhibiting 50% or greater, 55% or greater, 60% or greater, 65% or greater, 68% or greater, 70% or greater, 75% or greater, 80% or greater, 85% or greater, 90% or greater, 95% or greater homology, 97% or greater, and/or 99% or less, 95% or less, 90% or less, 85% or less, 80% or less, 75% or less, 70% or less, 65% or less, or 60% or less homology to this sequence. Combinations of these ranges are also possible (e.g., 55-90% homology, 68-90% homology, 75-90% homology, and 75-85% homology, etc.).

Non-limiting examples of such proteins include those described in Sequence List 1 and Sequence List 2 (shown in Example 2).

Any of the amino acid substitutions described anywhere herein may be a substitution with natural and/or unnatural amino acids, and may include 1 or 2, 3, 4, etc., amino acids that are substituted in. Those of ordinary skill in the art will be aware of amino acids. For instance, the naturally-occurring amino acids include are the 20 amino acids most commonly found in nature, typically in the L-isomer, i.e., alanine ("Ala" or "A"), arginine ("Arg" or "R"), asparagine ("Asn" or "N"), aspartic acid ("Asp" or "D"), cysteine ("Cys" or "C"), glutamine ("Gln" or "Q"), glutamic acid ("Glu" or "E"), glycine ("Gly" or "G"), histidine ("His" or "H"), isoleucine ("Ile" or "I"), leucine ("Leu" or "L"), lysine ("Lys" or "K"), methionine ("Met" or "M"), phenylalanine ("Phe" or "F"), proline ("Pro" or "P"), serine ("Ser" or "S"), threonine ("Thr" or "T"), tryptophan ("Trp" or "W"), tyrosine ("Tyr" or "Y"), and valine ("Val" or "V"). In some embodiments, only natural amino acids are used in the protein.

However, in some cases, one or more unnatural amino acids may be present. An unnatural amino acid is an amino acid (or an imino acid) that is not one of the 20 natural amino acids. Non-limiting examples of unnatural amino acids include D-isomers of the natural amino acids (with the exception of glycine, which is identical to its L-isomer), as well as other amino acids such as alloisoleucine, allothreonine, homophenylalanine, homoserine, homocysteine, 5-hydroxylysine, 4-hydroxyproline, 4-carboxyglutamic acid, cysteic acid, cyclohexylalanine, ethylglycine, norleucine, norvaline, 3-aminobutyric acid, beta-amino acids (e.g., beta-alanine), N-methylated amino acids such as N-methylglycine, N-methylalanine, N-methylvaline, N-methylleucine, N-methylisoleucine, N-methylnorleucine, N-methyl-2-aminobutyric acid, N-methyl-2-aminopentanoic acid, etc.

In some cases, the glycan-binding protein may have a relatively high melting temperature ($T_m$) or exhibit high thermal stability. For example, the glycan-binding protein may exhibit a melting temperature of greater than or equal to 50° C., greater than or equal to 60° C., greater than or equal to 70° C., greater than or equal to 80° C., greater than or equal to 90° C. greater than or equal to 100° C., greater than or equal to 125° C., greater than or equal to 150° C., etc. In some cases, the melting temperature may be less than or equal to 150° C., less than or equal to 125° C., less than or equal to 100° C., less than or equal to 90° C., or less than or equal to 80° C. Combinations of these ranges are also possible (e.g., 60° C. to 125° C. (inclusive)).

The glycan-binding protein may also be stable to a wide range of pH conditions. For example, the glycan-binding protein may be stable at a pH of greater than or equal to 1, greater than or equal to 2, greater than or equal to 3, greater than or equal to 4, greater than or equal to 5, or greater than or equal to 6. In some embodiments, the glycan-binding protein may be stable at a pH of less than or equal to 12, less than or equal to 11, less than or equal to 10, less than or equal to 9, or less than or equal to 8. Combinations of these ranges are also possible, for example, stable within a pH of between 2-11, or within a pH between 1-12, etc.

In one embodiment, the protein is not any one of the following sequences:

```
                                         (SEQ ID NO: 5)
ATVKFTYQGEEKQVDISKIKWV1RWGQHIAFKYDEGGGAAGYGWVSEKDA
PKELLQMLEKQ,
```

```
                                         (SEQ ID NO: 6)
ATVKFTYQGEEKQVDISKIKWVNRWGQRIYFKYDEGGGAAGYGWVSEKDA
PKELLQMLEKQ,
```

-continued (SEQ ID NO: 7)
ATVKYTYRGEEKRVDISKIKWVNRWGQHLAFKYDKGGGAAGYGWVSEKDA

PKELLQMLEKR, (SEQ ID NO: 8)
ATVKSTYRGEEKQVDISKIKWVIRWGQHLAFKYDEGGGAAGYGWVSEKDA

PKELLQMLEKQ, (SEQ ID NO: 9)
ATVKFTYRGEEKQVDISKIKWVNRWGQHLAFKYDVGGGAAGYGWMSEKDA

PKELLQMLEKR, (SEQ ID NO: 10)
ATVKFTYQGEEKQVDISKIKWVIRLGRTIMFKYDEGGGANGYGKVSEKDA

PKELLQMLEKQ, (SEQ ID NO: 11)
ATVKFTYQGEEKQVDISKIKWVVRLGQVIMFKYDEGGGANGYGKVSEKDA

PKELLQMLEKQ, (SEQ ID NO: 12)
ATVKFTYRGEEKQVDISKIKWVVRLGQVIMFKYGEGGGSNGYGRVSEKDA

PKELRQMLEKR,
or (SEQ ID NO: 13)
ATVKFTYRGEEKQVDISKIKWVVRLGQVIMFKYDEGGGASGYGRVSEKDA

PKELLQMLEK

In accordance with some embodiments, two or more proteins are linked directly to each other, or indirectly linked, e.g., by a suitable linker. Thus, in certain embodiments, the composition comprises one or more glycan-binding portions (e.g., a first glycan-binding portion and a second glycan-binding portion). The proteins can be linked, for example, C-terminus to C-terminus, N-terminus to N-terminus, C-terminus to N-terminus, or in other suitable configurations in certain instances. In some instances, the two or more proteins are joined in a linear structure. In certain cases, the two or more proteins are joined in a branched structure. In some embodiments, the two or more proteins are immobilized proximally as part of a surface immobilized array.

In some cases, two or more linked proteins may be useful to create compositions that can bind to longer glycans. For instance, a first glycan-binding portion may recognize a first binding determinant in a glycan while a second glycan-binding portion may recognize a second binding determinant in the same glycan. In this way, longer glycans comprised of more than one saccharide may be selectively bound or even sequenced in some cases, e.g., using suitable proteins such as those discussed herein. In certain embodiments, one or more of the glycan-binding portions may include protein structures such as any of these disclosed herein, for example, those generally based on Sso7d, reduced-charge variant of Sso7d (rcSso7d), etc. In some cases, such glycans may be sequenced or their identities may be determined, e.g., as discussed herein.

For example, in some cases, one or more linked proteins may be used to identify glycan structures within glycoproteins, glycolipids, glyconucleic acids, proteoglycans, or the like. For instance, glycan structures may comprise a plurality of saccharide units (e.g., Neu5Ac, Kdn, Neu5Gc, Neu, Neu2en5Ac, mannose, glucose, GlcNAc, galactose, Xyl, fucose, Leg, Pse, etc.) joined together in various configurations (e.g. by α- or β-glycosidic linkage) or onto various structures (e.g., via N-glycosylation, O-glycosylation, etc.), and the linked protein may be able to identify two, three, or more saccharide-binding determinants within such structures.

Figure 6:
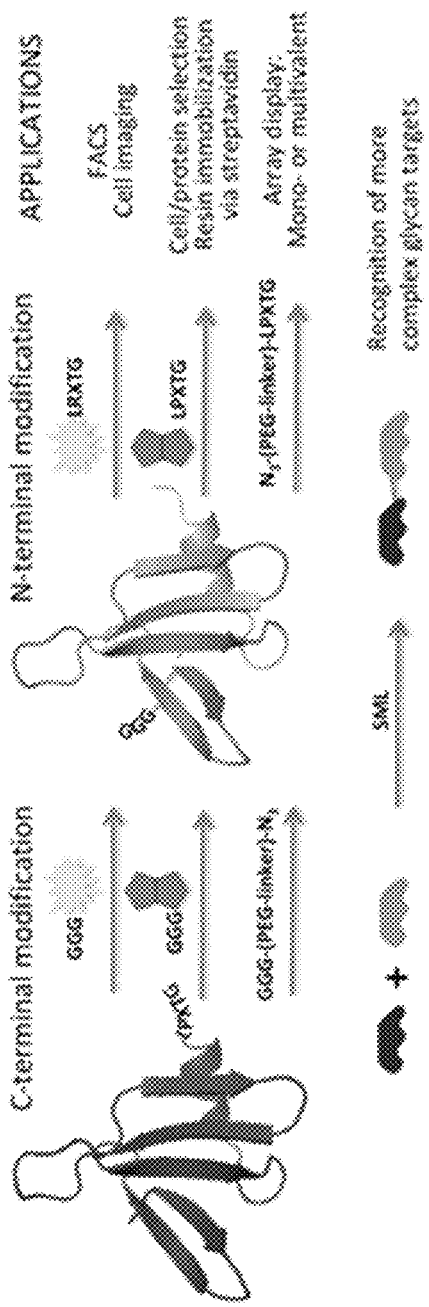
FIG. 6 illustrates conjugation of glycan-binding proteins, in accordance with various embodiments described herein.

In some embodiments, the linkage between the proteins can be accomplished indirectly. The linker, in certain embodiments, comprises a peptidic linker. For example, in FIG. 6, two proteins are linked together via an LPXTG (SEQ ID NO: 17) (or LRXTG (SEQ ID NO: 18)) sequence on one of the proteins (where X can be any amino acid) and a GGG sequence on the other protein. These may be linked together, for example, using sortase or other suitable enzymes. The LPXTG (SEQ ID NO: 17) (or LRXTG (SEQ ID NO: 18)) sequence may be found near the C-terminus of a first protein and the GGG sequence may be found near the N-terminus of a second protein, and sortase may thus covalently link the N-terminus of the first protein to a location near (within ~100 amino acids of) the C-terminus of the second protein. As another example, the peptidic linker may comprise a Gly-rich linker, e.g., a Gly-Gly linker or other $Gly_n$ linkers (n being any positive integer, e.g., 1, 2, 3, 4, 5, 6, etc.). Other amino acids may also be present in a Gly-rich linker, e.g. as in $(GGGGS)_n$ (SEQ ID NOs: 19-24).

The linker, in some instances, comprises a non-peptidic linker. A variety of non-peptidic linkers can be used, including click chemistry techniques, PEG, or the like. For example, a non-peptidic linker may comprise a polyethylene glycol (PEG) linker. For example, in FIG. 6, two proteins are linked via PEG in combination with an azide-alkyne click-chemistry linker.

According to certain embodiments, two proteins may be directly linked to each other by ligating or joining their nucleic acid sequences together such that the two proteins are expressed together. For instance, the two or more proteins may be genetically fused together.

In some cases, linking two proteins together may increase binding and/or binding selectivity to the target of interest (e.g., the monosaccharide or disaccharide-binding determinant).

In accordance with some embodiments, the composition further comprises an additional structure. For example, in some cases, the additional structure comprises a protein (e.g., a non-glycan-binding protein), enzyme, affinity tag (e.g. polyHis tag) and/or an oligonucleotide sequence, and/or small molecule (for instance, having a molecular weight of less than 2000 or 1000 Da). In some embodiments, the small molecule comprises a fluorophore. For example, in FIG. 6, one of the proteins is attached to a fluorophore.

The additional structure may be covalently attached to the protein, in certain instances. For example, in some instances, the additional structure is covalently attached to the protein via multivalent dendritic polymer backbones. According to certain embodiments, the additional structure comprises an oligomerization domain of a native protein (e.g., a non-glycan-binding protein), and the oligomerization domain is fused to the protein.

Figure 5:
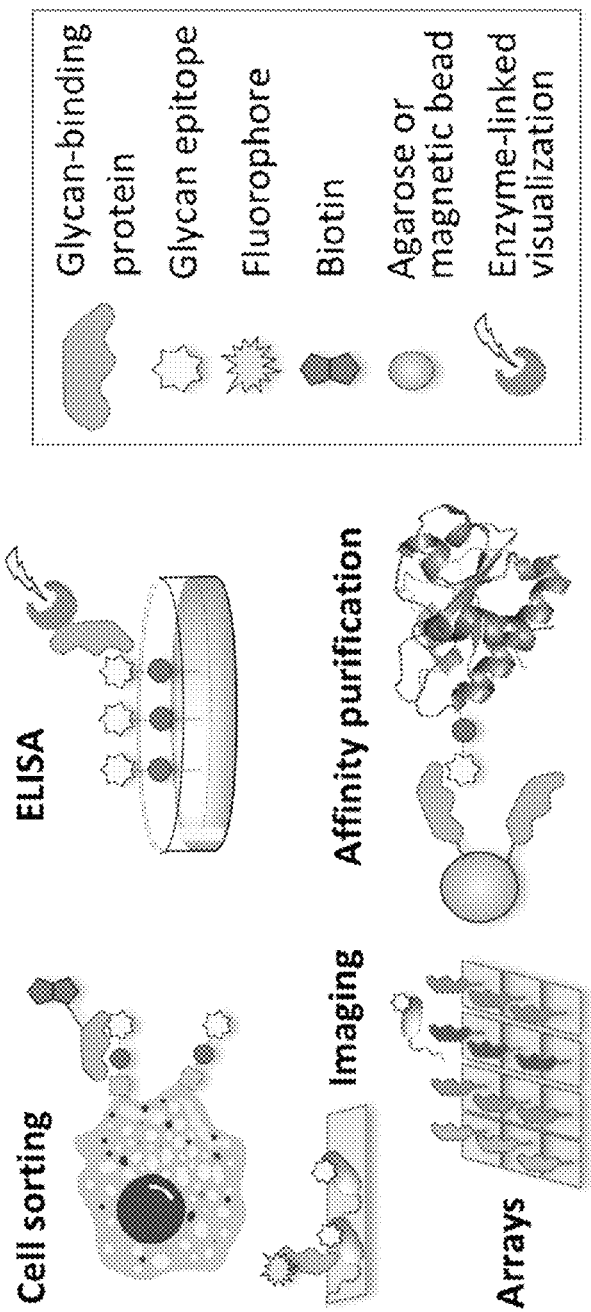
FIG. 5 illustrates functionalization and uses of the glycan-binding proteins, in accordance with some embodiments as described herein.

In some embodiments, the proteins, and compositions thereof, described herein have numerous applications, including in identification, manipulation, diagnostics, ELISAs, glycan characterization, cell selection, immunoblotting, flow cytometry, histology, imaging, arrays, affinity purification, and/or enzyme-linked visualization. For example, FIG. 5 shows some possible uses, in some cases, for the glycan-binding proteins, and compositions thereof, disclosed herein.

For instance, in some cases, the proteins disclosed herein may be useful as substitutes or analogs for antibodies and antibody-like biomolecules in immunological, therapeutic, diagnostic, or technological applications, such as flow cytometry, histology, and others. The generated proteins disclosed herein, in some instances, can be used to identify and/or manipulate a carbohydrate of interest regardless of size or composition. Many carbohydrates or biomolecules play significant roles in various diseases, and systems and methods for determining glycans, e.g., using glycan-binding proteins such as those discussed herein, may be useful for identifying, characterizing, or sequencing such glycans. As another example, such proteins could be used to determine human cancer-binding determinants, bacterial glycans, or the like.

In certain embodiments, proteins such as those disclosed herein can be attached to other groups, providing a vast array of applications. For example, in some cases, proteins such as those disclosed herein can be attached to a fluorophore. This could be useful, for example, in imaging of a glycan-binding determinant of interest (or molecules containing the glycan-binding determinant of interest). As another example, in certain instances, a protein can be attached to a molecule such as biotin. This could be useful, for example, various in cell selection applications. According to yet another example, a protein disclosed herein can be attached to a bead, such as an agarose bead or a magnetic bead. This could be useful, for example, in affinity purification of glycan-binding determinants of interest (or molecules containing the glycan-binding determinant of interest).

According to certain embodiments, the proteins (and compositions thereof) described herein have various advantages. For example, in some embodiments, the methods described herein can be used to generate a protein specific for any desired target, which can be useful, for example, where there are no native binders of that target. In some cases, the proteins described herein may be more stable (e.g., to temperature or pH) than other binders of the desired target. Moreover, in some instances, the proteins described herein are small enough that they can recognize single-atom differences between molecules (e.g., sugars), which may provide higher specificity for a target of interest than other binders, and/or which may prevent or reduce steric hindrance.

Without wishing to be bound by theory, it is believed that, in certain embodiments, generating a glycan-binding protein from a protein that does not typically bind sugars (e.g., from a DNA-binding protein or a protein-binding protein) can improve selectivity for the glycan of interest, for instance, as there is no possibility of lingering native sugar-binding functionality for a different sugar. Similarly, in some embodiments, the proteins described herein have higher binding constants for the target of interest than other binders. Further, in certain cases, the proteins described herein can be easily attached to one another (e.g., through sortase-mediated ligation or genetic fusion) or to other groups (e.g., fluorophores or chemical handles) for easy functionalization.

The following examples are intended to illustrate certain embodiments of the present invention, but do not exemplify the full scope of the invention.

Example 1

This example describes an archaeal DNA binding protein to bind and manipulate glycans, or carbohydrates and carbohydrate-containing biomolecules. As discussed herein, small DNA-binding proteins (based on Sso7d from *Sulfolobus solfataricus*) can be engineered using directed evolution to bind and specifically recognize targeted monosaccharides (e.g. hexose, heptulose, octulosonic and nonulosonic derivatives), disaccharides, and other more complex carbohydrates, although wild-type Sso7d is not able to bind to any glycans. As such, the engineered proteins may be able to substitute for antibody and antibody-like biomolecules in various immunological, diagnostic, and/or technological roles, such as flow cytometry, histology, and others. The proteins directly can also be used as a protein reagent capable of identifying and manipulating a carbohydrate of interest regardless of size or composition, filling a long-standing need in the glycosciences and medicine. Importantly, the proteins can also be assembled, e.g., in a "mix-and-match" fashion, to create custom reagents.

In some embodiments, the engineered proteins can tightly bind single copies of a sugar and distinguish single differences at the atomic level. The proteins may also be capable of straightforward chemical functionalization, do not require specialized training for use, and can be linked in some cases to assemble a reagent capable of specifically recognizing and manipulating complex oligosaccharide structures.

This example describes the preparation of glycan-binding proteins from an Sso7d library. The initial Sso7d library was prepared based on the methods described in Traxlmayr, M. W. et al. *J. Biol. Chem.* 2016, 291(43), 22496-22508. This library was prepared from a reduced charge-variant of Sso7d, a native DNA binder. Nine surface-exposed residues on one face of a reduced-charge variant of Sso7d were randomized with 18 different amino acids (all of the 20 naturally occurring amino acids, except the original amino acid itself and cysteine to avoid any sulfide groups) to generate a combinatorial library of approximately $10^9$ Sso7d variants. This was accomplished by PCR elongation and amplification of the SSo7d gene, followed by electroporation of PCR fragments and linearized vectors into yeast.

Sso7d has the following sequence:

(SEQ ID NO: 2)
ATVKFKYKGEEKQVDISKIKKVWRVGKMISFTYDEGGGKTGRGAVSEKDA

PKELLQMLEKQK while the reduced-charge variant of Sso7d has the following sequence:

(SEQ ID NO: 1)
ATVKFTYQGEEKQVDISKIK<u>KVWRV</u>GQMI<u>SFT</u>YDEGGGA<u>TGRGA</u>VSEKDA

PKELLQMLEKQ, where the underlining indicates the nine residues that were randomized.

After a Sso7d library was prepared as discussed above, the Sso7d library was then panned in these experiments via yeast-surface display (YSD) selections with magnetic bead-immobilized glycans for evolution of glycan binders using established techniques for yeast display. The beads were Dynabeads, which are made of polystyrene with a ferrous core. The bead-immobilized glycans used included a dihexose (e.g. Galβ1-3GalNAcα, the TF or Thomsen-Friedenrich antigen) or a nonulosonic acid (e.g. Neu5Ac.) Glycans were added by covalent chemical conjugation via a tosyl moiety or by non-covalent interactions between a biotin molecule on the glycan and a streptavidin tetramer on the bead surface.

Variants that bound glycans of interest with higher binding and/or binding selectivity were selected. In each bead selection (three or more were performed), yeast cells displaying Sso7d were selected by (i) their ability to stay bound to magnetic beads through rigorous, iterative rounds of washing, agitation, and/or presence of competitors, and/or (ii) their inability to stay bound on beads displaying undesired molecules, such as other saccharides or polymeric backbones. Once selected by bead selections and FACS sorts, Sso7d variants on yeast surfaces were required to bind polymeric sugar reagents (sugar-PAA-FITC) in solution state and any variants that did this moved forward in the process.

The selected variants were then mutated further. Mutated residues were no longer limited to the 9 surface exposed residues in order to allow for more possibilities for favorable properties to be found, by allowing mutations throughout the protein. FACS sorting allowed identification and physical selection of the tightest binding yeast cells, and these were propagated and their expression vectors removed for DNA sequencing. This DNA material was then used in any further mutagenesis by error-prone PCR or by rational site-directed mutagenesis. The process (i.e., mutating and selecting) was repeated numerous times.

After variants of proteins exhibiting desired binding and/or binding selectivities were obtained, the genes of the Sso7d variants of interest were amplified from yeast expression vectors by PCR, and the resulting PCR fragments were cloned into an *E. coli* expression vector bearing an affinity tag. Proteins were overexpressed in *E. coli* bearing the vector and the proteins were purified by affinity chromatography and characterized by SDS-Page for identity and purity.

In some cases, the variants were then conjugated to other variants (of the same or different types) and to other structures (e.g., fluorophores). For example, some expressed Sso7d variants were elongated to contain the sequence LPXTG (SEQ ID NO: 17). They were then ligated via sortase-mediated ligation to bear short peptides carrying a biotin molecule. They have also been sortagged to contain the FITC fluorophore. Sso7d variants have been attached to each other via genetic fusion, but also are attached by sortase-mediated mediated ligation.

Non-limiting examples of Sso7d variants that can bind to glycans are shown below. The exemplary variants in Sequence List 1 were engineered to bind one or more nonulsonic acids, while the exemplary variants in Sequence List 2 were engineered to bind one or more dihexoses. The disaccharides (or disaccharides motifs within trisaccharides) bound by variants in Sequence List 1 and 2 are shown in FIGS. 9A-9F. Every variant listed in Sequence List 1 and Sequence List 2 bound at least one disaccharide (or disaccharide motif within a trisaccharide) in FIGS. 9A-9F. These variants are not shown in any particular order.

```
Sequence List 1
                                         (SEQ ID NO: 25)
  1. ATVKFTYQGEEKQVDISKIKHVRRWGRWIWFIYEEGGGAKGRGGV

SEKDAPKELLQMLEKQGSEQKLISEED (SEQ ID NO: 26)
  2. ATGKFTYQGEKKQGDISKIKHGRRWGRGIWFIYEEGGGAKGRGGV

SEKDAPKELLQMLEKQGSEQKLISEED (SEQ ID NO: 27)
  3. ITVKFTYQGEEKQVDISKIEHVRRWGQWIWFTYDEGGGAKGRGGV

SEKGAPKELLQMLGKRGSEQKLISEED (SEQ ID NO: 28)
  4. ATVKFTYQGEEKQVDISKIKHVRRWGQWIWFIYDKGGGAKGRGGV

SEKDAPKELLQMLEKQGSEQKLISEED (SEQ ID NO: 29)
  5. ATVKFTYQGEEKQVDISKIKHVRRWGQWIWFIYDEGGGAKGKGSV

SEKDAPKELLQMLEKAGIRTKAYF (SEQ ID NO: 30)
  6. ATVEFTYQGEEKQVDISKIKHVRRWGQWIWFIYDEGGGAKGRGGV

SERDAPKELLQLLEKRGSEQKLISEED (SEQ ID NO: 31)
  7. ATVKFTYQGEEKQVDISKIKYVRRWGQAIIFRYDEGGGAEGKGSV

SEKGAPKELLQMLEKARIRTKAYF (SEQ ID NO: 32)
  8. ATVKFTYRGEEKQVGISRIKSVHRIGQWIKFWYDEGSGAYGRGYV

SEKDAPKELLQMLEKRGSEQKLISEED (SEQ ID NO: 33)
  9. AIVKFTYQGEEKQVDISKIKYVRRWGQYIWFGYDEGGGAHGRGRV

SGKDAPKELLQMLEKQGSEQKLISEED (SEQ ID NO: 34)
 10. ATVKFTYRGEEKQVDISKIKSVSRWGQAIIFRYDGGGGARGKGSV

SEKDAPKELLQMLEEARIRTKAYF (SEQ ID NO: 35)
 11. ATVKFTYRGEEKQVGISRIKSVHRIGQWIKFWYDEGSGAYGRGYV

SEKDAPKELLQMLEKRGSEQKLF (SEQ ID NO: 36)
 12. ATVKFTYRGKEKQVGISRIKSVHRIGQWIRFWYDEGSGAYGRGYV

SEKDAPKELLQMLEK (SEQ ID NO: 37)
 13. ATVKFTYRGEEKQVGISRIKSVHRIGQWIKFWYDEGSGAYGRGYV

SGKDAPKELLQMLEKRGSEQKLISEED (SEQ ID NO: 38)
 14. ATVKFTYRGKEKQVGISRIKSVHRIGQWIKFWYDEGSGAYGRGYV

SGKDAPKELLQMLEKRGSEQKLISEED (SEQ ID NO: 39)
 15. ATVKFTYRGEEKQVGINRIKSVHRIGQWIKFWYDEGSGAYGRGYV

SGKDAPKELLRMLEKRGSEQKLISEED (SEQ ID NO: 40)
 16. ATVKFTYRGEEKQVGISRIKSVHRIGRWIKFWYDEGSGAYGRGYV

SGKDAPKELLQMLEKRGSEQKLISEED (SEQ ID NO: 41)
 17. ATVKFTYRGEEKQVGISRIKSVRRIGQWIKFWYDEGSGAYGRGYV

SGKDAPKELLQMLEKRGSEQKLISEED (SEQ ID NO: 42)
 18. ATVKFTYRGEEKRVGISRIKSVRRIGQWIKFWYDEGSGAYGRGYV

SEKDAPKELLQMLGKRGSEQKLISEED (SEQ ID NO: 43)
 19. ATVKFTYRGEEKQVGISRIKSVRRIGQWIKFWYDEGSGAYGRGYV

SEKDAPKELLQMLGKRGSEQKLISEED
```

```
                                                    (SEQ ID NO: 44)
20. ATVRFTYRGEEKQVGISRIKSVRRIGQWIKFWYDEGSGAYGRGYV
SEKDAPKELLQMLGKRGSEQKLISEED (SEQ ID NO: 45)
21. ATVKFTYRGEEKQVGISRIKSVHRIGQWIKFWYDEGSGAYGRGYV
SEKGAPKELLQMLGKRGSEQKLISEED (SEQ ID NO: 46)
22. ATVKFTYRGEEKQVGISRIRSVHRIGQWIKFWYDEGSGACGRGYV
SEKGAPKELLQMLGKRGSEQKLISEED (SEQ ID NO: 47)
23. ATVKFTYRGEEKQVGISRIKSVHRIGQWIKFWYDEGSGAYGRGYV
SEKDAPKELLQMLGKRGSEQKLISEED (SEQ ID NO: 48)
24. ATVRFTYRGEEKQVGISRIKSVHRIGQWIKFWYDEGSGTYGRGYV
SEKDAPRELLQMLGKRGSEQKLISEED (SEQ ID NO: 49)
25. ATVKFTYRGEEKQVGISRIKSVRRIGQWIKFWYDEGSGAYGRGYV
SEKDAPKELLQMLEKRGSEQKLISEED (SEQ ID NO: 50)
26. ATVKFTYRGGEKQVGISRIKSVRRIGQWIKFWYDEGSGAYGRGYV
SEKDAPKELLQMLEKRGSEQKLISEED (SEQ ID NO: 51)
27. ATVKFTYRGKEKRVGVSRIKSVRRIGQWIKFWYDEGSGAYGRGYV
SEKDAPKELLQMLEKRGSEQKLISEED (SEQ ID NO: 52)
28. ATVKFTYRGEEKRVGISRIKSVRRIGQWIKFWYDEGSGAYGRGYV
SEKDAPKELLQMLEKRGSEQKLISEED (SEQ ID NO: 53)
29. ATVKFTYRGEEKQVGISRIKSVRRIGQWVKFWYDEGSGAYGRGYV
SEKDAPKELLQMLEKRGSEQKLISEED (SEQ ID NO: 54)
30. ATVKFTYRGEEKQVGISRIKSVRRIGQWVKFWYGEGSGAYGRGYV
SEKDAPKELLQMLEKRGSEQKLISEED (SEQ ID NO: 55)
31. ATVKFTYRGEEKQVGISRIRSVRRIGQWIKFWYDEGSGAYGRGYV
SEKDAPKELLQMLEKRGSEQKLISEED (SEQ ID NO: 56)
32. ATVKFTYRGEEKQVGISRIKSVRRIGQWIKFWYDEGRGAYGRGYV
SEKDAPKELLQMLEKRGSEQKLISEED (SEQ ID NO: 57)
33. ATVKFTYRGEEKQVGISRIKSVRRIGQWIKFWYDEGSGAYGRGYV
SEKDAPEELLQMLEKRGSEQKLISEED (SEQ ID NO: 58)
34. ATVKFTYRGEEKQVGISRIKSVHRIGQWIKFWYDEGSGAYGRGYV
SKKDAPKELLQMLEKRGSEQKLISEED (SEQ ID NO: 59)
35. ATVKFTYRGEEKQVGVSRIKSVHRIGRWIKFWYDEGSGAYGRGYV
SEKDAPKELLQMLEKRGSEQKLISEED (SEQ ID NO: 60)
36. ATVKFTYRGEEKQVGISRIKSVHRIGRWIKFWYDEGSGAYGRGYV
SEKDAPKELLQMLEKRGSEQKLISEED (SEQ ID NO: 61)
37. ATVKFTYRGEEKQVGISRIKSVHRVGRWIKFWYDEGSGAYGRGYV
SEKDAPKELLQMLEKRGSEQKLISEED (SEQ ID NO: 62)
38. ATVKFTYRGEEKQVGIGRIKSVHRIGRWIKFWYDEGSGAYGRGYV
SEKDAPKELLQMLEKRGSEQKLISEED (SEQ ID NO: 63)
39. ATVKFTYRGEEKQVGISRIKSVHRIGRWIKFWYDEGSGAYGRGYV
NEKDAPKELLQMLEKRGSEQKLISEED (SEQ ID NO: 64)
40. ATVKFTYRGEEKQVGISRIKFVHRIGRWIKFWYDEGSGAYGRGYV
SEKDAPKELLQMLEKRGSEQKLISEED (SEQ ID NO: 65)
41. ATVKFTYRGEEKQVGISRIKSVHRIGQWIKFWYDEGSGAYGRGYV
SEKNAPKELLQMLEKRGSEQKLISEED (SEQ ID NO: 66)
42. ATVKFTYRGEEKQVGISRIKSVHRIGQWIKFWYDEGSGAYGRGYV
SEKGAPKELLQMLEKRGSEQKLISEED (SEQ ID NO: 67)
43. ATVKFTYRGEGKQVGISRIKSVHRIGQWIKFWYDEGSGAYGRGYV
SEKDAPKELLQMLEKRGSEQKLISEED (SEQ ID NO: 68)
44. ATVKFTYRGEGKQVGISRIKSVHRIGQWIKFWYDEGSGAYGRGYV
SEKDAPKELLQMLKKRGSEQKLISEED (SEQ ID NO: 69)
45. ATVKFTYRGERKQVGISRIKSVHRIGQWIKFWYDEGSGAYGRGYV
SEKDAPKELLQMLEKRGSEQKLISEED (SEQ ID NO: 70)
46. ATVKFTYRGEEKQVGISRIKSVHRVGQWIKFWYDEGSGAYGRGYV
SEKDAPKELLQMLEKRGSEQKLISEED (SEQ ID NO: 71)
47. ATVKFTYRGEERQVGISRIKSVHRIGQWIKFWYDEGSGAYGRGYV
SEKDAPKELLQMLEKRGSEQKLISEED (SEQ ID NO: 72)
48. ATVKFTYRGEEKQVGISRIKSVHRIGQWIKFWYDEGSGAYGRGYV
GEKDAPKELLQMLEKRGSEQKLISEED (SEQ ID NO: 73)
49. ATVKFTYRGEEKRVGISRIKSVHRIGQWIKFWYDEGSGAYGRGYV
SEKDAPKELLQMLEKRGSEQKLISEED (SEQ ID NO: 74)
50. ATVKFTYRGEEKQVGISRIKSVHRIGQWIKFWYDEGSGAYGRGYV
SEKDAPKELLRMLEKRGSEQKLISEED (SEQ ID NO: 75)
51. ATVKFTYRGEEKQVGVSRIKSVHRIGQWIKFWYDGGSGAYGRGYV
SEKDAPKELLQMLEKRGSEQKLISEED
```

```
                                                         (SEQ ID NO: 76)
52. ATVKFTYRGEEKQVGISRIKSVHRIGQWIKFWYDGGSGAYGRGYV
SEKDAPKELLQMLEKRGSEQKLISEED (SEQ ID NO: 77)
53. ATVKFTYRGEEKQVGVSRVKSVHRIGQWIKFWYDEGSGAYGRGYV
SEKDAPEELLQMLEKRGSEQKLISEED (SEQ ID NO: 78)
54. ATVKFTYRGEEKQVGISRIKSVHRIGQWIKFWYDEGSGAHGRGYV
SEKDAPKELLQMLEKRGSEQKLISEED (SEQ ID NO: 79)
55. ATVKFTYRGEEKQVGISRIKSVHRIGQWIKFRYDEGSGAYGRGYV
SEKDAPKELLQMLEKRGSEQKLISEED (SEQ ID NO: 80)
56. VTVEFTYRGEEKQVDISKIKHVRRWGRWIWFIYEEGGGAKGRGGV
SEKDAPKELLQMLEKRGSEQKLISEED (SEQ ID NO: 81)
57. ATVKFTYQGEEKQVDISKIKHVRRWGRWIWFIYEEGGGAKGRGGV
SEKDAPKELLQMLEKRGSEQKLISEED (SEQ ID NO: 82)
58. ATVRFTYQGEEKQVDISKIKHVRRWGRWIWFIYEEGGGAKGRGGV
SEKDAPKELLQMLEKRGSEQKLISEED (SEQ ID NO: 83)
59. ATVKFTYQGEEKQVDISKIKHVRRWGRWIWFIYEEGGGGKGRGGV
SEKDAPKELLQMLEKRGSEQKLISEED (SEQ ID NO: 84)
60. ATVKFTHQGEEKQVDISKIKHVRRWGRWIWFIYEEGGGAKGRGGV
SEKDAPKELLQMLEKRGSEQKLISEED (SEQ ID NO: 85)
61. AIVKFTYQGEEKQVDISKIKHVRRWGRWIWFIYEEGGGAKGRGGV
SEKDAPKELLQMLEKRGSEQKLISEED (SEQ ID NO: 86)
62. AAVKFTYQGEEKQVDISKIKHVRRWGRWIWFIYEEGGGAKGRGGV
SEKDAPKELLQMLEKQGSEQKLISEED (SEQ ID NO: 87)
63. ATVKFTYQGEEKQVDISKIKHVRRWGRWIWFIYEAGGGAKGRGGV
SEKDAPKELLQMLEKQGSEQKLISEED (SEQ ID NO: 88)
64. ATVKFTYQGEEKQVDISKIKHVRRWGRWIWFIYEGGGGAKGRGGV
SEKDAPKELLQMLERRGSEQKLISEED (SEQ ID NO: 89)
65. ATVKFTYQGEEKQVDISKIKHVRRWGRWIWFIYEGGGGAKGRGGV
SEKDAPKELLQMLEKQGSEQKLISEED (SEQ ID NO: 90)
66. ATVKFTYRGEEKQVDISKIKHVRRWGQWIWFIYDEGGGAKGKGSV
SEKDAPKELLQMLEKAGIRTKAYF (SEQ ID NO: 91)
67. ATVKFTYQGEEKQVDVSKIKHVRRWGQWIWFIYDEGGGAKGKGSV
SEKDAPKELLQMLGKAGIRTKAYF (SEQ ID NO: 92)
68. ATVKFTYQGEEKQVDISKIKHVRRWGRWIWFIYDEGGGAKGKGSV
SEKDAPKELLQMLEKAGIRTKAYF (SEQ ID NO: 93)
69. ATVKFTYQGEEKQVDISKIKHVRRWGRWIWFIYEEGGGAKGKGSV
SEKDAPKELLQMLEKAGIRTKAYF (SEQ ID NO: 94)
70. ATVKFTYQGEEKQVDISKIKHVRRWGQRIWFIYGEGGGAKGRGSV
SEKDAPKELLQMLEKAGIRTKAYF (SEQ ID NO: 95)
71. ATVKFTYQGEEKQVDISKIKHVRRWGRWIWFIYEEGGAKGRGGVS
EKDAPKELLQMLEKQGSEQKLISEEDL (SEQ ID NO: 96)
72. ATVKFTYQGEEKQVDISKIKHVRRWGRWIWFTYEEGGGAKGRGGV
SEKDAPKELLQMLEKQGSEQKLILKRT (SEQ ID NO: 97)
73. ATVKFTYQGEEKQVDISKIKHVRRWGRWIWFTYEEGGGAKGRGGV
SEKDAPKELLQMLEKPGSEQKLISEED (SEQ ID NO: 98)
74. ATVKFTYQGEEKQVDISKIKHVRRWGRWIWFTYEEGGGARGRGGV
SEKDAPKELLQMLEKQGSEQKLISEED (SEQ ID NO: 99)
75. ATVKFTYQGEEKQVDVSKIKHVRRWGRWIWFTYEEGGGAKGRGGV
SEKDAPKELLQMLEKQGSEQKLISEED (SEQ ID NO: 100)
76. ATVKFTYQGEEKQVDISKIKHVRRWGRWIWFTYEEGGGAKGRGGV
SEKDAPRELLQMLEKRGSEQKLISEED (SEQ ID NO: 101)
77. ATVKFTYRGEEKQVDISEIKHVRRWGRWIWFTYEEGGGARGRGGV
SEKDAPKELLQMLEKRGSEQKLISEED (SEQ ID NO: 102)
78. ATVKFTYQGEEKQVDISKIRHVRRWGRRIWFTYEEGGGAKGRGGV
GEKDAPKELLQMLEKQGSEQKLISEED (SEQ ID NO: 103)
79. ATVKFTYQGEEKQVDISKIKHVRRWGRRIWFIYEEGGGAKGRGGV
SEKDAPKELLQMLEKQGSEQKLISEKD (SEQ ID NO: 104)
80. ATVKFTYQGEEKQVDISKIKHVRRWGRRIWFIYEEGGGAKGRGGV
SEKDAPKELLQMLEKQGSEQKLISEED (SEQ ID NO: 105)
81. ATVKFTYQGEEKQVDISKIKHVRRWGRWIWFIYEEGGGAKGRGGV
GEKDAPKELLQMLEKQGSEQKLISEED (SEQ ID NO: 106)
82. ATVKFTYQGEGKQVDISKIKHVRRWGRWIWFIYEEGGGAKGRGGV
SEKDAPKELLQMLEKQGSEQKLISEED (SEQ ID NO: 107)
83. ATVKFTYQGEEKQVDISKIKRVRRWGRWIWFIYEEGGGAKGRGGV
SEKDAPKELLQMLEKQGSEQKLISEED
```

```
                                              (SEQ ID NO: 108)
84. ITVKFTYQGEEKQVDISKIEHVRRWGRWIWFTYDEGGGAKGRGGV
SEKGAPKELLQMLGKRGSEQKLISEED (SEQ ID NO: 109)
85. ITVKFTYRGEEKQVDISKIEHVRRWGQWIWFTYDEGGGAKGRGGV
SEKGAPRELLQMLGKRGSEQKLISEED (SEQ ID NO: 110)
86. ATVKFTYQGEEKQVDISKIKHVRRWGRWIWFTYDEGGGAKGRGGV
SEKGAPKELLQMLGKRGSEQKLISEED (SEQ ID NO: 111)
87. ATVKFTYQGEEKQVDISKIKHVRRWGRWIWFTYEEGGGAKGRGGV
SEKDAPKELLQMLGKRGSEQKLISEED (SEQ ID NO: 112)
88. ATVKFTYQGEEKRVDISKIKHVRRWGRWIWFIYEEGGGAKGRGGV
SEKDAPKELLQMLGKRGSEQKLISEED (SEQ ID NO: 113)
89. ATVKFTYQGEEKQVDISKIKHVRRWGRWIWFIYEEGGGAKGRGGV
SEKDAPKELLQMLGKQGSEQKLISEED (SEQ ID NO: 114)
90. ATVKFTYRGEEKQVDISKIKHVRRWGRWIWFIYEEGGGAKGRGGV
SEKDAPKELLQMLGKQRSEQKLISEED (SEQ ID NO: 115)
91. ATVKFTYHGEEKQVDISKIKHVRRWGRWIWFIYEEGGGAKGRGGV
SEKDAPKELLQMLEKQGSEQKLISEED (SEQ ID NO: 116)
92. ATVKFTYRGEEKQVDISKIKHVRRWGQWIWFIYDKGGGAKGRGGV
SEKDAPKELLQMLEKQGSEQKLISEED (SEQ ID NO: 117)
93. ATVKFTYRGEEKQVDISKIKHVRCWGQWIWFIYDKGGGAKGRGGV
SEKGAPKELLQMLEKQGSEQKLISEED (SEQ ID NO: 118)
94. ATVKFTYRGEEKQVGISRIRSVHRIGQWIKFWYDEGSGAYGRGYV
SEKDAPKELLQMLEKRGSEQKLISEED (SEQ ID NO: 119)
95. TTVKFTYRGEEKQVGISRIKSVHRIGQWIKFWYDKGSGAYGRGYV
SEKDAPKELLQMLEKRGSEQKLISEED (SEQ ID NO: 120)
96. AIVKFTYRGEEKQVGISRIKSVHRIGQWIKFWYGEGSGAYGRGYV
SEKDAPKELLQMLEKRGSEQKLISEED (SEQ ID NO: 121)
97. ATVKFTYRGGEKQVGISRIKSVHRIGQWIKFRYDEGSGAYGRGYV
SEKDAPKELLQMLEKRGSEQKLISEED (SEQ ID NO: 122)
98. ATVKFTYRGKEKQVGISRIKSVHRIGQWIKFRYDEGSGAYGRGYV
SEKDAPKELLQMLEKRGSEQKLISEED (SEQ ID NO: 123)
99. ATVKFTYRGEEKQVDISRIKHVRRWGRWIWFIYEEGGGAKGRGGV
SEKDAPKELLQMLEKQGSEQKLISEED (SEQ ID NO: 124)
100. ATVKFTYRGEEKQVDISKIKHVRRWGRWIWFIYEEGGGAKGRGGV
SEKDAPKELLQMLEKQGSEQKLISEED (SEQ ID NO: 125)
101. ATVKFTYRGEEKQVDISKIKHVRRWGRWVWFIYEEGGGAKGRGGV
SEKDAPKELLQMLEKQGSEQKLISEED (SEQ ID NO: 126)
102. ATVKFTYRGEEKQVDISKVKHVRRWGRWIWFIYEEGGGAKGRGGV
SEKDAPKELLQMLEKQGSEQKLISEED (SEQ ID NO: 127)
103. ATVKFTYRGEEKQVDISKIKHVRRWGRWIWFIYEEGGGAKGRGGV
SEKDAPKELLRMLEKQGSEQKLISEED (SEQ ID NO: 128)
104. ATVKFTYRGEEKQVDISKIKHVRRWGRWIWFIYEEGGGAKGRGGV
SGKDAPKELLQMLEKQGSEQKLISEED (SEQ ID NO: 402)
105. ATVKFTYRGEEKQVGISRIKSVRRIGQWIKFWYDEGSGAYGRGYV
SEKDAPKELLQMLEKR (SEQ ID NO: 403)
106. ATVKFTYRGEEKQVGISRIKSVRRIGQWIKFWYDEGSGAYGRGYV
SGKDAPKELLQMLEKR (SEQ ID NO: 404)
107. ATVKFTYRGGEKQVGISRIKSVRRIGQWIKFWYDEGSGAYGRGYV
SEKDAPKELLQMLEKR (SEQ ID NO: 405)
108. ATVKFTYRGEEKQVGISRIKSVHRIGRWIKFWYDEGSGAYGRGYV
SEKDAPKELLQMLEKR (SEQ ID NO: 406)
109. ATVKFTYRGEEKQVGISRIKSVHRIGQWIKFWYDEGSGAYGRGYV
SKKDAPKELLQMLEKR

Sequence List 2
                                              (SEQ ID NO: 129)
110. ATVKFTYRGEEKQVGISRIKSVHRIGQWIKFWYDEGSGAYGRGYV
SEKDAPKELLQMLEKRGSEQKLF (SEQ ID NO: 130)
111. ATVKFTYRGKEKQVGISRIKSVHRIGQWIRFWYDEGSGAYGRGYV
SEKDAPKELLQMLEK (SEQ ID NO: 131)
112. ATVKFTYRGEEKQVGISRIKSVHRIGQWIKFWYDEGSGAYGRGYV
SGKDAPKELLQMLEKRGSEQKLISEED (SEQ ID NO: 132)
113. ATVKFTYRGKEKQVGISRIKSVHRIGQWIKFWYDEGSGAYGRGYV
SGKDAPKELLQMLEKRGSEQKLISEED (SEQ ID NO: 133)
114. ATVKFTYRGEEKQVGINRIKSVHRIGQWIKFWYDEGSGAYGRGYV
SGKDAPKELLRMLEKRGSEQKLISEED (SEQ ID NO: 134)
115. ATVKFTYRGEEKQVGISRIKSVHRIGRWIKFWYDEGSGAYGRGYV
SGKDAPKELLQMLEKRGSEQKLISEED
```

```
                                                    (SEQ ID NO: 135)
116. ATVKFTYRGEEKQVGISRIKSVRRIGQWIKFWYDEGSGAYGRGYV
     SGKDAPKELLQMLEKRGSEQKLISEED (SEQ ID NO: 136)
117. ATVKFTYRGEEKRVGISRIKSVRRIGQWIKFWYDEGSGAYGRGYV
     SEKDAPKELLQMLGKRGSEQKLISEED (SEQ ID NO: 137)
118. ATVKFTYRGEEKQVGISRIKSVRRIGQWIKFWYDEGSGAYGRGYV
     SEKDAPKELLQMLGKRGSEQKLISEED (SEQ ID NO: 138)
119. ATVRFTYRGEEKQVGISRIKSVRRIGQWIKFWYDEGSGAYGRGYV
     SEKDAPKELLQMLGKRGSEQKLISEED (SEQ ID NO: 139)
120. ATVKFTYRGEEKQVGISRIKSVHRIGQWIKFWYDEGSGAYGRGYV
     SEKGAPKELLQMLGKRGSEQKLISEED (SEQ ID NO: 140)
121. ITVKFTYQGEEKQVDISKIEHVRRWGQWIWFTYDEGGGAKGRGGV
     SEKGAPKELLQMLGKRGSEQKLISEED (SEQ ID NO: 141)
122. ATVKFTYRGEEKQVGISRIRSVHRIGQWIKFWYDEGSGACGRGYV
     SEKGAPKELLQMLGKRGSEQKLISEED (SEQ ID NO: 142)
123. ATVKFTYRGEEKQVGISRIKSVHRIGQWIKFWYDEGSGAYGRGYV
     SEKDAPKELLQMLGKRGSEQKLISEED (SEQ ID NO: 143)
124. ATVRFTYRGEEKQVGISRIKSVHRIGQWIKFWYDEGSGTYGRGYV
     SEKDAPRELLQMLGKRGSEQKLISEED (SEQ ID NO: 144)
125. ATVKFTYRGEEKQVGISRIKSVRRIGQWIKFWYDEGSGAYGRGYV
     SEKDAPKELLQMLEKRGSEQKLISEED (SEQ ID NO: 145)
126. ATVKFTYRGGEKQVGISRIKSVRRIGQWIKFWYDEGSGAYGRGYV
     SEKDAPKELLQMLEKRGSEQKLISEED (SEQ ID NO: 146)
127. ATVKFTYRGKEKRVGVSRIKSVRRIGQWIKFWYDEGSGAYGRGYV
     SEKDAPKELLQMLEKRGSEQKLISEED (SEQ ID NO: 147)
128. ATVKFTYRGEEKRVGISRIKSVRRIGQWIKFWYDEGSGAYGRGYV
     SEKDAPKELLQMLEKRGSEQKLISEED (SEQ ID NO: 148)
129. ATVKFTYRGEEKQVGISRIKSVRRIGQWVKFWYDEGSGAYGRGYV
     SEKDAPKELLQMLEKRGSEQKLISEED (SEQ ID NO: 149)
130. ATVKFTYRGEEKQVGISRIKSVRRIGQWVKFWYGEGSGAYGRGYV
     SEKDAPKELLQMLEKRGSEQKLISEED (SEQ ID NO: 150)
131. ATVKFTYRGEEKQVGISRIRSVRRIGQWIKFWYDEGSGAYGRGYV
     SEKDAPKELLQMLEKRGSEQKLISEED (SEQ ID NO: 151)
132. ATVKFTYRGEEKQVGISRIKSVRRIGQWIKFWYDEGRGAYGRGYV
     SEKDAPKELLQMLEKRGSEQKLISEED (SEQ ID NO: 152)
133. ATVKFTYRGEEKQVGISRIKSVRRIGQWIKFWYDEGSGAYGRGYV
     SEKDAPEELLQMLEKRGSEQKLISEED (SEQ ID NO: 153)
134. ATVKFTYRGEEKQVGISRIKSVHRIGQWIKFWYDEGSGAYGRGYV
     SKKDAPKELLQMLEKRGSEQKLISEED (SEQ ID NO: 154)
135. ATVKFTYRGEEKQVGVSRIKSVHRIGRWIKFWYDEGSGAYGRGYV
     SEKDAPKELLQMLEKRGSEQKLISEED (SEQ ID NO: 155)
136. ATVKFTYRGEEKQVGISRIKSVHRIGRWIKFWYDEGSGAYGRGYV
     SEKDAPKELLQMLEKRGSEQKLISEED (SEQ ID NO: 156)
137. ATVKFTYRGEEKQVGISRIKSVHRVGRWIKFWYDEGSGAYGRGYV
     SEKDAPKELLQMLEKRGSEQKLISEED (SEQ ID NO: 157)
138. ATVKFTYRGEEKQVGIGRIKSVHRIGRWIKFWYDEGSGAYGRGYV
     SEKDAPKELLQMLEKRGSEQKLISEED (SEQ ID NO: 158)
139. ATVKFTYRGEEKQVGISRIKSVHRIGRWIKFWYDEGSGAYGRGYV
     NEKDAPKELLQMLEKRGSEQKLISEED (SEQ ID NO: 159)
140. ATVKFTYRGEEKQVGISRIKFVHRIGRWIKFWYDEGSGAYGRGYV
     SEKDAPKELLQMLEKRGSEQKLISEED (SEQ ID NO: 160)
141. ATVKFTYRGEEKQVGISRIKSVHRIGQWIKFWYDEGSGAYGRGYV
     SEKNAPKELLQMLEKRGSEQKLISEED (SEQ ID NO: 161)
142. ATVKFTYRGEEKQVGISRIKSVHRIGQWIKFWYDEGSGAYGRGYV
     SEKGAPKELLQMLEKRGSEQKLISEED (SEQ ID NO: 162)
143. ATVKFTYRGEGKQVGISRIKSVHRIGQWIKFWYDEGSGAYGRGYV
     SEKDAPKELLQMLEKRGSEQKLISEED (SEQ ID NO: 163)
144. ATVKFTYRGEGKQVGISRIKSVHRIGQWIKFWYDEGSGAYGRGYV
     SEKDAPKELLQMLKKRGSEQKLISEED (SEQ ID NO: 164)
145. ATVKFTYRGERKQVGISRIKSVHRIGQWIKFWYDEGSGAYGRGYV
     SEKDAPKELLQMLEKRGSEQKLISEED (SEQ ID NO: 165)
146. ATVKFTYRGEEKQVGISRIKSVHRIGQWIKFWYDEGSGAYGRGYV
     SEKDAPKELLQMLEKRGSEQKLISEED (SEQ ID NO: 166)
147. ATVKFTYRGEEKQVGISRIKSVHRVGQWIKFWYDEGSGAYGRGYV
     SEKDAPKELLQMLEKRGSEQKLISEED
```

148. ATVKFTYRGEERQVGISRIKSVHRIGQWIKFWYDEGSGAYGRGYV
SEKDAPKELLQMLEKRGSEQKLISEED
(SEQ ID NO: 167)

149. ATVKFTYRGEEKQVGISRIKSVHRIGQWIKFWYDEGSGAYGRGYV
GEKDAPKELLQMLEKRGSEQKLISEED
(SEQ ID NO: 168)

150. ATVKFTYRGEEKRVGISRIKSVHRIGQWIKFWYDEGSGAYGRGYV
SEKDAPKELLQMLEKRGSEQKLISEED
(SEQ ID NO: 169)

151. ATVKFTYRGEEKQVGISRIKSVHRIGQWIKFWYDEGSGAYGRGYV
SEKDAPKELLRMLEKRGSEQKLISEED
(SEQ ID NO: 170)

152. ATVKFTYRGEEKQVGVSRIKSVHRIGQWIKFWYDGGSGAYGRGYV
SEKDAPKELLQMLEKRGSEQKLISEED
(SEQ ID NO: 171)

153. ATVKFTYRGEEKQVGISRIKSVHRIGQWIKFWYDGGSGAYGRGYV
SEKDAPKELLQMLEKRGSEQKLISEED
(SEQ ID NO: 172)

154. ATVKFTYRGEEKQVGVSRVKSVHRIGQWIKFWYDEGSGAYGRGYV
SEKDAPEELLQMLEKRGSEQKLISEED
(SEQ ID NO: 173)

155. ATVKFTYRGEEKQVGISRIKSVHRIGQWIKFWYDEGSGAHGRGYV
SEKDAPKELLQMLEKRGSEQKLISEED
(SEQ ID NO: 174)

156. ATVKFTYRGEEKQVGISRIKSVHRIGQWIKFRYDEGSGAYGRGYV
SEKDAPKELLQMLEKRGSEQKLISEED
(SEQ ID NO: 175)

157. VTVEFTYRGEEKQVDISKIKHVRRWGRWIWFIYEEGGGAKGRGGV
SEKDAPKELLQMLEKRGSEQKLISEED
(SEQ ID NO: 176)

158. ATVKFTYQGEEKQVDISKIKHVRRWGRWIWFIYEEGGGAKGRGGV
SEKDAPKELLQMLEKQGSEQKLISEED
(SEQ ID NO: 177)

159. ATVKFTYQGEEKQVDISKIKHVRRWGRWIWFIYEEGGGAKGRGGV
SEKDAPKELLQMLEKRGSEQKLISEED
(SEQ ID NO: 178)

160. ATVRFTYQGEEKQVDISKIKHVRRWGRWIWFIYEEGGGAKGRGGV
SEKDAPKELLQMLEKRGSEQKLISEED
(SEQ ID NO: 179)

161. ATVKFTYQGEEKQVDISKIKHVRRWGRWIWFIYEEGGGGKGRGGV
SEKDAPKELLQMLEKRGSEQKLISEED
(SEQ ID NO: 180)

162. ATVKFTHQGEEKQVDISKIKHVRRWGRWIWFIYEEGGGAKGRGGV
SEKDAPKELLQMLEKRGSEQKLISEED
(SEQ ID NO: 181)

163. AIVKFTYQGEEKQVDISKIKHVRRWGRWIWFIYEEGGGAKGRGGV
SEKDAPKELLQMLEKRGSEQKLISEED
(SEQ ID NO: 182)

164. AAVKFTYQGEEKQVDISKIKHVRRWGRWIWFIYEEGGGAKGRGGV
SEKDAPKELLQMLEKQGSEQKLISEED
(SEQ ID NO: 183)

165. ATVKFTYQGEEKQVDISKIKHVRRWGRWIWFIYEAGGGAKGRGGV
SEKDAPKELLQMLEKQGSEQKLISEED
(SEQ ID NO: 184)

166. ATVKFTYQGEEKQVDISKIKHVRRWGRWIWFIYEGGGGAKGRGGV
SEKDAPKELLQMLERRGSEQKLISEED
(SEQ ID NO: 185)

167. ATVKFTYQGEEKQVDISKIKHVRRWGRWIWFIYEGGGGAKGRGGV
SEKDAPKELLQMLEKQGSEQKLISEED
(SEQ ID NO: 186)

168. ATVKFTYRGEEKQVDISKIKHVRRWGQWIWFIYDEGGGAKGKGSV
SEKDAPKELLQMLEKAGIRTKAYF
(SEQ ID NO: 187)

169. ATVKFTYQGEEKQVDVSKIKHVRRWGQWIWFIYDEGGGAKGKGSV
SEKDAPKELLQMLGKAGIRTKAYF
(SEQ ID NO: 188)

170. ATVKFTYQGEEKQVDISKIKHVRRWGRWIWFIYDEGGGAKGKGSV
SEKDAPKELLQMLEKAGIRTKAYF
(SEQ ID NO: 189)

171. ATVKFTYQGEEKQVDISKIKHVRRWGRWIWFIYEEGGGAKGKGSV
SEKDAPKELLQMLEKAGIRTKAYF
(SEQ ID NO: 190)

172. ATVKFTYQGEEKQVDISKIKHVRRWGQRIWFIYGEGGGAKGRGSV
SEKDAPKELLQMLEKAGIRTKAYF
(SEQ ID NO: 191)

173. ATVKFTYQGEEKQVDISKIKHVRRWGRWIWFIYEEGGAKGRGGVS
EKDAPKELLQMLEKQGSEQKLISEEDL
(SEQ ID NO: 192)

174. ATVKFTYQGEEKQVDISKIKHVRRWGRWIWFTYEEGGGAKGRGGV
SEKDAPKELLQMLEKQGSEQKLILKRT
(SEQ ID NO: 193)

175. ATVKFTYQGEEKQVDISKIKHVRRWGRWIWFTYEEGGGAKGRGGV
SEKDAPKELLQMLEKPGSEQKLISEED
(SEQ ID NO: 194)

176. ATVKFTYQGEEKQVDISKIKHVRRWGRWIWFTYEEGGGARGRGGV
SEKDAPKELLQMLEKQGSEQKLISEED
(SEQ ID NO: 195)

177. ATVKFTYQGEEKQVDVSKIKHVRRWGRWIWFTYEEGGGAKGRGGV
SEKDAPKELLQMLEKQGSEQKLISEED
(SEQ ID NO: 196)

178. ATVKFTYQGEEKQVDISKIKHVRRWGRWIWFTYEEGGGAKGRGGV
SEKDAPRELLQMLEKRGSEQKLISEED
(SEQ ID NO: 197)

179. ATVKFTYRGEEKQVDISEIKHVRRWGRWIWFTYEEGGGARGRGGV
SEKDAPKELLQMLEKRGSEQKLISEED
(SEQ ID NO: 198)

180. ATVKFTYQGEEKQVDISKIRHVRRWGRRIWFTYEEGGGAKGRGGV
GEKDAPKELLQMLEKQGSEQKLISEED
(SEQ ID NO: 199)

181. ATVKFTYQGEEKQVDISKIKHVRRWGRRIWFIYEEGGGAKGRGGV
SEKDAPKELLQMLEKQGSEQKLISEKD
(SEQ ID NO: 200)

182. ATVKFTYQGEEKQVDISKIKHVRRWGRRIWFIYEEGGGAKGRGGV
SEKDAPKELLQMLEKQGSEQKLISEED
(SEQ ID NO: 201)

183. ATVKFTYQGEEKQVDISKIKHVRRWGRWIWFIYEEGGGAKGRGGV
GEKDAPKELLQMLEKQGSEQKLISEED
(SEQ ID NO: 202)

184. ATVKFTYQGEGKQVDISKIKHVRRWGRWIWFIYEEGGGAKGRGGV
SEKDAPKELLQMLEKQGSEQKLISEED
(SEQ ID NO: 203)

185. ATVKFTYQGEEKQVDISKIKRVRRWGRWIWFIYEEGGGAKGRGGV
SEKDAPKELLQMLEKQGSEQKLISEED
(SEQ ID NO: 204)

186. ITVKFTYQGEEKQVDISKIEHVRRWGRWIWFTYDEGGGAKGRGGV
SEKGAPKELLQMLGKRGSEQKLISEED
(SEQ ID NO: 205)

187. ITVKFTYRGEEKQVDISKIEHVRRWGQWIWFTYDEGGGAKGRGGV
SEKGAPRELLQMLGKRGSEQKLISEED
(SEQ ID NO: 206)

188. ATVKFTYQGEEKQVDISKIKHVRRWGRWIWFTYDEGGGAKGRGGV
SEKGAPKELLQMLGKRGSEQKLISEED
(SEQ ID NO: 207)

189. ATVKFTYQGEEKQVDISKIKHVRRWGRWIWFTYEEGGGAKGRGGV
SEKDAPKELLQMLGKRGSEQKLISEED
(SEQ ID NO: 208)

190. ATVKFTYQGEEKRVDISKIKHVRRWGRWIWFIYEEGGGAKGRGGV
SEKDAPKELLQMLGKRGSEQKLISEED
(SEQ ID NO: 209)

191. ATVKFTYQGEEKQVDISKIKHVRRWGRWIWFIYEEGGGAKGRGGV
SEKDAPKELLQMLGKQGSEQKLISEED
(SEQ ID NO: 210)

192. ATVKFTYRGEEKQVDISKIKHVRRWGRWIWFIYEEGGGAKGRGGV
SEKDAPKELLQMLGKQRSEQKLISEED
(SEQ ID NO: 211)

193. ATVKFTYHGEEKQVDISKIKHVRRWGRWIWFIYEEGGGAKGRGGV
SEKDAPKELLQMLEKQGSEQKLISEED
(SEQ ID NO: 212)

194. ATVKFTYRGEEKQVDISKIKHVRRWGQWIWFIYDKGGGAKGRGGV
SEKDAPKELLQMLEKQGSEQKLISEED
(SEQ ID NO: 213)

195. ATVKFTYRGEEKQVDISKIKHVRCWGQWIWFIYDKGGGAKGRGGV
SEKGAPKELLQMLEKQGSEQKLISEED
(SEQ ID NO: 214)

196. ATVKFTYRGEEKQVGISRIRSVHRIGQWIKFWYDEGSGAYGRGYV
SEKDAPKELLQMLEKRGSEQKLISEED
(SEQ ID NO: 215)

197. TTVKFTYRGEEKQVGISRIKSVHRIGQWIKFWYDKGSGAYGRGYV
SEKDAPKELLQMLEKRGSEQKLISEED
(SEQ ID NO: 216)

198. AIVKFTYRGEEKQVGISRIKSVHRIGQWIKFWYGEGSGAYGRGYV
SEKDAPKELLQMLEKRGSEQKLISEED
(SEQ ID NO: 217)

199. ATVKFTYRGGEKQVGISRIKSVHRIGQWIKFRYDEGSGAYGRGYV
SEKDAPKELLQMLEKRGSEQKLISEED
(SEQ ID NO: 218)

200. ATVKFTYRGKEKQVGISRIKSVHRIGQWIKFRYDEGSGAYGRGYV
SEKDAPKELLQMLEKRGSEQKLISEED
(SEQ ID NO: 219)

201. ATVKFTYRGEEKQVDISRIKHVRRWGRWIWFIYEEGGGAKGRGGV
SEKDAPKELLQMLEKQGSEQKLISEED
(SEQ ID NO: 220)

202. ATVKFTYRGEEKQVDISKIKHVRRWGRWIWFIYEEGGGAKGRGGV
SEKDAPKELLQMLEKQGSEQKLISEED
(SEQ ID NO: 221)

203. ATVKFTYRGEEKQVDISKIKHVRRWGRWVWFIYEEGGGAKGRGGV
SEKDAPKELLQMLEKQGSEQKLISEED
(SEQ ID NO: 222)

204. ATVKFTYRGEEKQVDISKVKHVRRWGRWIWFIYEEGGGAKGRGGV
SEKDAPKELLQMLEKQGSEQKLISEED
(SEQ ID NO: 223)

205. ATVKFTYRGEEKQVDISKIKHVRRWGRWIWFIYEEGGGAKGRGGV
SEKDAPKELLRMLEKQGSEQKLISEED
(SEQ ID NO: 224)

206. ATVKFTYRGEEKQVDISKIKHVRRWGRWIWFIYEEGGGAKGRGGV
SGKDAPKELLQMLEKQGSEQKLISEED
(SEQ ID NO: 225)

207. ATVRFTYRGEEKQVDISKIKYVRRWGQYIWFGYDGGGARGYGYV
SERDAPKELLQMLEEQGSEQKLISEED
(SEQ ID NO: 226)

208. ATVRFTYQGEEKQVDISKIKHVRRWGRYIWFGYDEGGGARHGYV
SEKDAPKELLQMLEKQGSEQKLISEED
(SEQ ID NO: 227)

209. ATVQFTYQGEERQVDISKIRHVRRWGRWIWFIYGEGGGAKGWGGV
SAKDAPKELLQMLEKQGSEQKLISEED
(SEQ ID NO: 228)

210. ATVKFTYQGGEKQVDISKIKHVRRWGQWIWFIYDEGGGAKGWGGV
SGKDAPKELLQMLEKRGSEQKLISEED
(SEQ ID NO: 229)

211. ATVKFTYRGEEKQVDISKIKYVRRWGQYIWFGYDEGGGARGYGYV
SERDAPKELLQMLEKQGSEQKLISEED
(SEQ ID NO: 230)

```
                                                    (SEQ ID NO: 231)
212. ATVKFTYRGEEKQVDISKIKHVRRWGQYIWFGYDEGGGARGYGYV
SEKDAPKGLLQMLEKQGSEQKLISEED (SEQ ID NO: 232)
213. ATVKFTYRGEEKQVDISKIKHVRRWGQWIWFIYDEGGGAKGWGGV
SERDAPKGLLQMLEKQGSEQKLISEED (SEQ ID NO: 233)
214. AAVKFTYQGEEKQVDISKIKYVWRWGRWIWFRYDEGGGAHGIGHV
SEKDVPKELLQMLEKQGSEQKLISEED (SEQ ID NO: 234)
215. ATVRFTYRGEEKQVDISRIKYVRRWGQYIWLGYDGGGARGYGYV
SEKGAPKELLQMLEKQGSEQKLISEED (SEQ ID NO: 235)
216. ATVKFTYRGEEKQVDISKIKYVRRWGQYIWFGYGEGGGARGYGYV
SEKDAPKELLQMLKKQGSEQKLISEED (SEQ ID NO: 236)
217. AAVKFTYQGEEKQVDTSKIKHVRRWGRYIWFGYDEGGGARGHGYV
SEKDAPKELLQMLEKQGSEQKLISEED (SEQ ID NO: 237)
218. ATVKFTYRGEEGQVDISKVKYVWRWGQWIWFRYDGGGGAHGIGYV
SEKDTPKELLQMLEKQGSEQKLISEED (SEQ ID NO: 238)
219. ATVKFTYQGEEKQVGISKIRYVRRWGQYIWFGYDEGGGTRGYGYV
SERDAPKELLQMLERRGSEQKLISEED (SEQ ID NO: 239)
220. ATVKFTYQGEEKQVDISKIKHVRRWGQWIWFIYDEGGGARGRGYV
SEKGAPEELLQMLGKQGSEQKLISEED (SEQ ID NO: 240)
221. ATVKFTYHGEGKQVDISKIKYVRRWGRYIWFGYDEGGGARGYGYV
SEKGAPEELLQMLEKQGSEQKLISEED (SEQ ID NO: 241)
222. ATVKFTYRGEEKQVDISKIKYVRRWGRYIWFGYDEGGGARGYGYV
SEKDAPKELLQMLEKQGSEQKLISEED (SEQ ID NO: 242)
223. ATVKFTYQGEEKQVDISKIKHVRRWGQWIWFIYDEGGGAKGWGGV
SGKDAPKELLQMLEKQGSEQKLISEED (SEQ ID NO: 243)
224. ATVKFTYQGEEKQVDISKIKYVRRWGQYIWFGYGEGGGARGYGHV
SERDAPKELLQMLEKQGSEQKLISEED (SEQ ID NO: 244)
225. ATVKFTYRGEEKQVAISKIKYVRRWGQHIWFGYDKGGGAHGIGYV
SERDAPKELLQMLDEQGSEQKLISEED (SEQ ID NO: 245)
226. ATVKFTYRGEEKRVDISKIKHVRRWGQWIWFIYDGGGGAKGWGGV
SEKDAPKELLQMLEEQGSEQKLISEED (SEQ ID NO: 246)
227. ATVKFTYRGEEKQVDISKIKYVRRWGQYIWFGYDEGGGARGYGYV
SEKDAPEELLQMLEKHGSEQKLISEED (SEQ ID NO: 247)
228. ATVRFTYHGEEKQVDISKIKYVRRWGQWIWFIYDEGGGANGKGSV
SEKDAPKELLQMLEKQGSEQKLISEED (SEQ ID NO: 248)
229. ATVKFTYRGEEKQVDISKIKYVRRWGQYIWFGYDEGGGARHGYV
SENDAPKELLQMLEKQGSEQKLISEED (SEQ ID NO: 249)
230. ATVEFTYRGEEKQVDISKIKYVRRWGQYIWFGYDGGGGARGYGYV
SEKDAPKELLQMLEEQGSEQKLISEED (SEQ ID NO: 250)
231. ATVKFTYRGEEKQVGISKIKYVRRWGQYIWFGYDEGGGARGYGYV
SEKDAPKELLQMLDKQGSEQKLISEED (SEQ ID NO: 251)
232. ATVKFTYRGEEKQVDISKIKHVRRWGQWIWFIYDGGGGAKGWGGV
SEKDAPKELLQMLEKQGSEQKLISEED (SEQ ID NO: 252)
233. ATVKFTYRGEEKQVDISKIKHVRRWGQWIWFIYDEGGGAKGWGGV
SEKDAPKELLQMLEKQGSEQKLISEED (SEQ ID NO: 253)
234. AVVRFTYRGEEKQVDISKIKYVRRWGQYIWFGYDEGGGARGYGYV
SEKDAPKELLRMLEK (SEQ ID NO: 254)
235. ATVKFTYQGEEKRVDISKIKYVRRWGQYIWFGYDGGGGARGYGHV
SEKDAPRELLQMLEKRGSEQKLISEED (SEQ ID NO: 255)
236. ATVKFTYQGEEKQVDISKIKYVWRWGQWIWFHYDEGGGARGYGYV
SEKDAPKELLQMLGKRGSEQKLISEED (SEQ ID NO: 256)
237. ATVKFTYQGEEKQVDISKIKYVRRWGQYIWFGYDGGGGARGYGHV
SEKDAPKELLQMLGGRGSEQKLISEED (SEQ ID NO: 257)
238. ATVKFTYRGEEKQVDISKIKYVRRWGQYIWFGYDGGGGARGYGHV
SEKDAPKELLQMLEEQGSEQKLISEED (SEQ ID NO: 258)
239. ATVRFTYQGEEKQVDISKTKHVRRWGQWIWFIYDEAGGAHGRGRV
SEKDAPKELLQMLEKQGSEQKLISEED (SEQ ID NO: 259)
240. ATVKFTYRGEEKQVDISKIKYVRRWGQYIWFGYDEGGGARGYGYV
SETDAPEKLLQMLEKQGSEQKLISEED (SEQ ID NO: 260)
241. ATVKFTYRGEEKQVDISKIKHVRRWGQWIWFIYDGGGGTKGWGGV
SEKDAPKELLQMLEKQGSEQKLISEED (SEQ ID NO: 261)
242. ATVKFTYQGEEKQVDISKIKHVRRWGRWIWFIYDEGGGAKGWGGV
SGRDAPKELLQMLEKQGSEQKLISEED (SEQ ID NO: 262)
243. ATVKFTYQGEEKQVGISRIKYVRRRGQYIWFGYDKGGGARGYGYV
SEKDAPKELLQMLEKQGSEQKLISEED
```

244. ATVRFTYQGEEKQVDISKIKHVRRWGQWIWFIYDEGGGAKGRGGVSEKDAPKELLQMLEKQGSEQKLISEED (SEQ ID NO: 263)

245. ATVKFTYRGEEKQVDISKIKYVRRWGQYIWFGYDEGGGARGYGYVSEKDAPKGLLQMLEKRGSEQKLISEED (SEQ ID NO: 264)

246. ATVKFTYQGEEKQVDISKIKYVRRWGQRISFIYDEGGGARGYGRVSEKDAPKELLQLLEKQGSEQKLISEED (SEQ ID NO: 265)

247. ATVKFTYRGEEEQVDISKIKYVWRWGQWIWLRYDEGGGAHGIGYVSRKDAPKELLQMLEKQGSEQKLISEED (SEQ ID NO: 266)

248. ATVRFTYQGEERRVDISKIKYVRRWGQHIWFGYDEGGGARGYGYVNEKGAPRELLRMLEKRGSEQKLISEED (SEQ ID NO: 267)

249. ATVKFTYQGEEKQVDISKIKHVRRWGRWIWFIYDEGGGAKGRGGVSEKDAPKELLQMLEKQGSEQKLISEED (SEQ ID NO: 268)

250. ATVKFTYQGEEKQVDISEIKYVRRRGQYIWFGYDEGGGARGYGYVSGKDAPKELLQMLERRGSEQKLISEED (SEQ ID NO: 269)

251. ATVKFTYQGKEGQVAISKIKYVRRWGQYIWFGYDEGGGARGYGYVSEKDAPKELLQMLGKQGSEQKLISEED (SEQ ID NO: 270)

252. ATVRFTYQGEEKQVDISKIKYVRRWGQYIWFGYDGGGARGYGYVSKKDAPKELLQMLERQGSEQKLISEED (SEQ ID NO: 271)

253. ATVKFTYQGEEKQVDISKIKYVWRWGRWIWFRYDEGGGAHGIGHVSEKGAPKELLRMLEKQGSEQKLISEED (SEQ ID NO: 272)

254. ATVKFTYQGEEKQVDISKIKHVRRWGRYIWFGYDEGGGARGYGYVSEKAAPKGLLQMLGKQGSEQKLISEED (SEQ ID NO: 273)

255. ATVKFTYRGEEKQVDISKIKYVRRWGQYIWFGYDEGGGARGYGYVSGKDAPKELLQMLEKQGSEQKLISEED (SEQ ID NO: 274)

256. ATVRFTYQGEEKQVDISRIKIVYRWGQRISFIYDKGGGARGYGRVSEKDAPKELLQMLEK (SEQ ID NO: 275)

257. ATVRFTYRGGEKQVDISKIKYVRRWGQYVWFGYDKGGGVRGYGYVSEKDAPRELLQMLEKQGSEQKLISEED (SEQ ID NO: 276)

258. ATVKFTYQGEEKQVDISKIKSVHRVGQWIKFWYDGGGGAYGRGYVSEKDAPKELLQMLE (SEQ ID NO: 415)

259. ATVKFTYRGEEKQVDISRIRSVSRWGQAIVFRYDEGGGAKGKGSVSEKDAPKELLQMLGKAGIRTKAYF (SEQ ID NO: 277)

260. ATVKFTYQGEEKQVGISKIKHVRRWGQWIWFIYDEGGGAKGRGSVSERDAPKELLQMLEKAGIRTKAYF (SEQ ID NO: 278)

261. ATVKFTYQGEEKQVDISKIKYVRRWGQYIWFGYDEGGGARGYGYVSEKDAPKGLLQMLEKARIRTKAYF (SEQ ID NO: 279)

262. ATVKFTYRGEEKRVDISKIKYVRRWGQYIWFGYDEGGGARGYGYVSGRDAPRELLQMLEKARIRTKAYF (SEQ ID NO: 280)

263. ATVQFTYQGGEKQVDISKIKYVRRWGRYIWLGYDEGGGARGHGYVSEKDAPKELLQMLEKARIRTKAYF (SEQ ID NO: 281)

264. ATVEFTYQGEEKQVDISKIKYVRRWGQYIWFGYDEGGGARGYGYVSEKDAPKELLQILEKARIRTKAYF (SEQ ID NO: 282)

265. ATVKFTYQGEEKQVDISKIKYVRRWGQYLWFGYDGGGGARGYGYVSEKDAPKELLQMLERARIRTKAYF (SEQ ID NO: 283)

266. ATVKFTYQGEERQVDISKVKHVRRWGQWVWFIYDEGGGAKGWGGVSEKDAPTELLQMLEKARIRTKAYF (SEQ ID NO: 284)

267. ATVKFTYQGEEKQVDISRIKSAFRWGQAIIFRYDEGGGAKGKGSVSEKDAPKELLQMLEKARIRTKAYF (SEQ ID NO: 285)

268. ATVEFTYRGEEKQVDISKIKYVRRWGQYIWFGYDEGGGARGYGYVSEKDAPKELLQMLEKAGIRTKAYF (SEQ ID NO: 286)

269. ATVKFTYQGEEKQVDISKIKYARRWGQYIWFGYDEGGGARGYGYVSEEDAPKELLQMLEKARIRTKAYF (SEQ ID NO: 287)

270. ATVKFTYRGEEKQVDISKIKSVSRWGQAIIFRYDEGGGAKGKGSVSEKDAPKELLQMLEKARIRTKAYF (SEQ ID NO: 288)

271. ATVKFAYQGEERQVDISKIEYVRRWGQYIWFGYDEGGGARGYGYVSEKDAPKELLQMLEKARIRTKAYF (SEQ ID NO: 289)

272. ATVKFTYQGEEKQVDVSKIKHVRRWGQWIWFIYDEGGGAKGWGGVSEKDAPKELLQMLEKARIRTKAYF (SEQ ID NO: 290)

273. ATVKFTYQGEEKQVGIGKIKHVRRWGQYIWFGYDGGGGARGYGYVSEKDAPKGLLQMLEKARIRTKAYF (SEQ ID NO: 291)

274. ATVKFTYQGEEKQVDISKIKYVWRWGQWIWFRYDEGGGAKGKGSVSEKDAPRELLQMLEKAGIRTKAYF (SEQ ID NO: 292)

275. ATVKFTYRGEEKQVDISKIKYVRRWGQYIWFGYDGGGGARGYGHVSEKDAPKELLQMLEEARIRTKAYF (SEQ ID NO: 293)

```
(SEQ ID NO: 294)
276. ATVKFTYQGEEKQVDIGKIKYVRRWGQYIWFGYDEGGGARGYGYV
SEEDAPKELLQMLEKARIRTKAYF (SEQ ID NO: 295)
277. ATVKFTYQGEEKQVDISKIKSVHRVGQWIKFWYDEGGGAYGRGYV
SERDAPRELLQMLEEARIRTKAYF (SEQ ID NO: 296)
278. ATVKFTYQGEEEQVAISKIKHVRRWGQWIWFRYDEGGGAHGIGYV
SEKDAPKELLQMLEKARIRTKAYF (SEQ ID NO: 297)
279. ATVKFTYQGEEKQVDISKIKYVWRWGQWIWFRYDEGGGAHGIGYM
SEKDAPRELLQMLGKARIRTKAYF (SEQ ID NO: 298)
280. ATVKFTYQGEEKQVEVSKIKYVRRWGQYIWFSYDEGGGARGYGYV
SERDAPRELLQMLEKARIRTKAYF (SEQ ID NO: 299)
281. ATVKFTYRGEEKQVDISKIKSVSRWGQAIIFRYDGGGGARGKGSV
SEKDAPKELLQMLEKAGIRTKAYF (SEQ ID NO: 300)
282. ATVKFTYQGEEKQVDISKIKHVRRWGQWIWFIYDEGGGAKGWGGV
SEKNAPKELLQMLEKARIRTKAYF (SEQ ID NO: 301)
283. ATVRFTYQGEEKQVDISKIKYVRRWGQYIWFGYDEGGGARGYGYV
SEKDTPKELLQLLEKARIRTKAYF (SEQ ID NO: 302)
284. ATVKFTYQGEEKQVDISKIKHVRRWGQWIWFIYDEGGGAKGKGSV
SEKDAPKELLQMLEKAGIRTKAYF (SEQ ID NO: 303)
285. ATVKFTYQGEEKQVDISKIKYVWRWGQAIIFRYDEGGGAKGKGSV
SEEDAPKELLQMLEKARIRTKAYF (SEQ ID NO: 304)
286. ATVKFTYRGEEKQVGISKIKYVRRWGQYIWFGYDEGGGARGHGYV
SEKDAPKELLQMLEKQGSEQKLISEED (SEQ ID NO: 305)
287. AAVKFTYQGEEKQVDIGRTKYVWRWGQWIWFRYDEGGGARGYGCV
GEKDAPRELLRVLEKQGSEQKLISEED (SEQ ID NO: 306)
288. ATVKFTYRGEEKQVDTSRIKYVWRWGQWIWFRYDEGGGARGYGYV
SEKDAPKELLQMLEKQGSEQKLISEED (SEQ ID NO: 307)
289. ATVRFTYQGEERQVGISKIKYVRRRGQYIWFGYDEGGGVRGYGYV
SEKGAPKELLRMLEKRGSEQKLISEED (SEQ ID NO: 308)
290. ATVKFTYQGEEKQVDISKIKHVRRWGQWIWFIYDEAGGAHGRGRV
SERGAPKELLQMLEKQGSEQKLISEED (SEQ ID NO: 309)
291. ATVKFTYRGEEEQVGISRIKYVWRWGQWIWFRYDGGGGARGYGHV
SDKDAPKELLQMLEKRGSEQKLISEED (SEQ ID NO: 310)
292. ATVKFTYQGEEKQVDISRIKHVRRWGQWIWFIYDGAGGAHGRGRV
SERGAPKELLQMLEKQGSEQKLISEED (SEQ ID NO: 311)
293. ATVKFTYQGEEKQVDISKVKYVRRRGQYIWFGYDEGDGAYGRGHV
SEKGAPKELLQMLKKQGSEQKLISEED (SEQ ID NO: 312)
294. VTVKFTYQGEEKQVDISRIKHVRRWGQWIWFIYGKGGGAKGRGGV
SEKDAPKELLQMLEKQGSEQKLISEED (SEQ ID NO: 313)
295. AAVKFTYRGEEKQVDISKIKYVRRWGQYIWFGYDKGGGARGYGYV
GEKGAPKELLQMLEKQGSEQKLISEED (SEQ ID NO: 314)
296. ATVKFTYRGEEKQVDISRIKYVRRWGQYIWFGYDEGGGARGHGHV
SEKEAPRELLQMLEKQGSEQKLISEED (SEQ ID NO: 315)
297. ATVKFTYQGEEKQVDISKIKHVRRWGQWIWFIYDEAGGAHGRGRV
SERGAPRELLQMLEKQGSEQKLISEED (SEQ ID NO: 316)
298. ATVRFTYRGEERQVGISKIKYVRRWGQYIWFGYDEGGGARGYGYV
SEKDAPKELLQMLDKQGSEQKLISEED (SEQ ID NO: 317)
299. ATVKFTYQGEEKQVGISRIKYVRRRGQYIWFGYDKGGGARGHGYV
GEKDAPKELLQMLGKQGSEQKLISEED (SEQ ID NO: 318)
300. ATVKFTYQGGEKQVDISKIKYVRRWGQHIWFGYDEGGGARGYGYV
SKKDAPKELLQMLEKRGSEQKLISEED (SEQ ID NO: 319)
301. ATVKFTYRGEEGQVDISKVKYVWRWGQWIWFRYDGGGAHGIGHV
SEKDTPKELLQMLEKQGSEQKLISEED (SEQ ID NO: 320)
302. ATVKFTYQGEEKQVDMSKIKHVRRWGQWIWFIYDEGGGARGRGYV
SEKGAPEELLQMLGKQGSEQKLISEED (SEQ ID NO: 321)
303. ATVKFTYQGREKQVDISKIKHVRRRGQYIWFGYDKGGGARGYGYV
SEGDAPKELLQMLEKQESEQKLISEED (SEQ ID NO: 322)
304. ATVKFTYQGEEKQVGISKIRHVRRWGQWIWFIYDEGGGAKGRGSV
SERDAPKELLQMLEKARIRTKAYF (SEQ ID NO: 323)
305. ATVKFTYQGGEKQVDISKIKHVWRWGQWVWFRYDEGGGARGYGRV
SEKGAPKELLQMLGKQGSEQKLISEED (SEQ ID NO: 324)
306. ATVKFTYHGEGKQVDISKIRYVRRWGRYIWFGYDEGGGARGYGYV
SEKGAPEELLQMLGKQGSEQKLISEED (SEQ ID NO: 325)
307. ATVKFTYRGEEKQVDISKIKHVRRWGQWIWFIYDEGGGAKGKGSV
SEEDAPKELLQMLEKVGIRTKAYF
```

-continued

308. ATVKFTYRGGEKQVDISRVKYVWRRGQWIWFRYDGGGGAHGTGCV (SEQ ID NO: 326)
SEKNAPKELLQMLGRQGSEQKLISEED

309. ATVKFTYQGEEKQVDISKIKHVRRWGQWIWFIYDKGGGAKGRGGV (SEQ ID NO: 327)
SDKDAPKELLQMLEKQGSEQKLISEED

310. ATVRFTYRGEEKQVDISKIKHVRRWGQWIWFIYDEGGGAKGRGGV (SEQ ID NO: 328)
SKEDAPKELLRMLGKQGSEQKLISEED

311. ATVKFTYHGEERQVDISKIKHARRWGQWIWFIYDEGGGAKGRGGV (SEQ ID NO: 329)
SERNAPKELLQMLEGRGSEQKLISEED

312. ATVRFTYQGEEKQVDISKIKYVRRRGQYIWFGYDEGGGARGYGYV (SEQ ID NO: 330)
SGKGAPKELLQMLEEHGSEQKLISEED

313. ATVKFTYRGEGKQVDISKIKHVRRWGQWIWFIYDEGGGAKGWGGV (SEQ ID NO: 331)
SEKGAPKALLQMLEKQGSEQKLISEED

314. ATVEFTYRGEEKQVDISKIKHVRRWGQWIWFIYDEGGGAKGRGGV (SEQ ID NO: 332)
SERDAPKELLQLLEKRGSEQKLISEED

315. ATVKFTYQGKEKQVDISKIKYVRRRGQYIWFGYDKSGGARGYGYV (SEQ ID NO: 333)
SEKGAPKELLQMLEKQGSEQKLISEED

316. ATVKFTYRGGEKQVDIGKIKYVRRWGQYVWFGYDEGGGARGYGYV (SEQ ID NO: 334)
SEKDAPKELLQMLEKRGSEQKLISEED

317. ATVKFTHRGEEKQVDASKIKYVRRWGRHIWFGYDEGGGARGYGYV (SEQ ID NO: 335)
GEKDAPKELLQMLERQGSEQKLISEED

318. ATVKFTYQGEEKQVDISKIKHVRRWGQWIWFTYDEGGGAKGRGGV (SEQ ID NO: 336)
SEKDAPKELLQMLEKQGSEQKLISEED

319. TTVKFTYQGEEKQVDISKIKHVRRWGRWIWFTYDEGGGAKGRGGV (SEQ ID NO: 337)
SEKDAPKELLQMLEKRGSEQKLISEED

320. TTVKFTYQGEEKQVDISKIKHVRRWGQWIWFTYDEGGGAKGRGGV (SEQ ID NO: 338)
SEKDAPKELLRMLEKQGSEQKLISEED

321. ATVKFTYRGEEKQVAISKIKYVRRWGQHIWFGYDKGGGVRGYGYV (SEQ ID NO: 339)
GEKGAPRGLLQMLEKQGSEQKLISEED

322. ATVRFTYQGEEKQVDINRIKHVRRWGQWIWFIYDEGGGAKGRGGV (SEQ ID NO: 340)
SGKDAPKELLQMLEKQGSEQKLISEED

323. ATVKYTYRGEEKQVGISRIKSVHRIGQWIKFWYDEGSGAYGRGYV (SEQ ID NO: 341)
SEKDAPRELLQMLGKRGSEQKLISEED

324. ATVKFTYQGEEKQVDISKIKHVRRWGQWIWFIYDKGGGAKGRGGV (SEQ ID NO: 342)
SEKDAPKELLQMLEKQGSEQKLISEED

325. ATVKFTYQGEEKQVDISKIKYVRRWGQYIWFGYDAGGGVRGYGYV (SEQ ID NO: 343)
SEKDAPKGLLQMLEKARIRTKAYF

326. ATVKFTYQGEEKQVNISKIKHVRRWGQWIWFVYDEGGGAKGRGGV (SEQ ID NO: 344)
SEKDAPKELLQMLEKQGSEQKLISEED

327. ATVKFTYRGEEKQVDISEIRYVWRRGQWIWFRYDEGGGAHGIGHV (SEQ ID NO: 345)
SEKGAPKELLQTLERQGSEQKLISEED

328. ATVKFTYRGEEKRVDISKIKHVRRWGQWIWFIYDEGGGAHGRGRV (SEQ ID NO: 346)
SEKDAPKELLQMLEKQGSEQKLISEED

329. ATVKFTYQGGKKQMDISKLKYVRRWGRYIWFGYDEGGGARGYGYV (SEQ ID NO: 347)
SGKDAPRELLQMLEKQGSEQKLISEED

330. ATVKFTYRGEEKQVDISKIKYVRRWGQYVWFGYDEGGGAKGRGGV (SEQ ID NO: 348)
SKKDAPKELLQMLERQGSEQKLISEED

331. ATVKFTYQGEEKQVDISKIKYVRRWGQYIWFGYDEGGGARGRGYV (SEQ ID NO: 349)
SGKDAPKELLQMLEKQGSEQKLISEED

332. ATVKFTYQGGEKQVGISRIKYVRRRGQYIWFGYDKGGGARGYGYV (SEQ ID NO: 350)
SEKDAPKELLQMLEKQGSEQKLISEED

333. ATVKFTYQGEEKQVDISKIKYVRRWGQYIWFGYDAGGGARGYGYV (SEQ ID NO: 351)
SEKDAPKGLLQMLEKRGSEQKLISEED

334. ATVKFTYQGEEKQVDISRIKYVRRWGQYIWFGYGEGGARGYGYV (SEQ ID NO: 352)
SEKDAPEGLLQMLGKRGSEQKLISEED

335. AAVKFTYQGEERQVDISKIKHVRRWGQWIWFIYDEGGGAKGRGGV (SEQ ID NO: 353)
SEKDAPKELLQMLERQGSEQKLISEED

336. ATVKFTYRGEEKQADISKIKYVRRWGQYVWFGYDEGGGVRGYGYV (SEQ ID NO: 354)
SEKDAPKELLQMLEKQGSEQKLISEED

337. ATVKFTYQGEEKQVDISKIKHVRRWGQWIWFVYDKGGGAKGRGGV (SEQ ID NO: 355)
SEKNAPKELLQMLERQGSEQKLISEED

338. AIVKFTYHGEEKQVDISKIKYVRRWGQYIWFGYDEGGGARGYGYV (SEQ ID NO: 356)
SERGAPKELLQMLEKRGSEQKLISEED

339. ATVKFTYRGGEKQVDISKIKYVRRRGQYIWFGYDEGGGARGYGYV (SEQ ID NO: 357)
SERDAPKELLQMLEKQGSEQKLISEED

```
                                                           (SEQ ID NO: 358)
340. ATVKFTYQGEEKQVDISKIKHVRRWGQWIWFIYDKGGGAKGRGGV
     SEKNAPKELLQMLEKQGSEQKLISEED (SEQ ID NO: 359)
341. ATVEFTYQGEEKQVDISKIKHVRRWGQWIWFIYDEGGGAKGRGGV
     SERDAPKELLQLLEKRGSEQKLISEED (SEQ ID NO: 360)
342. ATVKFTYRGEGKQVDISKIKYVRRWGQYVWFGYDEGGGARGYGYV
     SEKDAPKELLQMLEKQGSEQKLISEED (SEQ ID NO: 361)
343. ATVKFTYRGGEKQVDISRIKYVWRRGQWIWFRYDGGGGAHGTGCV
     SEKNAPKELLQMLGRQGSEQKLISEED (SEQ ID NO: 362)
344. ATVEFTYRGEEKQVDVSKIKYAWRWGRWIWFRYDEGGSAHGIGYV
     SEKDAPKELLQMLEKQGSEQKLISEED (SEQ ID NO: 363)
345. ATVKFTYQGEEKQVGVSRITYVRRRGQYIWFGYDKGGGARGYGYV
     SEKDAPKELLQMLEKQGSEQKLISEED (SEQ ID NO: 364)
346. ATVKFTYRGEEKQVDISKIKYVRRWGQYIWFGYDGGGGANGRGGV
     SERGAPKELLQMLGKQGSEQKLISEED (SEQ ID NO: 365)
347. ATVEFTYQGEEKQVDIGKIKYVRRWGQYIWFGYDEGGGARGYGYV
     SRKGAPKELLQMLEKRGSEQKLISEED (SEQ ID NO: 366)
348. AIVRFTYRGEEKRVDISEIKYVRRWGQYIWFGYDKGGGARGHGYV
     SEKDAPKELLQMLEEQGSEQKLISEED (SEQ ID NO: 367)
349. ATVKFTYRGEEKQVDISKIKHARRWGQYIWFGYDEGGGARGYGYV
     SEKDAPKELLRMLEKRGSEQKLISEED (SEQ ID NO: 368)
350. ATVKFTYQGEEKQVDISRIKHVRRRGQYIWFGYDEGGGARGYGYV
     SEKDAPKELLRMLEK (SEQ ID NO: 369)
351. ATVKFTYRGEEKQVDISKIKYVRRWGQYIWFGYDEGGGARGHGRV
     SEKDAPRGLLQMLEKQGSEQKLISEED (SEQ ID NO: 370)
352. AIVKFTHHGEEKQVDISKIKYVRRWGQYIWFGYDEGGGARGYGYV
     SERDAPKELLQMLEKRGSEQKLISEED (SEQ ID NO: 371)
353. TTVKFTYQGEEKQVGISRIKYVRRRGQYIWFGYDKGGGARGYGYV
     SGKDAPRELLQMLEKQGSEQKLISEED (SEQ ID NO: 372)
354. ATVRFTYHGEEKQVDISKIKYARRWGQYIWFGYDEGGGARGYGHV
     SGEDAPKELLQMLEKPGSEQKLISEED (SEQ ID NO: 373)
355. ATVKFTYQGEEKQVDISKIKYVRRWGRYIWFGYDGGGGARGYGHV
     SEKDAPKELLQMLGGRGSEQKLISEED (SEQ ID NO: 374)
356. ATVKFTYQGGEEKQVDISKVRHVRRWGRWIWFGYDEGGGAHGRGRV
     SGKDAPKELLQMLEKQGSEQKLISEED (SEQ ID NO: 375)
357. ATVKFTYRGEEKQVDISKIKRVRRWGQWIWFIYDEAGGAHGRGRV
     SERGAPKELLQMLEKQGSEQKLISEED (SEQ ID NO: 376)
358. ATVEFTYQGEEKQVDISKIKHVRRRGQYIWFGYDKGGGARGYGYV
     SEKDAPKELLQMLEKQGSEQKLISEED (SEQ ID NO: 377)
359. ATVKFTYRGEEKQVDISKIKHVRRWGQWIWFIYDEGGGAKGWGGV
     SEKDAPRGLLQMLERQGSEQKLISEED (SEQ ID NO: 378)
360. ATVKFTYQGEEKQVDISKIKYVRRWGQWIWFRYDGGGGAHGIGHV
     SEKDAPKELLQMLGKQGSEQKLISEED (SEQ ID NO: 379)
361. ATVKFTYHGEEKQVDISKIKYVRRWGQYIWFGYDEGGGARGYGYV
     SGKGAPEELLQMLEKQGSEQKLISEED (SEQ ID NO: 380)
362. ATVKFTYQGEGKQVDISKIKHVRRWGQWIWFIYDEGGGARGYGYV
     SGKDAPKKLLRMLEGRGSEQKLISEED (SEQ ID NO: 381)
363. AAVEFTYQGEEKQVDISKIKHVRRWGQWIWFIYDEAGGAHGRGRV
     SERGAPKELLQMLERQGSEQKLISEED (SEQ ID NO: 382)
364. ATVKFTYRGGEKQVDISKIKYVRRRGQYIWFGYDEGGGARGYGYV
     SERDAPRELLQMLEKQGSEQKLISEED (SEQ ID NO: 383)
365. ATVKFTYRGEEKQVDISKIKYVRRRGQYIWFGYDEGGGARGYGYV
     SEKDAPKELLQMLGKQGSEQKLISEED (SEQ ID NO: 384)
366. ATVKFTYRGEEKRVDTSKIKHVRRWGQWIWFTYDEGGGAKGRGGV
     SEKDAPKELLQMLEKQGSEQKLISEED (SEQ ID NO: 385)
367. ATVKFTYRGEEKQVDISKIKYVWRWGQWIWFRYDEGGGAHGIGHV
     SEKSAPKELLQTLGRQGSEQKLISEED (SEQ ID NO: 386)
368. ATVKSTYQGEEKQVDISKIKHVRRWGRWIWFIYDEGGGAKGWGGV
     SGRDAPKELLQMLEKQGSEQKLISEED (SEQ ID NO: 387)
369. AIVKFTYQGEERQVDISKIKYVRRWGQYIWFGYDEGGGAHGRGRV
     SGKDAPKELLQMLEKQGSEQKLISEED (SEQ ID NO: 388)
370. ATVKFTYHGEERQVDISKIKYVRRWGQYIWFGYGGGGARGYGYV
     SEKDAPKELLQMLEKQGSEQKLISEED (SEQ ID NO: 389)
371. ATVKFTYQGEEKQVDISKIKYVRRWGQYIWFGYDGGGGARGRGYV
     SEKDAPKELLQMLEKQGSEQKLISEED
```

-continued (SEQ ID NO: 390)
372. VAVKFTYQGEEKRVDISKIKYVRRRGQYIWFGYGEGGGARGYGYV

SEKDAPKELLQMLAKRGSEQKLISEED (SEQ ID NO: 391)
373. ATVKFTYQGEEKQVDISKIKHVRRWGQWIWFIYDGGGAKGRGGV

SEKDAPKELLQMLEKQGSEQKLISEED (SEQ ID NO: 392)
374. ATVKFTYRGEEKQVDASRIKYVRRWGQYIWFGYDEGGGARGYGYV

SGRDAPKELLQMLEKQGSEQKLISEED (SEQ ID NO: 393)
375. ATVKFTYQGEEKQVDISKIRYARRRGQYIWFGYGEGGGARGYGYV

SDKDAPKELLRMLEKQGSEQKLISEED (SEQ ID NO: 397)
376. ATVKFTYQGEEKQVDISKIKIVYRWGQRISFIYDEGGGARGYGRV

SEKDAPKELLQMLEKQGSEQKLISEEDL (SEQ ID NO: 398)
377. ATVKFTYQGEEKQVDISKIKHVRRWGQWIWFIYDEGGGAKGWGGV

SEKDAPKELLQMLEKQGSEQKLISEEDL (SEQ ID NO: 399)
378. ATVKFTYQGEEKQVDISKIKYVRRWGQYIWFGYDEGGGARGYGYV

SEKDAPKELLQMLEKQGSEQKLISEEDL (SEQ ID NO: 400)
379. ATVKFTYQGEEKQVDISKIKRVYRYGQWIWFRYDEGGGAYGGGWV

SEKDAPKELLQMLEKQGSEQKLISEEDL (SEQ ID NO: 401)
380. ATVKFTYQGEEKQVDISKIKSVSRWGQAIIFRYDEGGGAKGKGSV

SEKDAPKELLQMLEKARIRTKAYF

Example 2

This example describes some of the glycan-binding proteins of Example 1. The protein scaffold (SEQ ID NO: 1) of Example 1 is a reduced-charge variant of Sso7d, which is a native DNA binder. The protein scaffold was used to generate the glycan-binding proteins. It had 63 residues and a melting temperature of 98° C. The protein scaffold was stable to prolonged exposure to pH values with the range of 0.3-12.5 and was free of disulfides. The protein scaffold was compatible with yeast surface display, high-yield protein expression in E. coli, and functionalization. The protein scaffold formed an SH3-domain-like fold with five beta (β)-strands and an alpha (α)-helix at the C-terminus.

Figure 4:
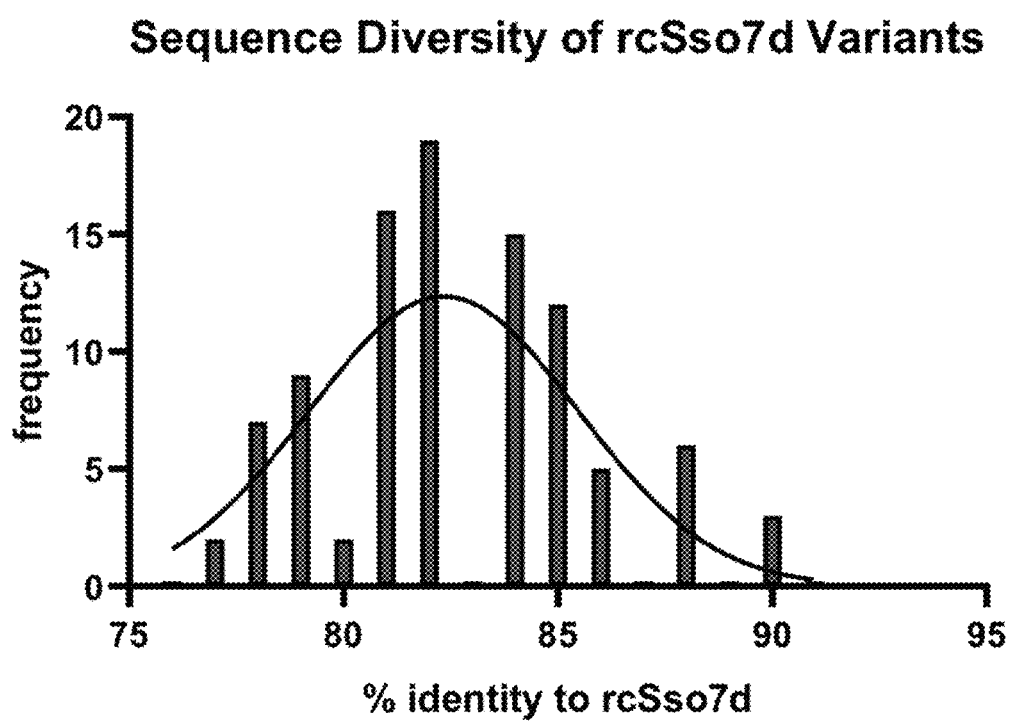
FIG. 4 illustrates, in accordance with certain embodiments, a histogram of the percent identity of the glycan-binding proteins in Sequence List 2 with rcSso7d.

The glycan-binding proteins that were found in Example 1 were generally stable to the described biochemical manipulations and were predicted to be well-folded both on yeast surfaces and as soluble expressed proteins based the observed binding properties. Anecdotally it also is known that proteins that are efficiently expressed on yeast cell surfaces must be well-folded. In addition, the glycan-binding proteins had sequences that diverged significantly from the protein scaffold. FIG. 4 shows a histogram of the number of variants in Sequence List 2 that bind glycans versus percent homology in sequence compared to the original protein scaffold (the reduced-charge variant of Sso7d, or rcSso7d). Notably, these sequences are significantly different than the protein scaffold, with the most divergent sequences having approximately 68-69% homology. For example, these histograms include the following sequences that have 68.852% homology to the protein scaffold:

(SEQ ID NO: 13)
ATVKFTYRGEEKQVGVSRVKSVHRIGQWIKFWYDEGSGAYGRGYVSEKDA

PEELLQMLEKRGSEQKLISEEDL (SEQ ID NO: 394)
ATVKFTYRGEEKQVGISRIRSVHRIGQWIKFWYDEGSGACGRGYVSEKGA

PKELLQMLGKRGSEQKLISEEDL (SEQ ID NO: 395)
ATVKFTYRGKEKRVGVSRIKSVRRIGQWIKFWYDEGSGAYGRGYVSEKDA

PKELLQMLEKRGSEQKLISEEDL (SEQ ID NO: 396)
ATVKFTYRGEEKQVGINRIKSVHRIGQWIKFWYDEGSGAYGRGYVSGKDA

PKELLRMLEKRGSEQKLISEEDL

Despite the differences in sequence, these variants are all predicted to form an SH3-domain-like fold with five beta (β)-strands and an alpha (α)-helix at the C-terminus. Other glycan-binding proteins with even more divergence are also predicted to exhibit a similar SH3-domain-like fold with five beta (β)-strands and an alpha (α)-helix at the C-terminus.

Example 3

This example describes some glycan-binding proteins from Example 1.

Some of the variants that were generated demonstrated high specificity for a target of interest and could distinguish small points of differences between molecules that were targeted and other, non-target molecules having similar structures. For instance, in this example, variants were evolved to bind Galβ1-3GalNAcα (TF antigen), as discussed in Example 1. These variants demonstrated $K_D$ values for the TF antigen of 3 nM to 150 nM. These variants were studied with biolayer interferometry (BLI).

FIGS. 2A-2C show the structure of the TF antigen compared to the structures of Galα1-3GalNAcα and GalNAcα1-3GalNAcα, with arrows pointing to the stereocenters and functional groups that vary from the TF antigen. Specifically, Galα1-3GalNAcα differs from the TF antigen in having a substituent in the axial position instead of an equatorial position. GalNAcα1-3GalNAcα has an additional differentiation, in that a hydroxyl group is replaced by an N-acetamide substituent.

Figure 2D:
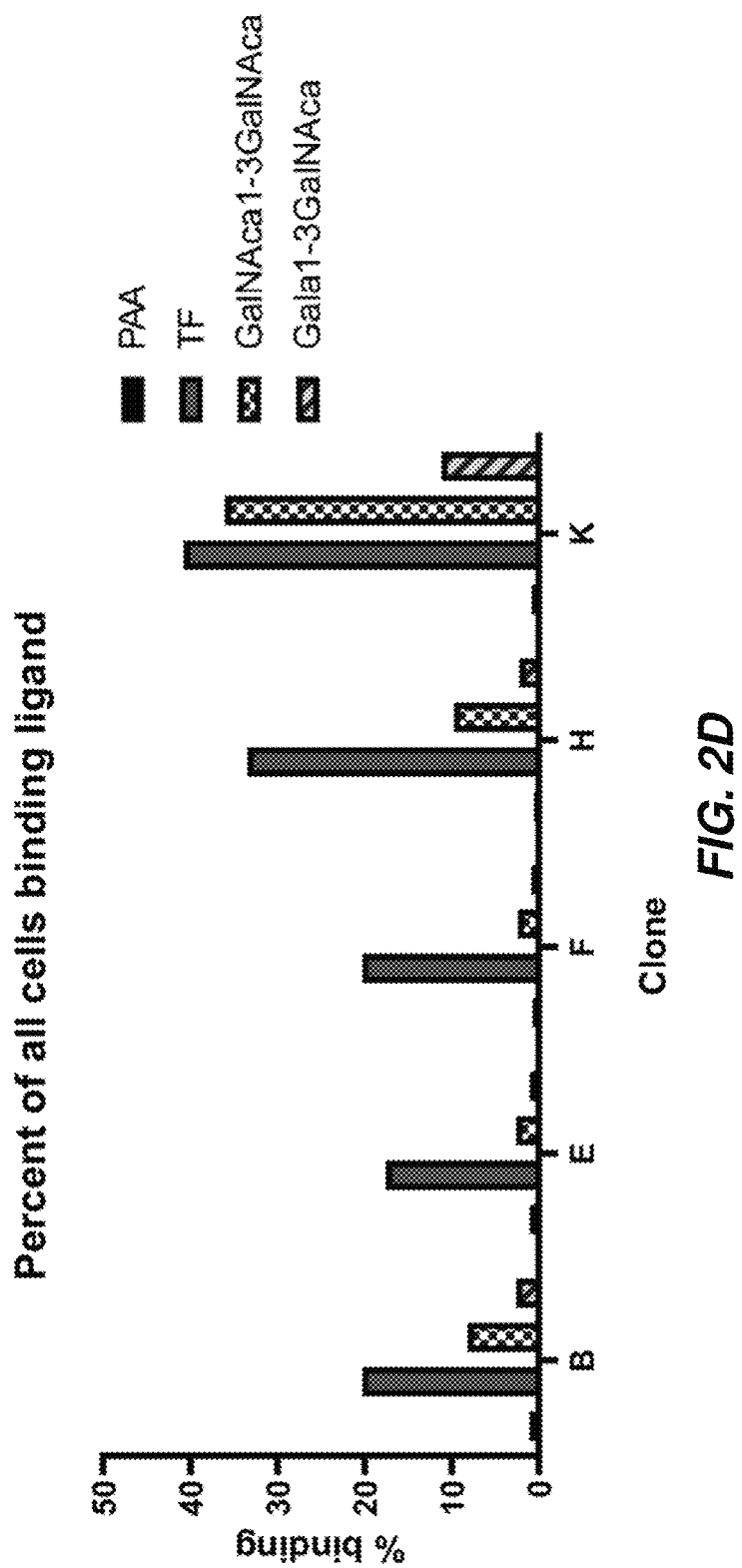
FIG. 2D illustrates, in accordance with certain embodiments, the percent binding of the three compounds of FIGS. 2A-2C and PAA-FITC (the control) for five different glycan-binding proteins.

FIG. 2D shows the percent binding of these three compounds and a sugar-polyacrylic acid (PAA)-FITC conjugate as a control for five different variants that were identified in these experiments. This binding was determined by analytical flow cytometry, wherein fluorescently labeled yeast and fluorescently labeled sugar-PAA-FITC were co-localized. These five variants (from Sequence List 2) have the following sequences:

(SEQ ID NO: 397)
ATVKFTYQGEEKQVDISKIKIVYRWGQRISFIYDEGGGARGYGRVSEKDA

PKELLQMLEKQGSEQKLISEEDL
(arbitrarily labeled clone B)

(SEQ ID NO: 398)
ATVKFTYQGEEKQVDISKIKHVRRWGQWIWFIYDEGGGAKGWGGVSEKDA

PKELLQMLEKQGSEQKLISEEDL
(arbitrarily labeled clone E)

(SEQ ID NO: 399)
ATVKFTYQGEEKQVDISKIKYVRRWGQYIWFGYDEGGGARGYGYVSEKDA

PKELLQMLEKQGSEQKLISEEDL
(arbitrarily labeled clone F)

(SEQ ID NO: 400)
ATVKFTYQGEEKQVDISKIKRVYRYGQWIWFRYDEGGGAYGGGWVSEKDA

PKELLQMLEKQGSEQKLISEEDL
(arbitrarily labeled clone H)

(SEQ ID NO 401)
ATVKFTYQGEEKQVDISKIKSVSRWGQAIIFRYDEGGGAKGKGSVSEKDA

PKELLQMLEKARIRTKAYF. (arbitrarily labeled clone K)

Notably, despite the small differences between the compounds in FIGS. 2A-2C, it was found that all of these variants preferentially bound the TF antigen versus the other compounds and the control. Thus, these data illustrate that proteins can be engineered to preferentially bind to specific sugars. Additionally, the variants differed from each other by 6 or fewer amino acids within the binding region.

Figure 2E:
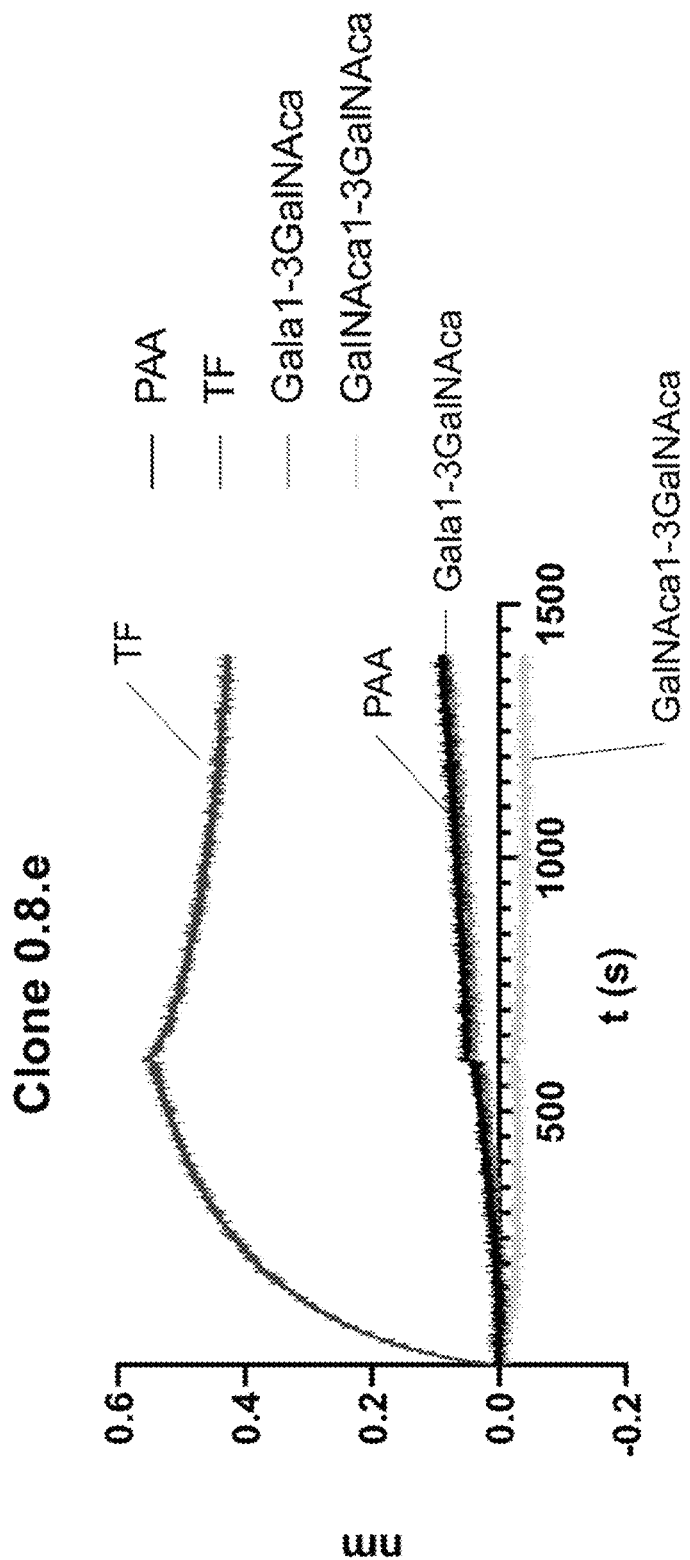
FIG. 2E illustrates biolayer interferometry traces of a glycan-binding protein in accordance with some embodiments.

FIG. 2E shows the biolayer interferometry traces for clone E. Clone E was immobilized on a Ni-NTA tip and dipped into a 1 uM solution of the sugar of interest. The traces show an increase in nm as sugar starts binding to protein on the tip, then a decrease in nm as the tip is moved from the sugar solution to buffer only. From this data, a curved was fitted and the binding affinity was determined from the rate of association and dissociation. FIG. 2E demonstrates that clone E bound to the TF antigen but did not bind to the negative control (PAA) and the other related disaccharides provided.

Example 4

This example describes certain glycan-binding proteins from Example 1. Some of the variants that were generated in Example 1 demonstrated high specificity for a target of interest and could distinguish small points of differences between molecules that were targeted and other, non-target molecules having similar structures. For instance, in this example, variants were evolved to bind sialic acid (Neu5Ac), as discussed in Example 1. These variants were then studied with flow cytometry and in particular, were determined to preferentially bind to Neu5Ac (sialic acid) relative to Neu5Gc. These variants (from Sequence List 1) have the following sequences:

(SEQ ID NO: 402)
ATVKFTYRGEEKQVGISRIKSVRRIGQWIKFWYDEGSGAYGRGYVSEKDA

PKELLQMLEKR (arbitrarily labeled clone A4)

(SEQ ID NO: 403)
ATVKFTYRGEEKQVGISRIKSVRRIGQWIKFWYDEGSGAYGRGYVSGKDA

PKELLQMLEKR (arbitrarily labeled clone B5)

(SEQ ID NO: 404)
ATVKFTYRGGEEKQVGISRIKSVRRIGQWIKFWYDEGSGAYGRGYVSEKDA

PKELLQMLEKR (arbitrarily labeled clone B6)

(SEQ ID NO: 405)
ATVKFTYRGEEKQVGISRIKSVHRIGRWIKFWYDEGSGAYGRGYVSEKDA

PKELLQMLEKR (arbitrarily labeled clone B8)

(SEQ ID NO: 406)
ATVKFTYRGEEKQVGISRIKSVHRIGQWIKFWYDEGSGAYGRGYVSKKDA

PKELLQMLEKR (arbitrarily labeled clone C11)

To analyze this specificity, yeast cells bearing the HA-epitope tag and displaying Sso7d variant Clone B5, for example, on their surface were labeled using fluorescent anti-HA antibody. These were provided 500 nM of the desired sugar-PAA-FITC for 1 hour, then analyzed by analytical flow cytometry for co-localization of both fluorophores, indicating glycan binding. Specific binding can be observed by the percentage of cells binding Neu5Ac versus Neu5Gc or PAA-FITC alone. Cells were gated in flow cytometry parameters to ensure single-cell analysis of live cells presenting Sso7d on their surface. As an example, the binding constant for Clone B5, as determined independently by BLI with soluble, expressed Clone B5, was 25-30 nM.

Figure 3B:
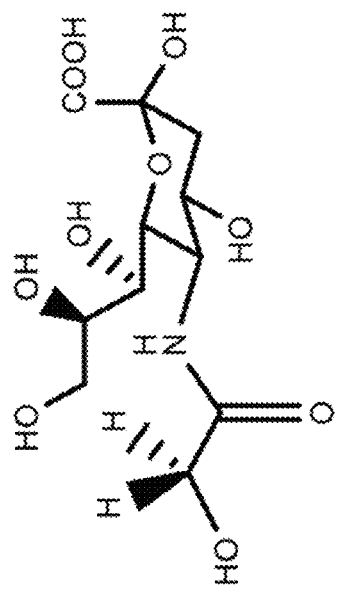
FIG. 3B illustrates the structure of Neu5Gc.
Figure 3A:
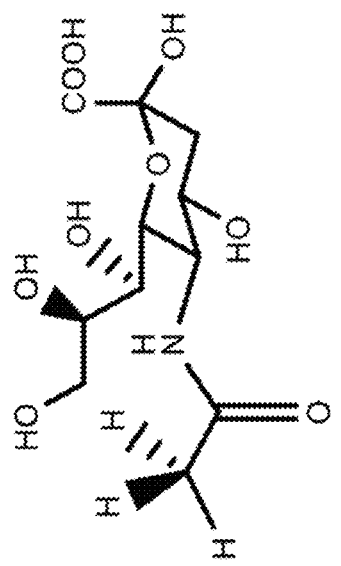
FIG. 3A illustrates the structure of Neu5Ac.

FIGS. 3A-3B show the structures of sialic acid (Neu5Ac) (FIG. 3A) and Neu5Gc (FIG. 3B). These binding determinants differ by one hydroxyl group.

Figure 3E:
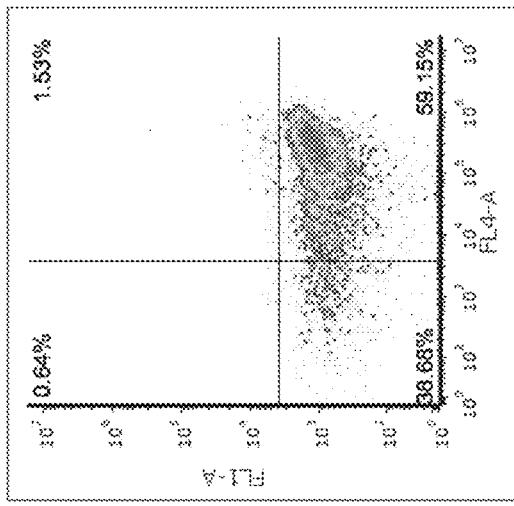
FIGS. 3C-3E illustrate flow cytometry results for sialic acid-PAA-FITC (FIG. 3C), NeuN5Gc-PAA-FITC (FIG. 3D), and PAA-FITC (FIG. 3E) for a glycan-binding protein, in accordance with certain embodiments.
Figure 3D:
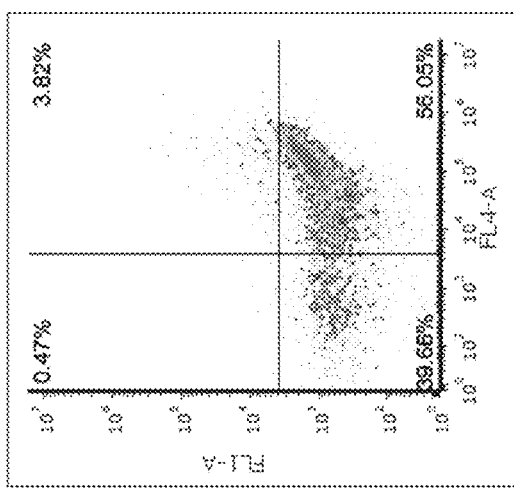
Figure 3C:
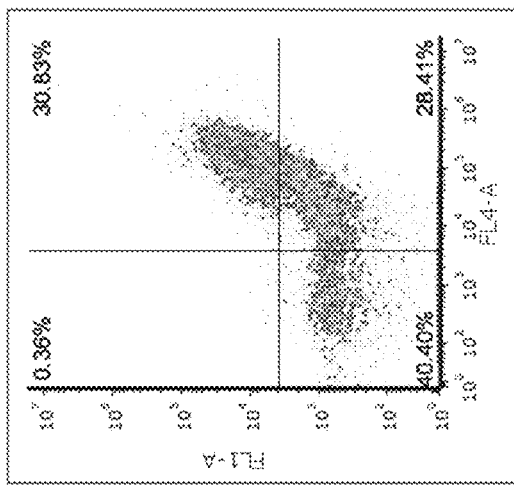

FIGS. 3C-3E show the flow cytometry results for Neu5Ac-PAA-FITC (FIG. 3C), Neu5Gc-PAA-FITC (FIG. 3D), and the control PAA-FITC (FIG. 3E) for clone B5. These results show that the variants tested preferentially bound to sialic acid relative to Neu5Gc-PAA-FITC or PAA-FITC. Similar results have been attained for other glycan-binding proteins from Example 1, such as clones A4, B6, B8, and C11.

Example 5

This example describes testing of glycan-binding proteins described herein against various glycans in flow cytometry binding studies.

Figure 10A:
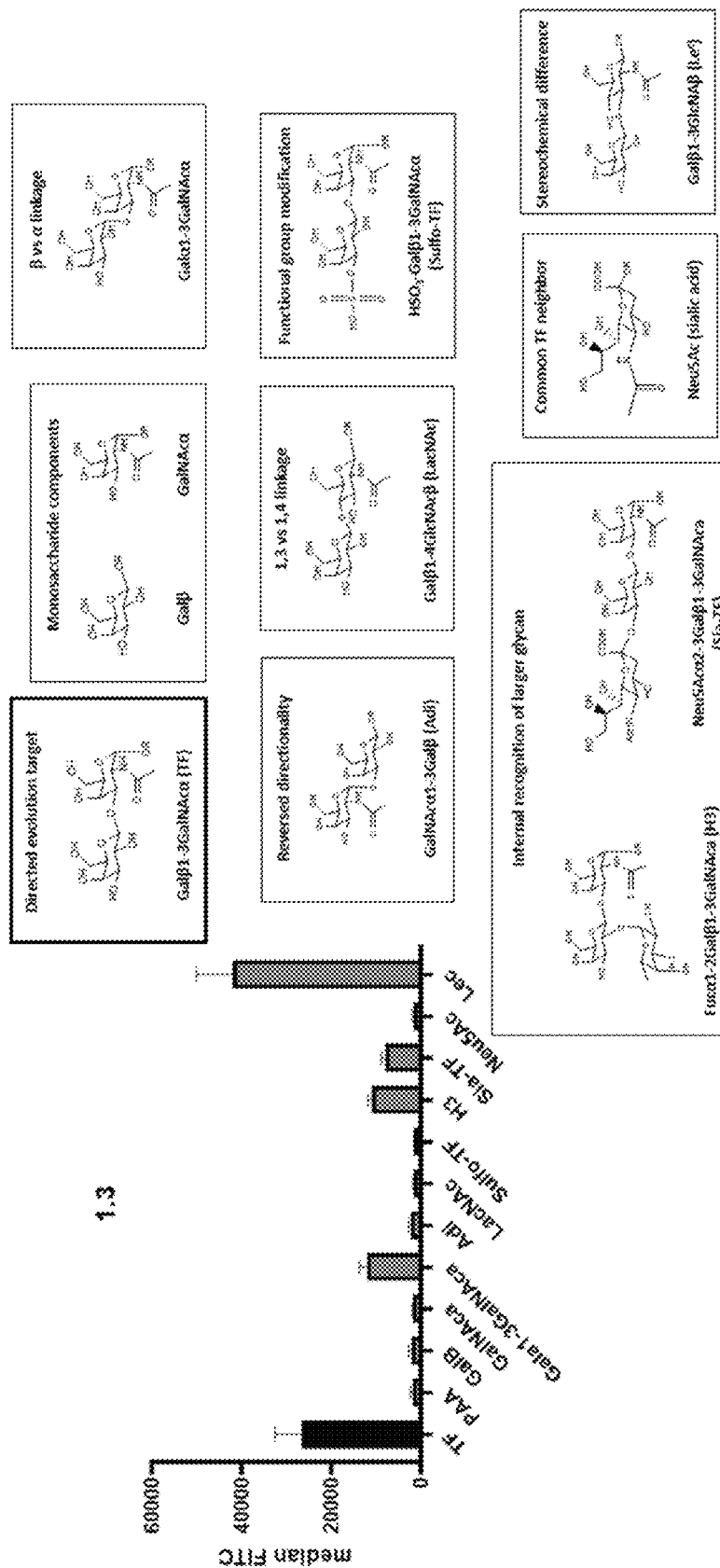
FIG. 10A illustrates median fluorescence intensity of a binding study of an embodiment described herein tested against various glycans.
Figure 10B:
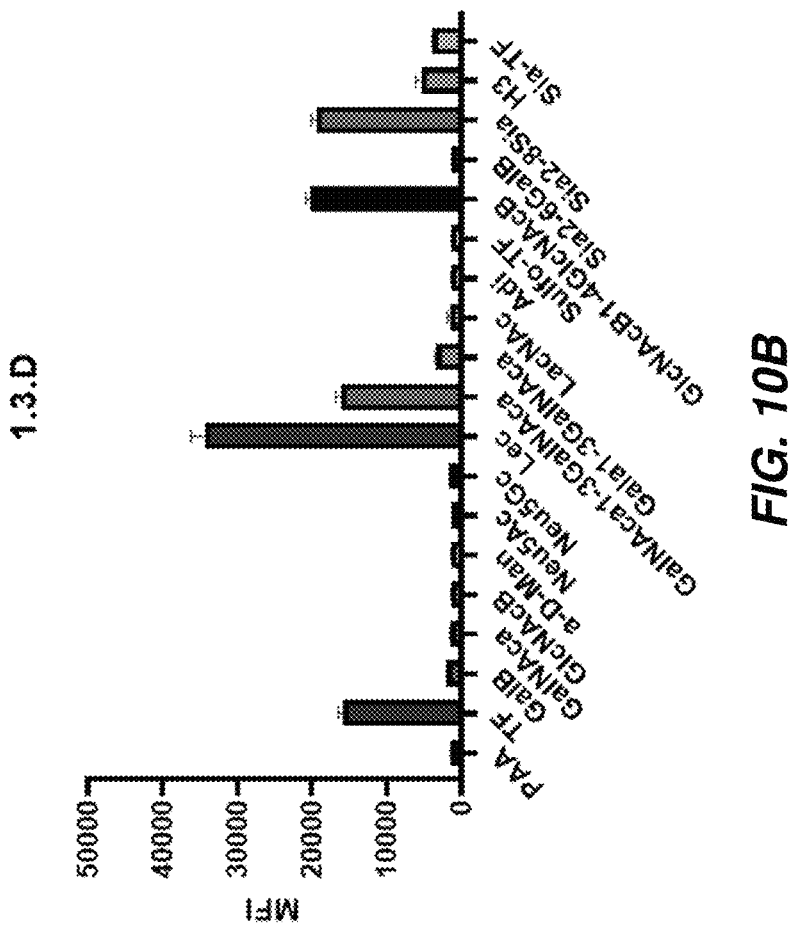
FIG. 10B illustrates binding specificity of an embodiment described herein tested against various glycans.
Figure 10C:
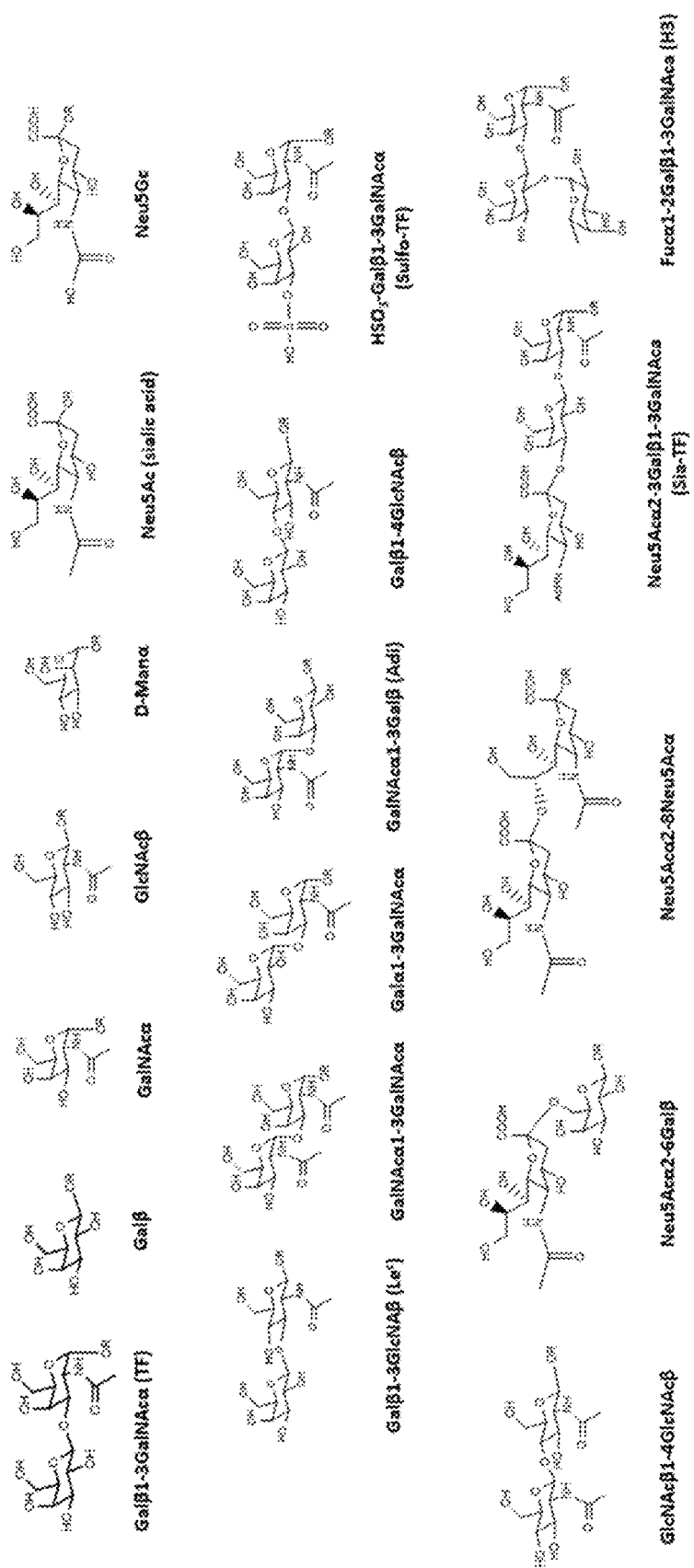
FIG. 10C illustrates structures of all glycans tested for binding.
Figure 10D:
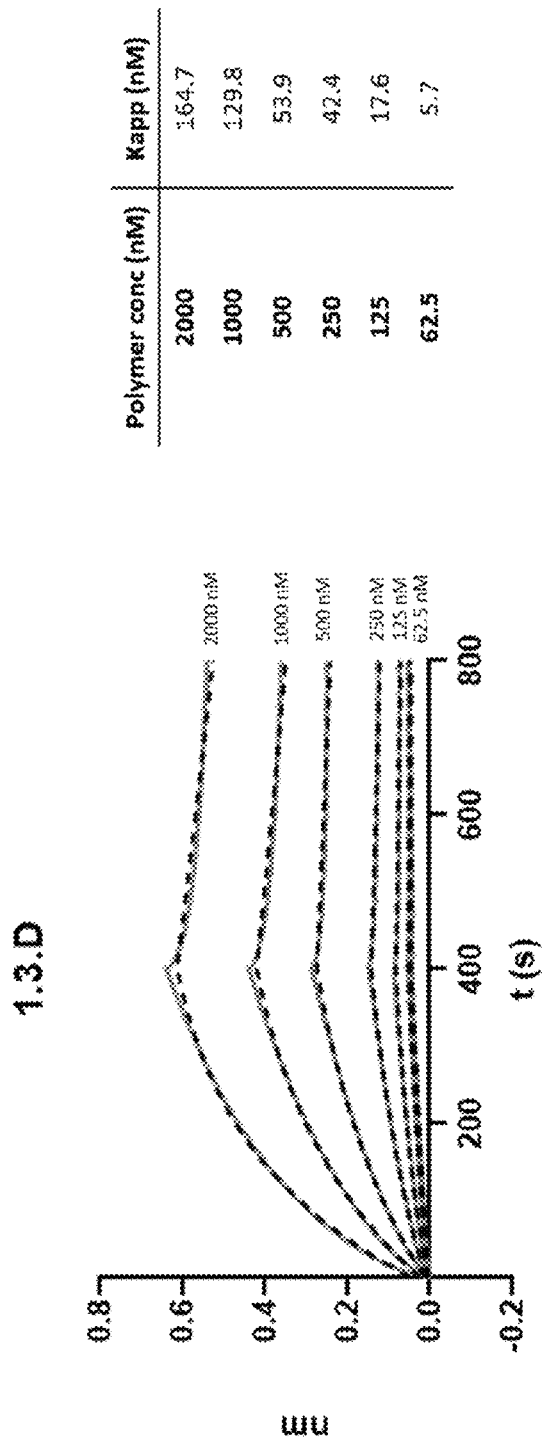
FIG. 10D illustrates biolayer interferometry traces of an embodiment described herein with apparent Kd values calculated.

A mixed library of clones was generated based upon the directed evolution target Galβ1-3GalNAcα (TF). Based upon the directed evolution target Galβ1-3GalNAcα (TF), glycans with structural variations were chosen for a flow cytometry study in which binding behavior was examined (FIG. 10C). Glycans were chosen that possess atom-level differences to each other, including but not limited to: glycans that differ by 1 inverted stereocenter (e.g., GlcNAc vs. GalNAc), glycans with sidechains on neighboring carbon atoms (e.g., OH— on C3 vs. OH— and C4), disaccharides that are comprised of identical monosaccharides whose positions have been flipped (e.g., Gal-GalNAc vs. GalNac-Gal) and others. These glycans with structural variations (FIG. 10 C) were all chosen to highlight the ability of this scaffold at distinguishing small structural differences essential to glycan recognition in nature. These results show that only glycan Galβ1-3GlcNAβ (Lec) demonstrated greater binding than the directed evolution target Galβ1-3GalNAcα for a mixed library of clones (FIG. 10A). In addition to the previously discussed binding study, a flow cytometry study in which the binding specificity was studied was carried out, and results show that glycans Galβ1-3GlcNAβ (Lec), GlcNAcβ1-4GlcNAcβ, and Sia2-8Sia had higher binding specificities than that of TF, while GalNAcα1-3GalNAcα had comparable binding specificity to TF (FIG. 10B). Biolayer interferometry was also used to calculate apparent $K_D$ values at varying polymer concentrations for Clone 1.3.D (FIG. 10D), which has the following sequence:

ATVKFTYRGEEKQVDISKIKYVRRWGQYIWFGYDEGGGARGYGYVSETDA PELLLQMLEKQ. (Clone 1.3.D) (SEQ ID NO: 416)

Figure 11A:
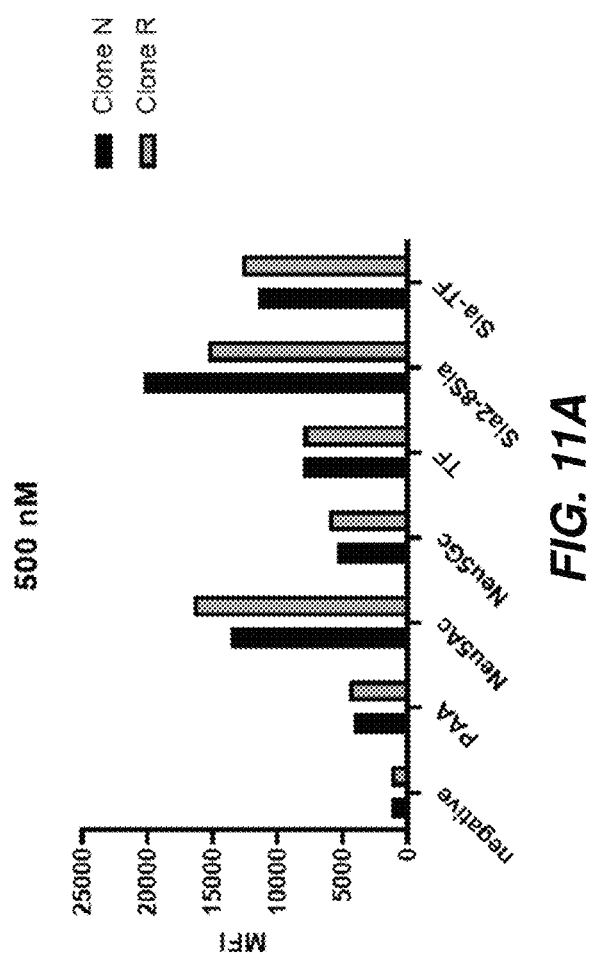
FIG. 11A illustrates the binding specificity of embodiments described herein.

Binding specificity was also tested for various glycans with Clone N and Clone R (FIG. 11A), which have the following sequences:

ATVKFTYRGEGKQVGISRIKSVRRIGQWIKFWYDEGSGAYGRGYVSGKDA PKELLQMLEKR (Clone N) (SEQ ID NO: 417)

ATVKFTYRGEEKQVGISRIKSVRRIGRWIKLWYDEGSGAYGRGYVSGKDA PKELLQMLEKR (Clone R) (SEQ ID NO: 418)

Figure 11B:
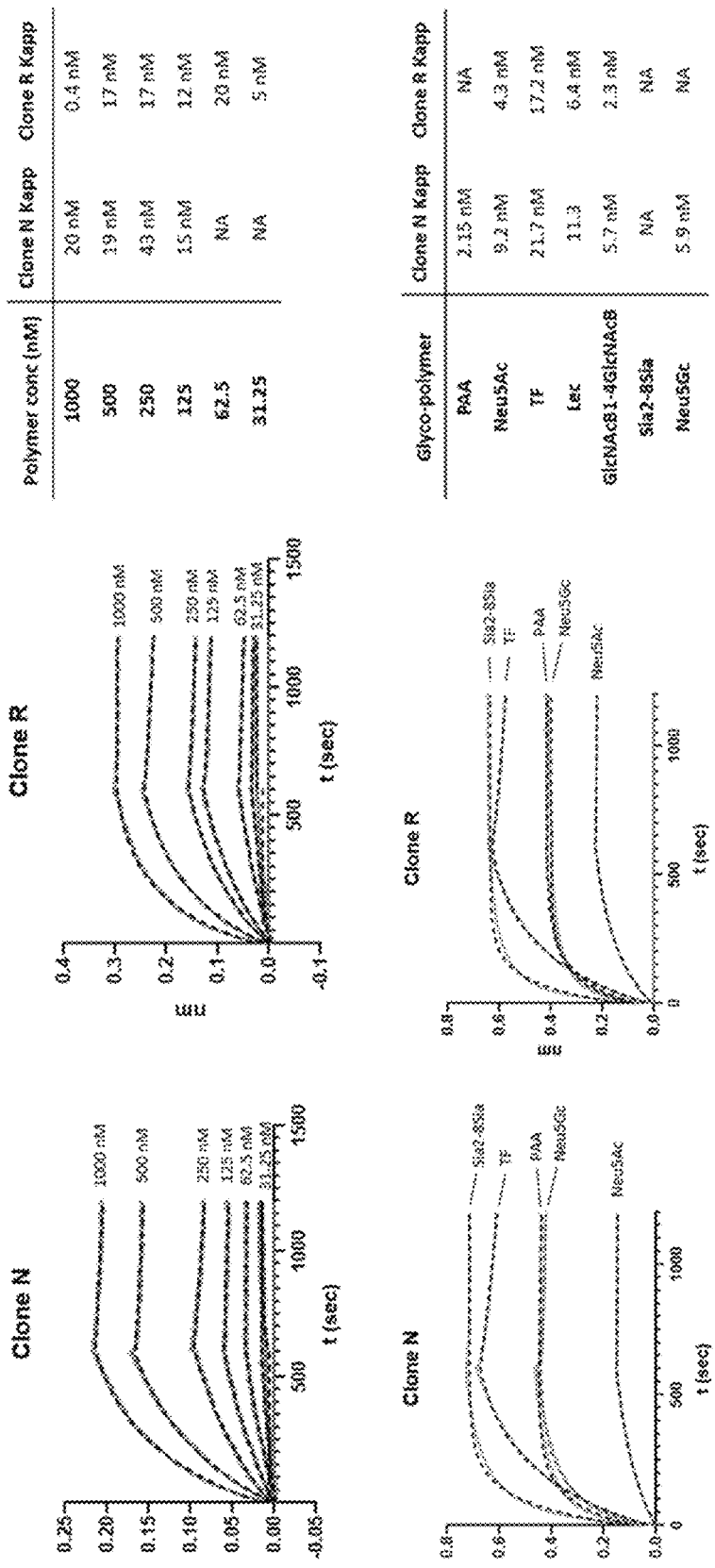
FIG. 11B illustrates biolayer interferometry traces of embodiments described herein with apparent Kd values calculated.

The results indicate that glycan Sia2-8Sia showed the most difference in preferential binding, as evidenced by the median fluorescence intensity values for Clone N and Clone R binding. Biolayer interferometry was used to calculate $K_D$ values for Clone N and Clone R at varying polymer concentrations and using various glycol-polymers (FIG. 11B). These biolayer inferometry results measure average apparent $K_D$ values for Clone N and Clone R to be 24 nM and 12 nM respectively, suggesting these scaffolds bind glycans 10- to 100-fold more tightly than glycan-binding proteins occurring in nature (i.e. lectins and mAbs).

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Some embodiments may be embodied as a method, of which various examples have been described. The acts performed as part of the methods may be ordered in any suitable way. Accordingly, embodiments may be constructed in which acts are performed in an order different than illustrated, which may include different (e.g., more or less) acts than those that are described, and/or that may involve performing some acts simultaneously, even though the acts are shown as being performed sequentially in the embodiments specifically described above. In some cases, the methods may also have intervening steps in addition to those described.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of producing a glycan-binding protein, comprising:

provide a protein scaffold comprising Sso7d, wherein the protein scaffold has no more than 200 amino acid residues, with a binding face area of less than or equal to 6 square nanometers (nm²);

generating one or more variants of the protein scaffold;

determining binding and/or binding selectivity of the one or more variants to a monosaccharide or disaccharide-binding determinant;

selecting, from the one or more variants, a variant exhibiting increased binding and/or binding selectivity to the monosaccharide or disaccharide-binding determinant, relative to the protein scaffold and/or prior steps; and repeating the generating, determining and selecting steps, using the variant exhibiting increased binding and/or binding selectivity to the monosaccharide or disaccharide-binding determinant in each repeat.

2. The method of claim 1, wherein the protein scaffold is free of disulfide bonds.

3. The method of claim 1, wherein the protein scaffold has no more than 100 amino acids.

4. The method of claim 1, wherein the protein scaffold has no more than 75 amino acids.

5. The method of claim 1, wherein the protein scaffold has a maximum dimension of less than or equal to 100 Angstroms.

6. The method of claim 1, wherein the protein scaffold exhibits a $T_m$ of at least 50° C.

7. The method of claim 1, wherein the repeating step is repeated at least 5 times.

8. The method of claim 1, wherein generating one or more variants of the protein scaffold comprises generating one or more variants of the protein scaffold that have, on average, greater than or equal to 1 amino acid mutation.

9. The method of claim 1, further comprising producing a variant exhibiting a $K_D$ of less than $10^{-5}$ M to the monosaccharide or disaccharide-binding determinant.

10. The method of claim 1, further comprising generating a variant having at least 68% or greater identity to the following sequence:

(SEQ ID NO: 3)
ATVKFTYQGEEKQVDISKIK(s1)(s2)DEGGG(s3)SEKDAPKELLQML
EKQ wherein:

(s1) is KX¹VX²RX³G (SEQ ID NO: 412), each of X¹, X², and X³ independently being an amino acid residue, with the proviso that X¹, X², and X³ cannot simultaneously be K, W, and V, respectively;

(s2) is QX⁴IX⁵FX⁶Y (SEQ ID NO: 413), each of X⁴, X⁵, and X⁶ independently being an amino acid residue, with the proviso that X⁴, X⁵, and X⁶ cannot simultaneously be M, S, and T, respectively;

(s3) is AX⁷GX⁸GX⁹V (SEQ ID NO: 414), each of X⁷, X⁸, and X⁹ independently being an amino acid residue, with the proviso that X⁷, X⁸, and X⁹ cannot simultaneously be T, R, and A, respectively;

and wherein the protein specifically binds to the monosaccharide or disaccharide-binding determinant.

11. A method of producing a glycan-binding protein, comprising:

providing a protein scaffold comprising Sso7d;

generating one or more variants of the protein scaffold;

determining binding and/or binding selectivity of the one or more variants to a monosaccharide or disaccharide-binding determinant;

selecting, from the one or more variants, a variant exhibiting increased binding and/or binding selectivity to the monosaccharide or disaccharide-binding determinant, relative to the protein scaffold and/or prior steps; and repeating the generating, determining and selecting steps, using the variant exhibiting increased binding and/or binding selectivity to the monosaccharide or disaccharide-binding determinant in each repeat.

12. The method of claim 11, wherein the protein scaffold is free of disulfide bonds.

13. The method of claim 11, wherein the protein scaffold has no more than 100 amino acids.

14. The method of claim 11, wherein the protein scaffold has no more than 75 amino acids.

15. The method of claim 11, wherein the protein scaffold exhibits a $T_m$ of at least 50° C.

16. The method of claim 11, wherein the protein scaffold exhibits a $T_m$ of at least 70° C.

17. The method of claim 11, wherein the protein scaffold exhibits a $T_m$ of at least 90° C.

18. The method of claim 11, wherein the protein scaffold is stable within a pH of between 1-12.

19. The method of claim 11, wherein the protein scaffold is stable within a pH of between 2-11.

20. The method of claim 1, wherein the protein scaffold has a maximum dimension of less than or equal to 50 Angstroms.

* * * * *

SEQUENCE LISTING

```
<160> NUMBER OF SEQ ID NOS: 418

<210> SEQ ID NO 1
<211> LENGTH: 61
<212> TYPE: PRT
<213> ORGANISM: Artificial Sequence
<220> FEATURE:
<223> OTHER INFORMATION: Synthetic Polypeptide

<400> SEQUENCE: 1

Ala Thr Val Lys Phe Thr Tyr Gln Gly Glu Glu Lys Gln Val Asp Ile
1               5                   10                  15

Ser Lys Ile Lys Lys Val Trp Arg Val Gly Gln Met Ile Ser Phe Thr
            20                  25                  30

Tyr Asp Glu Gly Gly Gly Ala Thr Gly Arg Gly Ala Val Ser Glu Lys
        35                  40                  45

Asp Ala Pro Lys Glu Leu Leu Gln Met Leu Glu Lys Gln
    50                  55                  60

<210> SEQ ID NO 2
<211> LENGTH: 62
<212> TYPE: PRT
<213> ORGANISM: S. solfataricus

<400> SEQUENCE: 2

Ala Thr Val Lys Phe Lys Tyr Lys Gly Glu Glu Lys Gln Val Asp Ile
1               5                   10                  15

Ser Lys Ile Lys Lys Val Trp Arg Val Gly Lys Met Ile Ser Phe Thr
            20                  25                  30

Tyr Asp Glu Gly Gly Gly Lys Thr Gly Arg Gly Ala Val Ser Glu Lys
        35                  40                  45

Asp Ala Pro Lys Glu Leu Leu Gln Met Leu Glu Lys Gln Lys
    50                  55                  60

<210> SEQ ID NO 3
<211> LENGTH: 62
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (21)..(27)
<223> OTHER INFORMATION: Xaa can be any naturally occurring amino acid
<220> FEATURE:
<221> NAME/KEY: misc_feature
<222> LOCATION: (21)..(27)
<223> OTHER INFORMATION: Xaas cannot sequentially be KKVWRVG
<220> FEATURE:
<221> NAME/KEY: misc_feature
<222> LOCATION: (28)..(34)
<223> OTHER INFORMATION: Xaa can be any naturally occurring amino acid
<220> FEATURE:
<221> NAME/KEY: misc_feature
<222> LOCATION: (28)..(34)
<223> OTHER INFORMATION: Xaas cannot sequentially be QMISFTY
<220> FEATURE:
<221> NAME/KEY: misc_feature
<222> LOCATION: (40)..(46)
```

```
<223> OTHER INFORMATION: Xaa can be any naturally occurring amino acid
<220> FEATURE:
<221> NAME/KEY: misc_feature
<222> LOCATION: (40)..(46)
<223> OTHER INFORMATION: Xaas cannot sequentially be ATGRGAV

<400> SEQUENCE: 3

Ala Thr Val Lys Phe Thr Tyr Gln Gly Glu Glu Lys Gln Val Asp Ile
1               5                   10                  15

Ser Lys Ile Lys Xaa Xaa Xaa Xaa Xaa Xaa Xaa Xaa Xaa Xaa
            20                  25                  30

Xaa Xaa Asp Glu Gly Gly Gly Xaa Xaa Xaa Xaa Xaa Xaa Ser Glu
        35                  40                  45

Lys Asp Ala Pro Lys Glu Leu Leu Gln Met Leu Glu Lys Gln
    50                  55                  60

<210> SEQ ID NO 4
<211> LENGTH: 62
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (22)..(45)
<223> OTHER INFORMATION: Xaas cannot simultaneously be K, W, V, M, S, T,
      T, R, and A, sequentially
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid

<400> SEQUENCE: 4

Ala Thr Val Lys Phe Thr Tyr Gln Gly Glu Glu Lys Gln Val Asp Ile
1               5                   10                  15

Ser Lys Ile Lys Lys Xaa Val Xaa Arg Xaa Gly Gln Xaa Ile Xaa Phe
            20                  25                  30

Xaa Tyr Asp Glu Gly Gly Gly Ala Xaa Gly Xaa Gly Xaa Val Ser Glu
        35                  40                  45
```

Lys Asp Ala Pro Lys Glu Leu Leu Gln Met Leu Glu Lys Gln
        50                  55                  60

<210> SEQ ID NO 5
<211> LENGTH: 61
<212> TYPE: PRT
<213> ORGANISM: Artificial Sequence
<220> FEATURE:
<223> OTHER INFORMATION: Synthetic Polypeptide

<400> SEQUENCE: 5

Ala Thr Val Lys Phe Thr Tyr Gln Gly Glu Glu Lys Gln Val Asp Ile
1               5                   10                  15

Ser Lys Ile Lys Trp Val Ile Arg Trp Gly Gln His Ile Ala Phe Lys
            20                  25                  30

Tyr Asp Glu Gly Gly Gly Ala Ala Gly Tyr Gly Trp Val Ser Glu Lys
        35                  40                  45

Asp Ala Pro Lys Glu Leu Leu Gln Met Leu Glu Lys Gln
    50                  55                  60

<210> SEQ ID NO 6
<211> LENGTH: 61
<212> TYPE: PRT
<213> ORGANISM: Artificial Sequence
<220> FEATURE:
<223> OTHER INFORMATION: Synthetic Polypeptide

<400> SEQUENCE: 6

Ala Thr Val Lys Phe Thr Tyr Gln Gly Glu Glu Lys Gln Val Asp Ile
1               5                   10                  15

Ser Lys Ile Lys Trp Val Asn Arg Trp Gly Gln Arg Ile Tyr Phe Lys
            20                  25                  30

Tyr Asp Glu Gly Gly Gly Ala Ala Gly Tyr Gly Trp Val Ser Glu Lys
        35                  40                  45

Asp Ala Pro Lys Glu Leu Leu Gln Met Leu Glu Lys Gln
    50                  55                  60

<210> SEQ ID NO 7
<211> LENGTH: 61
<212> TYPE: PRT
<213> ORGANISM: Artificial Sequence
<220> FEATURE:
<223> OTHER INFORMATION: Synthetic Polypeptide

<400> SEQUENCE: 7

Ala Thr Val Lys Tyr Thr Tyr Arg Gly Glu Glu Lys Arg Val Asp Ile
1               5                   10                  15

Ser Lys Ile Lys Trp Val Asn Arg Trp Gly Gln His Leu Ala Phe Lys
            20                  25                  30

Tyr Asp Lys Gly Gly Gly Ala Ala Gly Tyr Gly Trp Val Ser Glu Lys
        35                  40                  45

Asp Ala Pro Lys Glu Leu Leu Gln Met Leu Glu Lys Arg
    50                  55                  60

<210> SEQ ID NO 8
<211> LENGTH: 61
<212> TYPE: PRT
<213> ORGANISM: Artificial Sequence
<220> FEATURE:
<223> OTHER INFORMATION: Synthetic Polypeptide

<400> SEQUENCE: 8

```
Ala Thr Val Lys Ser Thr Tyr Arg Gly Glu Glu Lys Gln Val Asp Ile
1               5                   10                  15

Ser Lys Ile Lys Trp Val Ile Arg Trp Gly Gln His Leu Ala Phe Lys
            20                  25                  30

Tyr Asp Glu Gly Gly Gly Ala Ala Gly Tyr Gly Trp Val Ser Glu Lys
        35                  40                  45

Asp Ala Pro Lys Glu Leu Leu Gln Met Leu Glu Lys Gln
        50                  55                  60

<210> SEQ ID NO 9
<211> LENGTH: 61
<212> TYPE: PRT
<213> ORGANISM: Artificial Sequence
<220> FEATURE:
<223> OTHER INFORMATION: Synthetic Polypeptide

<400> SEQUENCE: 9

Ala Thr Val Lys Phe Thr Tyr Arg Gly Glu Glu Lys Gln Val Asp Ile
1               5                   10                  15

Ser Lys Ile Lys Trp Val Asn Arg Trp Gly Gln His Leu Ala Phe Lys
            20                  25                  30

Tyr Asp Val Gly Gly Gly Ala Ala Gly Tyr Gly Trp Met Ser Glu Lys
        35                  40                  45

Asp Ala Pro Lys Glu Leu Leu Gln Met Leu Glu Lys Arg
        50                  55                  60

<210> SEQ ID NO 10
<211> LENGTH: 61
<212> TYPE: PRT
<213> ORGANISM: Artificial Sequence
<220> FEATURE:
<223> OTHER INFORMATION: Synthetic Polypeptide

<400> SEQUENCE: 10

Ala Thr Val Lys Phe Thr Tyr Gln Gly Glu Glu Lys Gln Val Asp Ile
1               5                   10                  15

Ser Lys Ile Lys Trp Val Ile Arg Leu Gly Arg Thr Ile Met Phe Lys
            20                  25                  30

Tyr Asp Glu Gly Gly Gly Ala Asn Gly Tyr Gly Lys Val Ser Glu Lys
        35                  40                  45

Asp Ala Pro Lys Glu Leu Leu Gln Met Leu Glu Lys Gln
        50                  55                  60

<210> SEQ ID NO 11
<211> LENGTH: 61
<212> TYPE: PRT
<213> ORGANISM: Artificial Sequence
<220> FEATURE:
<223> OTHER INFORMATION: Synthetic Polypeptide

<400> SEQUENCE: 11

Ala Thr Val Lys Phe Thr Tyr Gln Gly Glu Glu Lys Gln Val Asp Ile
1               5                   10                  15

Ser Lys Ile Lys Trp Val Val Arg Leu Gly Gln Val Ile Met Phe Lys
            20                  25                  30

Tyr Asp Glu Gly Gly Gly Ala Asn Gly Tyr Gly Lys Val Ser Glu Lys
        35                  40                  45

Asp Ala Pro Lys Glu Leu Leu Gln Met Leu Glu Lys Gln
        50                  55                  60
```

<210> SEQ ID NO 12
<211> LENGTH: 61
<212> TYPE: PRT
<213> ORGANISM: Artificial Sequence
<220> FEATURE:
<223> OTHER INFORMATION: Synthetic Polypeptide

<400> SEQUENCE: 12

```
Ala Thr Val Lys Phe Thr Tyr Arg Gly Glu Glu Lys Gln Val Asp Ile
1               5                   10                  15

Ser Lys Ile Lys Trp Val Val Arg Leu Gly Gln Val Ile Met Phe Lys
            20                  25                  30

Tyr Gly Glu Gly Gly Gly Ser Asn Gly Tyr Gly Arg Val Ser Glu Lys
        35                  40                  45

Asp Ala Pro Lys Glu Leu Arg Gln Met Leu Glu Lys Arg
    50                  55                  60
```

<210> SEQ ID NO 13
<211> LENGTH: 60
<212> TYPE: PRT
<213> ORGANISM: Artificial Sequence
<220> FEATURE:
<223> OTHER INFORMATION: Synthetic Polypeptide

<400> SEQUENCE: 13

```
Ala Thr Val Lys Phe Thr Tyr Arg Gly Glu Glu Lys Gln Val Asp Ile
1               5                   10                  15

Ser Lys Ile Lys Trp Val Val Arg Leu Gly Gln Val Ile Met Phe Lys
            20                  25                  30

Tyr Asp Glu Gly Gly Gly Ala Ser Gly Tyr Gly Arg Val Ser Glu Lys
        35                  40                  45

Asp Ala Pro Lys Glu Leu Leu Gln Met Leu Glu Lys
    50                  55                  60
```

<210> SEQ ID NO 14
<211> LENGTH: 73
<212> TYPE: PRT
<213> ORGANISM: Artificial Sequence
<220> FEATURE:
<223> OTHER INFORMATION: Synthetic Polypeptide

<400> SEQUENCE: 14

```
Ala Thr Val Lys Phe Thr Tyr Arg Gly Glu Glu Lys Gln Val Gly Val
1               5                   10                  15

Ser Arg Val Lys Ser Val His Arg Ile Gly Gln Trp Ile Lys Phe Trp
            20                  25                  30

Tyr Asp Glu Gly Ser Gly Ala Tyr Gly Arg Gly Tyr Val Ser Glu Lys
        35                  40                  45

Asp Ala Pro Glu Glu Leu Leu Gln Met Leu Glu Lys Arg Gly Ser Glu
    50                  55                  60

Gln Lys Leu Ile Ser Glu Glu Asp Leu
65                  70
```

<210> SEQ ID NO 15
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 15

```
Ala Thr Val Lys Phe Thr Tyr
1               5

<210> SEQ ID NO 16
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 16

Gly Val Ser Arg Val Lys Ser Val His Arg Ile Gly Gln Trp Ile Lys
1               5                   10                  15

Phe Trp

<210> SEQ ID NO 17
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 17

Leu Pro Xaa Thr Gly
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 18

Leu Arg Xaa Thr Gly
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 19

Gly Gly Gly Gly Ser
1               5

<210> SEQ ID NO 20
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 20

Gly Gly Gly Gly Ser Gly Gly Gly Gly Ser
1               5                   10
```

```
<210> SEQ ID NO 21
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 21

Gly Gly Gly Gly Ser Gly Gly Gly Ser Gly Gly Gly Gly Ser
1               5                   10                  15

<210> SEQ ID NO 22
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 22

Gly Gly Gly Gly Ser Gly Gly Gly Gly Ser Gly Gly Gly Gly Ser Gly
1               5                   10                  15

Gly Gly Gly Ser
            20

<210> SEQ ID NO 23
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 23

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 24
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 24

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 25
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 25

Ala Thr Val Lys Phe Thr Tyr Gln Gly Glu Glu Lys Gln Val Asp Ile
1               5                   10                  15

Ser Lys Ile Lys His Val Arg Arg Trp Gly Arg Trp Ile Trp Phe Ile
            20                  25                  30

Tyr Glu Glu Gly Gly Gly Ala Lys Gly Arg Gly Val Ser Glu Lys
        35                  40                  45
```

Asp Ala Pro Lys Glu Leu Leu Gln Met Leu Glu Lys Gln Gly Ser Glu
         50                  55                  60

Gln Lys Leu Ile Ser Glu Glu Asp
 65                  70

<210> SEQ ID NO 26
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 26

Ala Thr Gly Lys Phe Thr Tyr Gln Gly Glu Lys Gln Gly Asp Ile
 1               5                  10                  15

Ser Lys Ile Lys His Gly Arg Arg Trp Gly Arg Gly Ile Trp Phe Ile
                 20                  25                  30

Tyr Glu Glu Gly Gly Gly Ala Lys Gly Arg Gly Gly Val Ser Glu Lys
             35                  40                  45

Asp Ala Pro Lys Glu Leu Leu Gln Met Leu Glu Lys Gln Gly Ser Glu
         50                  55                  60

Gln Lys Leu Ile Ser Glu Glu Asp
 65                  70

<210> SEQ ID NO 27
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 27

Ile Thr Val Lys Phe Thr Tyr Gln Gly Glu Lys Gln Val Asp Ile
 1               5                  10                  15

Ser Lys Ile Glu His Val Arg Arg Trp Gly Gln Trp Ile Trp Phe Thr
                 20                  25                  30

Tyr Asp Glu Gly Gly Gly Ala Lys Gly Arg Gly Gly Val Ser Glu Lys
             35                  40                  45

Gly Ala Pro Lys Glu Leu Leu Gln Met Leu Gly Lys Arg Gly Ser Glu
         50                  55                  60

Gln Lys Leu Ile Ser Glu Glu Asp
 65                  70

<210> SEQ ID NO 28
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 28

Ala Thr Val Lys Phe Thr Tyr Gln Gly Glu Lys Gln Val Asp Ile
 1               5                  10                  15

Ser Lys Ile Lys His Val Arg Arg Trp Gly Gln Trp Ile Trp Phe Ile
                 20                  25                  30

Tyr Asp Lys Gly Gly Gly Ala Lys Gly Arg Gly Gly Val Ser Glu Lys
             35                  40                  45

Asp Ala Pro Lys Glu Leu Leu Gln Met Leu Glu Lys Gln Gly Ser Glu
         50                  55                  60

Gln Lys Leu Ile Ser Glu Glu Asp

```
                                   65                  70
```

<210> SEQ ID NO 29
<211> LENGTH: 69
<212> TYPE: PRT
<213> ORGANISM: Artificial Sequence
<220> FEATURE:
<223> OTHER INFORMATION: Synthetic Polypeptide

<400> SEQUENCE: 29

```
Ala Thr Val Lys Phe Thr Tyr Gln Gly Glu Lys Gln Val Asp Ile
1               5                   10                  15

Ser Lys Ile Lys His Val Arg Arg Trp Gly Gln Trp Ile Trp Phe Ile
            20                  25                  30

Tyr Asp Glu Gly Gly Gly Ala Lys Gly Lys Gly Ser Val Ser Glu Lys
                35                  40                  45

Asp Ala Pro Lys Glu Leu Leu Gln Met Leu Glu Lys Ala Gly Ile Arg
        50                  55                  60

Thr Lys Ala Tyr Phe
65
```

<210> SEQ ID NO 30
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 30

```
Ala Thr Val Glu Phe Thr Tyr Gln Gly Glu Lys Gln Val Asp Ile
1               5                   10                  15

Ser Lys Ile Lys His Val Arg Arg Trp Gly Gln Trp Ile Trp Phe Ile
            20                  25                  30

Tyr Asp Glu Gly Gly Gly Ala Lys Gly Arg Gly Gly Val Ser Glu Arg
                35                  40                  45

Asp Ala Pro Lys Glu Leu Leu Gln Leu Leu Glu Lys Arg Gly Ser Glu
        50                  55                  60

Gln Lys Leu Ile Ser Glu Glu Asp
65                  70
```

<210> SEQ ID NO 31
<211> LENGTH: 69
<212> TYPE: PRT
<213> ORGANISM: Artificial Sequence
<220> FEATURE:
<223> OTHER INFORMATION: Synthetic Polypeptide

<400> SEQUENCE: 31

```
Ala Thr Val Lys Phe Thr Tyr Gln Gly Glu Lys Gln Val Asp Ile
1               5                   10                  15

Ser Lys Ile Lys Tyr Val Arg Arg Trp Gly Gln Ala Ile Ile Phe Arg
            20                  25                  30

Tyr Asp Glu Gly Gly Gly Ala Glu Gly Lys Gly Ser Val Ser Glu Lys
                35                  40                  45

Gly Ala Pro Lys Glu Leu Leu Gln Met Leu Glu Lys Ala Arg Ile Arg
        50                  55                  60

Thr Lys Ala Tyr Phe
65
```

<210> SEQ ID NO 32

<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 32

Ala Thr Val Lys Phe Thr Tyr Arg Gly Glu Glu Lys Gln Val Gly Ile
1               5                   10                  15

Ser Arg Ile Lys Ser Val His Arg Ile Gly Gln Trp Ile Lys Phe Trp
            20                  25                  30

Tyr Asp Glu Gly Ser Gly Ala Tyr Gly Arg Gly Tyr Val Ser Glu Lys
        35                  40                  45

Asp Ala Pro Lys Glu Leu Leu Gln Met Leu Glu Lys Arg Gly Ser Glu
    50                  55                  60

Gln Lys Leu Ile Ser Glu Glu Asp
65                  70

<210> SEQ ID NO 33
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 33

Ala Ile Val Lys Phe Thr Tyr Gln Gly Glu Glu Lys Gln Val Asp Ile
1               5                   10                  15

Ser Lys Ile Lys Tyr Val Arg Arg Trp Gly Gln Tyr Ile Trp Phe Gly
            20                  25                  30

Tyr Asp Glu Gly Gly Gly Ala His Gly Arg Gly Arg Val Ser Gly Lys
        35                  40                  45

Asp Ala Pro Lys Glu Leu Leu Gln Met Leu Glu Lys Gln Gly Ser Glu
    50                  55                  60

Gln Lys Leu Ile Ser Glu Glu Asp
65                  70

<210> SEQ ID NO 34
<211> LENGTH: 69
<212> TYPE: PRT
<213> ORGANISM: Artificial Sequence
<220> FEATURE:
<223> OTHER INFORMATION: Synthetic Polypeptide

<400> SEQUENCE: 34

Ala Thr Val Lys Phe Thr Tyr Arg Gly Glu Glu Lys Gln Val Asp Ile
1               5                   10                  15

Ser Lys Ile Lys Ser Val Ser Arg Trp Gly Gln Ala Ile Ile Phe Arg
            20                  25                  30

Tyr Asp Gly Gly Gly Gly Ala Arg Gly Lys Gly Ser Val Ser Glu Lys
        35                  40                  45

Asp Ala Pro Lys Glu Leu Leu Gln Met Leu Glu Glu Ala Arg Ile Arg
    50                  55                  60

Thr Lys Ala Tyr Phe
65

<210> SEQ ID NO 35
<211> LENGTH: 68
<212> TYPE: PRT
<213> ORGANISM: Artificial Sequence
<220> FEATURE:

<223> OTHER INFORMATION: Synthetic Polypeptide

<400> SEQUENCE: 35

Ala Thr Val Lys Phe Thr Tyr Arg Gly Glu Glu Lys Gln Val Gly Ile
1               5                   10                  15

Ser Arg Ile Lys Ser Val His Arg Ile Gly Gln Trp Ile Lys Phe Trp
            20                  25                  30

Tyr Asp Glu Gly Ser Gly Ala Tyr Gly Arg Gly Tyr Val Ser Glu Lys
        35                  40                  45

Asp Ala Pro Lys Glu Leu Leu Gln Met Leu Glu Lys Arg Gly Ser Glu
    50                  55                  60

Gln Lys Leu Phe
65

<210> SEQ ID NO 36
<211> LENGTH: 60
<212> TYPE: PRT
<213> ORGANISM: Artificial Sequence
<220> FEATURE:
<223> OTHER INFORMATION: Synthetic Polypeptide

<400> SEQUENCE: 36

Ala Thr Val Lys Phe Thr Tyr Arg Gly Lys Glu Lys Gln Val Gly Ile
1               5                   10                  15

Ser Arg Ile Lys Ser Val His Arg Ile Gly Gln Trp Ile Arg Phe Trp
            20                  25                  30

Tyr Asp Glu Gly Ser Gly Ala Tyr Gly Arg Gly Tyr Val Ser Glu Lys
        35                  40                  45

Asp Ala Pro Lys Glu Leu Leu Gln Met Leu Glu Lys
    50                  55                  60

<210> SEQ ID NO 37
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 37

Ala Thr Val Lys Phe Thr Tyr Arg Gly Glu Glu Lys Gln Val Gly Ile
1               5                   10                  15

Ser Arg Ile Lys Ser Val His Arg Ile Gly Gln Trp Ile Lys Phe Trp
            20                  25                  30

Tyr Asp Glu Gly Ser Gly Ala Tyr Gly Arg Gly Tyr Val Ser Gly Lys
        35                  40                  45

Asp Ala Pro Lys Glu Leu Leu Gln Met Leu Glu Lys Arg Gly Ser Glu
    50                  55                  60

Gln Lys Leu Ile Ser Glu Glu Asp
65                  70

<210> SEQ ID NO 38
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 38

Ala Thr Val Lys Phe Thr Tyr Arg Gly Lys Glu Lys Gln Val Gly Ile
1               5                   10                  15

```
Ser Arg Ile Lys Ser Val His Arg Ile Gly Gln Trp Ile Lys Phe Trp
            20                  25                  30

Tyr Asp Glu Gly Ser Gly Ala Tyr Gly Arg Gly Tyr Val Ser Gly Lys
            35                  40                  45

Asp Ala Pro Lys Glu Leu Leu Gln Met Leu Glu Lys Arg Gly Ser Glu
        50                  55                  60

Gln Lys Leu Ile Ser Glu Glu Asp
65                  70

<210> SEQ ID NO 39
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 39

Ala Thr Val Lys Phe Thr Tyr Arg Gly Glu Glu Lys Gln Val Gly Ile
1               5                   10                  15

Asn Arg Ile Lys Ser Val His Arg Ile Gly Gln Trp Ile Lys Phe Trp
            20                  25                  30

Tyr Asp Glu Gly Ser Gly Ala Tyr Gly Arg Gly Tyr Val Ser Gly Lys
            35                  40                  45

Asp Ala Pro Lys Glu Leu Leu Arg Met Leu Glu Lys Arg Gly Ser Glu
        50                  55                  60

Gln Lys Leu Ile Ser Glu Glu Asp
65                  70

<210> SEQ ID NO 40
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 40

Ala Thr Val Lys Phe Thr Tyr Arg Gly Glu Glu Lys Gln Val Gly Ile
1               5                   10                  15

Ser Arg Ile Lys Ser Val His Arg Ile Gly Arg Trp Ile Lys Phe Trp
            20                  25                  30

Tyr Asp Glu Gly Ser Gly Ala Tyr Gly Arg Gly Tyr Val Ser Gly Lys
            35                  40                  45

Asp Ala Pro Lys Glu Leu Leu Gln Met Leu Glu Lys Arg Gly Ser Glu
        50                  55                  60

Gln Lys Leu Ile Ser Glu Glu Asp
65                  70

<210> SEQ ID NO 41
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 41

Ala Thr Val Lys Phe Thr Tyr Arg Gly Glu Glu Lys Gln Val Gly Ile
1               5                   10                  15

Ser Arg Ile Lys Ser Val Arg Arg Ile Gly Gln Trp Ile Lys Phe Trp
            20                  25                  30

Tyr Asp Glu Gly Ser Gly Ala Tyr Gly Arg Gly Tyr Val Ser Gly Lys
```

```
              35                  40                  45
Asp Ala Pro Lys Glu Leu Leu Gln Met Leu Glu Lys Arg Gly Ser Glu
    50                  55                  60

Gln Lys Leu Ile Ser Glu Glu Asp
65                  70

<210> SEQ ID NO 42
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 42

Ala Thr Val Lys Phe Thr Tyr Arg Gly Glu Glu Lys Arg Val Gly Ile
1               5                   10                  15

Ser Arg Ile Lys Ser Val Arg Arg Ile Gly Gln Trp Ile Lys Phe Trp
                20                  25                  30

Tyr Asp Glu Gly Ser Gly Ala Tyr Gly Arg Gly Tyr Val Ser Glu Lys
            35                  40                  45

Asp Ala Pro Lys Glu Leu Leu Gln Met Leu Gly Lys Arg Gly Ser Glu
    50                  55                  60

Gln Lys Leu Ile Ser Glu Glu Asp
65                  70

<210> SEQ ID NO 43
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 43

Ala Thr Val Lys Phe Thr Tyr Arg Gly Glu Glu Lys Gln Val Gly Ile
1               5                   10                  15

Ser Arg Ile Lys Ser Val Arg Arg Ile Gly Gln Trp Ile Lys Phe Trp
                20                  25                  30

Tyr Asp Glu Gly Ser Gly Ala Tyr Gly Arg Gly Tyr Val Ser Glu Lys
            35                  40                  45

Asp Ala Pro Lys Glu Leu Leu Gln Met Leu Gly Lys Arg Gly Ser Glu
    50                  55                  60

Gln Lys Leu Ile Ser Glu Glu Asp
65                  70

<210> SEQ ID NO 44
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 44

Ala Thr Val Arg Phe Thr Tyr Arg Gly Glu Glu Lys Gln Val Gly Ile
1               5                   10                  15

Ser Arg Ile Lys Ser Val Arg Arg Ile Gly Gln Trp Ile Lys Phe Trp
                20                  25                  30

Tyr Asp Glu Gly Ser Gly Ala Tyr Gly Arg Gly Tyr Val Ser Glu Lys
            35                  40                  45

Asp Ala Pro Lys Glu Leu Leu Gln Met Leu Gly Lys Arg Gly Ser Glu
    50                  55                  60
```

```
Gln Lys Leu Ile Ser Glu Glu Asp
 65                 70

<210> SEQ ID NO 45
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 45

Ala Thr Val Lys Phe Thr Tyr Arg Gly Glu Glu Lys Gln Val Gly Ile
  1               5                  10                  15

Ser Arg Ile Lys Ser Val His Arg Ile Gly Gln Trp Ile Lys Phe Trp
                 20                  25                  30

Tyr Asp Glu Gly Ser Gly Ala Tyr Gly Arg Gly Tyr Val Ser Glu Lys
             35                  40                  45

Gly Ala Pro Lys Glu Leu Leu Gln Met Leu Gly Lys Arg Gly Ser Glu
         50                  55                  60

Gln Lys Leu Ile Ser Glu Glu Asp
 65                 70

<210> SEQ ID NO 46
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 46

Ala Thr Val Lys Phe Thr Tyr Arg Gly Glu Glu Lys Gln Val Gly Ile
  1               5                  10                  15

Ser Arg Ile Arg Ser Val His Arg Ile Gly Gln Trp Ile Lys Phe Trp
                 20                  25                  30

Tyr Asp Glu Gly Ser Gly Ala Cys Gly Arg Gly Tyr Val Ser Glu Lys
             35                  40                  45

Gly Ala Pro Lys Glu Leu Leu Gln Met Leu Gly Lys Arg Gly Ser Glu
         50                  55                  60

Gln Lys Leu Ile Ser Glu Glu Asp
 65                 70

<210> SEQ ID NO 47
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 47

Ala Thr Val Lys Phe Thr Tyr Arg Gly Glu Glu Lys Gln Val Gly Ile
  1               5                  10                  15

Ser Arg Ile Lys Ser Val His Arg Ile Gly Gln Trp Ile Lys Phe Trp
                 20                  25                  30

Tyr Asp Glu Gly Ser Gly Ala Tyr Gly Arg Gly Tyr Val Ser Glu Lys
             35                  40                  45

Asp Ala Pro Lys Glu Leu Leu Gln Met Leu Gly Lys Arg Gly Ser Glu
         50                  55                  60

Gln Lys Leu Ile Ser Glu Glu Asp
 65                 70
```

<210> SEQ ID NO 48
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 48

Ala Thr Val Arg Phe Thr Tyr Arg Gly Glu Glu Lys Gln Val Gly Ile
1               5                   10                  15

Ser Arg Ile Lys Ser Val His Arg Ile Gly Gln Trp Ile Lys Phe Trp
            20                  25                  30

Tyr Asp Glu Gly Ser Gly Thr Tyr Gly Arg Gly Tyr Val Ser Glu Lys
        35                  40                  45

Asp Ala Pro Arg Glu Leu Leu Gln Met Leu Gly Lys Arg Gly Ser Glu
    50                  55                  60

Gln Lys Leu Ile Ser Glu Glu Asp
65                  70

<210> SEQ ID NO 49
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 49

Ala Thr Val Lys Phe Thr Tyr Arg Gly Glu Glu Lys Gln Val Gly Ile
1               5                   10                  15

Ser Arg Ile Lys Ser Val Arg Arg Ile Gly Gln Trp Ile Lys Phe Trp
            20                  25                  30

Tyr Asp Glu Gly Ser Gly Ala Tyr Gly Arg Gly Tyr Val Ser Glu Lys
        35                  40                  45

Asp Ala Pro Lys Glu Leu Leu Gln Met Leu Gly Lys Arg Gly Ser Glu
    50                  55                  60

Gln Lys Leu Ile Ser Glu Glu Asp
65                  70

<210> SEQ ID NO 50
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 50

Ala Thr Val Lys Phe Thr Tyr Arg Gly Gly Glu Lys Gln Val Gly Ile
1               5                   10                  15

Ser Arg Ile Lys Ser Val Arg Arg Ile Gly Gln Trp Ile Lys Phe Trp
            20                  25                  30

Tyr Asp Glu Gly Ser Gly Ala Tyr Gly Arg Gly Tyr Val Ser Glu Lys
        35                  40                  45

Asp Ala Pro Lys Glu Leu Leu Gln Met Leu Gly Lys Arg Gly Ser Glu
    50                  55                  60

Gln Lys Leu Ile Ser Glu Glu Asp
65                  70

<210> SEQ ID NO 51
<211> LENGTH: 72
<212> TYPE: PRT

<213> ORGANISM: Artificial Sequence
<220> FEATURE:
<223> OTHER INFORMATION: Synthetic Polypeptide

<400> SEQUENCE: 51

```
Ala Thr Val Lys Phe Thr Tyr Arg Gly Lys Glu Lys Arg Val Gly Val
1               5                   10                  15

Ser Arg Ile Lys Ser Val Arg Arg Ile Gly Gln Trp Ile Lys Phe Trp
            20                  25                  30

Tyr Asp Glu Gly Ser Gly Ala Tyr Gly Arg Gly Tyr Val Ser Glu Lys
        35                  40                  45

Asp Ala Pro Lys Glu Leu Leu Gln Met Leu Glu Lys Arg Gly Ser Glu
    50                  55                  60

Gln Lys Leu Ile Ser Glu Glu Asp
65                  70
```

<210> SEQ ID NO 52
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 52

```
Ala Thr Val Lys Phe Thr Tyr Arg Gly Glu Glu Lys Arg Val Gly Ile
1               5                   10                  15

Ser Arg Ile Lys Ser Val Arg Arg Ile Gly Gln Trp Ile Lys Phe Trp
            20                  25                  30

Tyr Asp Glu Gly Ser Gly Ala Tyr Gly Arg Gly Tyr Val Ser Glu Lys
        35                  40                  45

Asp Ala Pro Lys Glu Leu Leu Gln Met Leu Glu Lys Arg Gly Ser Glu
    50                  55                  60

Gln Lys Leu Ile Ser Glu Glu Asp
65                  70
```

<210> SEQ ID NO 53
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 53

```
Ala Thr Val Lys Phe Thr Tyr Arg Gly Glu Glu Lys Gln Val Gly Ile
1               5                   10                  15

Ser Arg Ile Lys Ser Val Arg Arg Ile Gly Gln Trp Val Lys Phe Trp
            20                  25                  30

Tyr Asp Glu Gly Ser Gly Ala Tyr Gly Arg Gly Tyr Val Ser Glu Lys
        35                  40                  45

Asp Ala Pro Lys Glu Leu Leu Gln Met Leu Glu Lys Arg Gly Ser Glu
    50                  55                  60

Gln Lys Leu Ile Ser Glu Glu Asp
65                  70
```

<210> SEQ ID NO 54
<211> LENGTH: 72
<212> TYPE: PRT
<213> ORGANISM: Artificial Sequence
<220> FEATURE:
<223> OTHER INFORMATION: Synthetic Polypeptide -continued

<400> SEQUENCE: 54

Ala Thr Val Lys Phe Thr Tyr Arg Gly Glu Glu Lys Gln Val Gly Ile
1               5                   10                  15

Ser Arg Ile Lys Ser Val Arg Ile Gly Gln Trp Val Lys Phe Trp
            20                  25                  30

Tyr Gly Glu Gly Ser Gly Ala Tyr Gly Arg Gly Tyr Val Ser Glu Lys
            35                  40                  45

Asp Ala Pro Lys Glu Leu Leu Gln Met Leu Glu Lys Arg Gly Ser Glu
        50                  55                  60

Gln Lys Leu Ile Ser Glu Glu Asp
65                  70

<210> SEQ ID NO 55
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 55

Ala Thr Val Lys Phe Thr Tyr Arg Gly Glu Glu Lys Gln Val Gly Ile
1               5                   10                  15

Ser Arg Ile Arg Ser Val Arg Ile Gly Gln Trp Ile Lys Phe Trp
            20                  25                  30

Tyr Asp Glu Gly Ser Gly Ala Tyr Gly Arg Gly Tyr Val Ser Glu Lys
            35                  40                  45

Asp Ala Pro Lys Glu Leu Leu Gln Met Leu Glu Lys Arg Gly Ser Glu
        50                  55                  60

Gln Lys Leu Ile Ser Glu Glu Asp
65                  70

<210> SEQ ID NO 56
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 56

Ala Thr Val Lys Phe Thr Tyr Arg Gly Glu Glu Lys Gln Val Gly Ile
1               5                   10                  15

Ser Arg Ile Lys Ser Val Arg Ile Gly Gln Trp Ile Lys Phe Trp
            20                  25                  30

Tyr Asp Glu Gly Arg Gly Ala Tyr Gly Arg Gly Tyr Val Ser Glu Lys
            35                  40                  45

Asp Ala Pro Lys Glu Leu Leu Gln Met Leu Glu Lys Arg Gly Ser Glu
        50                  55                  60

Gln Lys Leu Ile Ser Glu Glu Asp
65                  70

<210> SEQ ID NO 57
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 57

Ala Thr Val Lys Phe Thr Tyr Arg Gly Glu Glu Lys Gln Val Gly Ile
1               5                   10                  15

```
Ser Arg Ile Lys Ser Val Arg Ile Gly Gln Trp Ile Lys Phe Trp
            20                  25                  30

Tyr Asp Glu Gly Ser Gly Ala Tyr Gly Arg Gly Tyr Val Ser Glu Lys
            35                  40                  45

Asp Ala Pro Glu Glu Leu Leu Gln Met Leu Glu Lys Arg Gly Ser Glu
50                  55                  60

Gln Lys Leu Ile Ser Glu Glu Asp
65                  70

<210> SEQ ID NO 58
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 58

Ala Thr Val Lys Phe Thr Tyr Arg Gly Glu Glu Lys Gln Val Gly Ile
1               5                   10                  15

Ser Arg Ile Lys Ser Val His Arg Ile Gly Gln Trp Ile Lys Phe Trp
            20                  25                  30

Tyr Asp Glu Gly Ser Gly Ala Tyr Gly Arg Gly Tyr Val Ser Lys Lys
            35                  40                  45

Asp Ala Pro Lys Glu Leu Leu Gln Met Leu Glu Lys Arg Gly Ser Glu
50                  55                  60

Gln Lys Leu Ile Ser Glu Glu Asp
65                  70

<210> SEQ ID NO 59
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 59

Ala Thr Val Lys Phe Thr Tyr Arg Gly Glu Glu Lys Gln Val Gly Val
1               5                   10                  15

Ser Arg Ile Lys Ser Val His Arg Ile Gly Arg Trp Ile Lys Phe Trp
            20                  25                  30

Tyr Asp Glu Gly Ser Gly Ala Tyr Gly Arg Gly Tyr Val Ser Glu Lys
            35                  40                  45

Asp Ala Pro Lys Glu Leu Leu Gln Met Leu Glu Lys Arg Gly Ser Glu
50                  55                  60

Gln Lys Leu Ile Ser Glu Glu Asp
65                  70

<210> SEQ ID NO 60
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 60

Ala Thr Val Lys Phe Thr Tyr Arg Gly Glu Glu Lys Gln Val Gly Ile
1               5                   10                  15

Ser Arg Ile Lys Ser Val His Arg Ile Gly Arg Trp Ile Lys Phe Trp
            20                  25                  30
```

Tyr Asp Glu Gly Ser Gly Ala Tyr Gly Arg Gly Tyr Val Ser Glu Lys
            35                  40                  45

Asp Ala Pro Lys Glu Leu Leu Gln Met Leu Glu Lys Arg Gly Ser Glu
    50                  55                  60

Gln Lys Leu Ile Ser Glu Glu Asp
65                  70

<210> SEQ ID NO 61
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 61

Ala Thr Val Lys Phe Thr Tyr Arg Gly Glu Glu Lys Gln Val Gly Ile
1               5                   10                  15

Ser Arg Ile Lys Ser Val His Arg Val Gly Arg Trp Ile Lys Phe Trp
            20                  25                  30

Tyr Asp Glu Gly Ser Gly Ala Tyr Gly Arg Gly Tyr Val Ser Glu Lys
            35                  40                  45

Asp Ala Pro Lys Glu Leu Leu Gln Met Leu Glu Lys Arg Gly Ser Glu
    50                  55                  60

Gln Lys Leu Ile Ser Glu Glu Asp
65                  70

<210> SEQ ID NO 62
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 62

Ala Thr Val Lys Phe Thr Tyr Arg Gly Glu Glu Lys Gln Val Gly Ile
1               5                   10                  15

Gly Arg Ile Lys Ser Val His Arg Ile Gly Arg Trp Ile Lys Phe Trp
            20                  25                  30

Tyr Asp Glu Gly Ser Gly Ala Tyr Gly Arg Gly Tyr Val Ser Glu Lys
            35                  40                  45

Asp Ala Pro Lys Glu Leu Leu Gln Met Leu Glu Lys Arg Gly Ser Glu
    50                  55                  60

Gln Lys Leu Ile Ser Glu Glu Asp
65                  70

<210> SEQ ID NO 63
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 63

Ala Thr Val Lys Phe Thr Tyr Arg Gly Glu Glu Lys Gln Val Gly Ile
1               5                   10                  15

Ser Arg Ile Lys Ser Val His Arg Ile Gly Arg Trp Ile Lys Phe Trp
            20                  25                  30

Tyr Asp Glu Gly Ser Gly Ala Tyr Gly Arg Gly Tyr Val Asn Glu Lys
            35                  40                  45

Asp Ala Pro Lys Glu Leu Leu Gln Met Leu Glu Lys Arg Gly Ser Glu

```
                50                  55                  60

Gln Lys Leu Ile Ser Glu Glu Asp
 65                 70

<210> SEQ ID NO 64
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 64

Ala Thr Val Lys Phe Thr Tyr Arg Gly Glu Glu Lys Gln Val Gly Ile
 1               5                  10                  15

Ser Arg Ile Lys Phe Val His Arg Ile Gly Arg Trp Ile Lys Phe Trp
                20                  25                  30

Tyr Asp Glu Gly Ser Gly Ala Tyr Gly Arg Gly Tyr Val Ser Glu Lys
                35                  40                  45

Asp Ala Pro Lys Glu Leu Leu Gln Met Leu Glu Lys Arg Gly Ser Glu
    50                  55                  60

Gln Lys Leu Ile Ser Glu Glu Asp
 65                 70

<210> SEQ ID NO 65
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 65

Ala Thr Val Lys Phe Thr Tyr Arg Gly Glu Glu Lys Gln Val Gly Ile
 1               5                  10                  15

Ser Arg Ile Lys Ser Val His Arg Ile Gly Gln Trp Ile Lys Phe Trp
                20                  25                  30

Tyr Asp Glu Gly Ser Gly Ala Tyr Gly Arg Gly Tyr Val Ser Glu Lys
                35                  40                  45

Asn Ala Pro Lys Glu Leu Leu Gln Met Leu Glu Lys Arg Gly Ser Glu
    50                  55                  60

Gln Lys Leu Ile Ser Glu Glu Asp
 65                 70

<210> SEQ ID NO 66
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 66

Ala Thr Val Lys Phe Thr Tyr Arg Gly Glu Glu Lys Gln Val Gly Ile
 1               5                  10                  15

Ser Arg Ile Lys Ser Val His Arg Ile Gly Gln Trp Ile Lys Phe Trp
                20                  25                  30

Tyr Asp Glu Gly Ser Gly Ala Tyr Gly Arg Gly Tyr Val Ser Glu Lys
                35                  40                  45

Gly Ala Pro Lys Glu Leu Leu Gln Met Leu Glu Lys Arg Gly Ser Glu
    50                  55                  60

Gln Lys Leu Ile Ser Glu Glu Asp
 65                 70
```

<210> SEQ ID NO 67
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 67

Ala Thr Val Lys Phe Thr Tyr Arg Gly Glu Gly Lys Gln Val Gly Ile
1               5                   10                  15

Ser Arg Ile Lys Ser Val His Arg Ile Gly Gln Trp Ile Lys Phe Trp
                20                  25                  30

Tyr Asp Glu Gly Ser Gly Ala Tyr Gly Arg Gly Tyr Val Ser Glu Lys
            35                  40                  45

Asp Ala Pro Lys Glu Leu Leu Gln Met Leu Glu Lys Arg Gly Ser Glu
        50                  55                  60

Gln Lys Leu Ile Ser Glu Glu Asp
65                  70

<210> SEQ ID NO 68
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 68

Ala Thr Val Lys Phe Thr Tyr Arg Gly Glu Gly Lys Gln Val Gly Ile
1               5                   10                  15

Ser Arg Ile Lys Ser Val His Arg Ile Gly Gln Trp Ile Lys Phe Trp
                20                  25                  30

Tyr Asp Glu Gly Ser Gly Ala Tyr Gly Arg Gly Tyr Val Ser Glu Lys
            35                  40                  45

Asp Ala Pro Lys Glu Leu Leu Gln Met Leu Lys Lys Arg Gly Ser Glu
        50                  55                  60

Gln Lys Leu Ile Ser Glu Glu Asp
65                  70

<210> SEQ ID NO 69
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 69

Ala Thr Val Lys Phe Thr Tyr Arg Gly Glu Arg Lys Gln Val Gly Ile
1               5                   10                  15

Ser Arg Ile Lys Ser Val His Arg Ile Gly Gln Trp Ile Lys Phe Trp
                20                  25                  30

Tyr Asp Glu Gly Ser Gly Ala Tyr Gly Arg Gly Tyr Val Ser Glu Lys
            35                  40                  45

Asp Ala Pro Lys Glu Leu Leu Gln Met Leu Glu Lys Arg Gly Ser Glu
        50                  55                  60

Gln Lys Leu Ile Ser Glu Glu Asp
65                  70

<210> SEQ ID NO 70
<211> LENGTH: 72

<212> TYPE: PRT
<213> ORGANISM: Artificial Sequence
<220> FEATURE:
<223> OTHER INFORMATION: Synthetic Polypeptide

<400> SEQUENCE: 70

Ala Thr Val Lys Phe Thr Tyr Arg Gly Glu Glu Lys Gln Val Gly Ile
1               5                   10                  15

Ser Arg Ile Lys Ser Val His Arg Val Gly Gln Trp Ile Lys Phe Trp
            20                  25                  30

Tyr Asp Glu Gly Ser Gly Ala Tyr Gly Arg Gly Tyr Val Ser Glu Lys
        35                  40                  45

Asp Ala Pro Lys Glu Leu Leu Gln Met Leu Glu Lys Arg Gly Ser Glu
    50                  55                  60

Gln Lys Leu Ile Ser Glu Glu Asp
65                  70

<210> SEQ ID NO 71
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 71

Ala Thr Val Lys Phe Thr Tyr Arg Gly Glu Glu Arg Gln Val Gly Ile
1               5                   10                  15

Ser Arg Ile Lys Ser Val His Arg Ile Gly Gln Trp Ile Lys Phe Trp
            20                  25                  30

Tyr Asp Glu Gly Ser Gly Ala Tyr Gly Arg Gly Tyr Val Ser Glu Lys
        35                  40                  45

Asp Ala Pro Lys Glu Leu Leu Gln Met Leu Glu Lys Arg Gly Ser Glu
    50                  55                  60

Gln Lys Leu Ile Ser Glu Glu Asp
65                  70

<210> SEQ ID NO 72
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 72

Ala Thr Val Lys Phe Thr Tyr Arg Gly Glu Glu Lys Gln Val Gly Ile
1               5                   10                  15

Ser Arg Ile Lys Ser Val His Arg Ile Gly Gln Trp Ile Lys Phe Trp
            20                  25                  30

Tyr Asp Glu Gly Ser Gly Ala Tyr Gly Arg Gly Tyr Val Gly Glu Lys
        35                  40                  45

Asp Ala Pro Lys Glu Leu Leu Gln Met Leu Glu Lys Arg Gly Ser Glu
    50                  55                  60

Gln Lys Leu Ile Ser Glu Glu Asp
65                  70

<210> SEQ ID NO 73
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 73

Ala Thr Val Lys Phe Thr Tyr Arg Gly Glu Glu Lys Arg Val Gly Ile
1               5                   10                  15

Ser Arg Ile Lys Ser Val His Arg Ile Gly Gln Trp Ile Lys Phe Trp
            20                  25                  30

Tyr Asp Glu Gly Ser Gly Ala Tyr Gly Arg Gly Tyr Val Ser Glu Lys
        35                  40                  45

Asp Ala Pro Lys Glu Leu Leu Gln Met Leu Glu Lys Arg Gly Ser Glu
    50                  55                  60

Gln Lys Leu Ile Ser Glu Glu Asp
65                  70

<210> SEQ ID NO 74
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 74

Ala Thr Val Lys Phe Thr Tyr Arg Gly Glu Glu Lys Gln Val Gly Ile
1               5                   10                  15

Ser Arg Ile Lys Ser Val His Arg Ile Gly Gln Trp Ile Lys Phe Trp
            20                  25                  30

Tyr Asp Glu Gly Ser Gly Ala Tyr Gly Arg Gly Tyr Val Ser Glu Lys
        35                  40                  45

Asp Ala Pro Lys Glu Leu Leu Arg Met Leu Glu Lys Arg Gly Ser Glu
    50                  55                  60

Gln Lys Leu Ile Ser Glu Glu Asp
65                  70

<210> SEQ ID NO 75
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 75

Ala Thr Val Lys Phe Thr Tyr Arg Gly Glu Glu Lys Gln Val Gly Val
1               5                   10                  15

Ser Arg Ile Lys Ser Val His Arg Ile Gly Gln Trp Ile Lys Phe Trp
            20                  25                  30

Tyr Asp Gly Gly Ser Gly Ala Tyr Gly Arg Gly Tyr Val Ser Glu Lys
        35                  40                  45

Asp Ala Pro Lys Glu Leu Leu Gln Met Leu Glu Lys Arg Gly Ser Glu
    50                  55                  60

Gln Lys Leu Ile Ser Glu Glu Asp
65                  70

<210> SEQ ID NO 76
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 76

Ala Thr Val Lys Phe Thr Tyr Arg Gly Glu Glu Lys Gln Val Gly Ile

```
                1               5                   10                  15
Ser Arg Ile Lys Ser Val His Arg Ile Gly Gln Trp Ile Lys Phe Trp
            20                  25                  30

Tyr Asp Gly Gly Ser Gly Ala Tyr Gly Arg Gly Tyr Val Ser Glu Lys
            35                  40                  45

Asp Ala Pro Lys Glu Leu Leu Gln Met Leu Glu Lys Arg Gly Ser Glu
        50                  55                  60

Gln Lys Leu Ile Ser Glu Glu Asp
65                  70

<210> SEQ ID NO 77
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 77

Ala Thr Val Lys Phe Thr Tyr Arg Gly Glu Glu Lys Gln Val Gly Val
1               5                   10                  15

Ser Arg Val Lys Ser Val His Arg Ile Gly Gln Trp Ile Lys Phe Trp
            20                  25                  30

Tyr Asp Glu Gly Ser Gly Ala Tyr Gly Arg Gly Tyr Val Ser Glu Lys
            35                  40                  45

Asp Ala Pro Glu Glu Leu Leu Gln Met Leu Glu Lys Arg Gly Ser Glu
        50                  55                  60

Gln Lys Leu Ile Ser Glu Glu Asp
65                  70

<210> SEQ ID NO 78
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 78

Ala Thr Val Lys Phe Thr Tyr Arg Gly Glu Glu Lys Gln Val Gly Ile
1               5                   10                  15

Ser Arg Ile Lys Ser Val His Arg Ile Gly Gln Trp Ile Lys Phe Trp
            20                  25                  30

Tyr Asp Glu Gly Ser Gly Ala His Gly Arg Gly Tyr Val Ser Glu Lys
            35                  40                  45

Asp Ala Pro Lys Glu Leu Leu Gln Met Leu Glu Lys Arg Gly Ser Glu
        50                  55                  60

Gln Lys Leu Ile Ser Glu Glu Asp
65                  70

<210> SEQ ID NO 79
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 79

Ala Thr Val Lys Phe Thr Tyr Arg Gly Glu Glu Lys Gln Val Gly Ile
1               5                   10                  15

Ser Arg Ile Lys Ser Val His Arg Ile Gly Gln Trp Ile Lys Phe Arg
            20                  25                  30
```

Tyr Asp Glu Gly Ser Gly Ala Tyr Gly Arg Gly Tyr Val Ser Glu Lys
            35                  40                  45

Asp Ala Pro Lys Glu Leu Leu Gln Met Leu Glu Lys Arg Gly Ser Glu
        50                  55                  60

Gln Lys Leu Ile Ser Glu Glu Asp
65                  70

<210> SEQ ID NO 80
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 80

Val Thr Val Glu Phe Thr Tyr Arg Gly Glu Lys Gln Val Asp Ile
1               5                   10                  15

Ser Lys Ile Lys His Val Arg Arg Trp Gly Arg Trp Ile Trp Phe Ile
            20                  25                  30

Tyr Glu Glu Gly Gly Gly Ala Lys Gly Arg Gly Gly Val Ser Glu Lys
            35                  40                  45

Asp Ala Pro Lys Glu Leu Leu Gln Met Leu Glu Lys Arg Gly Ser Glu
        50                  55                  60

Gln Lys Leu Ile Ser Glu Glu Asp
65                  70

<210> SEQ ID NO 81
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 81

Ala Thr Val Lys Phe Thr Tyr Gln Gly Glu Glu Lys Gln Val Asp Ile
1               5                   10                  15

Ser Lys Ile Lys His Val Arg Arg Trp Gly Arg Trp Ile Trp Phe Ile
            20                  25                  30

Tyr Glu Glu Gly Gly Gly Ala Lys Gly Arg Gly Gly Val Ser Glu Lys
            35                  40                  45

Asp Ala Pro Lys Glu Leu Leu Gln Met Leu Glu Lys Arg Gly Ser Glu
        50                  55                  60

Gln Lys Leu Ile Ser Glu Glu Asp
65                  70

<210> SEQ ID NO 82
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 82

Ala Thr Val Arg Phe Thr Tyr Gln Gly Glu Glu Lys Gln Val Asp Ile
1               5                   10                  15

Ser Lys Ile Lys His Val Arg Arg Trp Gly Arg Trp Ile Trp Phe Ile
            20                  25                  30

Tyr Glu Glu Gly Gly Gly Ala Lys Gly Arg Gly Gly Val Ser Glu Lys
            35                  40                  45

Asp Ala Pro Lys Glu Leu Leu Gln Met Leu Glu Lys Arg Gly Ser Glu
            50                  55                  60

Gln Lys Leu Ile Ser Glu Glu Asp
 65                  70

<210> SEQ ID NO 83
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 83

Ala Thr Val Lys Phe Thr Tyr Gln Gly Glu Glu Lys Gln Val Asp Ile
 1               5                  10                  15

Ser Lys Ile Lys His Val Arg Arg Trp Gly Arg Trp Ile Trp Phe Ile
                20                  25                  30

Tyr Glu Glu Gly Gly Gly Gly Lys Gly Arg Gly Gly Val Ser Glu Lys
                35                  40                  45

Asp Ala Pro Lys Glu Leu Leu Gln Met Leu Glu Lys Arg Gly Ser Glu
            50                  55                  60

Gln Lys Leu Ile Ser Glu Glu Asp
 65                  70

<210> SEQ ID NO 84
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 84

Ala Thr Val Lys Phe Thr His Gln Gly Glu Glu Lys Gln Val Asp Ile
 1               5                  10                  15

Ser Lys Ile Lys His Val Arg Arg Trp Gly Arg Trp Ile Trp Phe Ile
                20                  25                  30

Tyr Glu Glu Gly Gly Gly Ala Lys Gly Arg Gly Gly Val Ser Glu Lys
                35                  40                  45

Asp Ala Pro Lys Glu Leu Leu Gln Met Leu Glu Lys Arg Gly Ser Glu
            50                  55                  60

Gln Lys Leu Ile Ser Glu Glu Asp
 65                  70

<210> SEQ ID NO 85
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 85

Ala Ile Val Lys Phe Thr Tyr Gln Gly Glu Glu Lys Gln Val Asp Ile
 1               5                  10                  15

Ser Lys Ile Lys His Val Arg Arg Trp Gly Arg Trp Ile Trp Phe Ile
                20                  25                  30

Tyr Glu Glu Gly Gly Gly Ala Lys Gly Arg Gly Gly Val Ser Glu Lys
                35                  40                  45

Asp Ala Pro Lys Glu Leu Leu Gln Met Leu Glu Lys Arg Gly Ser Glu
            50                  55                  60

Gln Lys Leu Ile Ser Glu Glu Asp

```
65                  70

<210> SEQ ID NO 86
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 86

Ala Ala Val Lys Phe Thr Tyr Gln Gly Glu Glu Lys Gln Val Asp Ile
1               5                   10                  15

Ser Lys Ile Lys His Val Arg Arg Trp Gly Arg Trp Ile Trp Phe Ile
            20                  25                  30

Tyr Glu Glu Gly Gly Gly Ala Lys Gly Arg Gly Gly Val Ser Glu Lys
        35                  40                  45

Asp Ala Pro Lys Glu Leu Leu Gln Met Leu Glu Lys Gln Gly Ser Glu
    50                  55                  60

Gln Lys Leu Ile Ser Glu Glu Asp
65                  70

<210> SEQ ID NO 87
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 87

Ala Thr Val Lys Phe Thr Tyr Gln Gly Glu Glu Lys Gln Val Asp Ile
1               5                   10                  15

Ser Lys Ile Lys His Val Arg Arg Trp Gly Arg Trp Ile Trp Phe Ile
            20                  25                  30

Tyr Glu Ala Gly Gly Gly Ala Lys Gly Arg Gly Gly Val Ser Glu Lys
        35                  40                  45

Asp Ala Pro Lys Glu Leu Leu Gln Met Leu Glu Lys Gln Gly Ser Glu
    50                  55                  60

Gln Lys Leu Ile Ser Glu Glu Asp
65                  70

<210> SEQ ID NO 88
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 88

Ala Thr Val Lys Phe Thr Tyr Gln Gly Glu Glu Lys Gln Val Asp Ile
1               5                   10                  15

Ser Lys Ile Lys His Val Arg Arg Trp Gly Arg Trp Ile Trp Phe Ile
            20                  25                  30

Tyr Glu Gly Gly Gly Gly Ala Lys Gly Arg Gly Gly Val Ser Glu Lys
        35                  40                  45

Asp Ala Pro Lys Glu Leu Leu Gln Met Leu Glu Arg Arg Gly Ser Glu
    50                  55                  60

Gln Lys Leu Ile Ser Glu Glu Asp
65                  70

<210> SEQ ID NO 89
```

```
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 89

Ala Thr Val Lys Phe Thr Tyr Gln Gly Glu Glu Lys Gln Val Asp Ile
1               5                   10                  15

Ser Lys Ile Lys His Val Arg Arg Trp Gly Arg Trp Ile Trp Phe Ile
            20                  25                  30

Tyr Glu Gly Gly Gly Gly Ala Lys Gly Arg Gly Gly Val Ser Glu Lys
        35                  40                  45

Asp Ala Pro Lys Glu Leu Leu Gln Met Leu Glu Lys Gln Gly Ser Glu
    50                  55                  60

Gln Lys Leu Ile Ser Glu Glu Asp
65                  70

<210> SEQ ID NO 90
<211> LENGTH: 69
<212> TYPE: PRT
<213> ORGANISM: Artificial Sequence
<220> FEATURE:
<223> OTHER INFORMATION: Synthetic Polypeptide

<400> SEQUENCE: 90

Ala Thr Val Lys Phe Thr Tyr Arg Gly Glu Glu Lys Gln Val Asp Ile
1               5                   10                  15

Ser Lys Ile Lys His Val Arg Arg Trp Gly Gln Trp Ile Trp Phe Ile
            20                  25                  30

Tyr Asp Glu Gly Gly Gly Ala Lys Gly Lys Gly Ser Val Ser Glu Lys
        35                  40                  45

Asp Ala Pro Lys Glu Leu Leu Gln Met Leu Glu Lys Ala Gly Ile Arg
    50                  55                  60

Thr Lys Ala Tyr Phe
65

<210> SEQ ID NO 91
<211> LENGTH: 69
<212> TYPE: PRT
<213> ORGANISM: Artificial Sequence
<220> FEATURE:
<223> OTHER INFORMATION: Synthetic Polypeptide

<400> SEQUENCE: 91

Ala Thr Val Lys Phe Thr Tyr Gln Gly Glu Glu Lys Gln Val Asp Val
1               5                   10                  15

Ser Lys Ile Lys His Val Arg Arg Trp Gly Gln Trp Ile Trp Phe Ile
            20                  25                  30

Tyr Asp Glu Gly Gly Gly Ala Lys Gly Lys Gly Ser Val Ser Glu Lys
        35                  40                  45

Asp Ala Pro Lys Glu Leu Leu Gln Met Leu Gly Lys Ala Gly Ile Arg
    50                  55                  60

Thr Lys Ala Tyr Phe
65

<210> SEQ ID NO 92
<211> LENGTH: 69
<212> TYPE: PRT
<213> ORGANISM: Artificial Sequence
<220> FEATURE:
```

<223> OTHER INFORMATION: Synthetic Polypeptide

<400> SEQUENCE: 92

```
Ala Thr Val Lys Phe Thr Tyr Gln Gly Glu Glu Lys Gln Val Asp Ile
1               5                   10                  15

Ser Lys Ile Lys His Val Arg Arg Trp Gly Arg Trp Ile Trp Phe Ile
            20                  25                  30

Tyr Asp Glu Gly Gly Gly Ala Lys Gly Lys Gly Ser Val Ser Glu Lys
        35                  40                  45

Asp Ala Pro Lys Glu Leu Leu Gln Met Leu Glu Lys Ala Gly Ile Arg
    50                  55                  60

Thr Lys Ala Tyr Phe
65
```

<210> SEQ ID NO 93
<211> LENGTH: 69
<212> TYPE: PRT
<213> ORGANISM: Artificial Sequence
<220> FEATURE:
<223> OTHER INFORMATION: Synthetic Polypeptide

<400> SEQUENCE: 93

```
Ala Thr Val Lys Phe Thr Tyr Gln Gly Glu Glu Lys Gln Val Asp Ile
1               5                   10                  15

Ser Lys Ile Lys His Val Arg Arg Trp Gly Arg Trp Ile Trp Phe Ile
            20                  25                  30

Tyr Glu Glu Gly Gly Gly Ala Lys Gly Lys Gly Ser Val Ser Glu Lys
        35                  40                  45

Asp Ala Pro Lys Glu Leu Leu Gln Met Leu Glu Lys Ala Gly Ile Arg
    50                  55                  60

Thr Lys Ala Tyr Phe
65
```

<210> SEQ ID NO 94
<211> LENGTH: 69
<212> TYPE: PRT
<213> ORGANISM: Artificial Sequence
<220> FEATURE:
<223> OTHER INFORMATION: Synthetic Polypeptide

<400> SEQUENCE: 94

```
Ala Thr Val Lys Phe Thr Tyr Gln Gly Glu Glu Lys Gln Val Asp Ile
1               5                   10                  15

Ser Lys Ile Lys His Val Arg Arg Trp Gly Gln Arg Ile Trp Phe Ile
            20                  25                  30

Tyr Gly Glu Gly Gly Gly Ala Lys Gly Arg Gly Ser Val Ser Glu Lys
        35                  40                  45

Asp Ala Pro Lys Glu Leu Leu Gln Met Leu Glu Lys Ala Gly Ile Arg
    50                  55                  60

Thr Lys Ala Tyr Phe
65
```

<210> SEQ ID NO 95
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 95

Ala Thr Val Lys Phe Thr Tyr Gln Gly Glu Glu Lys Gln Val Asp Ile
1               5                   10                  15

Ser Lys Ile Lys His Val Arg Arg Trp Gly Arg Trp Ile Trp Phe Ile
            20                  25                  30

Tyr Glu Glu Gly Gly Ala Lys Gly Arg Gly Gly Val Ser Glu Lys Asp
            35                  40                  45

Ala Pro Lys Glu Leu Leu Gln Met Leu Glu Lys Gln Gly Ser Glu Gln
    50                  55                  60

Lys Leu Ile Ser Glu Glu Asp Leu
65                  70

<210> SEQ ID NO 96
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 96

Ala Thr Val Lys Phe Thr Tyr Gln Gly Glu Glu Lys Gln Val Asp Ile
1               5                   10                  15

Ser Lys Ile Lys His Val Arg Arg Trp Gly Arg Trp Ile Trp Phe Thr
            20                  25                  30

Tyr Glu Glu Gly Gly Ala Lys Gly Arg Gly Gly Val Ser Glu Lys
            35                  40                  45

Asp Ala Pro Lys Glu Leu Leu Gln Met Leu Glu Lys Gln Gly Ser Glu
    50                  55                  60

Gln Lys Leu Ile Leu Lys Arg Thr
65                  70

<210> SEQ ID NO 97
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 97

Ala Thr Val Lys Phe Thr Tyr Gln Gly Glu Glu Lys Gln Val Asp Ile
1               5                   10                  15

Ser Lys Ile Lys His Val Arg Arg Trp Gly Arg Trp Ile Trp Phe Thr
            20                  25                  30

Tyr Glu Glu Gly Gly Ala Lys Gly Arg Gly Gly Val Ser Glu Lys
            35                  40                  45

Asp Ala Pro Lys Glu Leu Leu Gln Met Leu Glu Lys Pro Gly Ser Glu
    50                  55                  60

Gln Lys Leu Ile Ser Glu Glu Asp
65                  70

<210> SEQ ID NO 98
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 98

Ala Thr Val Lys Phe Thr Tyr Gln Gly Glu Glu Lys Gln Val Asp Ile
1               5                   10                  15

Ser Lys Ile Lys His Val Arg Arg Trp Gly Arg Trp Ile Trp Phe Thr

```
            20                  25                  30

Tyr Glu Glu Gly Gly Gly Ala Arg Gly Arg Gly Gly Val Ser Glu Lys
            35                  40                  45

Asp Ala Pro Lys Glu Leu Leu Gln Met Leu Glu Lys Gln Gly Ser Glu
        50                  55                  60

Gln Lys Leu Ile Ser Glu Asp
 65                  70

<210> SEQ ID NO 99
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 99

Ala Thr Val Lys Phe Thr Tyr Gln Gly Glu Glu Lys Gln Val Asp Val
 1               5                  10                  15

Ser Lys Ile Lys His Val Arg Arg Trp Gly Arg Trp Ile Trp Phe Thr
            20                  25                  30

Tyr Glu Glu Gly Gly Gly Ala Lys Gly Arg Gly Gly Val Ser Glu Lys
            35                  40                  45

Asp Ala Pro Lys Glu Leu Leu Gln Met Leu Glu Lys Gln Gly Ser Glu
        50                  55                  60

Gln Lys Leu Ile Ser Glu Asp
 65                  70

<210> SEQ ID NO 100
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 100

Ala Thr Val Lys Phe Thr Tyr Gln Gly Glu Glu Lys Gln Val Asp Ile
 1               5                  10                  15

Ser Lys Ile Lys His Val Arg Arg Trp Gly Arg Trp Ile Trp Phe Thr
            20                  25                  30

Tyr Glu Glu Gly Gly Gly Ala Lys Gly Arg Gly Gly Val Ser Glu Lys
            35                  40                  45

Asp Ala Pro Arg Glu Leu Leu Gln Met Leu Glu Lys Arg Gly Ser Glu
        50                  55                  60

Gln Lys Leu Ile Ser Glu Asp
 65                  70

<210> SEQ ID NO 101
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 101

Ala Thr Val Lys Phe Thr Tyr Arg Gly Glu Glu Lys Gln Val Asp Ile
 1               5                  10                  15

Ser Glu Ile Lys His Val Arg Arg Trp Gly Arg Trp Ile Trp Phe Thr
            20                  25                  30

Tyr Glu Glu Gly Gly Gly Ala Arg Gly Arg Gly Gly Val Ser Glu Lys
            35                  40                  45
```

Asp Ala Pro Lys Glu Leu Leu Gln Met Leu Glu Lys Arg Gly Ser Glu
        50                  55                  60

Gln Lys Leu Ile Ser Glu Glu Asp
 65                  70

<210> SEQ ID NO 102
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 102

Ala Thr Val Lys Phe Thr Tyr Gln Gly Glu Glu Lys Gln Val Asp Ile
 1               5                  10                  15

Ser Lys Ile Arg His Val Arg Arg Trp Gly Arg Ile Trp Phe Thr
                20                  25                  30

Tyr Glu Glu Gly Gly Gly Ala Lys Gly Arg Gly Gly Val Gly Glu Lys
            35                  40                  45

Asp Ala Pro Lys Glu Leu Leu Gln Met Leu Glu Lys Gln Gly Ser Glu
        50                  55                  60

Gln Lys Leu Ile Ser Glu Glu Asp
 65                  70

<210> SEQ ID NO 103
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 103

Ala Thr Val Lys Phe Thr Tyr Gln Gly Glu Glu Lys Gln Val Asp Ile
 1               5                  10                  15

Ser Lys Ile Lys His Val Arg Arg Trp Gly Arg Arg Ile Trp Phe Ile
                20                  25                  30

Tyr Glu Glu Gly Gly Gly Ala Lys Gly Arg Gly Gly Val Ser Glu Lys
            35                  40                  45

Asp Ala Pro Lys Glu Leu Leu Gln Met Leu Glu Lys Gln Gly Ser Glu
        50                  55                  60

Gln Lys Leu Ile Ser Glu Lys Asp
 65                  70

<210> SEQ ID NO 104
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 104

Ala Thr Val Lys Phe Thr Tyr Gln Gly Glu Glu Lys Gln Val Asp Ile
 1               5                  10                  15

Ser Lys Ile Lys His Val Arg Arg Trp Gly Arg Arg Ile Trp Phe Ile
                20                  25                  30

Tyr Glu Glu Gly Gly Gly Ala Lys Gly Arg Gly Gly Val Ser Glu Lys
            35                  40                  45

Asp Ala Pro Lys Glu Leu Leu Gln Met Leu Glu Lys Gln Gly Ser Glu
        50                  55                  60

Gln Lys Leu Ile Ser Glu Glu Asp
65                  70

<210> SEQ ID NO 105
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 105

Ala Thr Val Lys Phe Thr Tyr Gln Gly Glu Glu Lys Gln Val Asp Ile
1               5                   10                  15

Ser Lys Ile Lys His Val Arg Arg Trp Gly Arg Trp Ile Trp Phe Ile
            20                  25                  30

Tyr Glu Glu Gly Gly Gly Ala Lys Gly Arg Gly Gly Val Gly Glu Lys
        35                  40                  45

Asp Ala Pro Lys Glu Leu Leu Gln Met Leu Glu Lys Gln Gly Ser Glu
    50                  55                  60

Gln Lys Leu Ile Ser Glu Glu Asp
65                  70

<210> SEQ ID NO 106
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 106

Ala Thr Val Lys Phe Thr Tyr Gln Gly Glu Gly Lys Gln Val Asp Ile
1               5                   10                  15

Ser Lys Ile Lys His Val Arg Arg Trp Gly Arg Trp Ile Trp Phe Ile
            20                  25                  30

Tyr Glu Glu Gly Gly Gly Ala Lys Gly Arg Gly Gly Val Ser Glu Lys
        35                  40                  45

Asp Ala Pro Lys Glu Leu Leu Gln Met Leu Glu Lys Gln Gly Ser Glu
    50                  55                  60

Gln Lys Leu Ile Ser Glu Glu Asp
65                  70

<210> SEQ ID NO 107
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 107

Ala Thr Val Lys Phe Thr Tyr Gln Gly Glu Glu Lys Gln Val Asp Ile
1               5                   10                  15

Ser Lys Ile Lys Arg Val Arg Arg Trp Gly Arg Trp Ile Trp Phe Ile
            20                  25                  30

Tyr Glu Glu Gly Gly Gly Ala Lys Gly Arg Gly Gly Val Ser Glu Lys
        35                  40                  45

Asp Ala Pro Lys Glu Leu Leu Gln Met Leu Glu Lys Gln Gly Ser Glu
    50                  55                  60

Gln Lys Leu Ile Ser Glu Glu Asp
65                  70

```
<210> SEQ ID NO 108
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 108

Ile Thr Val Lys Phe Thr Tyr Gln Gly Glu Glu Lys Gln Val Asp Ile
1               5                   10                  15

Ser Lys Ile Glu His Val Arg Arg Trp Gly Arg Trp Ile Trp Phe Thr
            20                  25                  30

Tyr Asp Glu Gly Gly Gly Ala Lys Gly Arg Gly Gly Val Ser Glu Lys
        35                  40                  45

Gly Ala Pro Lys Glu Leu Leu Gln Met Leu Gly Lys Arg Gly Ser Glu
    50                  55                  60

Gln Lys Leu Ile Ser Glu Glu Asp
65                  70

<210> SEQ ID NO 109
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 109

Ile Thr Val Lys Phe Thr Tyr Arg Gly Glu Glu Lys Gln Val Asp Ile
1               5                   10                  15

Ser Lys Ile Glu His Val Arg Arg Trp Gly Gln Trp Ile Trp Phe Thr
            20                  25                  30

Tyr Asp Glu Gly Gly Gly Ala Lys Gly Arg Gly Gly Val Ser Glu Lys
        35                  40                  45

Gly Ala Pro Arg Glu Leu Leu Gln Met Leu Gly Lys Arg Gly Ser Glu
    50                  55                  60

Gln Lys Leu Ile Ser Glu Glu Asp
65                  70

<210> SEQ ID NO 110
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 110

Ala Thr Val Lys Phe Thr Tyr Gln Gly Glu Glu Lys Gln Val Asp Ile
1               5                   10                  15

Ser Lys Ile Lys His Val Arg Arg Trp Gly Arg Trp Ile Trp Phe Thr
            20                  25                  30

Tyr Asp Glu Gly Gly Gly Ala Lys Gly Arg Gly Gly Val Ser Glu Lys
        35                  40                  45

Gly Ala Pro Lys Glu Leu Leu Gln Met Leu Gly Lys Arg Gly Ser Glu
    50                  55                  60

Gln Lys Leu Ile Ser Glu Glu Asp
65                  70

<210> SEQ ID NO 111
<211> LENGTH: 72
<212> TYPE: PRT
<213> ORGANISM: Artificial Sequence
```

<220> FEATURE:
<223> OTHER INFORMATION: Synthetic Polypeptide

<400> SEQUENCE: 111

Ala Thr Val Lys Phe Thr Tyr Gln Gly Glu Glu Lys Gln Val Asp Ile
1               5                   10                  15

Ser Lys Ile Lys His Val Arg Arg Trp Gly Arg Trp Ile Trp Phe Thr
            20                  25                  30

Tyr Glu Glu Gly Gly Gly Ala Lys Gly Arg Gly Val Ser Glu Lys
        35                  40                  45

Asp Ala Pro Lys Glu Leu Leu Gln Met Leu Gly Lys Arg Gly Ser Glu
    50                  55                  60

Gln Lys Leu Ile Ser Glu Glu Asp
65                  70

<210> SEQ ID NO 112
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 112

Ala Thr Val Lys Phe Thr Tyr Gln Gly Glu Glu Lys Arg Val Asp Ile
1               5                   10                  15

Ser Lys Ile Lys His Val Arg Arg Trp Gly Arg Trp Ile Trp Phe Ile
            20                  25                  30

Tyr Glu Glu Gly Gly Gly Ala Lys Gly Arg Gly Val Ser Glu Lys
        35                  40                  45

Asp Ala Pro Lys Glu Leu Leu Gln Met Leu Gly Lys Arg Gly Ser Glu
    50                  55                  60

Gln Lys Leu Ile Ser Glu Glu Asp
65                  70

<210> SEQ ID NO 113
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 113

Ala Thr Val Lys Phe Thr Tyr Gln Gly Glu Glu Lys Gln Val Asp Ile
1               5                   10                  15

Ser Lys Ile Lys His Val Arg Arg Trp Gly Arg Trp Ile Trp Phe Ile
            20                  25                  30

Tyr Glu Glu Gly Gly Gly Ala Lys Gly Arg Gly Val Ser Glu Lys
        35                  40                  45

Asp Ala Pro Lys Glu Leu Leu Gln Met Leu Gly Lys Gln Gly Ser Glu
    50                  55                  60

Gln Lys Leu Ile Ser Glu Glu Asp
65                  70

<210> SEQ ID NO 114
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 114

Ala Thr Val Lys Phe Thr Tyr Arg Gly Glu Glu Lys Gln Val Asp Ile
1               5                   10                  15

Ser Lys Ile Lys His Val Arg Arg Trp Gly Arg Trp Ile Trp Phe Ile
            20                  25                  30

Tyr Glu Glu Gly Gly Gly Ala Lys Gly Arg Gly Val Ser Glu Lys
        35                  40                  45

Asp Ala Pro Lys Glu Leu Leu Gln Met Leu Lys Gln Arg Ser Glu
    50                  55                  60

Gln Lys Leu Ile Ser Glu Glu Asp
65                  70

<210> SEQ ID NO 115
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 115

Ala Thr Val Lys Phe Thr Tyr His Gly Glu Glu Lys Gln Val Asp Ile
1               5                   10                  15

Ser Lys Ile Lys His Val Arg Arg Trp Gly Arg Trp Ile Trp Phe Ile
            20                  25                  30

Tyr Glu Glu Gly Gly Gly Ala Lys Gly Arg Gly Val Ser Glu Lys
        35                  40                  45

Asp Ala Pro Lys Glu Leu Leu Gln Met Leu Lys Gln Gly Ser Glu
    50                  55                  60

Gln Lys Leu Ile Ser Glu Glu Asp
65                  70

<210> SEQ ID NO 116
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 116

Ala Thr Val Lys Phe Thr Tyr Arg Gly Glu Glu Lys Gln Val Asp Ile
1               5                   10                  15

Ser Lys Ile Lys His Val Arg Arg Trp Gly Gln Trp Ile Trp Phe Ile
            20                  25                  30

Tyr Asp Lys Gly Gly Gly Ala Lys Gly Arg Gly Val Ser Glu Lys
        35                  40                  45

Asp Ala Pro Lys Glu Leu Leu Gln Met Leu Lys Gln Gly Ser Glu
    50                  55                  60

Gln Lys Leu Ile Ser Glu Glu Asp
65                  70

<210> SEQ ID NO 117
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 117

Ala Thr Val Lys Phe Thr Tyr Arg Gly Glu Glu Lys Gln Val Asp Ile
1               5                   10                  15

```
Ser Lys Ile Lys His Val Arg Cys Trp Gly Gln Trp Ile Trp Phe Ile
            20                  25                  30

Tyr Asp Lys Gly Gly Gly Ala Lys Gly Arg Gly Val Ser Glu Lys
            35                  40                  45

Gly Ala Pro Lys Glu Leu Leu Gln Met Leu Glu Lys Gln Gly Ser Glu
 50                      55                  60

Gln Lys Leu Ile Ser Glu Glu Asp
 65                  70

<210> SEQ ID NO 118
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 118

Ala Thr Val Lys Phe Thr Tyr Arg Gly Glu Glu Lys Gln Val Gly Ile
 1               5                  10                  15

Ser Arg Ile Arg Ser Val His Arg Ile Gly Gln Trp Ile Lys Phe Trp
            20                  25                  30

Tyr Asp Glu Gly Ser Gly Ala Tyr Gly Arg Gly Tyr Val Ser Glu Lys
            35                  40                  45

Asp Ala Pro Lys Glu Leu Leu Gln Met Leu Lys Arg Gly Ser Glu
 50                      55                  60

Gln Lys Leu Ile Ser Glu Glu Asp
 65                  70

<210> SEQ ID NO 119
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 119

Thr Thr Val Lys Phe Thr Tyr Arg Gly Glu Glu Lys Gln Val Gly Ile
 1               5                  10                  15

Ser Arg Ile Lys Ser Val His Arg Ile Gly Gln Trp Ile Lys Phe Trp
            20                  25                  30

Tyr Asp Lys Gly Ser Gly Ala Tyr Gly Arg Gly Tyr Val Ser Glu Lys
            35                  40                  45

Asp Ala Pro Lys Glu Leu Leu Gln Met Leu Lys Arg Gly Ser Glu
 50                      55                  60

Gln Lys Leu Ile Ser Glu Glu Asp
 65                  70

<210> SEQ ID NO 120
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 120

Ala Ile Val Lys Phe Thr Tyr Arg Gly Glu Glu Lys Gln Val Gly Ile
 1               5                  10                  15

Ser Arg Ile Lys Ser Val His Arg Ile Gly Gln Trp Ile Lys Phe Trp
            20                  25                  30

Tyr Gly Glu Gly Ser Gly Ala Tyr Gly Arg Gly Tyr Val Ser Glu Lys
```

```
                 35                  40                  45

Asp Ala Pro Lys Glu Leu Leu Gln Met Leu Glu Lys Arg Gly Ser Glu
             50                  55                  60

Gln Lys Leu Ile Ser Glu Glu Asp
 65                  70
```

<210> SEQ ID NO 121
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 121

```
Ala Thr Val Lys Phe Thr Tyr Arg Gly Gly Glu Lys Gln Val Gly Ile
 1               5                  10                  15

Ser Arg Ile Lys Ser Val His Arg Ile Gly Gln Trp Ile Lys Phe Arg
                 20                  25                  30

Tyr Asp Glu Gly Ser Gly Ala Tyr Gly Arg Gly Tyr Val Ser Glu Lys
             35                  40                  45

Asp Ala Pro Lys Glu Leu Leu Gln Met Leu Glu Lys Arg Gly Ser Glu
             50                  55                  60

Gln Lys Leu Ile Ser Glu Glu Asp
 65                  70
```

<210> SEQ ID NO 122
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 122

```
Ala Thr Val Lys Phe Thr Tyr Arg Gly Lys Glu Lys Gln Val Gly Ile
 1               5                  10                  15

Ser Arg Ile Lys Ser Val His Arg Ile Gly Gln Trp Ile Lys Phe Arg
                 20                  25                  30

Tyr Asp Glu Gly Ser Gly Ala Tyr Gly Arg Gly Tyr Val Ser Glu Lys
             35                  40                  45

Asp Ala Pro Lys Glu Leu Leu Gln Met Leu Glu Lys Arg Gly Ser Glu
             50                  55                  60

Gln Lys Leu Ile Ser Glu Glu Asp
 65                  70
```

<210> SEQ ID NO 123
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 123

```
Ala Thr Val Lys Phe Thr Tyr Arg Gly Glu Glu Lys Gln Val Asp Ile
 1               5                  10                  15

Ser Arg Ile Lys His Val Arg Arg Trp Gly Arg Trp Ile Trp Phe Ile
                 20                  25                  30

Tyr Glu Glu Gly Gly Gly Ala Lys Gly Arg Gly Gly Val Ser Glu Lys
             35                  40                  45

Asp Ala Pro Lys Glu Leu Leu Gln Met Leu Glu Lys Gln Gly Ser Glu
             50                  55                  60
```

```
Gln Lys Leu Ile Ser Glu Glu Asp
 65                  70
```

```
<210> SEQ ID NO 124
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 124

Ala Thr Val Lys Phe Thr Tyr Arg Gly Glu Glu Lys Gln Val Asp Ile
 1               5                  10                  15

Ser Lys Ile Lys His Val Arg Arg Trp Gly Arg Trp Ile Trp Phe Ile
                20                  25                  30

Tyr Glu Glu Gly Gly Gly Ala Lys Gly Arg Gly Gly Val Ser Glu Lys
            35                  40                  45

Asp Ala Pro Lys Glu Leu Leu Gln Met Leu Glu Lys Gln Gly Ser Glu
        50                  55                  60

Gln Lys Leu Ile Ser Glu Glu Asp
 65                  70
```

```
<210> SEQ ID NO 125
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 125

Ala Thr Val Lys Phe Thr Tyr Arg Gly Glu Glu Lys Gln Val Asp Ile
 1               5                  10                  15

Ser Lys Ile Lys His Val Arg Arg Trp Gly Arg Trp Val Trp Phe Ile
                20                  25                  30

Tyr Glu Glu Gly Gly Gly Ala Lys Gly Arg Gly Gly Val Ser Glu Lys
            35                  40                  45

Asp Ala Pro Lys Glu Leu Leu Gln Met Leu Glu Lys Gln Gly Ser Glu
        50                  55                  60

Gln Lys Leu Ile Ser Glu Glu Asp
 65                  70
```

```
<210> SEQ ID NO 126
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 126

Ala Thr Val Lys Phe Thr Tyr Arg Gly Glu Glu Lys Gln Val Asp Ile
 1               5                  10                  15

Ser Lys Val Lys His Val Arg Arg Trp Gly Arg Trp Ile Trp Phe Ile
                20                  25                  30

Tyr Glu Glu Gly Gly Gly Ala Lys Gly Arg Gly Gly Val Ser Glu Lys
            35                  40                  45

Asp Ala Pro Lys Glu Leu Leu Gln Met Leu Glu Lys Gln Gly Ser Glu
        50                  55                  60

Gln Lys Leu Ile Ser Glu Glu Asp
 65                  70
```

<210> SEQ ID NO 127
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 127

```
Ala Thr Val Lys Phe Thr Tyr Arg Gly Glu Glu Lys Gln Val Asp Ile
1               5                   10                  15

Ser Lys Ile Lys His Val Arg Arg Trp Gly Arg Trp Ile Trp Phe Ile
            20                  25                  30

Tyr Glu Glu Gly Gly Gly Ala Lys Gly Arg Gly Gly Val Ser Glu Lys
                35                  40                  45

Asp Ala Pro Lys Glu Leu Leu Arg Met Leu Lys Gln Gly Ser Glu
        50                  55                  60

Gln Lys Leu Ile Ser Glu Glu Asp
65                  70
```

<210> SEQ ID NO 128
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 128

```
Ala Thr Val Lys Phe Thr Tyr Arg Gly Glu Glu Lys Gln Val Asp Ile
1               5                   10                  15

Ser Lys Ile Lys His Val Arg Arg Trp Gly Arg Trp Ile Trp Phe Ile
            20                  25                  30

Tyr Glu Glu Gly Gly Gly Ala Lys Gly Arg Gly Gly Val Ser Gly Lys
                35                  40                  45

Asp Ala Pro Lys Glu Leu Leu Gln Met Leu Lys Gln Gly Ser Glu
        50                  55                  60

Gln Lys Leu Ile Ser Glu Glu Asp
65                  70
```

<210> SEQ ID NO 129
<211> LENGTH: 68
<212> TYPE: PRT
<213> ORGANISM: Artificial Sequence
<220> FEATURE:
<223> OTHER INFORMATION: Synthetic Polypeptide

<400> SEQUENCE: 129

```
Ala Thr Val Lys Phe Thr Tyr Arg Gly Glu Glu Lys Gln Val Gly Ile
1               5                   10                  15

Ser Arg Ile Lys Ser Val His Arg Ile Gly Gln Trp Ile Lys Phe Trp
            20                  25                  30

Tyr Asp Glu Gly Ser Gly Ala Tyr Gly Arg Gly Tyr Val Ser Glu Lys
                35                  40                  45

Asp Ala Pro Lys Glu Leu Leu Gln Met Leu Lys Arg Gly Ser Glu
        50                  55                  60

Gln Lys Leu Phe
65
```

<210> SEQ ID NO 130
<211> LENGTH: 60
<212> TYPE: PRT

<213> ORGANISM: Artificial Sequence
<220> FEATURE:
<223> OTHER INFORMATION: Synthetic Polypeptide

<400> SEQUENCE: 130

Ala Thr Val Lys Phe Thr Tyr Arg Gly Lys Glu Lys Gln Val Gly Ile
1               5                   10                  15

Ser Arg Ile Lys Ser Val His Arg Ile Gly Gln Trp Ile Arg Phe Trp
            20                  25                  30

Tyr Asp Glu Gly Ser Gly Ala Tyr Gly Arg Gly Tyr Val Ser Glu Lys
        35                  40                  45

Asp Ala Pro Lys Glu Leu Leu Gln Met Leu Glu Lys
    50                  55                  60

<210> SEQ ID NO 131
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 131

Ala Thr Val Lys Phe Thr Tyr Arg Gly Glu Glu Lys Gln Val Gly Ile
1               5                   10                  15

Ser Arg Ile Lys Ser Val His Arg Ile Gly Gln Trp Ile Lys Phe Trp
            20                  25                  30

Tyr Asp Glu Gly Ser Gly Ala Tyr Gly Arg Gly Tyr Val Ser Gly Lys
        35                  40                  45

Asp Ala Pro Lys Glu Leu Leu Gln Met Leu Glu Lys Arg Gly Ser Glu
    50                  55                  60

Gln Lys Leu Ile Ser Glu Glu Asp
65                  70

<210> SEQ ID NO 132
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 132

Ala Thr Val Lys Phe Thr Tyr Arg Gly Lys Glu Lys Gln Val Gly Ile
1               5                   10                  15

Ser Arg Ile Lys Ser Val His Arg Ile Gly Gln Trp Ile Lys Phe Trp
            20                  25                  30

Tyr Asp Glu Gly Ser Gly Ala Tyr Gly Arg Gly Tyr Val Ser Gly Lys
        35                  40                  45

Asp Ala Pro Lys Glu Leu Leu Gln Met Leu Glu Lys Arg Gly Ser Glu
    50                  55                  60

Gln Lys Leu Ile Ser Glu Glu Asp
65                  70

<210> SEQ ID NO 133
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 133

Ala Thr Val Lys Phe Thr Tyr Arg Gly Glu Glu Lys Gln Val Gly Ile

```
                1               5                  10                  15
Asn Arg Ile Lys Ser Val His Arg Ile Gly Gln Trp Ile Lys Phe Trp
                20                  25                  30
Tyr Asp Glu Gly Ser Gly Ala Tyr Gly Arg Gly Tyr Val Ser Gly Lys
                35                  40                  45
Asp Ala Pro Lys Glu Leu Leu Arg Met Leu Glu Lys Arg Gly Ser Glu
    50                  55                  60
Gln Lys Leu Ile Ser Glu Glu Asp
65                  70

<210> SEQ ID NO 134
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 134

Ala Thr Val Lys Phe Thr Tyr Arg Gly Glu Glu Lys Gln Val Gly Ile
1               5                   10                  15
Ser Arg Ile Lys Ser Val His Arg Ile Gly Arg Trp Ile Lys Phe Trp
                20                  25                  30
Tyr Asp Glu Gly Ser Gly Ala Tyr Gly Arg Gly Tyr Val Ser Gly Lys
                35                  40                  45
Asp Ala Pro Lys Glu Leu Leu Gln Met Leu Glu Lys Arg Gly Ser Glu
    50                  55                  60
Gln Lys Leu Ile Ser Glu Glu Asp
65                  70

<210> SEQ ID NO 135
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 135

Ala Thr Val Lys Phe Thr Tyr Arg Gly Glu Glu Lys Gln Val Gly Ile
1               5                   10                  15
Ser Arg Ile Lys Ser Val Arg Arg Ile Gly Gln Trp Ile Lys Phe Trp
                20                  25                  30
Tyr Asp Glu Gly Ser Gly Ala Tyr Gly Arg Gly Tyr Val Ser Gly Lys
                35                  40                  45
Asp Ala Pro Lys Glu Leu Leu Gln Met Leu Glu Lys Arg Gly Ser Glu
    50                  55                  60
Gln Lys Leu Ile Ser Glu Glu Asp
65                  70

<210> SEQ ID NO 136
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 136

Ala Thr Val Lys Phe Thr Tyr Arg Gly Glu Glu Lys Arg Val Gly Ile
1               5                   10                  15
Ser Arg Ile Lys Ser Val Arg Arg Ile Gly Gln Trp Ile Lys Phe Trp
                20                  25                  30
```

Tyr Asp Glu Gly Ser Gly Ala Tyr Gly Arg Gly Tyr Val Ser Glu Lys
            35                  40                  45

Asp Ala Pro Lys Glu Leu Leu Gln Met Leu Gly Lys Arg Gly Ser Glu
        50                  55                  60

Gln Lys Leu Ile Ser Glu Glu Asp
65                  70

<210> SEQ ID NO 137
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 137

Ala Thr Val Lys Phe Thr Tyr Arg Gly Glu Glu Lys Gln Val Gly Ile
1               5                   10                  15

Ser Arg Ile Lys Ser Val Arg Arg Ile Gly Gln Trp Ile Lys Phe Trp
            20                  25                  30

Tyr Asp Glu Gly Ser Gly Ala Tyr Gly Arg Gly Tyr Val Ser Glu Lys
            35                  40                  45

Asp Ala Pro Lys Glu Leu Leu Gln Met Leu Gly Lys Arg Gly Ser Glu
        50                  55                  60

Gln Lys Leu Ile Ser Glu Glu Asp
65                  70

<210> SEQ ID NO 138
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 138

Ala Thr Val Arg Phe Thr Tyr Arg Gly Glu Glu Lys Gln Val Gly Ile
1               5                   10                  15

Ser Arg Ile Lys Ser Val Arg Arg Ile Gly Gln Trp Ile Lys Phe Trp
            20                  25                  30

Tyr Asp Glu Gly Ser Gly Ala Tyr Gly Arg Gly Tyr Val Ser Glu Lys
            35                  40                  45

Asp Ala Pro Lys Glu Leu Leu Gln Met Leu Gly Lys Arg Gly Ser Glu
        50                  55                  60

Gln Lys Leu Ile Ser Glu Glu Asp
65                  70

<210> SEQ ID NO 139
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 139

Ala Thr Val Lys Phe Thr Tyr Arg Gly Glu Glu Lys Gln Val Gly Ile
1               5                   10                  15

Ser Arg Ile Lys Ser Val His Arg Ile Gly Gln Trp Ile Lys Phe Trp
            20                  25                  30

Tyr Asp Glu Gly Ser Gly Ala Tyr Gly Arg Gly Tyr Val Ser Glu Lys
            35                  40                  45

Gly Ala Pro Lys Glu Leu Leu Gln Met Leu Gly Lys Arg Gly Ser Glu
        50                  55                  60

Gln Lys Leu Ile Ser Glu Glu Asp
 65                  70

<210> SEQ ID NO 140
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 140

Ile Thr Val Lys Phe Thr Tyr Gln Gly Glu Lys Gln Val Asp Ile
 1               5                  10                  15

Ser Lys Ile Glu His Val Arg Arg Trp Gly Gln Trp Ile Trp Phe Thr
             20                  25                  30

Tyr Asp Glu Gly Gly Gly Ala Lys Gly Arg Gly Gly Val Ser Glu Lys
         35                  40                  45

Gly Ala Pro Lys Glu Leu Leu Gln Met Leu Gly Lys Arg Gly Ser Glu
     50                  55                  60

Gln Lys Leu Ile Ser Glu Glu Asp
 65                  70

<210> SEQ ID NO 141
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 141

Ala Thr Val Lys Phe Thr Tyr Arg Gly Glu Glu Lys Gln Val Gly Ile
 1               5                  10                  15

Ser Arg Ile Arg Ser Val His Arg Ile Gly Gln Trp Ile Lys Phe Trp
             20                  25                  30

Tyr Asp Glu Gly Ser Gly Ala Cys Gly Arg Gly Tyr Val Ser Glu Lys
         35                  40                  45

Gly Ala Pro Lys Glu Leu Leu Gln Met Leu Gly Lys Arg Gly Ser Glu
     50                  55                  60

Gln Lys Leu Ile Ser Glu Glu Asp
 65                  70

<210> SEQ ID NO 142
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 142

Ala Thr Val Lys Phe Thr Tyr Arg Gly Glu Glu Lys Gln Val Gly Ile
 1               5                  10                  15

Ser Arg Ile Lys Ser Val His Arg Ile Gly Gln Trp Ile Lys Phe Trp
             20                  25                  30

Tyr Asp Glu Gly Ser Gly Ala Tyr Gly Arg Gly Tyr Val Ser Glu Lys
         35                  40                  45

Asp Ala Pro Lys Glu Leu Leu Gln Met Leu Gly Lys Arg Gly Ser Glu
     50                  55                  60

Gln Lys Leu Ile Ser Glu Glu Asp 65                      70

<210> SEQ ID NO 143
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 143

Ala Thr Val Arg Phe Thr Tyr Arg Gly Glu Glu Lys Gln Val Gly Ile
1               5                   10                  15

Ser Arg Ile Lys Ser Val His Arg Ile Gly Gln Trp Ile Lys Phe Trp
            20                  25                  30

Tyr Asp Glu Gly Ser Gly Thr Tyr Gly Arg Gly Tyr Val Ser Glu Lys
        35                  40                  45

Asp Ala Pro Arg Glu Leu Leu Gln Met Leu Gly Lys Arg Gly Ser Glu
    50                  55                  60

Gln Lys Leu Ile Ser Glu Glu Asp
65                      70

<210> SEQ ID NO 144
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 144

Ala Thr Val Lys Phe Thr Tyr Arg Gly Glu Glu Lys Gln Val Gly Ile
1               5                   10                  15

Ser Arg Ile Lys Ser Val Arg Arg Ile Gly Gln Trp Ile Lys Phe Trp
            20                  25                  30

Tyr Asp Glu Gly Ser Gly Ala Tyr Gly Arg Gly Tyr Val Ser Glu Lys
        35                  40                  45

Asp Ala Pro Lys Glu Leu Leu Gln Met Leu Gly Lys Arg Gly Ser Glu
    50                  55                  60

Gln Lys Leu Ile Ser Glu Glu Asp
65                      70

<210> SEQ ID NO 145
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 145

Ala Thr Val Lys Phe Thr Tyr Arg Gly Gly Glu Lys Gln Val Gly Ile
1               5                   10                  15

Ser Arg Ile Lys Ser Val Arg Arg Ile Gly Gln Trp Ile Lys Phe Trp
            20                  25                  30

Tyr Asp Glu Gly Ser Gly Ala Tyr Gly Arg Gly Tyr Val Ser Glu Lys
        35                  40                  45

Asp Ala Pro Lys Glu Leu Leu Gln Met Leu Glu Lys Arg Gly Ser Glu
    50                  55                  60

Gln Lys Leu Ile Ser Glu Glu Asp
65                      70

<210> SEQ ID NO 146

```
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 146

Ala Thr Val Lys Phe Thr Tyr Arg Gly Glu Lys Arg Val Gly Val
1               5                   10                  15

Ser Arg Ile Lys Ser Val Arg Arg Ile Gly Gln Trp Ile Lys Phe Trp
            20                  25                  30

Tyr Asp Glu Gly Ser Gly Ala Tyr Gly Arg Gly Tyr Val Ser Glu Lys
        35                  40                  45

Asp Ala Pro Lys Glu Leu Leu Gln Met Leu Glu Lys Arg Gly Ser Glu
    50                  55                  60

Gln Lys Leu Ile Ser Glu Glu Asp
65                  70

<210> SEQ ID NO 147
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 147

Ala Thr Val Lys Phe Thr Tyr Arg Gly Glu Glu Lys Arg Val Gly Ile
1               5                   10                  15

Ser Arg Ile Lys Ser Val Arg Arg Ile Gly Gln Trp Ile Lys Phe Trp
            20                  25                  30

Tyr Asp Glu Gly Ser Gly Ala Tyr Gly Arg Gly Tyr Val Ser Glu Lys
        35                  40                  45

Asp Ala Pro Lys Glu Leu Leu Gln Met Leu Glu Lys Arg Gly Ser Glu
    50                  55                  60

Gln Lys Leu Ile Ser Glu Glu Asp
65                  70

<210> SEQ ID NO 148
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 148

Ala Thr Val Lys Phe Thr Tyr Arg Gly Glu Glu Lys Gln Val Gly Ile
1               5                   10                  15

Ser Arg Ile Lys Ser Val Arg Arg Ile Gly Gln Trp Val Lys Phe Trp
            20                  25                  30

Tyr Asp Glu Gly Ser Gly Ala Tyr Gly Arg Gly Tyr Val Ser Glu Lys
        35                  40                  45

Asp Ala Pro Lys Glu Leu Leu Gln Met Leu Glu Lys Arg Gly Ser Glu
    50                  55                  60

Gln Lys Leu Ile Ser Glu Glu Asp
65                  70

<210> SEQ ID NO 149
<211> LENGTH: 72
<212> TYPE: PRT
<213> ORGANISM: Artificial Sequence
<220> FEATURE:
```

<223> OTHER INFORMATION: Synthetic Polypeptide

<400> SEQUENCE: 149

Ala Thr Val Lys Phe Thr Tyr Arg Gly Glu Glu Lys Gln Val Gly Ile
1               5                   10                  15
Ser Arg Ile Lys Ser Val Arg Arg Ile Gly Gln Trp Val Lys Phe Trp
            20                  25                  30
Tyr Gly Glu Gly Ser Gly Ala Tyr Gly Arg Gly Tyr Val Ser Glu Lys
        35                  40                  45
Asp Ala Pro Lys Glu Leu Leu Gln Met Leu Glu Lys Arg Gly Ser Glu
    50                  55                  60
Gln Lys Leu Ile Ser Glu Glu Asp
65                  70

<210> SEQ ID NO 150
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 150

Ala Thr Val Lys Phe Thr Tyr Arg Gly Glu Glu Lys Gln Val Gly Ile
1               5                   10                  15
Ser Arg Ile Arg Ser Val Arg Arg Ile Gly Gln Trp Ile Lys Phe Trp
            20                  25                  30
Tyr Asp Glu Gly Ser Gly Ala Tyr Gly Arg Gly Tyr Val Ser Glu Lys
        35                  40                  45
Asp Ala Pro Lys Glu Leu Leu Gln Met Leu Glu Lys Arg Gly Ser Glu
    50                  55                  60
Gln Lys Leu Ile Ser Glu Glu Asp
65                  70

<210> SEQ ID NO 151
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 151

Ala Thr Val Lys Phe Thr Tyr Arg Gly Glu Glu Lys Gln Val Gly Ile
1               5                   10                  15
Ser Arg Ile Lys Ser Val Arg Arg Ile Gly Gln Trp Ile Lys Phe Trp
            20                  25                  30
Tyr Asp Glu Gly Arg Gly Ala Tyr Gly Arg Gly Tyr Val Ser Glu Lys
        35                  40                  45
Asp Ala Pro Lys Glu Leu Leu Gln Met Leu Glu Lys Arg Gly Ser Glu
    50                  55                  60
Gln Lys Leu Ile Ser Glu Glu Asp
65                  70

<210> SEQ ID NO 152
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 152

Ala Thr Val Lys Phe Thr Tyr Arg Gly Glu Glu Lys Gln Val Gly Ile
1               5                   10                  15

Ser Arg Ile Lys Ser Val Arg Arg Ile Gly Gln Trp Ile Lys Phe Trp
            20                  25                  30

Tyr Asp Glu Gly Ser Gly Ala Tyr Gly Arg Gly Tyr Val Ser Glu Lys
        35                  40                  45

Asp Ala Pro Glu Glu Leu Leu Gln Met Leu Glu Lys Arg Gly Ser Glu
    50                  55                  60

Gln Lys Leu Ile Ser Glu Glu Asp
65                  70

<210> SEQ ID NO 153
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 153

Ala Thr Val Lys Phe Thr Tyr Arg Gly Glu Glu Lys Gln Val Gly Ile
1               5                   10                  15

Ser Arg Ile Lys Ser Val His Arg Ile Gly Gln Trp Ile Lys Phe Trp
            20                  25                  30

Tyr Asp Glu Gly Ser Gly Ala Tyr Gly Arg Gly Tyr Val Ser Lys Lys
        35                  40                  45

Asp Ala Pro Lys Glu Leu Leu Gln Met Leu Glu Lys Arg Gly Ser Glu
    50                  55                  60

Gln Lys Leu Ile Ser Glu Glu Asp
65                  70

<210> SEQ ID NO 154
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 154

Ala Thr Val Lys Phe Thr Tyr Arg Gly Glu Glu Lys Gln Val Gly Val
1               5                   10                  15

Ser Arg Ile Lys Ser Val His Arg Ile Gly Arg Trp Ile Lys Phe Trp
            20                  25                  30

Tyr Asp Glu Gly Ser Gly Ala Tyr Gly Arg Gly Tyr Val Ser Glu Lys
        35                  40                  45

Asp Ala Pro Lys Glu Leu Leu Gln Met Leu Glu Lys Arg Gly Ser Glu
    50                  55                  60

Gln Lys Leu Ile Ser Glu Glu Asp
65                  70

<210> SEQ ID NO 155
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 155

Ala Thr Val Lys Phe Thr Tyr Arg Gly Glu Glu Lys Gln Val Gly Ile
1               5                   10                  15

Ser Arg Ile Lys Ser Val His Arg Ile Gly Arg Trp Ile Lys Phe Trp

```
                20                  25                  30

Tyr Asp Glu Gly Ser Gly Ala Tyr Gly Arg Gly Tyr Val Ser Glu Lys
            35                  40                  45

Asp Ala Pro Lys Glu Leu Leu Gln Met Leu Glu Lys Arg Gly Ser Glu
        50                  55                  60

Gln Lys Leu Ile Ser Glu Asp
65                  70

<210> SEQ ID NO 156
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 156

Ala Thr Val Lys Phe Thr Tyr Arg Gly Glu Glu Lys Gln Val Gly Ile
1               5                   10                  15

Ser Arg Ile Lys Ser Val His Arg Val Gly Arg Trp Ile Lys Phe Trp
            20                  25                  30

Tyr Asp Glu Gly Ser Gly Ala Tyr Gly Arg Gly Tyr Val Ser Glu Lys
            35                  40                  45

Asp Ala Pro Lys Glu Leu Leu Gln Met Leu Glu Lys Arg Gly Ser Glu
        50                  55                  60

Gln Lys Leu Ile Ser Glu Asp
65                  70

<210> SEQ ID NO 157
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 157

Ala Thr Val Lys Phe Thr Tyr Arg Gly Glu Glu Lys Gln Val Gly Ile
1               5                   10                  15

Gly Arg Ile Lys Ser Val His Arg Ile Gly Arg Trp Ile Lys Phe Trp
            20                  25                  30

Tyr Asp Glu Gly Ser Gly Ala Tyr Gly Arg Gly Tyr Val Ser Glu Lys
            35                  40                  45

Asp Ala Pro Lys Glu Leu Leu Gln Met Leu Glu Lys Arg Gly Ser Glu
        50                  55                  60

Gln Lys Leu Ile Ser Glu Asp
65                  70

<210> SEQ ID NO 158
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 158

Ala Thr Val Lys Phe Thr Tyr Arg Gly Glu Glu Lys Gln Val Gly Ile
1               5                   10                  15

Ser Arg Ile Lys Ser Val His Arg Ile Gly Arg Trp Ile Lys Phe Trp
            20                  25                  30

Tyr Asp Glu Gly Ser Gly Ala Tyr Gly Arg Gly Tyr Val Asn Glu Lys
            35                  40                  45
```

Asp Ala Pro Lys Glu Leu Leu Gln Met Leu Glu Lys Arg Gly Ser Glu
        50                  55                  60

Gln Lys Leu Ile Ser Glu Glu Asp
 65                  70

<210> SEQ ID NO 159
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 159

Ala Thr Val Lys Phe Thr Tyr Arg Gly Glu Glu Lys Gln Val Gly Ile
 1               5                  10                  15

Ser Arg Ile Lys Phe Val His Arg Ile Gly Arg Trp Ile Lys Phe Trp
            20                  25                  30

Tyr Asp Glu Gly Ser Gly Ala Tyr Gly Arg Gly Tyr Val Ser Glu Lys
        35                  40                  45

Asp Ala Pro Lys Glu Leu Leu Gln Met Leu Glu Lys Arg Gly Ser Glu
    50                  55                  60

Gln Lys Leu Ile Ser Glu Glu Asp
 65                  70

<210> SEQ ID NO 160
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 160

Ala Thr Val Lys Phe Thr Tyr Arg Gly Glu Glu Lys Gln Val Gly Ile
 1               5                  10                  15

Ser Arg Ile Lys Ser Val His Arg Ile Gly Gln Trp Ile Lys Phe Trp
            20                  25                  30

Tyr Asp Glu Gly Ser Gly Ala Tyr Gly Arg Gly Tyr Val Ser Glu Lys
        35                  40                  45

Asn Ala Pro Lys Glu Leu Leu Gln Met Leu Glu Lys Arg Gly Ser Glu
    50                  55                  60

Gln Lys Leu Ile Ser Glu Glu Asp
 65                  70

<210> SEQ ID NO 161
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 161

Ala Thr Val Lys Phe Thr Tyr Arg Gly Glu Glu Lys Gln Val Gly Ile
 1               5                  10                  15

Ser Arg Ile Lys Ser Val His Arg Ile Gly Gln Trp Ile Lys Phe Trp
            20                  25                  30

Tyr Asp Glu Gly Ser Gly Ala Tyr Gly Arg Gly Tyr Val Ser Glu Lys
        35                  40                  45

Gly Ala Pro Lys Glu Leu Leu Gln Met Leu Glu Lys Arg Gly Ser Glu
    50                  55                  60

Gln Lys Leu Ile Ser Glu Glu Asp
65                  70

<210> SEQ ID NO 162
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 162

Ala Thr Val Lys Phe Thr Tyr Arg Gly Glu Gly Lys Gln Val Gly Ile
1               5                   10                  15

Ser Arg Ile Lys Ser Val His Arg Ile Gly Gln Trp Ile Lys Phe Trp
            20                  25                  30

Tyr Asp Glu Gly Ser Gly Ala Tyr Gly Arg Gly Tyr Val Ser Glu Lys
        35                  40                  45

Asp Ala Pro Lys Glu Leu Leu Gln Met Leu Gly Lys Arg Gly Ser Glu
    50                  55                  60

Gln Lys Leu Ile Ser Glu Glu Asp
65                  70

<210> SEQ ID NO 163
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 163

Ala Thr Val Lys Phe Thr Tyr Arg Gly Glu Gly Lys Gln Val Gly Ile
1               5                   10                  15

Ser Arg Ile Lys Ser Val His Arg Ile Gly Gln Trp Ile Lys Phe Trp
            20                  25                  30

Tyr Asp Glu Gly Ser Gly Ala Tyr Gly Arg Gly Tyr Val Ser Glu Lys
        35                  40                  45

Asp Ala Pro Lys Glu Leu Leu Gln Met Leu Lys Lys Arg Gly Ser Glu
    50                  55                  60

Gln Lys Leu Ile Ser Glu Glu Asp
65                  70

<210> SEQ ID NO 164
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 164

Ala Thr Val Lys Phe Thr Tyr Arg Gly Glu Arg Lys Gln Val Gly Ile
1               5                   10                  15

Ser Arg Ile Lys Ser Val His Arg Ile Gly Gln Trp Ile Lys Phe Trp
            20                  25                  30

Tyr Asp Glu Gly Ser Gly Ala Tyr Gly Arg Gly Tyr Val Ser Glu Lys
        35                  40                  45

Asp Ala Pro Lys Glu Leu Leu Gln Met Leu Glu Lys Arg Gly Ser Glu
    50                  55                  60

Gln Lys Leu Ile Ser Glu Glu Asp
65                  70

-continued

<210> SEQ ID NO 165
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 165

Ala Thr Val Lys Phe Thr Tyr Arg Gly Glu Glu Lys Gln Val Gly Ile
1               5                   10                  15

Ser Arg Ile Lys Ser Val His Arg Ile Gly Gln Trp Ile Lys Phe Trp
            20                  25                  30

Tyr Asp Glu Gly Ser Gly Ala Tyr Gly Arg Gly Tyr Val Ser Glu Lys
        35                  40                  45

Asp Ala Pro Lys Glu Leu Leu Gln Met Leu Glu Lys Arg Gly Ser Glu
    50                  55                  60

Gln Lys Leu Ile Ser Glu Glu Asp
65                  70

<210> SEQ ID NO 166
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 166

Ala Thr Val Lys Phe Thr Tyr Arg Gly Glu Glu Lys Gln Val Gly Ile
1               5                   10                  15

Ser Arg Ile Lys Ser Val His Arg Val Gly Gln Trp Ile Lys Phe Trp
            20                  25                  30

Tyr Asp Glu Gly Ser Gly Ala Tyr Gly Arg Gly Tyr Val Ser Glu Lys
        35                  40                  45

Asp Ala Pro Lys Glu Leu Leu Gln Met Leu Glu Lys Arg Gly Ser Glu
    50                  55                  60

Gln Lys Leu Ile Ser Glu Glu Asp
65                  70

<210> SEQ ID NO 167
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 167

Ala Thr Val Lys Phe Thr Tyr Arg Gly Glu Glu Arg Gln Val Gly Ile
1               5                   10                  15

Ser Arg Ile Lys Ser Val His Arg Ile Gly Gln Trp Ile Lys Phe Trp
            20                  25                  30

Tyr Asp Glu Gly Ser Gly Ala Tyr Gly Arg Gly Tyr Val Ser Glu Lys
        35                  40                  45

Asp Ala Pro Lys Glu Leu Leu Gln Met Leu Glu Lys Arg Gly Ser Glu
    50                  55                  60

Gln Lys Leu Ile Ser Glu Glu Asp
65                  70

<210> SEQ ID NO 168
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 168

Ala Thr Val Lys Phe Thr Tyr Arg Gly Glu Glu Lys Gln Val Gly Ile
1               5                   10                  15

Ser Arg Ile Lys Ser Val His Arg Ile Gly Gln Trp Ile Lys Phe Trp
            20                  25                  30

Tyr Asp Glu Gly Ser Gly Ala Tyr Gly Arg Gly Tyr Val Gly Glu Lys
        35                  40                  45

Asp Ala Pro Lys Glu Leu Leu Gln Met Leu Gly Lys Arg Gly Ser Glu
    50                  55                  60

Gln Lys Leu Ile Ser Glu Glu Asp
65                  70

<210> SEQ ID NO 169
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 169

Ala Thr Val Lys Phe Thr Tyr Arg Gly Glu Glu Lys Arg Val Gly Ile
1               5                   10                  15

Ser Arg Ile Lys Ser Val His Arg Ile Gly Gln Trp Ile Lys Phe Trp
            20                  25                  30

Tyr Asp Glu Gly Ser Gly Ala Tyr Gly Arg Gly Tyr Val Ser Glu Lys
        35                  40                  45

Asp Ala Pro Lys Glu Leu Leu Gln Met Leu Gly Lys Arg Gly Ser Glu
    50                  55                  60

Gln Lys Leu Ile Ser Glu Glu Asp
65                  70

<210> SEQ ID NO 170
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 170

Ala Thr Val Lys Phe Thr Tyr Arg Gly Glu Glu Lys Gln Val Gly Ile
1               5                   10                  15

Ser Arg Ile Lys Ser Val His Arg Ile Gly Gln Trp Ile Lys Phe Trp
            20                  25                  30

Tyr Asp Glu Gly Ser Gly Ala Tyr Gly Arg Gly Tyr Val Ser Glu Lys
        35                  40                  45

Asp Ala Pro Lys Glu Leu Leu Arg Met Leu Gly Lys Arg Gly Ser Glu
    50                  55                  60

Gln Lys Leu Ile Ser Glu Glu Asp
65                  70

<210> SEQ ID NO 171
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 171

Ala Thr Val Lys Phe Thr Tyr Arg Gly Glu Glu Lys Gln Val Gly Val
1               5                   10                  15

Ser Arg Ile Lys Ser Val His Arg Ile Gly Gln Trp Ile Lys Phe Trp
                20                  25                  30

Tyr Asp Gly Gly Ser Gly Ala Tyr Gly Arg Gly Tyr Val Ser Glu Lys
            35                  40                  45

Asp Ala Pro Lys Glu Leu Leu Gln Met Leu Glu Lys Arg Gly Ser Glu
        50                  55                  60

Gln Lys Leu Ile Ser Glu Glu Asp
65                  70

<210> SEQ ID NO 172
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 172

Ala Thr Val Lys Phe Thr Tyr Arg Gly Glu Glu Lys Gln Val Gly Ile
1               5                   10                  15

Ser Arg Ile Lys Ser Val His Arg Ile Gly Gln Trp Ile Lys Phe Trp
                20                  25                  30

Tyr Asp Gly Gly Ser Gly Ala Tyr Gly Arg Gly Tyr Val Ser Glu Lys
            35                  40                  45

Asp Ala Pro Lys Glu Leu Leu Gln Met Leu Glu Lys Arg Gly Ser Glu
        50                  55                  60

Gln Lys Leu Ile Ser Glu Glu Asp
65                  70

<210> SEQ ID NO 173
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 173

Ala Thr Val Lys Phe Thr Tyr Arg Gly Glu Glu Lys Gln Val Gly Val
1               5                   10                  15

Ser Arg Val Lys Ser Val His Arg Ile Gly Gln Trp Ile Lys Phe Trp
                20                  25                  30

Tyr Asp Glu Gly Ser Gly Ala Tyr Gly Arg Gly Tyr Val Ser Glu Lys
            35                  40                  45

Asp Ala Pro Glu Glu Leu Leu Gln Met Leu Glu Lys Arg Gly Ser Glu
        50                  55                  60

Gln Lys Leu Ile Ser Glu Glu Asp
65                  70

<210> SEQ ID NO 174
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 174

Ala Thr Val Lys Phe Thr Tyr Arg Gly Glu Glu Lys Gln Val Gly Ile
1               5                   10                  15

Ser Arg Ile Lys Ser Val His Arg Ile Gly Gln Trp Ile Lys Phe Trp
           20                  25                  30

Tyr Asp Glu Gly Ser Gly Ala His Gly Arg Gly Tyr Val Ser Glu Lys
        35                  40                  45

Asp Ala Pro Lys Glu Leu Leu Gln Met Leu Glu Lys Arg Gly Ser Glu
    50                  55                  60

Gln Lys Leu Ile Ser Glu Glu Asp
65                  70

<210> SEQ ID NO 175
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 175

Ala Thr Val Lys Phe Thr Tyr Arg Gly Glu Glu Lys Gln Val Gly Ile
1               5                   10                  15

Ser Arg Ile Lys Ser Val His Arg Ile Gly Gln Trp Ile Lys Phe Arg
           20                  25                  30

Tyr Asp Glu Gly Ser Gly Ala Tyr Gly Arg Gly Tyr Val Ser Glu Lys
        35                  40                  45

Asp Ala Pro Lys Glu Leu Leu Gln Met Leu Glu Lys Arg Gly Ser Glu
    50                  55                  60

Gln Lys Leu Ile Ser Glu Glu Asp
65                  70

<210> SEQ ID NO 176
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 176

Val Thr Val Glu Phe Thr Tyr Arg Gly Glu Glu Lys Gln Val Asp Ile
1               5                   10                  15

Ser Lys Ile Lys His Val Arg Arg Trp Gly Arg Trp Ile Trp Phe Ile
           20                  25                  30

Tyr Glu Glu Gly Gly Gly Ala Lys Gly Arg Gly Val Ser Glu Lys
        35                  40                  45

Asp Ala Pro Lys Glu Leu Leu Gln Met Leu Glu Lys Arg Gly Ser Glu
    50                  55                  60

Gln Lys Leu Ile Ser Glu Glu Asp
65                  70

<210> SEQ ID NO 177
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 177

Ala Thr Val Lys Phe Thr Tyr Gln Gly Glu Glu Lys Gln Val Asp Ile
1               5                   10                  15

Ser Lys Ile Lys His Val Arg Arg Trp Gly Arg Trp Ile Trp Phe Ile
           20                  25                  30

Tyr Glu Glu Gly Gly Gly Ala Lys Gly Arg Gly Gly Val Ser Glu Lys

```
        35                  40                  45

Asp Ala Pro Lys Glu Leu Leu Gln Met Leu Glu Lys Gln Gly Ser Glu
    50                  55                  60

Gln Lys Leu Ile Ser Glu Glu Asp
65                  70

<210> SEQ ID NO 178
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 178

Ala Thr Val Lys Phe Thr Tyr Gln Gly Glu Glu Lys Gln Val Asp Ile
1               5                   10                  15

Ser Lys Ile Lys His Val Arg Arg Trp Gly Arg Trp Ile Trp Phe Ile
                20                  25                  30

Tyr Glu Glu Gly Gly Gly Ala Lys Gly Arg Gly Val Ser Glu Lys
            35                  40                  45

Asp Ala Pro Lys Glu Leu Leu Gln Met Leu Glu Lys Arg Gly Ser Glu
    50                  55                  60

Gln Lys Leu Ile Ser Glu Glu Asp
65                  70

<210> SEQ ID NO 179
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 179

Ala Thr Val Arg Phe Thr Tyr Gln Gly Glu Glu Lys Gln Val Asp Ile
1               5                   10                  15

Ser Lys Ile Lys His Val Arg Arg Trp Gly Arg Trp Ile Trp Phe Ile
                20                  25                  30

Tyr Glu Glu Gly Gly Gly Ala Lys Gly Arg Gly Val Ser Glu Lys
            35                  40                  45

Asp Ala Pro Lys Glu Leu Leu Gln Met Leu Glu Lys Arg Gly Ser Glu
    50                  55                  60

Gln Lys Leu Ile Ser Glu Glu Asp
65                  70

<210> SEQ ID NO 180
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 180

Ala Thr Val Lys Phe Thr Tyr Gln Gly Glu Glu Lys Gln Val Asp Ile
1               5                   10                  15

Ser Lys Ile Lys His Val Arg Arg Trp Gly Arg Trp Ile Trp Phe Ile
                20                  25                  30

Tyr Glu Glu Gly Gly Gly Gly Lys Gly Arg Gly Val Ser Glu Lys
            35                  40                  45

Asp Ala Pro Lys Glu Leu Leu Gln Met Leu Glu Lys Arg Gly Ser Glu
    50                  55                  60
```

Gln Lys Leu Ile Ser Glu Glu Asp
65                  70

<210> SEQ ID NO 181
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 181

Ala Thr Val Lys Phe Thr His Gln Gly Glu Glu Lys Gln Val Asp Ile
1               5                   10                  15

Ser Lys Ile Lys His Val Arg Arg Trp Gly Arg Trp Ile Trp Phe Ile
                20                  25                  30

Tyr Glu Glu Gly Gly Gly Ala Lys Gly Arg Gly Gly Val Ser Glu Lys
            35                  40                  45

Asp Ala Pro Lys Glu Leu Leu Gln Met Leu Glu Lys Arg Gly Ser Glu
        50                  55                  60

Gln Lys Leu Ile Ser Glu Glu Asp
65                  70

<210> SEQ ID NO 182
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 182

Ala Ile Val Lys Phe Thr Tyr Gln Gly Glu Glu Lys Gln Val Asp Ile
1               5                   10                  15

Ser Lys Ile Lys His Val Arg Arg Trp Gly Arg Trp Ile Trp Phe Ile
                20                  25                  30

Tyr Glu Glu Gly Gly Gly Ala Lys Gly Arg Gly Gly Val Ser Glu Lys
            35                  40                  45

Asp Ala Pro Lys Glu Leu Leu Gln Met Leu Glu Lys Arg Gly Ser Glu
        50                  55                  60

Gln Lys Leu Ile Ser Glu Glu Asp
65                  70

<210> SEQ ID NO 183
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 183

Ala Ala Val Lys Phe Thr Tyr Gln Gly Glu Glu Lys Gln Val Asp Ile
1               5                   10                  15

Ser Lys Ile Lys His Val Arg Arg Trp Gly Arg Trp Ile Trp Phe Ile
                20                  25                  30

Tyr Glu Glu Gly Gly Gly Ala Lys Gly Arg Gly Gly Val Ser Glu Lys
            35                  40                  45

Asp Ala Pro Lys Glu Leu Leu Gln Met Leu Glu Lys Gln Gly Ser Glu
        50                  55                  60

Gln Lys Leu Ile Ser Glu Glu Asp
65                  70

<210> SEQ ID NO 184
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 184

```
Ala Thr Val Lys Phe Thr Tyr Gln Gly Glu Glu Lys Gln Val Asp Ile
1               5                   10                  15

Ser Lys Ile Lys His Val Arg Arg Trp Gly Arg Trp Ile Trp Phe Ile
            20                  25                  30

Tyr Glu Ala Gly Gly Gly Ala Lys Gly Arg Gly Val Ser Glu Lys
        35                  40                  45

Asp Ala Pro Lys Glu Leu Leu Gln Met Leu Glu Lys Gln Gly Ser Glu
    50                  55                  60

Gln Lys Leu Ile Ser Glu Glu Asp
65                  70
```

<210> SEQ ID NO 185
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 185

```
Ala Thr Val Lys Phe Thr Tyr Gln Gly Glu Glu Lys Gln Val Asp Ile
1               5                   10                  15

Ser Lys Ile Lys His Val Arg Arg Trp Gly Arg Trp Ile Trp Phe Ile
            20                  25                  30

Tyr Glu Gly Gly Gly Ala Lys Gly Arg Gly Val Ser Glu Lys
        35                  40                  45

Asp Ala Pro Lys Glu Leu Leu Gln Met Leu Glu Arg Arg Gly Ser Glu
    50                  55                  60

Gln Lys Leu Ile Ser Glu Glu Asp
65                  70
```

<210> SEQ ID NO 186
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 186

```
Ala Thr Val Lys Phe Thr Tyr Gln Gly Glu Glu Lys Gln Val Asp Ile
1               5                   10                  15

Ser Lys Ile Lys His Val Arg Arg Trp Gly Arg Trp Ile Trp Phe Ile
            20                  25                  30

Tyr Glu Gly Gly Gly Ala Lys Gly Arg Gly Val Ser Glu Lys
        35                  40                  45

Asp Ala Pro Lys Glu Leu Leu Gln Met Leu Glu Lys Gln Gly Ser Glu
    50                  55                  60

Gln Lys Leu Ile Ser Glu Glu Asp
65                  70
```

<210> SEQ ID NO 187
<211> LENGTH: 69
<212> TYPE: PRT

<210> SEQ ID NO 187
<211> LENGTH: 69
<212> TYPE: PRT
<213> ORGANISM: Artificial Sequence
<220> FEATURE:
<223> OTHER INFORMATION: Synthetic Polypeptide

<400> SEQUENCE: 187

```
Ala Thr Val Lys Phe Thr Tyr Arg Gly Glu Glu Lys Gln Val Asp Ile
1               5                   10                  15

Ser Lys Ile Lys His Val Arg Arg Trp Gly Gln Trp Ile Trp Phe Ile
            20                  25                  30

Tyr Asp Glu Gly Gly Gly Ala Lys Gly Lys Gly Ser Val Ser Glu Lys
        35                  40                  45

Asp Ala Pro Lys Glu Leu Leu Gln Met Leu Glu Lys Ala Gly Ile Arg
    50                  55                  60

Thr Lys Ala Tyr Phe
65
```

<210> SEQ ID NO 188
<211> LENGTH: 69
<212> TYPE: PRT
<213> ORGANISM: Artificial Sequence
<220> FEATURE:
<223> OTHER INFORMATION: Synthetic Polypeptide

<400> SEQUENCE: 188

```
Ala Thr Val Lys Phe Thr Tyr Gln Gly Glu Glu Lys Gln Val Asp Val
1               5                   10                  15

Ser Lys Ile Lys His Val Arg Arg Trp Gly Gln Trp Ile Trp Phe Ile
            20                  25                  30

Tyr Asp Glu Gly Gly Gly Ala Lys Gly Lys Gly Ser Val Ser Glu Lys
        35                  40                  45

Asp Ala Pro Lys Glu Leu Leu Gln Met Leu Glu Lys Ala Gly Ile Arg
    50                  55                  60

Thr Lys Ala Tyr Phe
65
```

<210> SEQ ID NO 189
<211> LENGTH: 69
<212> TYPE: PRT
<213> ORGANISM: Artificial Sequence
<220> FEATURE:
<223> OTHER INFORMATION: Synthetic Polypeptide

<400> SEQUENCE: 189

```
Ala Thr Val Lys Phe Thr Tyr Gln Gly Glu Glu Lys Gln Val Asp Ile
1               5                   10                  15

Ser Lys Ile Lys His Val Arg Arg Trp Gly Arg Trp Ile Trp Phe Ile
            20                  25                  30

Tyr Asp Glu Gly Gly Gly Ala Lys Gly Lys Gly Ser Val Ser Glu Lys
        35                  40                  45

Asp Ala Pro Lys Glu Leu Leu Gln Met Leu Glu Lys Ala Gly Ile Arg
    50                  55                  60

Thr Lys Ala Tyr Phe
65
```

<210> SEQ ID NO 190
<211> LENGTH: 69
<212> TYPE: PRT
<213> ORGANISM: Artificial Sequence
<220> FEATURE:
<223> OTHER INFORMATION: Synthetic Polypeptide

<400> SEQUENCE: 190

Ala Thr Val Lys Phe Thr Tyr Gln Gly Glu Glu Lys Gln Val Asp Ile
1               5                   10                  15

Ser Lys Ile Lys His Val Arg Arg Trp Gly Arg Trp Ile Trp Phe Ile
            20                  25                  30

Tyr Glu Glu Gly Gly Ala Lys Gly Lys Gly Ser Val Ser Glu Lys
        35                  40                  45

Asp Ala Pro Lys Glu Leu Leu Gln Met Leu Glu Lys Ala Gly Ile Arg
    50                  55                  60

Thr Lys Ala Tyr Phe
65

<210> SEQ ID NO 191
<211> LENGTH: 69
<212> TYPE: PRT
<213> ORGANISM: Artificial Sequence
<220> FEATURE:
<223> OTHER INFORMATION: Synthetic Polypeptide

<400> SEQUENCE: 191

Ala Thr Val Lys Phe Thr Tyr Gln Gly Glu Glu Lys Gln Val Asp Ile
1               5                   10                  15

Ser Lys Ile Lys His Val Arg Arg Trp Gly Gln Arg Ile Trp Phe Ile
            20                  25                  30

Tyr Gly Glu Gly Gly Ala Lys Gly Arg Gly Ser Val Ser Glu Lys
        35                  40                  45

Asp Ala Pro Lys Glu Leu Leu Gln Met Leu Glu Lys Ala Gly Ile Arg
    50                  55                  60

Thr Lys Ala Tyr Phe
65

<210> SEQ ID NO 192
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 192

Ala Thr Val Lys Phe Thr Tyr Gln Gly Glu Glu Lys Gln Val Asp Ile
1               5                   10                  15

Ser Lys Ile Lys His Val Arg Arg Trp Gly Arg Trp Ile Trp Phe Ile
            20                  25                  30

Tyr Glu Glu Gly Gly Ala Lys Gly Arg Gly Gly Val Ser Glu Lys Asp
        35                  40                  45

Ala Pro Lys Glu Leu Leu Gln Met Leu Glu Lys Gln Gly Ser Glu Gln
    50                  55                  60

Lys Leu Ile Ser Glu Glu Asp Leu
65                  70

<210> SEQ ID NO 193
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 193

Ala Thr Val Lys Phe Thr Tyr Gln Gly Glu Glu Lys Gln Val Asp Ile
1               5                   10                  15

Ser Lys Ile Lys His Val Arg Arg Trp Gly Arg Trp Ile Trp Phe Thr
            20                  25                  30

Tyr Glu Glu Gly Gly Gly Ala Lys Gly Arg Gly Gly Val Ser Glu Lys
            35                  40                  45

Asp Ala Pro Lys Glu Leu Leu Gln Met Leu Glu Lys Gln Gly Ser Glu
        50                  55                  60

Gln Lys Leu Ile Leu Lys Arg Thr
65                  70

<210> SEQ ID NO 194
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 194

Ala Thr Val Lys Phe Thr Tyr Gln Gly Glu Glu Lys Gln Val Asp Ile
1               5                   10                  15

Ser Lys Ile Lys His Val Arg Arg Trp Gly Arg Trp Ile Trp Phe Thr
            20                  25                  30

Tyr Glu Glu Gly Gly Gly Ala Lys Gly Arg Gly Gly Val Ser Glu Lys
            35                  40                  45

Asp Ala Pro Lys Glu Leu Leu Gln Met Leu Glu Lys Pro Gly Ser Glu
        50                  55                  60

Gln Lys Leu Ile Ser Glu Glu Asp
65                  70

<210> SEQ ID NO 195
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 195

Ala Thr Val Lys Phe Thr Tyr Gln Gly Glu Glu Lys Gln Val Asp Ile
1               5                   10                  15

Ser Lys Ile Lys His Val Arg Arg Trp Gly Arg Trp Ile Trp Phe Thr
            20                  25                  30

Tyr Glu Glu Gly Gly Gly Ala Arg Gly Arg Gly Gly Val Ser Glu Lys
            35                  40                  45

Asp Ala Pro Lys Glu Leu Leu Gln Met Leu Glu Lys Gln Gly Ser Glu
        50                  55                  60

Gln Lys Leu Ile Ser Glu Glu Asp
65                  70

<210> SEQ ID NO 196
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 196

Ala Thr Val Lys Phe Thr Tyr Gln Gly Glu Glu Lys Gln Val Asp Val
1               5                   10                  15

Ser Lys Ile Lys His Val Arg Arg Trp Gly Arg Trp Ile Trp Phe Thr
            20                  25                  30

Tyr Glu Glu Gly Gly Gly Ala Lys Gly Arg Gly Val Ser Glu Lys
            35                  40                  45

Asp Ala Pro Lys Glu Leu Leu Gln Met Leu Glu Lys Gln Gly Ser Glu
 50                      55                  60

Gln Lys Leu Ile Ser Glu Glu Asp
 65                  70

<210> SEQ ID NO 197
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 197

Ala Thr Val Lys Phe Thr Tyr Gln Gly Glu Glu Lys Gln Val Asp Ile
 1               5                  10                  15

Ser Lys Ile Lys His Val Arg Arg Trp Gly Arg Trp Ile Trp Phe Thr
            20                  25                  30

Tyr Glu Glu Gly Gly Gly Ala Lys Gly Arg Gly Gly Val Ser Glu Lys
            35                  40                  45

Asp Ala Pro Arg Glu Leu Leu Gln Met Leu Glu Lys Arg Gly Ser Glu
 50                      55                  60

Gln Lys Leu Ile Ser Glu Glu Asp
 65                  70

<210> SEQ ID NO 198
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 198

Ala Thr Val Lys Phe Thr Tyr Arg Gly Glu Glu Lys Gln Val Asp Ile
 1               5                  10                  15

Ser Glu Ile Lys His Val Arg Arg Trp Gly Arg Trp Ile Trp Phe Thr
            20                  25                  30

Tyr Glu Glu Gly Gly Gly Ala Arg Gly Arg Gly Gly Val Ser Glu Lys
            35                  40                  45

Asp Ala Pro Lys Glu Leu Leu Gln Met Leu Glu Lys Arg Gly Ser Glu
 50                      55                  60

Gln Lys Leu Ile Ser Glu Glu Asp
 65                  70

<210> SEQ ID NO 199
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 199

Ala Thr Val Lys Phe Thr Tyr Gln Gly Glu Glu Lys Gln Val Asp Ile
 1               5                  10                  15

Ser Lys Ile Arg His Val Arg Arg Trp Gly Arg Arg Ile Trp Phe Thr
            20                  25                  30

Tyr Glu Glu Gly Gly Gly Ala Lys Gly Arg Gly Gly Val Gly Glu Lys
            35                  40                  45

Asp Ala Pro Lys Glu Leu Leu Gln Met Leu Glu Lys Gln Gly Ser Glu

Gln Lys Leu Ile Ser Glu Glu Asp
65                  70

<210> SEQ ID NO 200
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 200

Ala Thr Val Lys Phe Thr Tyr Gln Gly Glu Glu Lys Gln Val Asp Ile
1               5                   10                  15

Ser Lys Ile Lys His Val Arg Arg Trp Gly Arg Arg Ile Trp Phe Ile
            20                  25                  30

Tyr Glu Glu Gly Gly Gly Ala Lys Gly Arg Gly Gly Val Ser Glu Lys
        35                  40                  45

Asp Ala Pro Lys Glu Leu Leu Gln Met Leu Glu Lys Gln Gly Ser Glu
    50                  55                  60

Gln Lys Leu Ile Ser Glu Lys Asp
65                  70

<210> SEQ ID NO 201
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 201

Ala Thr Val Lys Phe Thr Tyr Gln Gly Glu Glu Lys Gln Val Asp Ile
1               5                   10                  15

Ser Lys Ile Lys His Val Arg Arg Trp Gly Arg Arg Ile Trp Phe Ile
            20                  25                  30

Tyr Glu Glu Gly Gly Gly Ala Lys Gly Arg Gly Gly Val Ser Glu Lys
        35                  40                  45

Asp Ala Pro Lys Glu Leu Leu Gln Met Leu Glu Lys Gln Gly Ser Glu
    50                  55                  60

Gln Lys Leu Ile Ser Glu Glu Asp
65                  70

<210> SEQ ID NO 202
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 202

Ala Thr Val Lys Phe Thr Tyr Gln Gly Glu Glu Lys Gln Val Asp Ile
1               5                   10                  15

Ser Lys Ile Lys His Val Arg Arg Trp Gly Arg Trp Ile Trp Phe Ile
            20                  25                  30

Tyr Glu Glu Gly Gly Gly Ala Lys Gly Arg Gly Gly Val Gly Glu Lys
        35                  40                  45

Asp Ala Pro Lys Glu Leu Leu Gln Met Leu Lys Gln Gly Ser Glu
    50                  55                  60

Gln Lys Leu Ile Ser Glu Glu Asp
65                  70

<210> SEQ ID NO 203
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 203

Ala Thr Val Lys Phe Thr Tyr Gln Gly Glu Gly Lys Gln Val Asp Ile
1               5                   10                  15

Ser Lys Ile Lys His Val Arg Arg Trp Gly Arg Trp Ile Trp Phe Ile
            20                  25                  30

Tyr Glu Glu Gly Gly Gly Ala Lys Gly Arg Gly Gly Val Ser Glu Lys
        35                  40                  45

Asp Ala Pro Lys Glu Leu Leu Gln Met Leu Glu Lys Gln Gly Ser Glu
    50                  55                  60

Gln Lys Leu Ile Ser Glu Glu Asp
65                  70

<210> SEQ ID NO 204
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 204

Ala Thr Val Lys Phe Thr Tyr Gln Gly Glu Glu Lys Gln Val Asp Ile
1               5                   10                  15

Ser Lys Ile Lys Arg Val Arg Arg Trp Gly Arg Trp Ile Trp Phe Ile
            20                  25                  30

Tyr Glu Glu Gly Gly Gly Ala Lys Gly Arg Gly Gly Val Ser Glu Lys
        35                  40                  45

Asp Ala Pro Lys Glu Leu Leu Gln Met Leu Glu Lys Gln Gly Ser Glu
    50                  55                  60

Gln Lys Leu Ile Ser Glu Glu Asp
65                  70

<210> SEQ ID NO 205
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 205

Ile Thr Val Lys Phe Thr Tyr Gln Gly Glu Glu Lys Gln Val Asp Ile
1               5                   10                  15

Ser Lys Ile Glu His Val Arg Arg Trp Gly Arg Trp Ile Trp Phe Thr
            20                  25                  30

Tyr Asp Glu Gly Gly Gly Ala Lys Gly Arg Gly Gly Val Ser Glu Lys
        35                  40                  45

Gly Ala Pro Lys Glu Leu Leu Gln Met Leu Gly Lys Arg Gly Ser Glu
    50                  55                  60

Gln Lys Leu Ile Ser Glu Glu Asp
65                  70

<210> SEQ ID NO 206
<211> LENGTH: 72

<212> TYPE: PRT
<213> ORGANISM: Artificial Sequence
<220> FEATURE:
<223> OTHER INFORMATION: Synthetic Polypeptide

<400> SEQUENCE: 206

Ile Thr Val Lys Phe Thr Tyr Arg Gly Glu Glu Lys Gln Val Asp Ile
1               5                   10                  15

Ser Lys Ile Glu His Val Arg Arg Trp Gly Gln Trp Ile Trp Phe Thr
            20                  25                  30

Tyr Asp Glu Gly Gly Gly Ala Lys Gly Arg Gly Gly Val Ser Glu Lys
        35                  40                  45

Gly Ala Pro Arg Glu Leu Leu Gln Met Leu Gly Lys Arg Gly Ser Glu
    50                  55                  60

Gln Lys Leu Ile Ser Glu Glu Asp
65                  70

<210> SEQ ID NO 207
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 207

Ala Thr Val Lys Phe Thr Tyr Gln Gly Glu Glu Lys Gln Val Asp Ile
1               5                   10                  15

Ser Lys Ile Lys His Val Arg Arg Trp Gly Arg Trp Ile Trp Phe Thr
            20                  25                  30

Tyr Asp Glu Gly Gly Gly Ala Lys Gly Arg Gly Gly Val Ser Glu Lys
        35                  40                  45

Gly Ala Pro Lys Glu Leu Leu Gln Met Leu Gly Lys Arg Gly Ser Glu
    50                  55                  60

Gln Lys Leu Ile Ser Glu Glu Asp
65                  70

<210> SEQ ID NO 208
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 208

Ala Thr Val Lys Phe Thr Tyr Gln Gly Glu Glu Lys Gln Val Asp Ile
1               5                   10                  15

Ser Lys Ile Lys His Val Arg Arg Trp Gly Arg Trp Ile Trp Phe Thr
            20                  25                  30

Tyr Glu Glu Gly Gly Gly Ala Lys Gly Arg Gly Gly Val Ser Glu Lys
        35                  40                  45

Asp Ala Pro Lys Glu Leu Leu Gln Met Leu Gly Lys Arg Gly Ser Glu
    50                  55                  60

Gln Lys Leu Ile Ser Glu Glu Asp
65                  70

<210> SEQ ID NO 209
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 209

Ala Thr Val Lys Phe Thr Tyr Gln Gly Glu Glu Lys Arg Val Asp Ile
1               5                   10                  15

Ser Lys Ile Lys His Val Arg Arg Trp Gly Arg Trp Ile Trp Phe Ile
            20                  25                  30

Tyr Glu Glu Gly Gly Gly Ala Lys Gly Arg Gly Gly Val Ser Glu Lys
        35                  40                  45

Asp Ala Pro Lys Glu Leu Leu Gln Met Leu Gly Lys Arg Gly Ser Glu
    50                  55                  60

Gln Lys Leu Ile Ser Glu Glu Asp
65                  70

<210> SEQ ID NO 210
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 210

Ala Thr Val Lys Phe Thr Tyr Gln Gly Glu Glu Lys Gln Val Asp Ile
1               5                   10                  15

Ser Lys Ile Lys His Val Arg Arg Trp Gly Arg Trp Ile Trp Phe Ile
            20                  25                  30

Tyr Glu Glu Gly Gly Gly Ala Lys Gly Arg Gly Gly Val Ser Glu Lys
        35                  40                  45

Asp Ala Pro Lys Glu Leu Leu Gln Met Leu Gly Lys Gln Gly Ser Glu
    50                  55                  60

Gln Lys Leu Ile Ser Glu Glu Asp
65                  70

<210> SEQ ID NO 211
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 211

Ala Thr Val Lys Phe Thr Tyr Arg Gly Glu Glu Lys Gln Val Asp Ile
1               5                   10                  15

Ser Lys Ile Lys His Val Arg Arg Trp Gly Arg Trp Ile Trp Phe Ile
            20                  25                  30

Tyr Glu Glu Gly Gly Gly Ala Lys Gly Arg Gly Gly Val Ser Glu Lys
        35                  40                  45

Asp Ala Pro Lys Glu Leu Leu Gln Met Leu Gly Lys Gln Arg Ser Glu
    50                  55                  60

Gln Lys Leu Ile Ser Glu Glu Asp
65                  70

<210> SEQ ID NO 212
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 212

Ala Thr Val Lys Phe Thr Tyr His Gly Glu Glu Lys Gln Val Asp Ile

```
                1               5                  10                  15
Ser Lys Ile Lys His Val Arg Arg Trp Gly Arg Trp Ile Trp Phe Ile
            20                  25                  30

Tyr Glu Glu Gly Gly Gly Ala Lys Gly Arg Gly Gly Val Ser Glu Lys
            35                  40                  45

Asp Ala Pro Lys Glu Leu Leu Gln Met Leu Glu Lys Gln Gly Ser Glu
        50                  55                  60

Gln Lys Leu Ile Ser Glu Glu Asp
65                  70
```

<210> SEQ ID NO 213
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 213

```
Ala Thr Val Lys Phe Thr Tyr Arg Gly Glu Glu Lys Gln Val Asp Ile
1               5                  10                  15

Ser Lys Ile Lys His Val Arg Arg Trp Gly Gln Trp Ile Trp Phe Ile
            20                  25                  30

Tyr Asp Lys Gly Gly Gly Ala Lys Gly Arg Gly Gly Val Ser Glu Lys
            35                  40                  45

Asp Ala Pro Lys Glu Leu Leu Gln Met Leu Glu Lys Gln Gly Ser Glu
        50                  55                  60

Gln Lys Leu Ile Ser Glu Glu Asp
65                  70
```

<210> SEQ ID NO 214
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 214

```
Ala Thr Val Lys Phe Thr Tyr Arg Gly Glu Glu Lys Gln Val Asp Ile
1               5                  10                  15

Ser Lys Ile Lys His Val Arg Cys Trp Gly Gln Trp Ile Trp Phe Ile
            20                  25                  30

Tyr Asp Lys Gly Gly Gly Ala Lys Gly Arg Gly Gly Val Ser Glu Lys
            35                  40                  45

Gly Ala Pro Lys Glu Leu Leu Gln Met Leu Glu Lys Gln Gly Ser Glu
        50                  55                  60

Gln Lys Leu Ile Ser Glu Glu Asp
65                  70
```

<210> SEQ ID NO 215
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 215

```
Ala Thr Val Lys Phe Thr Tyr Arg Gly Glu Glu Lys Gln Val Gly Ile
1               5                  10                  15

Ser Arg Ile Arg Ser Val His Arg Ile Gly Gln Trp Ile Lys Phe Trp
            20                  25                  30
```

Tyr Asp Glu Gly Ser Gly Ala Tyr Gly Arg Gly Tyr Val Ser Glu Lys
        35                  40                  45

Asp Ala Pro Lys Glu Leu Leu Gln Met Leu Glu Lys Arg Gly Ser Glu
    50                  55                  60

Gln Lys Leu Ile Ser Glu Glu Asp
65                  70

<210> SEQ ID NO 216
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 216

Thr Thr Val Lys Phe Thr Tyr Arg Gly Glu Lys Gln Val Gly Ile
1               5                   10                  15

Ser Arg Ile Lys Ser Val His Arg Ile Gly Gln Trp Ile Lys Phe Trp
            20                  25                  30

Tyr Asp Lys Gly Ser Gly Ala Tyr Gly Arg Gly Tyr Val Ser Glu Lys
        35                  40                  45

Asp Ala Pro Lys Glu Leu Leu Gln Met Leu Glu Lys Arg Gly Ser Glu
    50                  55                  60

Gln Lys Leu Ile Ser Glu Glu Asp
65                  70

<210> SEQ ID NO 217
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 217

Ala Ile Val Lys Phe Thr Tyr Arg Gly Glu Lys Gln Val Gly Ile
1               5                   10                  15

Ser Arg Ile Lys Ser Val His Arg Ile Gly Gln Trp Ile Lys Phe Trp
            20                  25                  30

Tyr Gly Glu Gly Ser Gly Ala Tyr Gly Arg Gly Tyr Val Ser Glu Lys
        35                  40                  45

Asp Ala Pro Lys Glu Leu Leu Gln Met Leu Glu Lys Arg Gly Ser Glu
    50                  55                  60

Gln Lys Leu Ile Ser Glu Glu Asp
65                  70

<210> SEQ ID NO 218
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 218

Ala Thr Val Lys Phe Thr Tyr Arg Gly Gly Glu Lys Gln Val Gly Ile
1               5                   10                  15

Ser Arg Ile Lys Ser Val His Arg Ile Gly Gln Trp Ile Lys Phe Arg
            20                  25                  30

Tyr Asp Glu Gly Ser Gly Ala Tyr Gly Arg Gly Tyr Val Ser Glu Lys
        35                  40                  45

Asp Ala Pro Lys Glu Leu Leu Gln Met Leu Glu Lys Arg Gly Ser Glu
         50                  55                  60

Gln Lys Leu Ile Ser Glu Glu Asp
 65                  70

<210> SEQ ID NO 219
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 219

Ala Thr Val Lys Phe Thr Tyr Arg Gly Lys Glu Lys Gln Val Gly Ile
 1               5                  10                  15

Ser Arg Ile Lys Ser Val His Arg Ile Gly Gln Trp Ile Lys Phe Arg
                20                  25                  30

Tyr Asp Glu Gly Ser Gly Ala Tyr Gly Arg Gly Tyr Val Ser Glu Lys
            35                  40                  45

Asp Ala Pro Lys Glu Leu Leu Gln Met Leu Glu Lys Arg Gly Ser Glu
         50                  55                  60

Gln Lys Leu Ile Ser Glu Glu Asp
 65                  70

<210> SEQ ID NO 220
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 220

Ala Thr Val Lys Phe Thr Tyr Arg Gly Glu Glu Lys Gln Val Asp Ile
 1               5                  10                  15

Ser Arg Ile Lys His Val Arg Arg Trp Gly Arg Trp Ile Trp Phe Ile
                20                  25                  30

Tyr Glu Glu Gly Gly Gly Ala Lys Gly Arg Gly Gly Val Ser Glu Lys
            35                  40                  45

Asp Ala Pro Lys Glu Leu Leu Gln Met Leu Glu Lys Gln Gly Ser Glu
         50                  55                  60

Gln Lys Leu Ile Ser Glu Glu Asp
 65                  70

<210> SEQ ID NO 221
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 221

Ala Thr Val Lys Phe Thr Tyr Arg Gly Glu Glu Lys Gln Val Asp Ile
 1               5                  10                  15

Ser Lys Ile Lys His Val Arg Arg Trp Gly Arg Trp Ile Trp Phe Ile
                20                  25                  30

Tyr Glu Glu Gly Gly Gly Ala Lys Gly Arg Gly Gly Val Ser Glu Lys
            35                  40                  45

Asp Ala Pro Lys Glu Leu Leu Gln Met Leu Glu Lys Gln Gly Ser Glu
         50                  55                  60

Gln Lys Leu Ile Ser Glu Glu Asp

<210> SEQ ID NO 222
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 222

```
Ala Thr Val Lys Phe Thr Tyr Arg Gly Glu Glu Lys Gln Val Asp Ile
1               5                   10                  15
Ser Lys Ile Lys His Val Arg Arg Trp Gly Arg Trp Val Trp Phe Ile
            20                  25                  30
Tyr Glu Glu Gly Gly Gly Ala Lys Gly Arg Gly Gly Val Ser Glu Lys
        35                  40                  45
Asp Ala Pro Lys Glu Leu Leu Gln Met Leu Glu Lys Gln Gly Ser Glu
    50                  55                  60
Gln Lys Leu Ile Ser Glu Glu Asp
65                  70
```

<210> SEQ ID NO 223
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 223

```
Ala Thr Val Lys Phe Thr Tyr Arg Gly Glu Glu Lys Gln Val Asp Ile
1               5                   10                  15
Ser Lys Val Lys His Val Arg Arg Trp Gly Arg Trp Ile Trp Phe Ile
            20                  25                  30
Tyr Glu Glu Gly Gly Gly Ala Lys Gly Arg Gly Gly Val Ser Glu Lys
        35                  40                  45
Asp Ala Pro Lys Glu Leu Leu Gln Met Leu Glu Lys Gln Gly Ser Glu
    50                  55                  60
Gln Lys Leu Ile Ser Glu Glu Asp
65                  70
```

<210> SEQ ID NO 224
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 224

```
Ala Thr Val Lys Phe Thr Tyr Arg Gly Glu Glu Lys Gln Val Asp Ile
1               5                   10                  15
Ser Lys Ile Lys His Val Arg Arg Trp Gly Arg Trp Ile Trp Phe Ile
            20                  25                  30
Tyr Glu Glu Gly Gly Gly Ala Lys Gly Arg Gly Gly Val Ser Glu Lys
        35                  40                  45
Asp Ala Pro Lys Glu Leu Leu Arg Met Leu Glu Lys Gln Gly Ser Glu
    50                  55                  60
Gln Lys Leu Ile Ser Glu Glu Asp
65                  70
```

<210> SEQ ID NO 225

```
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 225

Ala Thr Val Lys Phe Thr Tyr Arg Gly Glu Glu Lys Gln Val Asp Ile
1               5                   10                  15

Ser Lys Ile Lys His Val Arg Arg Trp Gly Arg Trp Ile Trp Phe Ile
            20                  25                  30

Tyr Glu Glu Gly Gly Gly Ala Lys Gly Arg Gly Gly Val Ser Gly Lys
            35                  40                  45

Asp Ala Pro Lys Glu Leu Leu Gln Met Leu Glu Lys Gln Gly Ser Glu
    50                  55                  60

Gln Lys Leu Ile Ser Glu Glu Asp
65                  70

<210> SEQ ID NO 226
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 226

Ala Thr Val Arg Phe Thr Tyr Arg Gly Glu Glu Lys Gln Val Asp Ile
1               5                   10                  15

Ser Lys Ile Lys Tyr Val Arg Arg Trp Gly Gln Tyr Ile Trp Phe Gly
            20                  25                  30

Tyr Asp Gly Gly Gly Gly Ala Arg Gly Tyr Gly Tyr Val Ser Glu Arg
            35                  40                  45

Asp Ala Pro Lys Glu Leu Leu Gln Met Leu Glu Gln Gln Gly Ser Glu
    50                  55                  60

Gln Lys Leu Ile Ser Glu Glu Asp
65                  70

<210> SEQ ID NO 227
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 227

Ala Thr Val Arg Phe Thr Tyr Gln Gly Glu Glu Lys Gln Val Asp Ile
1               5                   10                  15

Ser Lys Ile Lys His Val Arg Arg Trp Gly Arg Tyr Ile Trp Phe Gly
            20                  25                  30

Tyr Asp Glu Gly Gly Gly Ala Arg Gly His Gly Tyr Val Ser Glu Lys
            35                  40                  45

Asp Ala Pro Lys Glu Leu Leu Gln Met Leu Glu Lys Gln Gly Ser Glu
    50                  55                  60

Gln Lys Leu Ile Ser Glu Glu Asp
65                  70

<210> SEQ ID NO 228
<211> LENGTH: 72
<212> TYPE: PRT
<213> ORGANISM: Artificial Sequence
<220> FEATURE:
```

<223> OTHER INFORMATION: Synthetic Polypeptide

<400> SEQUENCE: 228

Ala Thr Val Gln Phe Thr Tyr Gln Gly Glu Arg Gln Val Asp Ile
1               5                   10                  15

Ser Lys Ile Arg His Val Arg Arg Trp Gly Arg Trp Ile Trp Phe Ile
            20                  25                  30

Tyr Gly Glu Gly Gly Ala Lys Gly Trp Gly Val Ser Ala Lys
        35                  40                  45

Asp Ala Pro Lys Glu Leu Leu Gln Met Leu Glu Lys Gln Gly Ser Glu
    50                  55                  60

Gln Lys Leu Ile Ser Glu Glu Asp
65                  70

<210> SEQ ID NO 229
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 229

Ala Thr Val Lys Phe Thr Tyr Gln Gly Gly Glu Lys Gln Val Asp Ile
1               5                   10                  15

Ser Lys Ile Lys His Val Arg Arg Trp Gly Gln Trp Ile Trp Phe Ile
            20                  25                  30

Tyr Asp Glu Gly Gly Ala Lys Gly Trp Gly Val Ser Gly Lys
        35                  40                  45

Asp Ala Pro Lys Glu Leu Leu Gln Met Leu Glu Lys Arg Gly Ser Glu
    50                  55                  60

Gln Lys Leu Ile Ser Glu Glu Asp
65                  70

<210> SEQ ID NO 230
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 230

Ala Thr Val Lys Phe Thr Tyr Arg Gly Glu Glu Lys Gln Val Asp Ile
1               5                   10                  15

Ser Lys Ile Lys Tyr Val Arg Arg Trp Gly Gln Tyr Ile Trp Phe Gly
            20                  25                  30

Tyr Asp Glu Gly Gly Ala Arg Gly Tyr Gly Tyr Val Ser Glu Arg
        35                  40                  45

Asp Ala Pro Lys Glu Leu Leu Gln Met Leu Glu Lys Gln Gly Ser Glu
    50                  55                  60

Gln Lys Leu Ile Ser Glu Glu Asp
65                  70

<210> SEQ ID NO 231
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 231

```
Ala Thr Val Lys Phe Thr Tyr Arg Gly Glu Glu Lys Gln Val Asp Ile
1               5                   10                  15

Ser Lys Ile Lys His Val Arg Arg Trp Gly Gln Tyr Ile Trp Phe Gly
            20                  25                  30

Tyr Asp Glu Gly Gly Gly Ala Arg Gly Tyr Gly Tyr Val Ser Glu Lys
            35                  40                  45

Asp Ala Pro Lys Gly Leu Leu Gln Met Leu Glu Lys Gln Gly Ser Glu
        50                  55                  60

Gln Lys Leu Ile Ser Glu Asp
65                  70
```

<210> SEQ ID NO 232
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 232

```
Ala Thr Val Lys Phe Thr Tyr Arg Gly Glu Glu Lys Gln Val Asp Ile
1               5                   10                  15

Ser Lys Ile Lys His Val Arg Arg Trp Gly Gln Trp Ile Trp Phe Ile
            20                  25                  30

Tyr Asp Glu Gly Gly Gly Ala Lys Gly Trp Gly Gly Val Ser Glu Arg
            35                  40                  45

Asp Ala Pro Lys Gly Leu Leu Gln Met Leu Glu Lys Gln Gly Ser Glu
        50                  55                  60

Gln Lys Leu Ile Ser Glu Asp
65                  70
```

<210> SEQ ID NO 233
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 233

```
Ala Ala Val Lys Phe Thr Tyr Gln Gly Glu Glu Lys Gln Val Asp Ile
1               5                   10                  15

Ser Lys Ile Lys Tyr Val Trp Arg Trp Gly Arg Trp Ile Trp Phe Arg
            20                  25                  30

Tyr Asp Glu Gly Gly Gly Ala His Gly Ile Gly His Val Ser Glu Lys
            35                  40                  45

Asp Val Pro Lys Glu Leu Leu Gln Met Leu Glu Lys Gln Gly Ser Glu
        50                  55                  60

Gln Lys Leu Ile Ser Glu Asp
65                  70
```

<210> SEQ ID NO 234
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 234

```
Ala Thr Val Arg Phe Thr Tyr Arg Gly Glu Glu Lys Gln Val Asp Ile
1               5                   10                  15

Ser Arg Ile Lys Tyr Val Arg Arg Trp Gly Gln Tyr Ile Trp Leu Gly
```

```
            20                  25                  30

Tyr Asp Gly Gly Gly Gly Ala Arg Gly Tyr Gly Tyr Val Ser Glu Lys
            35                  40                  45

Gly Ala Pro Lys Glu Leu Leu Gln Met Leu Glu Lys Gln Gly Ser Glu
    50                  55                  60

Gln Lys Leu Ile Ser Glu Glu Asp
65                  70

<210> SEQ ID NO 235
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 235

Ala Thr Val Lys Phe Thr Tyr Arg Gly Glu Glu Lys Gln Val Asp Ile
1               5                   10                  15

Ser Lys Ile Lys Tyr Val Arg Arg Trp Gly Gln Tyr Ile Trp Phe Gly
            20                  25                  30

Tyr Gly Glu Gly Gly Gly Ala Arg Gly Tyr Gly Tyr Val Ser Glu Lys
            35                  40                  45

Asp Ala Pro Lys Glu Leu Leu Gln Met Leu Lys Lys Gln Gly Ser Glu
    50                  55                  60

Gln Lys Leu Ile Ser Glu Glu Asp
65                  70

<210> SEQ ID NO 236
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 236

Ala Ala Val Lys Phe Thr Tyr Gln Gly Glu Glu Lys Gln Val Asp Thr
1               5                   10                  15

Ser Lys Ile Lys His Val Arg Arg Trp Gly Arg Tyr Ile Trp Phe Gly
            20                  25                  30

Tyr Asp Glu Gly Gly Gly Ala Arg Gly His Gly Tyr Val Ser Glu Lys
            35                  40                  45

Asp Ala Pro Lys Glu Leu Leu Gln Met Leu Glu Lys Gln Gly Ser Glu
    50                  55                  60

Gln Lys Leu Ile Ser Glu Glu Asp
65                  70

<210> SEQ ID NO 237
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 237

Ala Thr Val Lys Phe Thr Tyr Arg Gly Glu Glu Gly Gln Val Asp Ile
1               5                   10                  15

Ser Lys Val Lys Tyr Val Trp Arg Trp Gly Gln Trp Ile Trp Phe Arg
            20                  25                  30

Tyr Asp Gly Gly Gly Ala His Gly Ile Gly Tyr Val Ser Glu Lys
            35                  40                  45
```

```
Asp Thr Pro Lys Glu Leu Leu Gln Met Leu Glu Lys Gln Gly Ser Glu
        50                  55                  60

Gln Lys Leu Ile Ser Glu Glu Asp
 65                  70

<210> SEQ ID NO 238
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 238

Ala Thr Val Lys Phe Thr Tyr Gln Gly Glu Glu Lys Gln Val Gly Ile
  1               5                  10                  15

Ser Lys Ile Arg Tyr Val Arg Arg Trp Gly Gln Tyr Ile Trp Phe Gly
                 20                  25                  30

Tyr Asp Glu Gly Gly Gly Thr Arg Gly Tyr Tyr Val Ser Glu Arg
             35                  40                  45

Asp Ala Pro Lys Glu Leu Leu Gln Met Leu Glu Arg Arg Gly Ser Glu
        50                  55                  60

Gln Lys Leu Ile Ser Glu Glu Asp
 65                  70

<210> SEQ ID NO 239
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 239

Ala Thr Val Lys Phe Thr Tyr Gln Gly Glu Glu Lys Gln Val Asp Ile
  1               5                  10                  15

Ser Lys Ile Lys His Val Arg Arg Trp Gly Gln Trp Ile Trp Phe Ile
                 20                  25                  30

Tyr Asp Glu Gly Gly Gly Ala Arg Gly Arg Gly Tyr Val Ser Glu Lys
             35                  40                  45

Gly Ala Pro Glu Glu Leu Leu Gln Met Leu Lys Gln Gly Ser Glu
        50                  55                  60

Gln Lys Leu Ile Ser Glu Glu Asp
 65                  70

<210> SEQ ID NO 240
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 240

Ala Thr Val Lys Phe Thr Tyr His Gly Glu Gly Lys Gln Val Asp Ile
  1               5                  10                  15

Ser Lys Ile Lys Tyr Val Arg Arg Trp Gly Arg Tyr Ile Trp Phe Gly
                 20                  25                  30

Tyr Asp Glu Gly Gly Gly Ala Arg Gly Tyr Tyr Val Ser Glu Lys
             35                  40                  45

Gly Ala Pro Glu Glu Leu Leu Gln Met Leu Glu Lys Gln Gly Ser Glu
        50                  55                  60
```

Gln Lys Leu Ile Ser Glu Glu Asp
65                  70

<210> SEQ ID NO 241
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 241

Ala Thr Val Lys Phe Thr Tyr Arg Gly Glu Lys Gln Val Asp Ile
1               5                   10                  15

Ser Lys Ile Lys Tyr Val Arg Arg Trp Gly Arg Tyr Ile Trp Phe Gly
            20                  25                  30

Tyr Asp Glu Gly Gly Gly Ala Arg Gly Tyr Tyr Val Ser Glu Lys
        35                  40                  45

Asp Ala Pro Lys Glu Leu Leu Gln Met Leu Lys Gln Gly Ser Glu
    50                  55                  60

Gln Lys Leu Ile Ser Glu Glu Asp
65                  70

<210> SEQ ID NO 242
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 242

Ala Thr Val Lys Phe Thr Tyr Gln Gly Glu Glu Lys Gln Val Asp Ile
1               5                   10                  15

Ser Lys Ile Lys His Val Arg Arg Trp Gly Gln Trp Ile Trp Phe Ile
            20                  25                  30

Tyr Asp Glu Gly Gly Gly Ala Lys Gly Trp Gly Val Ser Gly Lys
        35                  40                  45

Asp Ala Pro Lys Glu Leu Leu Gln Met Leu Lys Gln Gly Ser Glu
    50                  55                  60

Gln Lys Leu Ile Ser Glu Glu Asp
65                  70

<210> SEQ ID NO 243
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 243

Ala Thr Val Lys Phe Thr Tyr Gln Gly Glu Glu Lys Gln Val Asp Ile
1               5                   10                  15

Ser Lys Ile Lys Tyr Val Arg Arg Trp Gly Gln Tyr Ile Trp Phe Gly
            20                  25                  30

Tyr Gly Glu Gly Gly Gly Ala Arg Gly Tyr Gly His Val Ser Glu Arg
        35                  40                  45

Asp Ala Pro Lys Glu Leu Leu Gln Met Leu Lys Gln Gly Ser Glu
    50                  55                  60

Gln Lys Leu Ile Ser Glu Glu Asp
65                  70

```
<210> SEQ ID NO 244
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 244

Ala Thr Val Lys Phe Thr Tyr Arg Gly Glu Glu Lys Gln Val Ala Ile
1               5                   10                  15

Ser Lys Ile Lys Tyr Val Arg Arg Trp Gly Gln His Ile Trp Phe Gly
            20                  25                  30

Tyr Asp Lys Gly Gly Gly Ala His Gly Ile Gly Tyr Val Ser Glu Arg
        35                  40                  45

Asp Ala Pro Lys Glu Leu Leu Gln Met Leu Asp Glu Gln Gly Ser Glu
    50                  55                  60

Gln Lys Leu Ile Ser Glu Glu Asp
65                  70

<210> SEQ ID NO 245
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 245

Ala Thr Val Lys Phe Thr Tyr Arg Gly Glu Glu Lys Arg Val Asp Ile
1               5                   10                  15

Ser Lys Ile Lys His Val Arg Arg Trp Gly Gln Trp Ile Trp Phe Ile
            20                  25                  30

Tyr Asp Gly Gly Gly Gly Ala Lys Gly Trp Gly Val Ser Glu Lys
        35                  40                  45

Asp Ala Pro Lys Glu Leu Leu Gln Met Leu Glu Glu Gln Gly Ser Glu
    50                  55                  60

Gln Lys Leu Ile Ser Glu Glu Asp
65                  70

<210> SEQ ID NO 246
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 246

Ala Thr Val Lys Phe Thr Tyr Arg Gly Glu Glu Lys Gln Val Asp Ile
1               5                   10                  15

Ser Lys Ile Lys Tyr Val Arg Arg Trp Gly Gln Tyr Ile Trp Phe Gly
            20                  25                  30

Tyr Asp Glu Gly Gly Gly Ala Arg Gly Tyr Gly Tyr Val Ser Glu Lys
        35                  40                  45

Asp Ala Pro Glu Glu Leu Leu Gln Met Leu Glu Lys His Gly Ser Glu
    50                  55                  60

Gln Lys Leu Ile Ser Glu Glu Asp
65                  70

<210> SEQ ID NO 247
<211> LENGTH: 72
<212> TYPE: PRT
<213> ORGANISM: Artificial Sequence
```

<220> FEATURE:
<223> OTHER INFORMATION: Synthetic Polypeptide

<400> SEQUENCE: 247

Ala Thr Val Arg Phe Thr Tyr His Gly Glu Glu Lys Gln Val Asp Ile
1               5                   10                  15

Ser Lys Ile Lys Tyr Val Arg Arg Trp Gly Gln Trp Ile Trp Phe Ile
            20                  25                  30

Tyr Asp Glu Gly Gly Gly Ala Asn Gly Lys Gly Ser Val Ser Glu Lys
        35                  40                  45

Asp Ala Pro Lys Glu Leu Leu Gln Met Leu Lys Gln Gly Ser Glu
    50                  55                  60

Gln Lys Leu Ile Ser Glu Glu Asp
65                  70

<210> SEQ ID NO 248
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 248

Ala Thr Val Lys Phe Thr Tyr Arg Gly Glu Glu Lys Gln Val Asp Ile
1               5                   10                  15

Ser Lys Ile Lys Tyr Val Arg Arg Trp Gly Gln Tyr Ile Trp Phe Gly
            20                  25                  30

Tyr Asp Glu Gly Gly Gly Ala Arg Gly His Gly Tyr Val Ser Glu Asn
        35                  40                  45

Asp Ala Pro Lys Glu Leu Leu Gln Met Leu Lys Gln Gly Ser Glu
    50                  55                  60

Gln Lys Leu Ile Ser Glu Glu Asp
65                  70

<210> SEQ ID NO 249
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 249

Ala Thr Val Glu Phe Thr Tyr Arg Gly Glu Glu Lys Gln Val Asp Ile
1               5                   10                  15

Ser Lys Ile Lys Tyr Val Arg Arg Trp Gly Gln Tyr Ile Trp Phe Gly
            20                  25                  30

Tyr Asp Gly Gly Gly Gly Ala Arg Gly Tyr Gly Tyr Val Ser Glu Lys
        35                  40                  45

Asp Ala Pro Lys Glu Leu Leu Gln Met Leu Glu Gln Gly Ser Glu
    50                  55                  60

Gln Lys Leu Ile Ser Glu Glu Asp
65                  70

<210> SEQ ID NO 250
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 250

Ala Thr Val Lys Phe Thr Tyr Arg Gly Glu Glu Lys Gln Val Gly Ile
1               5                   10                  15

Ser Lys Ile Lys Tyr Val Arg Arg Trp Gly Gln Tyr Ile Trp Phe Gly
            20                  25                  30

Tyr Asp Glu Gly Gly Gly Ala Arg Gly Tyr Tyr Val Ser Glu Lys
        35                  40                  45

Asp Ala Pro Lys Glu Leu Leu Gln Met Leu Asp Lys Gln Gly Ser Glu
    50                  55                  60

Gln Lys Leu Ile Ser Glu Glu Asp
65                  70

<210> SEQ ID NO 251
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 251

Ala Thr Val Lys Phe Thr Tyr Arg Gly Glu Glu Lys Gln Val Asp Ile
1               5                   10                  15

Ser Lys Ile Lys His Val Arg Arg Trp Gly Gln Trp Ile Trp Phe Ile
            20                  25                  30

Tyr Asp Gly Gly Gly Gly Ala Lys Gly Trp Gly Val Ser Glu Lys
        35                  40                  45

Asp Ala Pro Lys Glu Leu Leu Gln Met Leu Glu Lys Gln Gly Ser Glu
    50                  55                  60

Gln Lys Leu Ile Ser Glu Glu Asp
65                  70

<210> SEQ ID NO 252
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 252

Ala Thr Val Lys Phe Thr Tyr Arg Gly Glu Glu Lys Gln Val Asp Ile
1               5                   10                  15

Ser Lys Ile Lys His Val Arg Arg Trp Gly Gln Trp Ile Trp Phe Ile
            20                  25                  30

Tyr Asp Glu Gly Gly Gly Ala Lys Gly Trp Gly Val Ser Glu Lys
        35                  40                  45

Asp Ala Pro Lys Glu Leu Leu Gln Met Leu Glu Lys Gln Gly Ser Glu
    50                  55                  60

Gln Lys Leu Ile Ser Glu Glu Asp
65                  70

<210> SEQ ID NO 253
<211> LENGTH: 60
<212> TYPE: PRT
<213> ORGANISM: Artificial Sequence
<220> FEATURE:
<223> OTHER INFORMATION: Synthetic Polypeptide

<400> SEQUENCE: 253

Ala Val Val Arg Phe Thr Tyr Arg Gly Glu Glu Lys Gln Val Asp Ile
1               5                   10                  15

Ser Lys Ile Lys Tyr Val Arg Arg Trp Gly Gln Tyr Ile Trp Phe Gly
            20                  25                  30

Tyr Asp Glu Gly Gly Gly Ala Arg Gly Tyr Gly Tyr Val Ser Glu Lys
        35                  40                  45

Asp Ala Pro Lys Glu Leu Leu Arg Met Leu Glu Lys
    50                  55                  60

<210> SEQ ID NO 254
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 254

Ala Thr Val Lys Phe Thr Tyr Gln Gly Glu Glu Lys Arg Val Asp Ile
1               5                   10                  15

Ser Lys Ile Lys Tyr Val Arg Arg Trp Gly Gln Tyr Ile Trp Phe Gly
            20                  25                  30

Tyr Asp Gly Gly Gly Gly Ala Arg Gly Tyr Gly His Val Ser Glu Lys
        35                  40                  45

Asp Ala Pro Arg Glu Leu Leu Gln Met Leu Glu Lys Arg Gly Ser Glu
    50                  55                  60

Gln Lys Leu Ile Ser Glu Glu Asp
65                  70

<210> SEQ ID NO 255
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 255

Ala Thr Val Lys Phe Thr Tyr Gln Gly Glu Glu Lys Gln Val Asp Ile
1               5                   10                  15

Ser Lys Ile Lys Tyr Val Trp Arg Trp Gly Gln Trp Ile Trp Phe His
            20                  25                  30

Tyr Asp Glu Gly Gly Gly Ala Arg Gly Tyr Gly Tyr Val Ser Glu Lys
        35                  40                  45

Asp Ala Pro Lys Glu Leu Leu Gln Met Leu Gly Lys Arg Gly Ser Glu
    50                  55                  60

Gln Lys Leu Ile Ser Glu Glu Asp
65                  70

<210> SEQ ID NO 256
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 256

Ala Thr Val Lys Phe Thr Tyr Gln Gly Glu Glu Lys Gln Val Asp Ile
1               5                   10                  15

Ser Lys Ile Lys Tyr Val Arg Arg Trp Gly Gln Tyr Ile Trp Phe Gly
            20                  25                  30

Tyr Asp Gly Gly Gly Gly Ala Arg Gly Tyr Gly His Val Ser Glu Lys
        35                  40                  45

Asp Ala Pro Lys Glu Leu Leu Gln Met Leu Gly Gly Arg Gly Ser Glu

```
                50                  55                  60

Gln Lys Leu Ile Ser Glu Glu Asp
 65                 70

<210> SEQ ID NO 257
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 257

Ala Thr Val Lys Phe Thr Tyr Arg Gly Glu Glu Lys Gln Val Asp Ile
 1               5                  10                  15

Ser Lys Ile Lys Tyr Val Arg Arg Trp Gly Gln Tyr Ile Trp Phe Gly
                20                  25                  30

Tyr Asp Gly Gly Gly Ala Arg Gly Tyr Gly His Val Ser Glu Lys
                35                  40                  45

Asp Ala Pro Lys Glu Leu Leu Gln Met Leu Glu Glu Gln Gly Ser Glu
            50                  55                  60

Gln Lys Leu Ile Ser Glu Glu Asp
 65                 70

<210> SEQ ID NO 258
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 258

Ala Thr Val Arg Phe Thr Tyr Gln Gly Glu Glu Lys Gln Val Asp Ile
 1               5                  10                  15

Ser Lys Thr Lys His Val Arg Arg Trp Gly Gln Trp Ile Trp Phe Ile
                20                  25                  30

Tyr Asp Glu Ala Gly Gly Ala His Gly Arg Gly Arg Val Ser Glu Lys
                35                  40                  45

Asp Ala Pro Lys Glu Leu Leu Gln Met Leu Glu Lys Gln Gly Ser Glu
            50                  55                  60

Gln Lys Leu Ile Ser Glu Glu Asp
 65                 70

<210> SEQ ID NO 259
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 259

Ala Thr Val Lys Phe Thr Tyr Arg Gly Glu Glu Lys Gln Val Asp Ile
 1               5                  10                  15

Ser Lys Ile Lys Tyr Val Arg Arg Trp Gly Gln Tyr Ile Trp Phe Gly
                20                  25                  30

Tyr Asp Glu Gly Gly Ala Arg Gly Tyr Gly Tyr Val Ser Glu Thr
                35                  40                  45

Asp Ala Pro Glu Lys Leu Leu Gln Met Leu Lys Gln Gly Ser Glu
            50                  55                  60

Gln Lys Leu Ile Ser Glu Glu Asp
 65                 70
```

<210> SEQ ID NO 260
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 260

Ala Thr Val Lys Phe Thr Tyr Arg Gly Glu Glu Lys Gln Val Asp Ile
1               5                   10                  15

Ser Lys Ile Lys His Val Arg Arg Trp Gly Gln Trp Ile Trp Phe Ile
            20                  25                  30

Tyr Asp Gly Gly Gly Thr Lys Gly Trp Gly Val Ser Glu Lys
            35                  40                  45

Asp Ala Pro Lys Glu Leu Leu Gln Met Leu Glu Lys Gln Gly Ser Glu
    50                  55                  60

Gln Lys Leu Ile Ser Glu Glu Asp
65                  70

<210> SEQ ID NO 261
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 261

Ala Thr Val Lys Phe Thr Tyr Gln Gly Glu Glu Lys Gln Val Asp Ile
1               5                   10                  15

Ser Lys Ile Lys His Val Arg Arg Trp Gly Arg Trp Ile Trp Phe Ile
            20                  25                  30

Tyr Asp Glu Gly Gly Gly Ala Lys Gly Trp Gly Val Ser Gly Arg
            35                  40                  45

Asp Ala Pro Lys Glu Leu Leu Gln Met Leu Glu Lys Gln Gly Ser Glu
    50                  55                  60

Gln Lys Leu Ile Ser Glu Glu Asp
65                  70

<210> SEQ ID NO 262
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 262

Ala Thr Val Lys Phe Thr Tyr Gln Gly Glu Glu Lys Gln Val Gly Ile
1               5                   10                  15

Ser Arg Ile Lys Tyr Val Arg Arg Gly Gln Tyr Ile Trp Phe Gly
            20                  25                  30

Tyr Asp Lys Gly Gly Gly Ala Arg Gly Tyr Gly Tyr Val Ser Glu Lys
            35                  40                  45

Asp Ala Pro Lys Glu Leu Leu Gln Met Leu Glu Lys Gln Gly Ser Glu
    50                  55                  60

Gln Lys Leu Ile Ser Glu Glu Asp
65                  70

<210> SEQ ID NO 263
<211> LENGTH: 72

<212> TYPE: PRT
<213> ORGANISM: Artificial Sequence
<220> FEATURE:
<223> OTHER INFORMATION: Synthetic Polypeptide

<400> SEQUENCE: 263

Ala Thr Val Arg Phe Thr Tyr Gln Gly Glu Glu Lys Gln Val Asp Ile
1               5                   10                  15

Ser Lys Ile Lys His Val Arg Arg Trp Gly Gln Trp Ile Trp Phe Ile
            20                  25                  30

Tyr Asp Glu Gly Gly Gly Ala Lys Gly Arg Gly Gly Val Ser Glu Lys
        35                  40                  45

Asp Ala Pro Lys Glu Leu Leu Gln Met Leu Glu Lys Gln Gly Ser Glu
    50                  55                  60

Gln Lys Leu Ile Ser Glu Glu Asp
65                  70

<210> SEQ ID NO 264
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 264

Ala Thr Val Lys Phe Thr Tyr Arg Gly Glu Glu Lys Gln Val Asp Ile
1               5                   10                  15

Ser Lys Ile Lys Tyr Val Arg Arg Trp Gly Gln Tyr Ile Trp Phe Gly
            20                  25                  30

Tyr Asp Glu Gly Gly Gly Ala Arg Gly Tyr Gly Tyr Val Ser Glu Lys
        35                  40                  45

Asp Ala Pro Lys Gly Leu Leu Gln Met Leu Glu Lys Arg Gly Ser Glu
    50                  55                  60

Gln Lys Leu Ile Ser Glu Glu Asp
65                  70

<210> SEQ ID NO 265
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 265

Ala Thr Val Lys Phe Thr Tyr Gln Gly Glu Glu Lys Gln Val Asp Ile
1               5                   10                  15

Ser Lys Ile Lys Tyr Val Arg Arg Trp Gly Gln Arg Ile Ser Phe Ile
            20                  25                  30

Tyr Asp Glu Gly Gly Gly Ala Arg Gly Tyr Gly Arg Val Ser Glu Lys
        35                  40                  45

Asp Ala Pro Lys Glu Leu Leu Gln Leu Leu Glu Lys Gln Gly Ser Glu
    50                  55                  60

Gln Lys Leu Ile Ser Glu Glu Asp
65                  70

<210> SEQ ID NO 266
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 266

Ala Thr Val Lys Phe Thr Tyr Arg Gly Glu Glu Gln Val Asp Ile
1               5                   10                  15

Ser Lys Ile Lys Tyr Val Trp Arg Trp Gly Gln Trp Ile Trp Leu Arg
            20                  25                  30

Tyr Asp Glu Gly Gly Gly Ala His Gly Ile Gly Tyr Val Ser Arg Lys
        35                  40                  45

Asp Ala Pro Lys Glu Leu Leu Gln Met Leu Glu Lys Gln Gly Ser Glu
    50                  55                  60

Gln Lys Leu Ile Ser Glu Glu Asp
65                  70

<210> SEQ ID NO 267
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 267

Ala Thr Val Arg Phe Thr Tyr Gln Gly Glu Glu Arg Arg Val Asp Ile
1               5                   10                  15

Ser Lys Ile Lys Tyr Val Arg Arg Trp Gly Gln His Ile Trp Phe Gly
            20                  25                  30

Tyr Asp Glu Gly Gly Gly Ala Arg Gly Tyr Gly Tyr Val Asn Glu Lys
        35                  40                  45

Gly Ala Pro Arg Glu Leu Leu Arg Met Leu Glu Lys Arg Gly Ser Glu
    50                  55                  60

Gln Lys Leu Ile Ser Glu Glu Asp
65                  70

<210> SEQ ID NO 268
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 268

Ala Thr Val Lys Phe Thr Tyr Gln Gly Glu Glu Lys Gln Val Asp Ile
1               5                   10                  15

Ser Lys Ile Lys His Val Arg Arg Trp Gly Arg Trp Ile Trp Phe Ile
            20                  25                  30

Tyr Asp Glu Gly Gly Gly Ala Lys Gly Arg Gly Gly Val Ser Glu Lys
        35                  40                  45

Asp Ala Pro Lys Glu Leu Leu Gln Met Leu Glu Lys Gln Gly Ser Glu
    50                  55                  60

Gln Lys Leu Ile Ser Glu Glu Asp
65                  70

<210> SEQ ID NO 269
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 269

Ala Thr Val Lys Phe Thr Tyr Gln Gly Glu Glu Lys Gln Val Asp Ile

```
                1               5                   10                  15
Ser Glu Ile Lys Tyr Val Arg Arg Gly Gln Tyr Ile Trp Phe Gly
                20                  25                  30

Tyr Asp Glu Gly Gly Gly Ala Arg Gly Tyr Gly Tyr Val Ser Gly Lys
                35                  40                  45

Asp Ala Pro Lys Glu Leu Leu Gln Met Leu Glu Arg Arg Gly Ser Glu
    50                  55                  60

Gln Lys Leu Ile Ser Glu Glu Asp
65                  70

<210> SEQ ID NO 270
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 270

Ala Thr Val Lys Phe Thr Tyr Gln Gly Lys Glu Gly Gln Val Ala Ile
1               5                   10                  15

Ser Lys Ile Lys Tyr Val Arg Arg Trp Gly Gln Tyr Ile Trp Phe Gly
                20                  25                  30

Tyr Asp Glu Gly Gly Gly Ala Arg Gly Tyr Gly Tyr Val Ser Glu Lys
                35                  40                  45

Asp Ala Pro Lys Glu Leu Leu Gln Met Leu Gly Lys Gln Gly Ser Glu
    50                  55                  60

Gln Lys Leu Ile Ser Glu Glu Asp
65                  70

<210> SEQ ID NO 271
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 271

Ala Thr Val Arg Phe Thr Tyr Gln Gly Glu Lys Gln Val Asp Ile
1               5                   10                  15

Ser Lys Ile Lys Tyr Val Arg Arg Trp Gly Gln Tyr Ile Trp Phe Gly
                20                  25                  30

Tyr Asp Gly Gly Gly Gly Ala Arg Gly Tyr Gly Tyr Val Ser Lys Lys
                35                  40                  45

Asp Ala Pro Lys Glu Leu Leu Gln Met Leu Glu Arg Gln Gly Ser Glu
    50                  55                  60

Gln Lys Leu Ile Ser Glu Glu Asp
65                  70

<210> SEQ ID NO 272
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 272

Ala Thr Val Lys Phe Thr Tyr Gln Gly Glu Glu Lys Gln Val Asp Ile
1               5                   10                  15

Ser Lys Ile Lys Tyr Val Trp Arg Trp Gly Arg Trp Ile Trp Phe Arg
                20                  25                  30
```

```
Tyr Asp Glu Gly Gly Gly Ala His Gly Ile Gly His Val Ser Glu Lys
        35                  40                  45

Gly Ala Pro Lys Glu Leu Leu Arg Met Leu Glu Lys Gln Gly Ser Glu
    50                  55                  60

Gln Lys Leu Ile Ser Glu Glu Asp
65                  70

<210> SEQ ID NO 273
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 273

Ala Thr Val Lys Phe Thr Tyr Gln Gly Glu Glu Lys Gln Val Asp Ile
1               5                   10                  15

Ser Lys Ile Lys His Val Arg Arg Trp Gly Arg Tyr Ile Trp Phe Gly
            20                  25                  30

Tyr Asp Glu Gly Gly Gly Ala Arg Gly Tyr Gly Tyr Val Ser Glu Lys
        35                  40                  45

Ala Ala Pro Lys Gly Leu Leu Gln Met Leu Gly Lys Gln Gly Ser Glu
    50                  55                  60

Gln Lys Leu Ile Ser Glu Glu Asp
65                  70

<210> SEQ ID NO 274
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 274

Ala Thr Val Lys Phe Thr Tyr Arg Gly Glu Glu Lys Gln Val Asp Ile
1               5                   10                  15

Ser Lys Ile Lys Tyr Val Arg Arg Trp Gly Gln Tyr Ile Trp Phe Gly
            20                  25                  30

Tyr Asp Glu Gly Gly Gly Ala Arg Gly Tyr Gly Tyr Val Ser Gly Lys
        35                  40                  45

Asp Ala Pro Lys Glu Leu Leu Gln Met Leu Gly Lys Gln Gly Ser Glu
    50                  55                  60

Gln Lys Leu Ile Ser Glu Glu Asp
65                  70

<210> SEQ ID NO 275
<211> LENGTH: 60
<212> TYPE: PRT
<213> ORGANISM: Artificial Sequence
<220> FEATURE:
<223> OTHER INFORMATION: Synthetic Polypeptide

<400> SEQUENCE: 275

Ala Thr Val Arg Phe Thr Tyr Gln Gly Glu Glu Lys Gln Val Asp Ile
1               5                   10                  15

Ser Arg Ile Lys Ile Val Tyr Arg Trp Gly Gln Arg Ile Ser Phe Ile
            20                  25                  30

Tyr Asp Lys Gly Gly Gly Ala Arg Gly Tyr Gly Arg Val Ser Glu Lys
        35                  40                  45
```

```
Asp Ala Pro Lys Glu Leu Leu Gln Met Leu Glu Lys
        50                  55                  60

<210> SEQ ID NO 276
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 276

Ala Thr Val Arg Phe Thr Tyr Arg Gly Gly Glu Lys Gln Val Asp Ile
1               5                   10                  15

Ser Lys Ile Lys Tyr Val Arg Arg Trp Gly Gln Tyr Val Trp Phe Gly
            20                  25                  30

Tyr Asp Lys Gly Gly Gly Val Arg Gly Tyr Gly Tyr Val Ser Glu Lys
        35                  40                  45

Asp Ala Pro Arg Glu Leu Leu Gln Met Leu Glu Lys Gln Gly Ser Glu
    50                  55                  60

Gln Lys Leu Ile Ser Glu Glu Asp
65                  70

<210> SEQ ID NO 277
<211> LENGTH: 69
<212> TYPE: PRT
<213> ORGANISM: Artificial Sequence
<220> FEATURE:
<223> OTHER INFORMATION: Synthetic Polypeptide

<400> SEQUENCE: 277

Ala Thr Val Lys Phe Thr Tyr Arg Gly Glu Glu Lys Gln Val Asp Ile
1               5                   10                  15

Ser Arg Ile Arg Ser Val Ser Arg Trp Gly Gln Ala Ile Val Phe Arg
            20                  25                  30

Tyr Asp Glu Gly Gly Gly Ala Lys Gly Lys Gly Ser Val Ser Glu Lys
        35                  40                  45

Asp Ala Pro Lys Glu Leu Leu Gln Met Leu Glu Lys Ala Gly Ile Arg
    50                  55                  60

Thr Lys Ala Tyr Phe
65

<210> SEQ ID NO 278
<211> LENGTH: 69
<212> TYPE: PRT
<213> ORGANISM: Artificial Sequence
<220> FEATURE:
<223> OTHER INFORMATION: Synthetic Polypeptide

<400> SEQUENCE: 278

Ala Thr Val Lys Phe Thr Tyr Gln Gly Glu Glu Lys Gln Val Gly Ile
1               5                   10                  15

Ser Lys Ile Lys His Val Arg Arg Trp Gly Gln Trp Ile Trp Phe Ile
            20                  25                  30

Tyr Asp Glu Gly Gly Gly Ala Lys Gly Arg Gly Ser Val Ser Glu Arg
        35                  40                  45

Asp Ala Pro Lys Glu Leu Leu Gln Met Leu Glu Lys Ala Gly Ile Arg
    50                  55                  60

Thr Lys Ala Tyr Phe
65
```

-continued

```
<210> SEQ ID NO 279
<211> LENGTH: 69
<212> TYPE: PRT
<213> ORGANISM: Artificial Sequence
<220> FEATURE:
<223> OTHER INFORMATION: Synthetic Polypeptide

<400> SEQUENCE: 279

Ala Thr Val Lys Phe Thr Tyr Gln Gly Glu Glu Lys Gln Val Asp Ile
1               5                   10                  15

Ser Lys Ile Lys Tyr Val Arg Arg Trp Gly Gln Tyr Ile Trp Phe Gly
            20                  25                  30

Tyr Asp Glu Gly Gly Gly Ala Arg Gly Tyr Tyr Val Ser Glu Lys
        35                  40                  45

Asp Ala Pro Lys Gly Leu Leu Gln Met Leu Glu Lys Ala Arg Ile Arg
    50                  55                  60

Thr Lys Ala Tyr Phe
65

<210> SEQ ID NO 280
<211> LENGTH: 69
<212> TYPE: PRT
<213> ORGANISM: Artificial Sequence
<220> FEATURE:
<223> OTHER INFORMATION: Synthetic Polypeptide

<400> SEQUENCE: 280

Ala Thr Val Lys Phe Thr Tyr Arg Gly Glu Glu Lys Arg Val Asp Ile
1               5                   10                  15

Ser Lys Ile Lys Tyr Val Arg Arg Trp Gly Gln Tyr Ile Trp Phe Gly
            20                  25                  30

Tyr Asp Glu Gly Gly Gly Ala Arg Gly Tyr Tyr Val Ser Gly Arg
        35                  40                  45

Asp Ala Pro Arg Glu Leu Leu Gln Met Leu Glu Lys Ala Arg Ile Arg
    50                  55                  60

Thr Lys Ala Tyr Phe
65

<210> SEQ ID NO 281
<211> LENGTH: 69
<212> TYPE: PRT
<213> ORGANISM: Artificial Sequence
<220> FEATURE:
<223> OTHER INFORMATION: Synthetic Polypeptide

<400> SEQUENCE: 281

Ala Thr Val Gln Phe Thr Tyr Gln Gly Gly Glu Lys Gln Val Asp Ile
1               5                   10                  15

Ser Lys Ile Lys Tyr Val Arg Arg Trp Gly Arg Tyr Ile Trp Leu Gly
            20                  25                  30

Tyr Asp Glu Gly Gly Gly Ala Arg Gly His Gly Tyr Val Ser Glu Lys
        35                  40                  45

Asp Ala Pro Lys Glu Leu Leu Gln Met Leu Glu Lys Ala Arg Ile Arg
    50                  55                  60

Thr Lys Ala Tyr Phe
65

<210> SEQ ID NO 282
<211> LENGTH: 69
<212> TYPE: PRT
<213> ORGANISM: Artificial Sequence
```

<220> FEATURE:
<223> OTHER INFORMATION: Synthetic Polypeptide

<400> SEQUENCE: 282

Ala Thr Val Glu Phe Thr Tyr Gln Gly Glu Glu Lys Gln Val Asp Ile
1               5                   10                  15

Ser Lys Ile Lys Tyr Val Arg Arg Trp Gly Gln Tyr Ile Trp Phe Gly
            20                  25                  30

Tyr Asp Glu Gly Gly Gly Ala Arg Gly Tyr Tyr Val Ser Glu Lys
        35                  40                  45

Asp Ala Pro Lys Glu Leu Leu Gln Ile Leu Glu Lys Ala Arg Ile Arg
    50                  55                  60

Thr Lys Ala Tyr Phe
65

<210> SEQ ID NO 283
<211> LENGTH: 69
<212> TYPE: PRT
<213> ORGANISM: Artificial Sequence
<220> FEATURE:
<223> OTHER INFORMATION: Synthetic Polypeptide

<400> SEQUENCE: 283

Ala Thr Val Lys Phe Thr Tyr Gln Gly Glu Glu Lys Gln Val Asp Ile
1               5                   10                  15

Ser Lys Ile Lys Tyr Val Arg Arg Trp Gly Gln Tyr Leu Trp Phe Gly
            20                  25                  30

Tyr Asp Gly Gly Gly Gly Ala Arg Gly Tyr Tyr Val Ser Glu Lys
        35                  40                  45

Asp Ala Pro Lys Glu Leu Leu Gln Met Leu Glu Arg Ala Arg Ile Arg
    50                  55                  60

Thr Lys Ala Tyr Phe
65

<210> SEQ ID NO 284
<211> LENGTH: 69
<212> TYPE: PRT
<213> ORGANISM: Artificial Sequence
<220> FEATURE:
<223> OTHER INFORMATION: Synthetic Polypeptide

<400> SEQUENCE: 284

Ala Thr Val Lys Phe Thr Tyr Gln Gly Glu Arg Gln Val Asp Ile
1               5                   10                  15

Ser Lys Val Lys His Val Arg Arg Trp Gly Gln Val Trp Phe Ile
            20                  25                  30

Tyr Asp Glu Gly Gly Gly Ala Lys Gly Trp Gly Val Ser Glu Lys
        35                  40                  45

Asp Ala Pro Thr Glu Leu Leu Gln Met Leu Glu Lys Ala Arg Ile Arg
    50                  55                  60

Thr Lys Ala Tyr Phe
65

<210> SEQ ID NO 285
<211> LENGTH: 69
<212> TYPE: PRT
<213> ORGANISM: Artificial Sequence
<220> FEATURE:
<223> OTHER INFORMATION: Synthetic Polypeptide

<400> SEQUENCE: 285

```
Ala Thr Val Lys Phe Thr Tyr Gln Gly Glu Glu Lys Gln Val Asp Ile
1               5                   10                  15

Ser Arg Ile Lys Ser Ala Phe Arg Trp Gly Gln Ala Ile Ile Phe Arg
            20                  25                  30

Tyr Asp Glu Gly Gly Gly Ala Lys Gly Lys Ser Val Ser Glu Lys
        35                  40                  45

Asp Ala Pro Lys Glu Leu Leu Gln Met Leu Lys Ala Arg Ile Arg
    50                  55                  60

Thr Lys Ala Tyr Phe
65
```

<210> SEQ ID NO 286
<211> LENGTH: 69
<212> TYPE: PRT
<213> ORGANISM: Artificial Sequence
<220> FEATURE:
<223> OTHER INFORMATION: Synthetic Polypeptide

<400> SEQUENCE: 286

```
Ala Thr Val Glu Phe Thr Tyr Arg Gly Glu Glu Lys Gln Val Asp Ile
1               5                   10                  15

Ser Lys Ile Lys Tyr Val Arg Arg Trp Gly Gln Tyr Ile Trp Phe Gly
            20                  25                  30

Tyr Asp Glu Gly Gly Gly Ala Arg Gly Tyr Gly Tyr Val Ser Glu Lys
        35                  40                  45

Asp Ala Pro Lys Glu Leu Leu Gln Met Leu Lys Ala Gly Ile Arg
    50                  55                  60

Thr Lys Ala Tyr Phe
65
```

<210> SEQ ID NO 287
<211> LENGTH: 69
<212> TYPE: PRT
<213> ORGANISM: Artificial Sequence
<220> FEATURE:
<223> OTHER INFORMATION: Synthetic Polypeptide

<400> SEQUENCE: 287

```
Ala Thr Val Lys Phe Thr Tyr Gln Gly Glu Glu Lys Gln Val Asp Ile
1               5                   10                  15

Ser Lys Ile Lys Tyr Ala Arg Arg Trp Gly Gln Tyr Ile Trp Phe Gly
            20                  25                  30

Tyr Asp Glu Gly Gly Gly Ala Arg Gly Tyr Gly Tyr Val Ser Glu Glu
        35                  40                  45

Asp Ala Pro Lys Glu Leu Leu Gln Met Leu Lys Ala Arg Ile Arg
    50                  55                  60

Thr Lys Ala Tyr Phe
65
```

<210> SEQ ID NO 288
<211> LENGTH: 69
<212> TYPE: PRT
<213> ORGANISM: Artificial Sequence
<220> FEATURE:
<223> OTHER INFORMATION: Synthetic Polypeptide

<400> SEQUENCE: 288

```
Ala Thr Val Lys Phe Thr Tyr Arg Gly Glu Glu Lys Gln Val Asp Ile
1               5                   10                  15
```

Ser Lys Ile Lys Ser Val Ser Arg Trp Gly Gln Ala Ile Ile Phe Arg
            20                  25                  30

Tyr Asp Glu Gly Gly Gly Ala Lys Gly Lys Gly Ser Val Ser Glu Lys
            35                  40                  45

Asp Ala Pro Lys Glu Leu Leu Gln Met Leu Gly Lys Ala Arg Ile Arg
    50                  55                  60

Thr Lys Ala Tyr Phe
65

<210> SEQ ID NO 289
<211> LENGTH: 69
<212> TYPE: PRT
<213> ORGANISM: Artificial Sequence
<220> FEATURE:
<223> OTHER INFORMATION: Synthetic Polypeptide

<400> SEQUENCE: 289

Ala Thr Val Lys Phe Ala Tyr Gln Gly Glu Glu Arg Gln Val Asp Ile
1               5                   10                  15

Ser Lys Ile Glu Tyr Val Arg Arg Trp Gly Gln Tyr Ile Trp Phe Gly
            20                  25                  30

Tyr Asp Glu Gly Gly Gly Ala Arg Gly Tyr Gly Tyr Val Ser Glu Lys
            35                  40                  45

Asp Ala Pro Lys Glu Leu Leu Gln Met Leu Gly Lys Ala Arg Ile Arg
    50                  55                  60

Thr Lys Ala Tyr Phe
65

<210> SEQ ID NO 290
<211> LENGTH: 69
<212> TYPE: PRT
<213> ORGANISM: Artificial Sequence
<220> FEATURE:
<223> OTHER INFORMATION: Synthetic Polypeptide

<400> SEQUENCE: 290

Ala Thr Val Lys Phe Thr Tyr Gln Gly Glu Glu Lys Gln Val Asp Val
1               5                   10                  15

Ser Lys Ile Lys His Val Arg Arg Trp Gly Gln Trp Ile Trp Phe Ile
            20                  25                  30

Tyr Asp Glu Gly Gly Gly Ala Lys Gly Trp Gly Gly Val Ser Glu Lys
            35                  40                  45

Asp Ala Pro Lys Glu Leu Leu Gln Met Leu Gly Lys Ala Arg Ile Arg
    50                  55                  60

Thr Lys Ala Tyr Phe
65

<210> SEQ ID NO 291
<211> LENGTH: 69
<212> TYPE: PRT
<213> ORGANISM: Artificial Sequence
<220> FEATURE:
<223> OTHER INFORMATION: Synthetic Polypeptide

<400> SEQUENCE: 291

Ala Thr Val Lys Phe Thr Tyr Gln Gly Glu Glu Lys Gln Val Gly Ile
1               5                   10                  15

Gly Lys Ile Lys His Val Arg Arg Trp Gly Gln Tyr Ile Trp Phe Gly
            20                  25                  30

Tyr Asp Gly Gly Gly Gly Ala Arg Gly Tyr Gly Tyr Val Ser Glu Lys

```
              35                  40                  45
Asp Ala Pro Lys Gly Leu Leu Gln Met Leu Glu Lys Ala Arg Ile Arg
    50                  55                  60

Thr Lys Ala Tyr Phe
65

<210> SEQ ID NO 292
<211> LENGTH: 69
<212> TYPE: PRT
<213> ORGANISM: Artificial Sequence
<220> FEATURE:
<223> OTHER INFORMATION: Synthetic Polypeptide

<400> SEQUENCE: 292

Ala Thr Val Lys Phe Thr Tyr Gln Gly Glu Glu Lys Gln Val Asp Ile
1               5                   10                  15

Ser Lys Ile Lys Tyr Val Trp Arg Trp Gly Gln Trp Ile Trp Phe Arg
            20                  25                  30

Tyr Asp Glu Gly Gly Gly Ala Lys Gly Lys Gly Ser Val Ser Glu Lys
            35                  40                  45

Asp Ala Pro Arg Glu Leu Leu Gln Met Leu Glu Lys Ala Gly Ile Arg
    50                  55                  60

Thr Lys Ala Tyr Phe
65

<210> SEQ ID NO 293
<211> LENGTH: 69
<212> TYPE: PRT
<213> ORGANISM: Artificial Sequence
<220> FEATURE:
<223> OTHER INFORMATION: Synthetic Polypeptide

<400> SEQUENCE: 293

Ala Thr Val Lys Phe Thr Tyr Arg Gly Glu Glu Lys Gln Val Asp Ile
1               5                   10                  15

Ser Lys Ile Lys Tyr Val Arg Arg Trp Gly Gln Tyr Ile Trp Phe Gly
            20                  25                  30

Tyr Asp Gly Gly Gly Gly Ala Arg Gly Tyr Gly His Val Ser Glu Lys
            35                  40                  45

Asp Ala Pro Lys Glu Leu Leu Gln Met Leu Glu Ala Arg Ile Arg
    50                  55                  60

Thr Lys Ala Tyr Phe
65

<210> SEQ ID NO 294
<211> LENGTH: 69
<212> TYPE: PRT
<213> ORGANISM: Artificial Sequence
<220> FEATURE:
<223> OTHER INFORMATION: Synthetic Polypeptide

<400> SEQUENCE: 294

Ala Thr Val Lys Phe Thr Tyr Gln Gly Glu Glu Lys Gln Val Asp Ile
1               5                   10                  15

Gly Lys Ile Lys Tyr Val Arg Arg Trp Gly Gln Tyr Ile Trp Phe Gly
            20                  25                  30

Tyr Asp Glu Gly Gly Gly Ala Arg Gly Tyr Gly Tyr Val Ser Glu Glu
            35                  40                  45

Asp Ala Pro Lys Glu Leu Leu Gln Met Leu Glu Lys Ala Arg Ile Arg
    50                  55                  60
```

Thr Lys Ala Tyr Phe
65

<210> SEQ ID NO 295
<211> LENGTH: 69
<212> TYPE: PRT
<213> ORGANISM: Artificial Sequence
<220> FEATURE:
<223> OTHER INFORMATION: Synthetic Polypeptide

<400> SEQUENCE: 295

Ala Thr Val Lys Phe Thr Tyr Gln Gly Glu Glu Lys Gln Val Asp Ile
1               5                   10                  15

Ser Lys Ile Lys Ser Val His Arg Val Gly Gln Trp Ile Lys Phe Trp
            20                  25                  30

Tyr Asp Glu Gly Gly Gly Ala Tyr Gly Arg Gly Tyr Val Ser Glu Arg
        35                  40                  45

Asp Ala Pro Arg Glu Leu Leu Gln Met Leu Glu Ala Arg Ile Arg
    50                  55                  60

Thr Lys Ala Tyr Phe
65

<210> SEQ ID NO 296
<211> LENGTH: 69
<212> TYPE: PRT
<213> ORGANISM: Artificial Sequence
<220> FEATURE:
<223> OTHER INFORMATION: Synthetic Polypeptide

<400> SEQUENCE: 296

Ala Thr Val Lys Phe Thr Tyr Gln Gly Glu Glu Gln Val Ala Ile
1               5                   10                  15

Ser Lys Ile Lys His Val Arg Arg Trp Gly Gln Trp Ile Trp Phe Arg
            20                  25                  30

Tyr Asp Glu Gly Gly Gly Ala His Gly Ile Gly Tyr Val Ser Glu Lys
        35                  40                  45

Asp Ala Pro Lys Glu Leu Leu Gln Met Leu Glu Lys Ala Arg Ile Arg
    50                  55                  60

Thr Lys Ala Tyr Phe
65

<210> SEQ ID NO 297
<211> LENGTH: 69
<212> TYPE: PRT
<213> ORGANISM: Artificial Sequence
<220> FEATURE:
<223> OTHER INFORMATION: Synthetic Polypeptide

<400> SEQUENCE: 297

Ala Thr Val Lys Phe Thr Tyr Gln Gly Glu Glu Lys Gln Val Asp Ile
1               5                   10                  15

Ser Lys Ile Lys Tyr Val Trp Arg Trp Gly Gln Trp Ile Trp Phe Arg
            20                  25                  30

Tyr Asp Glu Gly Gly Gly Ala His Gly Ile Gly Tyr Met Ser Glu Lys
        35                  40                  45

Asp Ala Pro Arg Glu Leu Leu Gln Met Leu Gly Lys Ala Arg Ile Arg
    50                  55                  60

Thr Lys Ala Tyr Phe
65

<210> SEQ ID NO 298
<211> LENGTH: 69
<212> TYPE: PRT
<213> ORGANISM: Artificial Sequence
<220> FEATURE:
<223> OTHER INFORMATION: Synthetic Polypeptide

<400> SEQUENCE: 298

Ala Thr Val Lys Phe Thr Tyr Gln Gly Glu Glu Lys Gln Val Glu Val
1               5                   10                  15

Ser Lys Ile Lys Tyr Val Arg Arg Trp Gly Gln Tyr Ile Trp Phe Ser
            20                  25                  30

Tyr Asp Glu Gly Gly Gly Ala Arg Gly Tyr Gly Tyr Val Ser Glu Arg
        35                  40                  45

Asp Ala Pro Arg Glu Leu Leu Gln Met Leu Glu Lys Ala Arg Ile Arg
    50                  55                  60

Thr Lys Ala Tyr Phe
65

<210> SEQ ID NO 299
<211> LENGTH: 69
<212> TYPE: PRT
<213> ORGANISM: Artificial Sequence
<220> FEATURE:
<223> OTHER INFORMATION: Synthetic Polypeptide

<400> SEQUENCE: 299

Ala Thr Val Lys Phe Thr Tyr Arg Gly Glu Glu Lys Gln Val Asp Ile
1               5                   10                  15

Ser Lys Ile Lys Ser Val Ser Arg Trp Gly Gln Ala Ile Ile Phe Arg
            20                  25                  30

Tyr Asp Gly Gly Gly Gly Ala Arg Gly Lys Gly Ser Val Ser Glu Lys
        35                  40                  45

Asp Ala Pro Lys Glu Leu Leu Gln Met Leu Glu Lys Ala Gly Ile Arg
    50                  55                  60

Thr Lys Ala Tyr Phe
65

<210> SEQ ID NO 300
<211> LENGTH: 69
<212> TYPE: PRT
<213> ORGANISM: Artificial Sequence
<220> FEATURE:
<223> OTHER INFORMATION: Synthetic Polypeptide

<400> SEQUENCE: 300

Ala Thr Val Lys Phe Thr Tyr Gln Gly Glu Glu Lys Gln Val Asp Ile
1               5                   10                  15

Ser Lys Ile Lys His Val Arg Arg Trp Gly Gln Trp Ile Trp Phe Ile
            20                  25                  30

Tyr Asp Glu Gly Gly Gly Ala Lys Gly Trp Gly Val Ser Glu Lys
        35                  40                  45

Asn Ala Pro Lys Glu Leu Leu Gln Met Leu Glu Lys Ala Arg Ile Arg
    50                  55                  60

Thr Lys Ala Tyr Phe
65

<210> SEQ ID NO 301
<211> LENGTH: 69
<212> TYPE: PRT

<213> ORGANISM: Artificial Sequence
<220> FEATURE:
<223> OTHER INFORMATION: Synthetic Polypeptide

<400> SEQUENCE: 301

```
Ala Thr Val Arg Phe Thr Tyr Gln Gly Glu Glu Lys Gln Val Asp Ile
1               5                   10                  15

Ser Lys Ile Lys Tyr Val Arg Arg Trp Gly Gln Tyr Ile Trp Phe Gly
            20                  25                  30

Tyr Asp Glu Gly Gly Gly Ala Arg Gly Tyr Gly Tyr Val Ser Glu Lys
        35                  40                  45

Asp Thr Pro Lys Glu Leu Leu Gln Leu Leu Glu Lys Ala Arg Ile Arg
    50                  55                  60

Thr Lys Ala Tyr Phe
65
```

<210> SEQ ID NO 302
<211> LENGTH: 69
<212> TYPE: PRT
<213> ORGANISM: Artificial Sequence
<220> FEATURE:
<223> OTHER INFORMATION: Synthetic Polypeptide

<400> SEQUENCE: 302

```
Ala Thr Val Lys Phe Thr Tyr Gln Gly Glu Glu Lys Gln Val Asp Ile
1               5                   10                  15

Ser Lys Ile Lys His Val Arg Arg Trp Gly Gln Trp Ile Trp Phe Ile
            20                  25                  30

Tyr Asp Glu Gly Gly Gly Ala Lys Gly Lys Gly Ser Val Ser Glu Lys
        35                  40                  45

Asp Ala Pro Lys Glu Leu Leu Gln Met Leu Glu Lys Ala Gly Ile Arg
    50                  55                  60

Thr Lys Ala Tyr Phe
65
```

<210> SEQ ID NO 303
<211> LENGTH: 69
<212> TYPE: PRT
<213> ORGANISM: Artificial Sequence
<220> FEATURE:
<223> OTHER INFORMATION: Synthetic Polypeptide

<400> SEQUENCE: 303

```
Ala Thr Val Lys Phe Thr Tyr Gln Gly Glu Glu Lys Gln Val Asp Ile
1               5                   10                  15

Ser Lys Ile Lys Tyr Val Trp Arg Trp Gly Gln Ala Ile Ile Phe Arg
            20                  25                  30

Tyr Asp Glu Gly Gly Gly Ala Lys Gly Lys Gly Ser Val Ser Glu Glu
        35                  40                  45

Asp Ala Pro Lys Glu Leu Leu Gln Met Leu Glu Lys Ala Arg Ile Arg
    50                  55                  60

Thr Lys Ala Tyr Phe
65
```

<210> SEQ ID NO 304
<211> LENGTH: 72
<212> TYPE: PRT
<213> ORGANISM: Artificial Sequence
<220> FEATURE:
<223> OTHER INFORMATION: Synthetic Polypeptide

```
<400> SEQUENCE: 304

Ala Thr Val Lys Phe Thr Tyr Arg Gly Glu Glu Lys Gln Val Gly Ile
1               5                   10                  15

Ser Lys Ile Lys Tyr Val Arg Arg Trp Gly Gln Tyr Ile Trp Phe Gly
            20                  25                  30

Tyr Asp Glu Gly Gly Gly Ala Arg Gly His Gly Tyr Val Ser Glu Lys
        35                  40                  45

Asp Ala Pro Lys Glu Leu Leu Gln Met Leu Glu Lys Gln Gly Ser Glu
    50                  55                  60

Gln Lys Leu Ile Ser Glu Glu Asp
65                  70

<210> SEQ ID NO 305
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 305

Ala Ala Val Lys Phe Thr Tyr Gln Gly Glu Glu Lys Gln Val Asp Ile
1               5                   10                  15

Gly Arg Thr Lys Tyr Val Trp Arg Trp Gly Gln Trp Ile Trp Phe Arg
            20                  25                  30

Tyr Asp Glu Gly Gly Gly Ala Arg Gly Tyr Gly Cys Val Gly Glu Lys
        35                  40                  45

Asp Ala Pro Arg Glu Leu Leu Arg Val Leu Glu Lys Gln Gly Ser Glu
    50                  55                  60

Gln Lys Leu Ile Ser Glu Glu Asp
65                  70

<210> SEQ ID NO 306
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 306

Ala Thr Val Lys Phe Thr Tyr Arg Gly Glu Glu Lys Gln Val Asp Thr
1               5                   10                  15

Ser Arg Ile Lys Tyr Val Trp Arg Trp Gly Gln Trp Ile Trp Phe Arg
            20                  25                  30

Tyr Asp Glu Gly Gly Gly Ala Arg Gly Tyr Gly Tyr Val Ser Glu Lys
        35                  40                  45

Asp Ala Pro Lys Glu Leu Leu Gln Met Leu Glu Lys Gln Gly Ser Glu
    50                  55                  60

Gln Lys Leu Ile Ser Glu Glu Asp
65                  70

<210> SEQ ID NO 307
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 307

Ala Thr Val Arg Phe Thr Tyr Gln Gly Glu Glu Arg Gln Val Gly Ile
1               5                   10                  15
```

```
Ser Lys Ile Lys Tyr Val Arg Arg Gly Gln Tyr Ile Trp Phe Gly
            20                  25                  30

Tyr Asp Glu Gly Gly Val Arg Gly Tyr Gly Tyr Val Ser Glu Lys
            35                  40                  45

Gly Ala Pro Lys Glu Leu Leu Arg Met Leu Glu Lys Arg Gly Ser Glu
 50                  55                  60

Gln Lys Leu Ile Ser Glu Glu Asp
 65                  70

<210> SEQ ID NO 308
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 308

Ala Thr Val Lys Phe Thr Tyr Gln Gly Glu Glu Lys Gln Val Asp Ile
 1               5                  10                  15

Ser Lys Ile Lys His Val Arg Arg Trp Gly Gln Trp Ile Trp Phe Ile
            20                  25                  30

Tyr Asp Glu Ala Gly Gly Ala His Gly Arg Gly Arg Val Ser Glu Arg
            35                  40                  45

Gly Ala Pro Lys Glu Leu Leu Gln Met Leu Glu Lys Gln Gly Ser Glu
 50                  55                  60

Gln Lys Leu Ile Ser Glu Glu Asp
 65                  70

<210> SEQ ID NO 309
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 309

Ala Thr Val Lys Phe Thr Tyr Arg Gly Glu Glu Glu Gln Val Gly Ile
 1               5                  10                  15

Ser Arg Ile Lys Tyr Val Trp Arg Trp Gly Gln Trp Ile Trp Phe Arg
            20                  25                  30

Tyr Asp Gly Gly Gly Ala Arg Gly Tyr Gly His Val Ser Asp Lys
            35                  40                  45

Asp Ala Pro Lys Glu Leu Leu Gln Met Leu Glu Lys Arg Gly Ser Glu
 50                  55                  60

Gln Lys Leu Ile Ser Glu Glu Asp
 65                  70

<210> SEQ ID NO 310
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 310

Ala Thr Val Lys Phe Thr Tyr Gln Gly Glu Glu Lys Gln Val Asp Ile
 1               5                  10                  15

Ser Arg Ile Lys His Val Arg Arg Trp Gly Gln Trp Ile Trp Phe Ile
            20                  25                  30
```

Tyr Asp Gly Ala Gly Gly Ala His Gly Arg Gly Arg Val Ser Glu Arg
                35                  40                  45

Gly Ala Pro Lys Glu Leu Leu Gln Met Leu Lys Gln Gly Ser Glu
    50                  55                  60

Gln Lys Leu Ile Ser Glu Glu Asp
 65                  70

<210> SEQ ID NO 311
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 311

Ala Thr Val Lys Phe Thr Tyr Gln Gly Glu Glu Lys Gln Val Asp Ile
 1               5                  10                  15

Ser Lys Val Lys Tyr Val Arg Arg Gly Gln Tyr Ile Trp Phe Gly
                20                  25                  30

Tyr Asp Glu Gly Asp Gly Ala Tyr Gly Arg Gly His Val Ser Glu Lys
                35                  40                  45

Gly Ala Pro Lys Glu Leu Leu Gln Met Leu Lys Lys Gln Gly Ser Glu
    50                  55                  60

Gln Lys Leu Ile Ser Glu Glu Asp
 65                  70

<210> SEQ ID NO 312
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 312

Val Thr Val Lys Phe Thr Tyr Gln Gly Glu Glu Lys Gln Val Asp Ile
 1               5                  10                  15

Ser Arg Ile Lys His Val Arg Arg Trp Gly Gln Trp Ile Trp Phe Ile
                20                  25                  30

Tyr Gly Lys Gly Gly Gly Ala Lys Gly Arg Gly Gly Val Ser Glu Lys
                35                  40                  45

Asp Ala Pro Lys Glu Leu Leu Gln Met Leu Glu Lys Gln Gly Ser Glu
    50                  55                  60

Gln Lys Leu Ile Ser Glu Glu Asp
 65                  70

<210> SEQ ID NO 313
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 313

Ala Ala Val Lys Phe Thr Tyr Arg Gly Glu Glu Lys Gln Val Asp Ile
 1               5                  10                  15

Ser Lys Ile Lys Tyr Val Arg Arg Trp Gly Gln Tyr Ile Trp Phe Gly
                20                  25                  30

Tyr Asp Lys Gly Gly Gly Ala Arg Gly Tyr Gly Tyr Val Gly Glu Lys
                35                  40                  45

Gly Ala Pro Lys Glu Leu Leu Gln Met Leu Glu Lys Gln Gly Ser Glu

Gln Lys Leu Ile Ser Glu Glu Asp
65                  70

<210> SEQ ID NO 314
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 314

Ala Thr Val Lys Phe Thr Tyr Arg Gly Glu Glu Lys Gln Val Asp Ile
1               5                   10                  15

Ser Arg Ile Lys Tyr Val Arg Arg Trp Gly Gln Tyr Ile Trp Phe Gly
                20                  25                  30

Tyr Asp Glu Gly Gly Gly Ala Arg Gly His Gly His Val Ser Glu Lys
            35                  40                  45

Glu Ala Pro Arg Glu Leu Leu Gln Met Leu Glu Lys Gln Gly Ser Glu
        50                  55                  60

Gln Lys Leu Ile Ser Glu Glu Asp
65                  70

<210> SEQ ID NO 315
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 315

Ala Thr Val Lys Phe Thr Tyr Gln Gly Glu Glu Lys Gln Val Asp Ile
1               5                   10                  15

Ser Lys Ile Lys His Val Arg Arg Trp Gly Gln Trp Ile Trp Phe Ile
                20                  25                  30

Tyr Asp Glu Ala Gly Gly Ala His Gly Arg Gly Arg Val Ser Glu Arg
            35                  40                  45

Gly Ala Pro Arg Glu Leu Leu Gln Met Leu Glu Lys Gln Gly Ser Glu
        50                  55                  60

Gln Lys Leu Ile Ser Glu Glu Asp
65                  70

<210> SEQ ID NO 316
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 316

Ala Thr Val Arg Phe Thr Tyr Arg Gly Glu Glu Arg Gln Val Gly Ile
1               5                   10                  15

Ser Lys Ile Lys Tyr Val Arg Arg Trp Gly Gln Tyr Ile Trp Phe Gly
                20                  25                  30

Tyr Asp Glu Gly Gly Gly Ala Arg Gly Tyr Gly Tyr Val Ser Glu Lys
            35                  40                  45

Asp Ala Pro Lys Glu Leu Leu Gln Met Leu Lys Gln Gly Ser Glu
        50                  55                  60

Gln Lys Leu Ile Ser Glu Glu Asp
65                  70

<210> SEQ ID NO 317
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 317

Ala Thr Val Lys Phe Thr Tyr Gln Gly Glu Glu Lys Gln Val Gly Ile
1               5                   10                  15

Ser Arg Ile Lys Tyr Val Arg Arg Gly Gln Tyr Ile Trp Phe Gly
            20                  25                  30

Tyr Asp Lys Gly Gly Gly Ala Arg Gly His Gly Tyr Val Gly Glu Lys
            35                  40                  45

Asp Ala Pro Lys Glu Leu Leu Gln Met Leu Gly Lys Gly Ser Glu
    50                  55                  60

Gln Lys Leu Ile Ser Glu Glu Asp
65                  70

<210> SEQ ID NO 318
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 318

Ala Thr Val Lys Phe Thr Tyr Gln Gly Gly Glu Lys Gln Val Asp Ile
1               5                   10                  15

Ser Lys Ile Lys Tyr Val Arg Arg Trp Gly Gln His Ile Trp Phe Gly
            20                  25                  30

Tyr Asp Glu Gly Gly Gly Ala Arg Gly Tyr Gly Tyr Val Ser Lys Lys
            35                  40                  45

Asp Ala Pro Lys Glu Leu Leu Gln Met Leu Glu Lys Arg Gly Ser Glu
    50                  55                  60

Gln Lys Leu Ile Ser Glu Glu Asp
65                  70

<210> SEQ ID NO 319
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 319

Ala Thr Val Lys Phe Thr Tyr Arg Gly Glu Glu Gly Gln Val Asp Ile
1               5                   10                  15

Ser Lys Val Lys Tyr Val Trp Arg Trp Gly Gln Trp Ile Trp Phe Arg
            20                  25                  30

Tyr Asp Gly Gly Gly Ala His Gly Ile Gly His Val Ser Glu Lys
            35                  40                  45

Asp Thr Pro Lys Glu Leu Leu Gln Met Leu Glu Lys Gln Gly Ser Glu
    50                  55                  60

Gln Lys Leu Ile Ser Glu Glu Asp
65                  70

<210> SEQ ID NO 320
<211> LENGTH: 72

```
<212> TYPE: PRT
<213> ORGANISM: Artificial Sequence
<220> FEATURE:
<223> OTHER INFORMATION: Synthetic Polypeptide

<400> SEQUENCE: 320

Ala Thr Val Lys Phe Thr Tyr Gln Gly Glu Glu Lys Gln Val Asp Met
1               5                   10                  15

Ser Lys Ile Lys His Val Arg Arg Trp Gly Gln Trp Ile Trp Phe Ile
            20                  25                  30

Tyr Asp Glu Gly Gly Gly Ala Arg Gly Arg Gly Tyr Val Ser Glu Lys
        35                  40                  45

Gly Ala Pro Glu Glu Leu Leu Gln Met Leu Gly Lys Gln Gly Ser Glu
    50                  55                  60

Gln Lys Leu Ile Ser Glu Glu Asp
65                  70

<210> SEQ ID NO 321
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 321

Ala Thr Val Lys Phe Thr Tyr Gln Gly Arg Glu Lys Gln Val Asp Ile
1               5                   10                  15

Ser Lys Ile Lys His Val Arg Arg Gly Gln Tyr Ile Trp Phe Gly
            20                  25                  30

Tyr Asp Lys Gly Gly Gly Ala Arg Gly Tyr Gly Tyr Val Ser Glu Gly
        35                  40                  45

Asp Ala Pro Lys Glu Leu Leu Gln Met Leu Glu Lys Gln Glu Ser Glu
    50                  55                  60

Gln Lys Leu Ile Ser Glu Glu Asp
65                  70

<210> SEQ ID NO 322
<211> LENGTH: 69
<212> TYPE: PRT
<213> ORGANISM: Artificial Sequence
<220> FEATURE:
<223> OTHER INFORMATION: Synthetic Polypeptide

<400> SEQUENCE: 322

Ala Thr Val Lys Phe Thr Tyr Gln Gly Glu Glu Lys Gln Val Gly Ile
1               5                   10                  15

Ser Lys Ile Arg His Val Arg Arg Trp Gly Gln Trp Ile Trp Phe Ile
            20                  25                  30

Tyr Asp Glu Gly Gly Gly Ala Lys Gly Arg Gly Ser Val Ser Glu Arg
        35                  40                  45

Asp Ala Pro Lys Glu Leu Leu Gln Met Leu Glu Lys Ala Arg Ile Arg
    50                  55                  60

Thr Lys Ala Tyr Phe
65

<210> SEQ ID NO 323
<211> LENGTH: 72
<212> TYPE: PRT
<213> ORGANISM: Artificial Sequence
<220> FEATURE:
<223> OTHER INFORMATION: Synthetic Polypeptide
```

-continued

<400> SEQUENCE: 323

Ala Thr Val Lys Phe Thr Tyr Gln Gly Gly Glu Lys Gln Val Asp Ile
1               5                   10                  15

Ser Lys Ile Lys His Val Trp Arg Trp Gly Gln Trp Val Trp Phe Arg
            20                  25                  30

Tyr Asp Glu Gly Gly Gly Ala Arg Gly Tyr Gly Arg Val Ser Glu Lys
        35                  40                  45

Gly Ala Pro Lys Glu Leu Leu Gln Met Leu Gly Lys Gln Gly Ser Glu
    50                  55                  60

Gln Lys Leu Ile Ser Glu Glu Asp
65                  70

<210> SEQ ID NO 324
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 324

Ala Thr Val Lys Phe Thr Tyr His Gly Glu Gly Lys Gln Val Asp Ile
1               5                   10                  15

Ser Lys Ile Arg Tyr Val Arg Arg Trp Gly Arg Tyr Ile Trp Phe Gly
            20                  25                  30

Tyr Asp Glu Gly Gly Gly Ala Arg Gly Tyr Gly Tyr Val Ser Glu Lys
        35                  40                  45

Gly Ala Pro Glu Glu Leu Leu Gln Met Leu Gly Lys Gln Gly Ser Glu
    50                  55                  60

Gln Lys Leu Ile Ser Glu Glu Asp
65                  70

<210> SEQ ID NO 325
<211> LENGTH: 69
<212> TYPE: PRT
<213> ORGANISM: Artificial Sequence
<220> FEATURE:
<223> OTHER INFORMATION: Synthetic Polypeptide

<400> SEQUENCE: 325

Ala Thr Val Lys Phe Thr Tyr Arg Gly Glu Gly Lys Gln Val Asp Ile
1               5                   10                  15

Ser Lys Ile Lys His Val Arg Arg Trp Gly Gln Trp Ile Trp Phe Ile
            20                  25                  30

Tyr Asp Glu Gly Gly Gly Ala Lys Gly Lys Gly Ser Val Ser Glu Glu
        35                  40                  45

Asp Ala Pro Lys Glu Leu Leu Gln Met Leu Glu Lys Val Gly Ile Arg
    50                  55                  60

Thr Lys Ala Tyr Phe
65

<210> SEQ ID NO 326
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 326

Ala Thr Val Lys Phe Thr Tyr Arg Gly Gly Glu Lys Gln Val Asp Ile

```
                1               5                  10                 15
Ser Arg Val Lys Tyr Val Trp Arg Arg Gly Gln Trp Ile Trp Phe Arg
                20                 25                 30

Tyr Asp Gly Gly Gly Ala His Gly Thr Gly Cys Val Ser Glu Lys
        35                 40                 45

Asn Ala Pro Lys Glu Leu Leu Gln Met Leu Gly Arg Gln Gly Ser Glu
    50                 55                 60

Gln Lys Leu Ile Ser Glu Glu Asp
65                 70

<210> SEQ ID NO 327
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 327

Ala Thr Val Lys Phe Thr Tyr Gln Gly Glu Glu Lys Gln Val Asp Ile
1               5                  10                 15

Ser Lys Ile Lys His Val Arg Arg Trp Gly Gln Trp Ile Trp Phe Ile
                20                 25                 30

Tyr Asp Lys Gly Gly Gly Ala Lys Gly Arg Gly Gly Val Ser Asp Lys
        35                 40                 45

Asp Ala Pro Lys Glu Leu Leu Gln Met Leu Glu Lys Gly Ser Glu
    50                 55                 60

Gln Lys Leu Ile Ser Glu Glu Asp
65                 70

<210> SEQ ID NO 328
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 328

Ala Thr Val Arg Phe Thr Tyr Arg Gly Glu Glu Lys Gln Val Asp Ile
1               5                  10                 15

Ser Lys Ile Lys His Val Arg Arg Trp Gly Gln Trp Ile Trp Phe Ile
                20                 25                 30

Tyr Asp Glu Gly Gly Gly Ala Lys Gly Arg Gly Gly Val Ser Lys Glu
        35                 40                 45

Asp Ala Pro Lys Glu Leu Leu Arg Met Leu Gly Lys Gln Gly Ser Glu
    50                 55                 60

Gln Lys Leu Ile Ser Glu Glu Asp
65                 70

<210> SEQ ID NO 329
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 329

Ala Thr Val Lys Phe Thr Tyr His Gly Glu Glu Arg Gln Val Asp Ile
1               5                  10                 15

Ser Lys Ile Lys His Ala Arg Arg Trp Gly Gln Trp Ile Trp Phe Ile
                20                 25                 30
```

```
Tyr Asp Glu Gly Gly Gly Ala Lys Gly Arg Gly Val Ser Glu Arg
        35                  40                  45

Asn Ala Pro Lys Glu Leu Leu Gln Met Leu Glu Arg Gly Ser Glu
 50                  55                  60

Gln Lys Leu Ile Ser Glu Glu Asp
 65                  70

<210> SEQ ID NO 330
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 330

Ala Thr Val Arg Phe Thr Tyr Gln Gly Glu Glu Lys Gln Val Asp Ile
 1               5                  10                  15

Ser Lys Ile Lys Tyr Val Arg Arg Gly Gln Tyr Ile Trp Phe Gly
                 20                  25                  30

Tyr Asp Glu Gly Gly Gly Ala Arg Gly Tyr Gly Tyr Val Ser Gly Lys
        35                  40                  45

Gly Ala Pro Lys Glu Leu Leu Gln Met Leu Glu His Gly Ser Glu
 50                  55                  60

Gln Lys Leu Ile Ser Glu Glu Asp
 65                  70

<210> SEQ ID NO 331
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 331

Ala Thr Val Lys Phe Thr Tyr Arg Gly Glu Gly Lys Gln Val Asp Ile
 1               5                  10                  15

Ser Lys Ile Lys His Val Arg Arg Trp Gly Gln Trp Ile Trp Phe Ile
                 20                  25                  30

Tyr Asp Glu Gly Gly Gly Ala Lys Gly Trp Gly Gly Val Ser Glu Lys
        35                  40                  45

Gly Ala Pro Lys Ala Leu Leu Gln Met Leu Glu Lys Gln Gly Ser Glu
 50                  55                  60

Gln Lys Leu Ile Ser Glu Glu Asp
 65                  70

<210> SEQ ID NO 332
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 332

Ala Thr Val Glu Phe Thr Tyr Arg Gly Glu Glu Lys Gln Val Asp Ile
 1               5                  10                  15

Ser Lys Ile Lys His Val Arg Arg Trp Gly Gln Trp Ile Trp Phe Ile
                 20                  25                  30

Tyr Asp Glu Gly Gly Gly Ala Lys Gly Arg Gly Val Ser Glu Arg
        35                  40                  45
```

Asp Ala Pro Lys Glu Leu Leu Gln Leu Leu Glu Lys Arg Gly Ser Glu
    50                  55                  60

Gln Lys Leu Ile Ser Glu Glu Asp
 65                  70

<210> SEQ ID NO 333
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 333

Ala Thr Val Lys Phe Thr Tyr Gln Gly Lys Glu Lys Gln Val Asp Ile
  1               5                  10                  15

Ser Lys Ile Lys Tyr Val Arg Arg Gly Gln Tyr Ile Trp Phe Gly
                 20                  25                  30

Tyr Asp Lys Ser Gly Gly Ala Arg Gly Tyr Gly Tyr Val Ser Glu Lys
             35                  40                  45

Gly Ala Pro Lys Glu Leu Leu Gln Met Leu Glu Lys Gln Gly Ser Glu
    50                  55                  60

Gln Lys Leu Ile Ser Glu Glu Asp
 65                  70

<210> SEQ ID NO 334
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 334

Ala Thr Val Lys Phe Thr Tyr Arg Gly Gly Glu Lys Gln Val Asp Ile
  1               5                  10                  15

Gly Lys Ile Lys Tyr Val Arg Arg Trp Gly Gln Tyr Val Trp Phe Gly
                 20                  25                  30

Tyr Asp Glu Gly Gly Gly Ala Arg Gly Tyr Gly Tyr Val Ser Glu Lys
             35                  40                  45

Asp Ala Pro Lys Glu Leu Leu Gln Met Leu Glu Lys Arg Gly Ser Glu
    50                  55                  60

Gln Lys Leu Ile Ser Glu Glu Asp
 65                  70

<210> SEQ ID NO 335
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 335

Ala Thr Val Lys Phe Thr His Arg Gly Glu Lys Gln Val Asp Ala
  1               5                  10                  15

Ser Lys Ile Lys Tyr Val Arg Arg Trp Gly Arg His Ile Trp Phe Gly
                 20                  25                  30

Tyr Asp Glu Gly Gly Gly Ala Arg Gly Tyr Gly Tyr Val Gly Glu Lys
             35                  40                  45

Asp Ala Pro Lys Glu Leu Leu Gln Met Leu Arg Gln Gly Ser Glu
    50                  55                  60

Gln Lys Leu Ile Ser Glu Glu Asp 65                  70

<210> SEQ ID NO 336
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 336

Ala Thr Val Lys Phe Thr Tyr Gln Gly Glu Glu Lys Gln Val Asp Ile
1               5                   10                  15

Ser Lys Ile Lys His Val Arg Arg Trp Gly Gln Trp Ile Trp Phe Thr
            20                  25                  30

Tyr Asp Glu Gly Gly Gly Ala Lys Gly Arg Gly Gly Val Ser Glu Lys
        35                  40                  45

Asp Ala Pro Lys Glu Leu Leu Gln Met Leu Glu Lys Gln Gly Ser Glu
    50                  55                  60

Gln Lys Leu Ile Ser Glu Glu Asp
65                  70

<210> SEQ ID NO 337
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 337

Thr Thr Val Lys Phe Thr Tyr Gln Gly Glu Glu Lys Gln Val Asp Ile
1               5                   10                  15

Ser Lys Ile Lys His Val Arg Arg Trp Gly Arg Trp Ile Trp Phe Thr
            20                  25                  30

Tyr Asp Glu Gly Gly Gly Ala Lys Gly Arg Gly Gly Val Ser Glu Lys
        35                  40                  45

Asp Ala Pro Lys Glu Leu Leu Gln Met Leu Glu Lys Arg Gly Ser Glu
    50                  55                  60

Gln Lys Leu Ile Ser Glu Glu Asp
65                  70

<210> SEQ ID NO 338
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 338

Thr Thr Val Lys Phe Thr Tyr Gln Gly Glu Glu Lys Gln Val Asp Ile
1               5                   10                  15

Ser Lys Ile Lys His Val Arg Arg Trp Gly Gln Trp Ile Trp Phe Thr
            20                  25                  30

Tyr Asp Glu Gly Gly Gly Ala Lys Gly Arg Gly Gly Val Ser Glu Lys
        35                  40                  45

Asp Ala Pro Lys Glu Leu Leu Arg Met Leu Glu Lys Gln Gly Ser Glu
    50                  55                  60

Gln Lys Leu Ile Ser Glu Glu Asp
65                  70

<210> SEQ ID NO 339

```
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 339

Ala Thr Val Lys Phe Thr Tyr Arg Gly Glu Glu Lys Gln Val Ala Ile
1               5                   10                  15

Ser Lys Ile Lys Tyr Val Arg Arg Trp Gly Gln His Ile Trp Phe Gly
            20                  25                  30

Tyr Asp Lys Gly Gly Val Arg Gly Tyr Gly Tyr Val Gly Glu Lys
        35                  40                  45

Gly Ala Pro Arg Gly Leu Leu Gln Met Leu Glu Lys Gln Gly Ser Glu
    50                  55                  60

Gln Lys Leu Ile Ser Glu Glu Asp
65                  70

<210> SEQ ID NO 340
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 340

Ala Thr Val Arg Phe Thr Tyr Gln Gly Glu Glu Lys Gln Val Asp Ile
1               5                   10                  15

Asn Arg Ile Lys His Val Arg Arg Trp Gly Gln Trp Ile Trp Phe Ile
            20                  25                  30

Tyr Asp Glu Gly Gly Gly Ala Lys Gly Arg Gly Val Ser Gly Lys
        35                  40                  45

Asp Ala Pro Lys Glu Leu Leu Gln Met Leu Glu Lys Gln Gly Ser Glu
    50                  55                  60

Gln Lys Leu Ile Ser Glu Glu Asp
65                  70

<210> SEQ ID NO 341
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 341

Ala Thr Val Lys Tyr Thr Tyr Arg Gly Glu Glu Lys Gln Val Gly Ile
1               5                   10                  15

Ser Arg Ile Lys Ser Val His Arg Ile Gly Gln Trp Ile Lys Phe Trp
            20                  25                  30

Tyr Asp Glu Gly Ser Gly Ala Tyr Gly Arg Gly Tyr Val Ser Glu Lys
        35                  40                  45

Asp Ala Pro Arg Glu Leu Leu Gln Met Leu Gly Lys Arg Gly Ser Glu
    50                  55                  60

Gln Lys Leu Ile Ser Glu Glu Asp
65                  70

<210> SEQ ID NO 342
<211> LENGTH: 72
<212> TYPE: PRT
<213> ORGANISM: Artificial Sequence
<220> FEATURE:
```

<223> OTHER INFORMATION: Synthetic Polypeptide

<400> SEQUENCE: 342

Ala Thr Val Lys Phe Thr Tyr Gln Gly Glu Glu Lys Gln Val Asp Ile
1               5                   10                  15
Ser Lys Ile Lys His Val Arg Arg Trp Gly Gln Trp Ile Trp Phe Ile
            20                  25                  30
Tyr Asp Lys Gly Gly Gly Ala Lys Gly Arg Gly Gly Val Ser Glu Lys
        35                  40                  45
Asp Ala Pro Lys Glu Leu Leu Gln Met Leu Glu Lys Gln Gly Ser Glu
    50                  55                  60
Gln Lys Leu Ile Ser Glu Glu Asp
65                  70

<210> SEQ ID NO 343
<211> LENGTH: 69
<212> TYPE: PRT
<213> ORGANISM: Artificial Sequence
<220> FEATURE:
<223> OTHER INFORMATION: Synthetic Polypeptide

<400> SEQUENCE: 343

Ala Thr Val Lys Phe Thr Tyr Gln Gly Glu Glu Lys Gln Val Asp Ile
1               5                   10                  15
Ser Lys Ile Lys Tyr Val Arg Arg Trp Gly Gln Tyr Ile Trp Phe Gly
            20                  25                  30
Tyr Asp Ala Gly Gly Gly Val Arg Gly Tyr Gly Tyr Val Ser Glu Lys
        35                  40                  45
Asp Ala Pro Lys Gly Leu Leu Gln Met Leu Glu Lys Ala Arg Ile Arg
    50                  55                  60
Thr Lys Ala Tyr Phe
65

<210> SEQ ID NO 344
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 344

Ala Thr Val Lys Phe Thr Tyr Gln Gly Glu Glu Lys Gln Val Asn Ile
1               5                   10                  15
Ser Lys Ile Lys His Val Arg Arg Trp Gly Gln Trp Ile Trp Phe Val
            20                  25                  30
Tyr Asp Glu Gly Gly Gly Ala Lys Gly Arg Gly Gly Val Ser Glu Lys
        35                  40                  45
Asp Ala Pro Lys Glu Leu Leu Gln Met Leu Glu Lys Gln Gly Ser Glu
    50                  55                  60
Gln Lys Leu Ile Ser Glu Glu Asp
65                  70

<210> SEQ ID NO 345
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 345

Ala Thr Val Lys Phe Thr Tyr Arg Gly Glu Lys Gln Val Asp Ile
1               5                   10                  15

Ser Glu Ile Arg Tyr Val Trp Arg Arg Gly Gln Trp Ile Trp Phe Arg
            20                  25                  30

Tyr Asp Glu Gly Gly Gly Ala His Gly Ile Gly His Val Ser Glu Lys
                35                  40                  45

Gly Ala Pro Lys Glu Leu Leu Gln Thr Leu Glu Arg Gln Gly Ser Glu
        50                  55                  60

Gln Lys Leu Ile Ser Glu Glu Asp
65                  70

<210> SEQ ID NO 346
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 346

Ala Thr Val Lys Phe Thr Tyr Arg Gly Glu Glu Lys Arg Val Asp Ile
1               5                   10                  15

Ser Lys Ile Lys His Val Arg Arg Trp Gly Gln Trp Ile Trp Phe Ile
            20                  25                  30

Tyr Asp Glu Gly Gly Gly Ala His Gly Arg Gly Arg Val Ser Glu Lys
                35                  40                  45

Asp Ala Pro Lys Glu Leu Leu Gln Met Leu Glu Lys Gln Gly Ser Glu
        50                  55                  60

Gln Lys Leu Ile Ser Glu Glu Asp
65                  70

<210> SEQ ID NO 347
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 347

Ala Thr Val Lys Phe Thr Tyr Gln Gly Gly Lys Lys Gln Met Asp Ile
1               5                   10                  15

Ser Lys Leu Lys Tyr Val Arg Arg Trp Gly Arg Tyr Ile Trp Phe Gly
            20                  25                  30

Tyr Asp Glu Gly Gly Gly Ala Arg Gly Tyr Gly Tyr Val Ser Gly Lys
                35                  40                  45

Asp Ala Pro Arg Glu Leu Leu Gln Met Leu Glu Lys Gln Gly Ser Glu
        50                  55                  60

Gln Lys Leu Ile Ser Glu Glu Asp
65                  70

<210> SEQ ID NO 348
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 348

Ala Thr Val Lys Phe Thr Tyr Arg Gly Glu Glu Lys Gln Val Asp Ile
1               5                   10                  15

Ser Lys Ile Lys Tyr Val Arg Arg Trp Gly Gln Tyr Val Trp Phe Gly

```
                20                  25                  30

Tyr Asp Glu Gly Gly Gly Ala Lys Gly Arg Gly Gly Val Ser Lys Lys
            35                  40                  45

Asp Ala Pro Lys Glu Leu Leu Gln Met Leu Glu Arg Gln Gly Ser Glu
        50                  55                  60

Gln Lys Leu Ile Ser Glu Asp
65                  70

<210> SEQ ID NO 349
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 349

Ala Thr Val Lys Phe Thr Tyr Gln Gly Glu Glu Lys Gln Val Asp Ile
1               5                   10                  15

Ser Lys Ile Lys Tyr Val Arg Arg Trp Gly Gln Tyr Ile Trp Phe Gly
                20                  25                  30

Tyr Asp Glu Gly Gly Gly Ala Arg Gly Arg Gly Tyr Val Ser Gly Lys
            35                  40                  45

Asp Ala Pro Lys Glu Leu Leu Gln Met Leu Lys Gln Gly Ser Glu
        50                  55                  60

Gln Lys Leu Ile Ser Glu Asp
65                  70

<210> SEQ ID NO 350
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 350

Ala Thr Val Lys Phe Thr Tyr Gln Gly Gly Glu Lys Gln Val Gly Ile
1               5                   10                  15

Ser Arg Ile Lys Tyr Val Arg Arg Arg Gly Gln Tyr Ile Trp Phe Gly
                20                  25                  30

Tyr Asp Lys Gly Gly Gly Ala Arg Gly Tyr Gly Tyr Val Ser Glu Lys
            35                  40                  45

Asp Ala Pro Lys Glu Leu Leu Gln Met Leu Lys Gln Gly Ser Glu
        50                  55                  60

Gln Lys Leu Ile Ser Glu Asp
65                  70

<210> SEQ ID NO 351
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 351

Ala Thr Val Lys Phe Thr Tyr Gln Gly Glu Glu Lys Gln Val Asp Ile
1               5                   10                  15

Ser Lys Ile Lys Tyr Val Arg Arg Trp Gly Gln Tyr Ile Trp Phe Gly
                20                  25                  30

Tyr Asp Ala Gly Gly Gly Ala Arg Gly Tyr Gly Tyr Val Ser Glu Lys
            35                  40                  45
```

Asp Ala Pro Lys Gly Leu Leu Gln Met Leu Glu Lys Arg Gly Ser Glu
            50                  55                  60

Gln Lys Leu Ile Ser Glu Glu Asp
 65                  70

<210> SEQ ID NO 352
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 352

Ala Thr Val Lys Phe Thr Tyr Gln Gly Glu Glu Lys Gln Val Asp Ile
 1               5                   10                  15

Ser Arg Ile Lys Tyr Val Arg Arg Trp Gly Gln Tyr Ile Trp Phe Gly
                20                  25                  30

Tyr Gly Glu Gly Gly Gly Ala Arg Gly Tyr Gly Tyr Val Ser Glu Lys
            35                  40                  45

Asp Ala Pro Glu Gly Leu Leu Gln Met Leu Gly Lys Arg Gly Ser Glu
            50                  55                  60

Gln Lys Leu Ile Ser Glu Glu Asp
 65                  70

<210> SEQ ID NO 353
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 353

Ala Ala Val Lys Phe Thr Tyr Gln Gly Glu Glu Arg Gln Val Asp Ile
 1               5                   10                  15

Ser Lys Ile Lys His Val Arg Arg Trp Gly Gln Trp Ile Trp Phe Ile
                20                  25                  30

Tyr Asp Glu Gly Gly Gly Ala Lys Gly Arg Gly Gly Val Ser Glu Lys
            35                  40                  45

Asp Ala Pro Lys Glu Leu Leu Gln Met Leu Glu Arg Gln Gly Ser Glu
            50                  55                  60

Gln Lys Leu Ile Ser Glu Glu Asp
 65                  70

<210> SEQ ID NO 354
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 354

Ala Thr Val Lys Phe Thr Tyr Arg Gly Glu Glu Lys Gln Ala Asp Ile
 1               5                   10                  15

Ser Lys Ile Lys Tyr Val Arg Arg Trp Gly Gln Tyr Val Trp Phe Gly
                20                  25                  30

Tyr Asp Glu Gly Gly Gly Val Arg Gly Tyr Gly Tyr Val Ser Glu Lys
            35                  40                  45

Asp Ala Pro Lys Glu Leu Leu Gln Met Leu Glu Lys Gln Gly Ser Glu
            50                  55                  60

Gln Lys Leu Ile Ser Glu Glu Asp
65                  70

<210> SEQ ID NO 355
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 355

Ala Thr Val Lys Phe Thr Tyr Gln Gly Glu Glu Lys Gln Val Asp Ile
1               5                   10                  15

Ser Lys Ile Lys His Val Arg Arg Trp Gly Gln Trp Ile Trp Phe Val
            20                  25                  30

Tyr Asp Lys Gly Gly Gly Ala Lys Gly Arg Gly Gly Val Ser Glu Lys
        35                  40                  45

Asn Ala Pro Lys Glu Leu Leu Gln Met Leu Glu Arg Gln Gly Ser Glu
    50                  55                  60

Gln Lys Leu Ile Ser Glu Glu Asp
65                  70

<210> SEQ ID NO 356
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 356

Ala Ile Val Lys Phe Thr Tyr His Gly Glu Glu Lys Gln Val Asp Ile
1               5                   10                  15

Ser Lys Ile Lys Tyr Val Arg Arg Trp Gly Gln Tyr Ile Trp Phe Gly
            20                  25                  30

Tyr Asp Glu Gly Gly Gly Ala Arg Gly Tyr Gly Tyr Val Ser Glu Arg
        35                  40                  45

Gly Ala Pro Lys Glu Leu Leu Gln Met Leu Glu Lys Arg Gly Ser Glu
    50                  55                  60

Gln Lys Leu Ile Ser Glu Glu Asp
65                  70

<210> SEQ ID NO 357
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 357

Ala Thr Val Lys Phe Thr Tyr Arg Gly Gly Glu Lys Gln Val Asp Ile
1               5                   10                  15

Ser Lys Ile Lys Tyr Val Arg Arg Gly Gln Tyr Ile Trp Phe Gly
            20                  25                  30

Tyr Asp Glu Gly Gly Gly Ala Arg Gly Tyr Gly Tyr Val Ser Glu Arg
        35                  40                  45

Asp Ala Pro Lys Glu Leu Leu Gln Met Leu Glu Lys Gln Gly Ser Glu
    50                  55                  60

Gln Lys Leu Ile Ser Glu Glu Asp
65                  70

```
<210> SEQ ID NO 358
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 358

Ala Thr Val Lys Phe Thr Tyr Gln Gly Glu Glu Lys Gln Val Asp Ile
1               5                   10                  15

Ser Lys Ile Lys His Val Arg Arg Trp Gly Gln Trp Ile Trp Phe Ile
            20                  25                  30

Tyr Asp Lys Gly Gly Gly Ala Lys Gly Arg Gly Val Ser Glu Lys
        35                  40                  45

Asn Ala Pro Lys Glu Leu Leu Gln Met Leu Glu Lys Gln Gly Ser Glu
    50                  55                  60

Gln Lys Leu Ile Ser Glu Glu Asp
65                  70

<210> SEQ ID NO 359
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 359

Ala Thr Val Glu Phe Thr Tyr Gln Gly Glu Glu Lys Gln Val Asp Ile
1               5                   10                  15

Ser Lys Ile Lys His Val Arg Arg Trp Gly Gln Trp Ile Trp Phe Ile
            20                  25                  30

Tyr Asp Glu Gly Gly Gly Ala Lys Gly Arg Gly Val Ser Glu Arg
        35                  40                  45

Asp Ala Pro Lys Glu Leu Leu Gln Leu Leu Lys Arg Gly Ser Glu
    50                  55                  60

Gln Lys Leu Ile Ser Glu Glu Asp
65                  70

<210> SEQ ID NO 360
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 360

Ala Thr Val Lys Phe Thr Tyr Arg Gly Glu Gly Lys Gln Val Asp Ile
1               5                   10                  15

Ser Lys Ile Lys Tyr Val Arg Arg Trp Gly Gln Tyr Val Trp Phe Gly
            20                  25                  30

Tyr Asp Glu Gly Gly Gly Ala Arg Gly Tyr Gly Tyr Val Ser Glu Lys
        35                  40                  45

Asp Ala Pro Lys Glu Leu Leu Gln Met Leu Glu Lys Gln Gly Ser Glu
    50                  55                  60

Gln Lys Leu Ile Ser Glu Glu Asp
65                  70

<210> SEQ ID NO 361
<211> LENGTH: 72
<212> TYPE: PRT
<213> ORGANISM: Artificial Sequence
```

<220> FEATURE:
<223> OTHER INFORMATION: Synthetic Polypeptide

<400> SEQUENCE: 361

Ala Thr Val Lys Phe Thr Tyr Arg Gly Gly Glu Lys Gln Val Asp Ile
1               5                   10                  15

Ser Arg Ile Lys Tyr Val Trp Arg Arg Gly Gln Trp Ile Trp Phe Arg
            20                  25                  30

Tyr Asp Gly Gly Gly Gly Ala His Gly Thr Gly Cys Val Ser Glu Lys
        35                  40                  45

Asn Ala Pro Lys Glu Leu Leu Gln Met Leu Gly Arg Gln Gly Ser Glu
    50                  55                  60

Gln Lys Leu Ile Ser Glu Glu Asp
65                  70

<210> SEQ ID NO 362
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 362

Ala Thr Val Glu Phe Thr Tyr Arg Gly Glu Glu Lys Gln Val Asp Val
1               5                   10                  15

Ser Lys Ile Lys Tyr Ala Trp Arg Trp Gly Arg Trp Ile Trp Phe Arg
            20                  25                  30

Tyr Asp Glu Gly Gly Ser Ala His Gly Ile Gly Tyr Val Ser Glu Lys
        35                  40                  45

Asp Ala Pro Lys Glu Leu Leu Gln Met Leu Lys Gln Gly Ser Glu
    50                  55                  60

Gln Lys Leu Ile Ser Glu Glu Asp
65                  70

<210> SEQ ID NO 363
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 363

Ala Thr Val Lys Phe Thr Tyr Gln Gly Glu Glu Lys Gln Val Gly Val
1               5                   10                  15

Ser Arg Ile Thr Tyr Val Arg Arg Gly Gln Tyr Ile Trp Phe Gly
            20                  25                  30

Tyr Asp Lys Gly Gly Gly Ala Arg Gly Tyr Gly Tyr Val Ser Glu Lys
        35                  40                  45

Asp Ala Pro Lys Glu Leu Leu Gln Met Leu Lys Gln Gly Ser Glu
    50                  55                  60

Gln Lys Leu Ile Ser Glu Glu Asp
65                  70

<210> SEQ ID NO 364
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 364

```
Ala Thr Val Lys Phe Thr Tyr Arg Gly Glu Glu Lys Gln Val Asp Ile
1               5                   10                  15

Ser Lys Ile Lys Tyr Val Arg Arg Trp Gly Gln Tyr Ile Trp Phe Gly
                20                  25                  30

Tyr Asp Gly Gly Gly Gly Ala Asn Gly Arg Gly Val Ser Glu Arg
                35                  40                  45

Gly Ala Pro Lys Glu Leu Leu Gln Met Leu Lys Gln Gly Ser Glu
        50                  55                  60

Gln Lys Leu Ile Ser Glu Glu Asp
65                  70

<210> SEQ ID NO 365
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 365

Ala Thr Val Glu Phe Thr Tyr Gln Gly Glu Glu Lys Gln Val Asp Ile
1               5                   10                  15

Gly Lys Ile Lys Tyr Val Arg Arg Trp Gly Gln Tyr Ile Trp Phe Gly
                20                  25                  30

Tyr Asp Glu Gly Gly Gly Ala Arg Gly Tyr Gly Tyr Val Ser Arg Lys
                35                  40                  45

Gly Ala Pro Lys Glu Leu Leu Gln Met Leu Lys Arg Gly Ser Glu
        50                  55                  60

Gln Lys Leu Ile Ser Glu Glu Asp
65                  70

<210> SEQ ID NO 366
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 366

Ala Ile Val Arg Phe Thr Tyr Arg Gly Glu Glu Lys Arg Val Asp Ile
1               5                   10                  15

Ser Glu Ile Lys Tyr Val Arg Arg Trp Gly Gln Tyr Ile Trp Phe Gly
                20                  25                  30

Tyr Asp Lys Gly Gly Gly Ala Arg Gly His Gly Tyr Val Ser Glu Lys
                35                  40                  45

Asp Ala Pro Lys Glu Leu Leu Gln Met Leu Glu Gln Gly Ser Glu
        50                  55                  60

Gln Lys Leu Ile Ser Glu Glu Asp
65                  70

<210> SEQ ID NO 367
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 367

Ala Thr Val Lys Phe Thr Tyr Arg Gly Glu Glu Lys Gln Val Asp Ile
1               5                   10                  15
```

```
Ser Lys Ile Lys His Ala Arg Arg Trp Gly Gln Tyr Ile Trp Phe Gly
            20                  25                  30

Tyr Asp Glu Gly Gly Gly Ala Arg Gly Tyr Gly Tyr Val Ser Glu Lys
        35                  40                  45

Asp Ala Pro Lys Glu Leu Leu Arg Met Leu Glu Lys Arg Gly Ser Glu
    50                  55                  60

Gln Lys Leu Ile Ser Glu Glu Asp
65                  70

<210> SEQ ID NO 368
<211> LENGTH: 60
<212> TYPE: PRT
<213> ORGANISM: Artificial Sequence
<220> FEATURE:
<223> OTHER INFORMATION: Synthetic Polypeptide

<400> SEQUENCE: 368

Ala Thr Val Lys Phe Thr Tyr Gln Gly Glu Glu Lys Gln Val Asp Ile
1               5                   10                  15

Ser Arg Ile Lys His Val Arg Arg Gly Gln Tyr Ile Trp Phe Gly
            20                  25                  30

Tyr Asp Glu Gly Gly Gly Ala Arg Gly Tyr Gly Tyr Val Ser Glu Lys
        35                  40                  45

Asp Ala Pro Lys Glu Leu Leu Arg Met Leu Glu Lys
    50                  55                  60

<210> SEQ ID NO 369
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 369

Ala Thr Val Lys Phe Thr Tyr Arg Gly Glu Glu Lys Gln Val Asp Ile
1               5                   10                  15

Ser Lys Ile Lys Tyr Val Arg Arg Trp Gly Gln Tyr Ile Trp Phe Gly
            20                  25                  30

Tyr Asp Glu Gly Gly Gly Ala Arg Gly His Gly Arg Val Ser Glu Lys
        35                  40                  45

Asp Ala Pro Arg Gly Leu Leu Gln Met Leu Glu Lys Gln Gly Ser Glu
    50                  55                  60

Gln Lys Leu Ile Ser Glu Glu Asp
65                  70

<210> SEQ ID NO 370
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 370

Ala Ile Val Lys Phe Thr His His Gly Glu Glu Lys Gln Val Asp Ile
1               5                   10                  15

Ser Lys Ile Lys Tyr Val Arg Arg Trp Gly Gln Tyr Ile Trp Phe Gly
            20                  25                  30

Tyr Asp Glu Gly Gly Gly Ala Arg Gly Tyr Gly Tyr Val Ser Glu Arg
        35                  40                  45

Asp Ala Pro Lys Glu Leu Leu Gln Met Leu Glu Lys Arg Gly Ser Glu
```

-continued

```
                50                  55                  60

Gln Lys Leu Ile Ser Glu Glu Asp
 65                  70

<210> SEQ ID NO 371
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 371

Thr Thr Val Lys Phe Thr Tyr Gln Gly Glu Glu Lys Gln Val Gly Ile
 1               5                  10                  15

Ser Arg Ile Lys Tyr Val Arg Arg Gly Gln Tyr Ile Trp Phe Gly
                20                  25                  30

Tyr Asp Lys Gly Gly Gly Ala Arg Gly Tyr Gly Tyr Val Ser Gly Lys
                35                  40                  45

Asp Ala Pro Arg Glu Leu Leu Gln Met Leu Glu Lys Gln Gly Ser Glu
            50                  55                  60

Gln Lys Leu Ile Ser Glu Glu Asp
 65                  70

<210> SEQ ID NO 372
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 372

Ala Thr Val Arg Phe Thr Tyr His Gly Glu Glu Lys Gln Val Asp Ile
 1               5                  10                  15

Ser Lys Ile Lys Tyr Ala Arg Arg Trp Gly Gln Tyr Ile Trp Phe Gly
                20                  25                  30

Tyr Asp Glu Gly Gly Gly Ala Arg Gly Tyr Gly His Val Ser Gly Glu
                35                  40                  45

Asp Ala Pro Lys Glu Leu Leu Gln Met Leu Glu Lys Pro Gly Ser Glu
            50                  55                  60

Gln Lys Leu Ile Ser Glu Glu Asp
 65                  70

<210> SEQ ID NO 373
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 373

Ala Thr Val Lys Phe Thr Tyr Gln Gly Glu Glu Lys Gln Val Asp Ile
 1               5                  10                  15

Ser Lys Ile Lys Tyr Val Arg Arg Trp Gly Arg Tyr Ile Trp Phe Gly
                20                  25                  30

Tyr Asp Gly Gly Gly Gly Ala Arg Gly Tyr Gly His Val Ser Glu Lys
                35                  40                  45

Asp Ala Pro Lys Glu Leu Leu Gln Met Leu Gly Gly Arg Gly Ser Glu
            50                  55                  60

Gln Lys Leu Ile Ser Glu Glu Asp
 65                  70
```

<210> SEQ ID NO 374
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 374

Ala Thr Val Lys Phe Thr Tyr Gln Gly Gly Glu Lys Gln Val Asp Ile
1               5                   10                  15

Ser Lys Val Arg His Val Arg Arg Trp Gly Arg Trp Ile Trp Phe Gly
            20                  25                  30

Tyr Asp Glu Gly Gly Gly Ala His Gly Arg Gly Arg Val Ser Gly Lys
        35                  40                  45

Asp Ala Pro Lys Glu Leu Leu Gln Met Leu Glu Lys Gly Gly Ser Glu
    50                  55                  60

Gln Lys Leu Ile Ser Glu Glu Asp
65                  70

<210> SEQ ID NO 375
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 375

Ala Thr Val Lys Phe Thr Tyr Arg Gly Glu Glu Lys Gln Val Asp Ile
1               5                   10                  15

Ser Lys Ile Lys Arg Val Arg Arg Trp Gly Gln Trp Ile Trp Phe Ile
            20                  25                  30

Tyr Asp Glu Ala Gly Gly Ala His Gly Arg Gly Arg Val Ser Glu Arg
        35                  40                  45

Gly Ala Pro Lys Glu Leu Leu Gln Met Leu Glu Lys Gln Gly Ser Glu
    50                  55                  60

Gln Lys Leu Ile Ser Glu Glu Asp
65                  70

<210> SEQ ID NO 376
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 376

Ala Thr Val Glu Phe Thr Tyr Gln Gly Glu Glu Lys Gln Val Asp Ile
1               5                   10                  15

Ser Lys Ile Lys His Val Arg Arg Gly Gln Tyr Ile Trp Phe Gly
            20                  25                  30

Tyr Asp Lys Gly Gly Gly Ala Arg Gly Tyr Gly Tyr Val Ser Glu Lys
        35                  40                  45

Asp Ala Pro Lys Glu Leu Leu Gln Met Leu Glu Lys Gln Gly Ser Glu
    50                  55                  60

Gln Lys Leu Ile Ser Glu Glu Asp
65                  70

<210> SEQ ID NO 377
<211> LENGTH: 72

```
<212> TYPE: PRT
<213> ORGANISM: Artificial Sequence
<220> FEATURE:
<223> OTHER INFORMATION: Synthetic Polypeptide

<400> SEQUENCE: 377
```

Ala Thr Val Lys Phe Thr Tyr Arg Gly Glu Glu Lys Gln Val Asp Ile
1               5                   10                  15

Ser Lys Ile Lys His Val Arg Arg Trp Gly Gln Trp Ile Trp Phe Ile
            20                  25                  30

Tyr Asp Glu Gly Gly Gly Ala Lys Gly Trp Gly Val Ser Glu Lys
            35                  40                  45

Asp Ala Pro Arg Gly Leu Leu Gln Met Leu Glu Arg Gln Gly Ser Glu
    50                  55                  60

Gln Lys Leu Ile Ser Glu Glu Asp
65                  70

```
<210> SEQ ID NO 378
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 378
```

Ala Thr Val Lys Phe Thr Tyr Gln Gly Glu Glu Lys Gln Val Asp Ile
1               5                   10                  15

Ser Lys Ile Lys Tyr Val Arg Arg Trp Gly Gln Trp Ile Trp Phe Arg
            20                  25                  30

Tyr Asp Gly Gly Gly Gly Ala His Gly Ile Gly His Val Ser Glu Lys
            35                  40                  45

Asp Ala Pro Lys Glu Leu Leu Gln Met Leu Gly Lys Gln Gly Ser Glu
    50                  55                  60

Gln Lys Leu Ile Ser Glu Glu Asp
65                  70

```
<210> SEQ ID NO 379
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 379
```

Ala Thr Val Lys Phe Thr Tyr His Gly Glu Glu Lys Gln Val Asp Ile
1               5                   10                  15

Ser Lys Ile Lys Tyr Val Arg Arg Trp Gly Gln Tyr Ile Trp Phe Gly
            20                  25                  30

Tyr Asp Glu Gly Gly Gly Ala Arg Gly Tyr Gly Tyr Val Ser Gly Lys
            35                  40                  45

Gly Ala Pro Glu Glu Leu Leu Gln Met Leu Glu Lys Gln Gly Ser Glu
    50                  55                  60

Gln Lys Leu Ile Ser Glu Glu Asp
65                  70

```
<210> SEQ ID NO 380
<211> LENGTH: 72
<212> TYPE: PRT
<213> ORGANISM: Artificial Sequence
<220> FEATURE:
<223> OTHER INFORMATION: Synthetic Polypeptide
```

<400> SEQUENCE: 380

Ala Thr Val Lys Phe Thr Tyr Gln Gly Glu Gly Lys Gln Val Asp Ile
1               5                   10                  15

Ser Lys Ile Lys His Val Arg Arg Trp Gly Gln Trp Ile Trp Phe Ile
            20                  25                  30

Tyr Asp Glu Gly Gly Gly Ala Arg Gly Tyr Gly Tyr Val Ser Gly Lys
        35                  40                  45

Asp Ala Pro Lys Lys Leu Leu Arg Met Leu Glu Gly Arg Gly Ser Glu
    50                  55                  60

Gln Lys Leu Ile Ser Glu Glu Asp
65                  70

<210> SEQ ID NO 381
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 381

Ala Ala Val Glu Phe Thr Tyr Gln Gly Glu Gly Lys Gln Val Asp Ile
1               5                   10                  15

Ser Lys Ile Lys His Val Arg Arg Trp Gly Gln Trp Ile Trp Phe Ile
            20                  25                  30

Tyr Asp Glu Ala Gly Gly Ala His Gly Arg Gly Arg Val Ser Glu Arg
        35                  40                  45

Gly Ala Pro Lys Glu Leu Leu Gln Met Leu Glu Arg Gly Gly Ser Glu
    50                  55                  60

Gln Lys Leu Ile Ser Glu Glu Asp
65                  70

<210> SEQ ID NO 382
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 382

Ala Thr Val Lys Phe Thr Tyr Arg Gly Glu Gly Lys Gln Val Asp Ile
1               5                   10                  15

Ser Lys Ile Lys Tyr Val Arg Arg Arg Gly Gln Tyr Ile Trp Phe Gly
            20                  25                  30

Tyr Asp Glu Gly Gly Gly Ala Arg Gly Tyr Gly Tyr Val Ser Glu Arg
        35                  40                  45

Asp Ala Pro Arg Glu Leu Leu Gln Met Leu Glu Lys Gly Gly Ser Glu
    50                  55                  60

Gln Lys Leu Ile Ser Glu Glu Asp
65                  70

<210> SEQ ID NO 383
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 383

Ala Thr Val Lys Phe Thr Tyr Arg Gly Glu Glu Lys Gln Val Asp Ile

```
                1               5                  10                 15
            Ser Lys Ile Lys Tyr Val Arg Arg Gly Gln Tyr Ile Trp Phe Gly
                            20                  25                  30

Tyr Asp Glu Gly Gly Gly Ala Arg Gly Tyr Gly Tyr Val Ser Glu Lys
                            35                  40                  45

Asp Ala Pro Lys Glu Leu Leu Gln Met Leu Gly Lys Gly Ser Glu
                            50                  55                  60

Gln Lys Leu Ile Ser Glu Glu Asp
            65                          70

<210> SEQ ID NO 384
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 384

Ala Thr Val Lys Phe Thr Tyr Arg Gly Glu Lys Arg Val Asp Thr
1               5                   10                  15

Ser Lys Ile Lys His Val Arg Arg Trp Gly Gln Trp Ile Trp Phe Thr
                20                  25                  30

Tyr Asp Glu Gly Gly Gly Ala Lys Gly Arg Gly Gly Val Ser Glu Lys
                35                  40                  45

Asp Ala Pro Lys Glu Leu Leu Gln Met Leu Glu Lys Gly Ser Glu
                50                  55                  60

Gln Lys Leu Ile Ser Glu Glu Asp
65                          70

<210> SEQ ID NO 385
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 385

Ala Thr Val Lys Phe Thr Tyr Arg Gly Glu Glu Lys Gln Val Asp Ile
1               5                   10                  15

Ser Lys Ile Lys Tyr Val Trp Arg Trp Gly Gln Trp Ile Trp Phe Arg
                20                  25                  30

Tyr Asp Glu Gly Gly Gly Ala His Gly Ile Gly His Val Ser Glu Lys
                35                  40                  45

Ser Ala Pro Lys Glu Leu Leu Gln Thr Leu Gly Arg Gln Gly Ser Glu
                50                  55                  60

Gln Lys Leu Ile Ser Glu Glu Asp
65                          70

<210> SEQ ID NO 386
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 386

Ala Thr Val Lys Ser Thr Tyr Gln Gly Glu Glu Lys Gln Val Asp Ile
1               5                   10                  15

Ser Lys Ile Lys His Val Arg Arg Trp Gly Arg Trp Ile Trp Phe Ile
                20                  25                  30
```

Tyr Asp Glu Gly Gly Gly Ala Lys Gly Trp Gly Gly Val Ser Gly Arg
            35                  40                  45

Asp Ala Pro Lys Glu Leu Leu Gln Met Leu Glu Lys Gln Gly Ser Glu
    50                  55                  60

Gln Lys Leu Ile Ser Glu Glu Asp
65                  70

<210> SEQ ID NO 387
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 387

Ala Ile Val Lys Phe Thr Tyr Gln Gly Glu Arg Gln Val Asp Ile
1               5                   10                  15

Ser Lys Ile Lys Tyr Val Arg Arg Trp Gly Gln Tyr Ile Trp Phe Gly
            20                  25                  30

Tyr Asp Glu Gly Gly Gly Ala His Gly Arg Gly Arg Val Ser Gly Lys
            35                  40                  45

Asp Ala Pro Lys Glu Leu Leu Gln Met Leu Glu Lys Gln Gly Ser Glu
    50                  55                  60

Gln Lys Leu Ile Ser Glu Glu Asp
65                  70

<210> SEQ ID NO 388
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 388

Ala Thr Val Lys Phe Thr Tyr His Gly Glu Glu Arg Gln Val Asp Ile
1               5                   10                  15

Ser Lys Ile Lys Tyr Val Arg Arg Trp Gly Gln Tyr Ile Trp Phe Gly
            20                  25                  30

Tyr Gly Gly Gly Gly Gly Ala Arg Gly Tyr Gly Tyr Val Ser Glu Lys
            35                  40                  45

Asp Ala Pro Lys Glu Leu Leu Gln Met Leu Glu Lys Gln Gly Ser Glu
    50                  55                  60

Gln Lys Leu Ile Ser Glu Glu Asp
65                  70

<210> SEQ ID NO 389
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 389

Ala Thr Val Lys Phe Thr Tyr Gln Gly Glu Glu Lys Gln Val Asp Ile
1               5                   10                  15

Ser Lys Ile Lys Tyr Val Arg Arg Trp Gly Gln Tyr Ile Trp Phe Gly
            20                  25                  30

Tyr Asp Gly Gly Gly Gly Ala Arg Gly Arg Gly Tyr Val Ser Glu Lys
            35                  40                  45

Asp Ala Pro Lys Glu Leu Leu Gln Met Leu Glu Lys Gln Gly Ser Glu
            50                  55                  60

Gln Lys Leu Ile Ser Glu Glu Asp
 65                  70

<210> SEQ ID NO 390
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 390

Val Ala Val Lys Phe Thr Tyr Gln Gly Glu Lys Arg Val Asp Ile
 1               5                  10                  15

Ser Lys Ile Lys Tyr Val Arg Arg Gly Gln Tyr Ile Trp Phe Gly
                20                  25                  30

Tyr Gly Glu Gly Gly Gly Ala Arg Gly Tyr Gly Tyr Val Ser Glu Lys
            35                  40                  45

Asp Ala Pro Lys Glu Leu Leu Gln Met Leu Ala Lys Arg Gly Ser Glu
            50                  55                  60

Gln Lys Leu Ile Ser Glu Glu Asp
 65                  70

<210> SEQ ID NO 391
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 391

Ala Thr Val Lys Phe Thr Tyr Gln Gly Glu Lys Gln Val Asp Ile
 1               5                  10                  15

Ser Lys Ile Lys His Val Arg Arg Trp Gly Gln Trp Ile Trp Phe Ile
                20                  25                  30

Tyr Asp Gly Gly Gly Gly Ala Lys Gly Arg Gly Gly Val Ser Glu Lys
            35                  40                  45

Asp Ala Pro Lys Glu Leu Leu Gln Met Leu Glu Lys Gln Gly Ser Glu
            50                  55                  60

Gln Lys Leu Ile Ser Glu Glu Asp
 65                  70

<210> SEQ ID NO 392
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 392

Ala Thr Val Lys Phe Thr Tyr Arg Gly Glu Lys Gln Val Asp Ala
 1               5                  10                  15

Ser Arg Ile Lys Tyr Val Arg Arg Trp Gly Gln Tyr Ile Trp Phe Gly
                20                  25                  30

Tyr Asp Glu Gly Gly Gly Ala Arg Gly Tyr Gly Tyr Val Ser Gly Arg
            35                  40                  45

Asp Ala Pro Lys Glu Leu Leu Gln Met Leu Glu Lys Gln Gly Ser Glu
            50                  55                  60

Gln Lys Leu Ile Ser Glu Glu Asp

<210> SEQ ID NO 393
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 393

```
Ala Thr Val Lys Phe Thr Tyr Gln Gly Glu Lys Gln Val Asp Ile
1               5                   10                  15

Ser Lys Ile Arg Tyr Ala Arg Arg Gly Gln Tyr Ile Trp Phe Gly
                20                  25                  30

Tyr Gly Glu Gly Gly Gly Ala Arg Gly Tyr Gly Tyr Val Ser Asp Lys
            35                  40                  45

Asp Ala Pro Lys Glu Leu Leu Arg Met Leu Glu Lys Gln Gly Ser Glu
        50                  55                  60

Gln Lys Leu Ile Ser Glu Glu Asp
65                  70
```

<210> SEQ ID NO 394
<211> LENGTH: 73
<212> TYPE: PRT
<213> ORGANISM: Artificial Sequence
<220> FEATURE:
<223> OTHER INFORMATION: Synthetic Polypeptide

<400> SEQUENCE: 394

```
Ala Thr Val Lys Phe Thr Tyr Arg Gly Glu Lys Gln Val Gly Ile
1               5                   10                  15

Ser Arg Ile Arg Ser Val His Arg Ile Gly Gln Trp Ile Lys Phe Trp
                20                  25                  30

Tyr Asp Glu Gly Ser Gly Ala Cys Gly Arg Gly Tyr Val Ser Glu Lys
            35                  40                  45

Gly Ala Pro Lys Glu Leu Leu Gln Met Leu Gly Lys Arg Gly Ser Glu
        50                  55                  60

Gln Lys Leu Ile Ser Glu Glu Asp Leu
65                  70
```

<210> SEQ ID NO 395
<211> LENGTH: 73
<212> TYPE: PRT
<213> ORGANISM: Artificial Sequence
<220> FEATURE:
<223> OTHER INFORMATION: Synthetic Polypeptide

<400> SEQUENCE: 395

```
Ala Thr Val Lys Phe Thr Tyr Arg Gly Lys Glu Lys Arg Val Gly Val
1               5                   10                  15

Ser Arg Ile Lys Ser Val Arg Arg Ile Gly Gln Trp Ile Lys Phe Trp
                20                  25                  30

Tyr Asp Glu Gly Ser Gly Ala Tyr Gly Arg Gly Tyr Val Ser Glu Lys
            35                  40                  45

Asp Ala Pro Lys Glu Leu Leu Gln Met Leu Glu Lys Arg Gly Ser Glu
        50                  55                  60

Gln Lys Leu Ile Ser Glu Glu Asp Leu
65                  70
```

<210> SEQ ID NO 396

<211> LENGTH: 73
<212> TYPE: PRT
<213> ORGANISM: Artificial Sequence
<220> FEATURE:
<223> OTHER INFORMATION: Synthetic Polypeptide

<400> SEQUENCE: 396

Ala Thr Val Lys Phe Thr Tyr Arg Gly Glu Glu Lys Gln Val Gly Ile
1               5                   10                  15

Asn Arg Ile Lys Ser Val His Arg Ile Gly Gln Trp Ile Lys Phe Trp
            20                  25                  30

Tyr Asp Glu Gly Ser Gly Ala Tyr Gly Arg Gly Tyr Val Ser Gly Lys
        35                  40                  45

Asp Ala Pro Lys Glu Leu Leu Arg Met Leu Glu Lys Arg Gly Ser Glu
    50                  55                  60

Gln Lys Leu Ile Ser Glu Glu Asp Leu
65                  70

<210> SEQ ID NO 397
<211> LENGTH: 73
<212> TYPE: PRT
<213> ORGANISM: Artificial Sequence
<220> FEATURE:
<223> OTHER INFORMATION: Synthetic Polypeptide

<400> SEQUENCE: 397

Ala Thr Val Lys Phe Thr Tyr Gln Gly Glu Glu Lys Gln Val Asp Ile
1               5                   10                  15

Ser Lys Ile Lys Ile Val Tyr Arg Trp Gly Gln Arg Ile Ser Phe Ile
            20                  25                  30

Tyr Asp Glu Gly Gly Gly Ala Arg Gly Tyr Gly Arg Val Ser Glu Lys
        35                  40                  45

Asp Ala Pro Lys Glu Leu Leu Gln Met Leu Glu Lys Gln Gly Ser Glu
    50                  55                  60

Gln Lys Leu Ile Ser Glu Glu Asp Leu
65                  70

<210> SEQ ID NO 398
<211> LENGTH: 73
<212> TYPE: PRT
<213> ORGANISM: Artificial Sequence
<220> FEATURE:
<223> OTHER INFORMATION: Synthetic Polypeptide

<400> SEQUENCE: 398

Ala Thr Val Lys Phe Thr Tyr Gln Gly Glu Glu Lys Gln Val Asp Ile
1               5                   10                  15

Ser Lys Ile Lys His Val Arg Arg Trp Gly Gln Trp Ile Trp Phe Ile
            20                  25                  30

Tyr Asp Glu Gly Gly Gly Ala Lys Gly Trp Gly Gly Val Ser Glu Lys
        35                  40                  45

Asp Ala Pro Lys Glu Leu Leu Gln Met Leu Glu Lys Gln Gly Ser Glu
    50                  55                  60

Gln Lys Leu Ile Ser Glu Glu Asp Leu
65                  70

<210> SEQ ID NO 399
<211> LENGTH: 73
<212> TYPE: PRT
<213> ORGANISM: Artificial Sequence
<220> FEATURE:

<223> OTHER INFORMATION: Synthetic Polypeptide

<400> SEQUENCE: 399

```
Ala Thr Val Lys Phe Thr Tyr Gln Gly Glu Glu Lys Gln Val Asp Ile
1               5                   10                  15
Ser Lys Ile Lys Tyr Val Arg Arg Trp Gly Tyr Ile Trp Phe Gly
            20                  25                  30
Tyr Asp Glu Gly Gly Gly Ala Arg Gly Tyr Gly Tyr Val Ser Glu Lys
            35                  40                  45
Asp Ala Pro Lys Glu Leu Leu Gln Met Leu Glu Lys Gln Gly Ser Glu
        50                  55                  60
Gln Lys Leu Ile Ser Glu Glu Asp Leu
65                  70
```

<210> SEQ ID NO 400
<211> LENGTH: 73
<212> TYPE: PRT
<213> ORGANISM: Artificial Sequence
<220> FEATURE:
<223> OTHER INFORMATION: Synthetic Polypeptide

<400> SEQUENCE: 400

```
Ala Thr Val Lys Phe Thr Tyr Gln Gly Glu Glu Lys Gln Val Asp Ile
1               5                   10                  15
Ser Lys Ile Lys Arg Val Tyr Arg Tyr Gly Gln Trp Ile Trp Phe Arg
            20                  25                  30
Tyr Asp Glu Gly Gly Gly Ala Tyr Gly Gly Gly Trp Val Ser Glu Lys
            35                  40                  45
Asp Ala Pro Lys Glu Leu Leu Gln Met Leu Glu Lys Gln Gly Ser Glu
        50                  55                  60
Gln Lys Leu Ile Ser Glu Glu Asp Leu
65                  70
```

<210> SEQ ID NO 401
<211> LENGTH: 69
<212> TYPE: PRT
<213> ORGANISM: Artificial Sequence
<220> FEATURE:
<223> OTHER INFORMATION: Synthetic Polypeptide

<400> SEQUENCE: 401

```
Ala Thr Val Lys Phe Thr Tyr Gln Gly Glu Glu Lys Gln Val Asp Ile
1               5                   10                  15
Ser Lys Ile Lys Ser Val Ser Arg Trp Gly Gln Ala Ile Ile Phe Arg
            20                  25                  30
Tyr Asp Glu Gly Gly Gly Ala Lys Gly Lys Gly Ser Val Ser Glu Lys
            35                  40                  45
Asp Ala Pro Lys Glu Leu Leu Gln Met Leu Glu Lys Ala Arg Ile Arg
        50                  55                  60
Thr Lys Ala Tyr Phe
65
```

<210> SEQ ID NO 402
<211> LENGTH: 61
<212> TYPE: PRT
<213> ORGANISM: Artificial Sequence
<220> FEATURE:
<223> OTHER INFORMATION: Synthetic Polypeptide

<400> SEQUENCE: 402

Ala Thr Val Lys Phe Thr Tyr Arg Gly Glu Glu Lys Gln Val Gly Ile
1               5                   10                  15

Ser Arg Ile Lys Ser Val Arg Arg Ile Gly Gln Trp Ile Lys Phe Trp
            20                  25                  30

Tyr Asp Glu Gly Ser Gly Ala Tyr Gly Arg Gly Tyr Val Ser Glu Lys
        35                  40                  45

Asp Ala Pro Lys Glu Leu Leu Gln Met Leu Glu Lys Arg
    50                  55                  60

<210> SEQ ID NO 403
<211> LENGTH: 61
<212> TYPE: PRT
<213> ORGANISM: Artificial Sequence
<220> FEATURE:
<223> OTHER INFORMATION: Synthetic Polypeptide

<400> SEQUENCE: 403

Ala Thr Val Lys Phe Thr Tyr Arg Gly Glu Glu Lys Gln Val Gly Ile
1               5                   10                  15

Ser Arg Ile Lys Ser Val Arg Arg Ile Gly Gln Trp Ile Lys Phe Trp
            20                  25                  30

Tyr Asp Glu Gly Ser Gly Ala Tyr Gly Arg Gly Tyr Val Ser Gly Lys
        35                  40                  45

Asp Ala Pro Lys Glu Leu Leu Gln Met Leu Glu Lys Arg
    50                  55                  60

<210> SEQ ID NO 404
<211> LENGTH: 61
<212> TYPE: PRT
<213> ORGANISM: Artificial Sequence
<220> FEATURE:
<223> OTHER INFORMATION: Synthetic Polypeptide

<400> SEQUENCE: 404

Ala Thr Val Lys Phe Thr Tyr Arg Gly Gly Glu Lys Gln Val Gly Ile
1               5                   10                  15

Ser Arg Ile Lys Ser Val Arg Arg Ile Gly Gln Trp Ile Lys Phe Trp
            20                  25                  30

Tyr Asp Glu Gly Ser Gly Ala Tyr Gly Arg Gly Tyr Val Ser Glu Lys
        35                  40                  45

Asp Ala Pro Lys Glu Leu Leu Gln Met Leu Glu Lys Arg
    50                  55                  60

<210> SEQ ID NO 405
<211> LENGTH: 61
<212> TYPE: PRT
<213> ORGANISM: Artificial Sequence
<220> FEATURE:
<223> OTHER INFORMATION: Synthetic Polypeptide

<400> SEQUENCE: 405

Ala Thr Val Lys Phe Thr Tyr Arg Gly Glu Glu Lys Gln Val Gly Ile
1               5                   10                  15

Ser Arg Ile Lys Ser Val His Arg Ile Gly Arg Trp Ile Lys Phe Trp
            20                  25                  30

Tyr Asp Glu Gly Ser Gly Ala Tyr Gly Arg Gly Tyr Val Ser Glu Lys
        35                  40                  45

Asp Ala Pro Lys Glu Leu Leu Gln Met Leu Glu Lys Arg
    50                  55                  60

```
<210> SEQ ID NO 406
<211> LENGTH: 61
<212> TYPE: PRT
<213> ORGANISM: Artificial Sequence
<220> FEATURE:
<223> OTHER INFORMATION: Synthetic Polypeptide

<400> SEQUENCE: 406

Ala Thr Val Lys Phe Thr Tyr Arg Gly Glu Glu Lys Gln Val Gly Ile
1               5                   10                  15

Ser Arg Ile Lys Ser Val His Arg Ile Gly Gln Trp Ile Lys Phe Trp
            20                  25                  30

Tyr Asp Glu Gly Ser Gly Ala Tyr Gly Arg Gly Tyr Val Ser Lys Lys
        35                  40                  45

Asp Ala Pro Lys Glu Leu Leu Gln Met Leu Glu Lys Arg
    50                  55                  60

<210> SEQ ID NO 407
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 407

Lys Lys Val Trp Arg Val Gly
1               5

<210> SEQ ID NO 408
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 408

Gln Met Ile Ser Phe Thr Tyr
1               5

<210> SEQ ID NO 409
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 409

Ala Thr Gly Arg Gly Ala Val
1               5

<210> SEQ ID NO 410
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 410

Gln Val Gly Val Ser Arg Val Lys Ser Val
1               5                   10

<210> SEQ ID NO 411
<211> LENGTH: 10
<212> TYPE: PRT
<213> ORGANISM: Artificial Sequence
<220> FEATURE:
```

<223> OTHER INFORMATION: Synthetic Polypeptide

<400> SEQUENCE: 411

Gln Val Asp Ile Ser Lys Ile Lys Lys Val
1               5                   10

<210> SEQ ID NO 412
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (2)..(6)
<223> OTHER INFORMATION: Xaas cannot simultaneously be KWV, sequentially
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 412

Lys Xaa Val Xaa Arg Xaa Gly
1               5

<210> SEQ ID NO 413
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (2)..(6)
<223> OTHER INFORMATION: Xaas cannot simultaneously be MST, sequentially
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 413

Gln Xaa Ile Xaa Phe Xaa Tyr
1               5

<210> SEQ ID NO 414
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (2)..(6)

```
<223> OTHER INFORMATION: Xaas cannot simultaneously be TRA, sequentially
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 414

Ala Xaa Gly Xaa Gly Xaa Val
1               5

<210> SEQ ID NO 415
<211> LENGTH: 59
<212> TYPE: PRT
<213> ORGANISM: Artificial Sequence
<220> FEATURE:
<223> OTHER INFORMATION: Synthetic Polypeptide

<400> SEQUENCE: 415

Ala Thr Val Lys Phe Thr Tyr Gln Gly Glu Glu Lys Gln Val Asp Ile
1               5                   10                  15

Ser Lys Ile Lys Ser Val His Arg Val Gly Gln Trp Ile Lys Phe Trp
            20                  25                  30

Tyr Asp Gly Gly Gly Gly Ala Tyr Gly Arg Gly Tyr Val Ser Glu Lys
        35                  40                  45

Asp Ala Pro Lys Glu Leu Leu Gln Met Leu Glu
    50                  55

<210> SEQ ID NO 416
<211> LENGTH: 61
<212> TYPE: PRT
<213> ORGANISM: Artificial Sequence
<220> FEATURE:
<223> OTHER INFORMATION: Synthetic Polypeptide

<400> SEQUENCE: 416

Ala Thr Val Lys Phe Thr Tyr Arg Gly Glu Glu Lys Gln Val Asp Ile
1               5                   10                  15

Ser Lys Ile Lys Tyr Val Arg Arg Trp Gly Gln Tyr Ile Trp Phe Gly
            20                  25                  30

Tyr Asp Glu Gly Gly Gly Ala Arg Gly Tyr Gly Tyr Val Ser Glu Thr
        35                  40                  45

Asp Ala Pro Glu Leu Leu Leu Gln Met Leu Glu Lys Gln
    50                  55                  60

<210> SEQ ID NO 417
<211> LENGTH: 61
<212> TYPE: PRT
<213> ORGANISM: Artificial Sequence
<220> FEATURE:
<223> OTHER INFORMATION: Synthetic Polypeptide

<400> SEQUENCE: 417

Ala Thr Val Lys Phe Thr Tyr Arg Gly Glu Gly Lys Gln Val Gly Ile
1               5                   10                  15

Ser Arg Ile Lys Ser Val Arg Arg Ile Gly Gln Trp Ile Lys Phe Trp
            20                  25                  30

Tyr Asp Glu Gly Ser Gly Ala Tyr Gly Arg Gly Tyr Val Ser Gly Lys
        35                  40                  45

Asp Ala Pro Lys Glu Leu Leu Gln Met Leu Glu Lys Arg
```

```
<210> SEQ ID NO 418
<211> LENGTH: 61
<212> TYPE: PRT
<213> ORGANISM: Artificial Sequence
<220> FEATURE:
<223> OTHER INFORMATION: Synthetic Polypeptide

<400> SEQUENCE: 418

Ala Thr Val Lys Phe Thr Tyr Arg Gly Glu Glu Lys Gln Val Gly Ile
1               5                   10                  15

Ser Arg Ile Lys Ser Val Arg Arg Ile Gly Arg Trp Ile Lys Leu Trp
                20                  25                  30

Tyr Asp Glu Gly Ser Gly Ala Tyr Gly Arg Gly Tyr Val Ser Gly Lys
            35                  40                  45

Asp Ala Pro Lys Glu Leu Leu Gln Met Leu Glu Lys Arg
        50                  55                  60
```